United States Patent

Kogen et al.

Patent Number: 5,827,855
Date of Patent: Oct. 27, 1998

[54] HEXAHYDRONAPHTHALENE ESTER DERIVATIVES THEIR PREPARATION AND THEIR THERAPEUTIC USES

[75] Inventors: Hiroshi Kogen; Sadao Ishihara; Teiichiro Koga; Eiichi Kitazawa; Nobufusa Serizawa; Kiyoshi Hamano, all of Tokyo, Japan

[73] Assignee: Sankyo Company, Limited, Tokyo, Japan

[21] Appl. No.: 579,840

[22] Filed: Dec. 28, 1995

Related U.S. Application Data

[62] Division of Ser. No. 435,725, May 5, 1995, abandoned, which is a division of Ser. No. 174,661, Dec. 28, 1993, Pat. No. 5,451,688.

[30] Foreign Application Priority Data

Dec. 28, 1992 [JP] Japan ................................. 4-349034

[51] Int. Cl.⁶ ..................... C07D 309/30; C07C 67/74; A01N 43/42
[52] U.S. Cl. ..................... 514/292; 560/119; 560/127; 549/292; 514/460; 514/547; 514/292; 562/467
[58] Field of Search ..................... 424/234.1, 287.1; 435/135, 146, 252.1, 253.2, 872; 514/256, 236, 319, 365, 374, 452, 448, 424, 427, 445, 292, 460, 547; 560/119, 75, 251, 256, 254, 255, 127; 548/344, 201, 562, 561, 248, 236; 562/467; 549/292

[56] References Cited

U.S. PATENT DOCUMENTS

| | | | |
|---|---|---|---|
| 4,137,322 | 1/1979 | Endo et al. | 424/273 |
| 4,346,227 | 8/1982 | Terahara et al. | 560/119 |
| 4,537,859 | 8/1985 | Terahara et al. | 435/146 |
| 4,997,848 | 3/1991 | Kurabayashi et al. | 514/452 |
| 5,049,696 | 9/1991 | Lee et al. | 560/75 |
| 5,491,167 | 2/1996 | Ishihara et al. | |

FOREIGN PATENT DOCUMENTS

| | | |
|---|---|---|
| 0 033 538 | 8/1981 | European Pat. Off. |
| 0 314 435 | 5/1989 | European Pat. Off. |
| A-0 381 478 | 8/1990 | European Pat. Off. |
| 58-10572 | 1/1983 | Japan |
| 59-17545 | 4/1984 | Japan |
| 59-175450 | 10/1984 | Japan |
| A-0 381 478 | 6/1984 | Switzerland |
| 2 077 264 | 12/1981 | United Kingdom |
| 2 111 052 | 6/1983 | United Kingdom |

OTHER PUBLICATIONS

Patent Abstracts of Japan, unexamined applications, C section, vol. 9, No. 32, The Patent Office Japanese Government, p. 4 C 265, 1985, of JP 59–175450.

The Journal of Organic Chemistry, vol. 51, 1986, Issues 9–14, G.E. Keck et al, "A Highly Covergent Total Synthesis, of (+)–Compactin", p. 2487–2493.

Pike and Brown, *Nutrition,* pp. 531–535 (1984).

Primary Examiner—Marian C. Knode
Assistant Examiner—Datquan Lee
Attorney, Agent, or Firm—Frishauf, Holtz, Goodman, Langer & Chick, P.C.

[57] ABSTRACT

Compounds of formula (I):

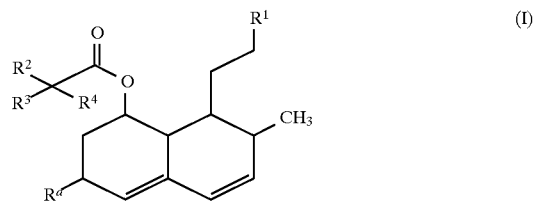

wherein $R^1$ represents a group of formula (II) or (III):

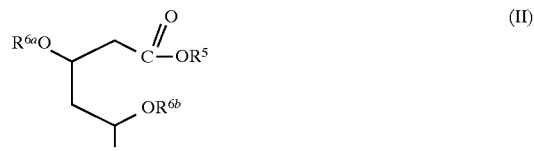

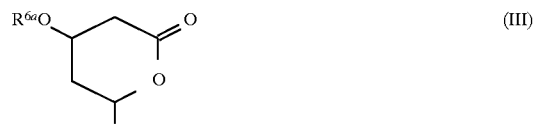

$R^2$ is alkyl, alkenyl or alkynyl; $R^3$ and $R^4$ are each hydrogen, alkyl, alkenyl or alkynyl; $R^5$ is hydrogen or a carboxy-protecting group; $R^a$ is a group of formula $-OR^6$; $R^6$ is hydrogen; $R^{6a}$ and $R^{6b}$ are each hydrogen, a hydroxy-protecting group, alkyl, alkanesulfonyl, halogenated alkanesulfonyl or arysulfonyl, and their salts and esters. Such compounds inhibit the synthesis of cholesterol, and can be used for the treatment and prophylaxis of hypercholesterolemia and of various cardiac disorders.

7 Claims, No Drawings

HEXAHYDRONAPHTHALENE ESTER DERIVATIVES THEIR PREPARATION AND THEIR THERAPEUTIC USES

This application is divisional application of Ser. No. 08/435,725 filed May 5, 1995, now abandoned, which is a divisional application of Ser. No. 08/174,661 filed Dec. 28, 1993, now U.S. Pat. No. 5,451,688.

BACKGROUND OF THE INVENTION

The present invention relates to a series of new hexahydronaphthalene derivatives related to the class of compounds known as "ML-236B", which have the ability to inhibit the synthesis of cholesterol, and which can thus be used for the treatment and prophylaxis of hypercholesterolemia and of various cardiac disorders. The invention also provides methods and compositions using these compounds as well as processes for their preparation.

Excessive levels of cholesterol in the body have been implicated in many life-threatening disorders and there is, therefore, a need for drugs which have the effect of reducing blood cholesterol levels. One method by which a drug may achieve this is to inhibit the biosynthesis of cholesterol.

A number of compounds which may be generally described as 7-[substituted 1,2,3,5,6,7,8,8a-octahydro-1-naphthyl]-3,5-dihydroxyheptanoates is known, and such compounds are disclosed, inter alia, in European Patent Publication No. 314 435, which also describes in greater detail than herein the development and forerunners of these types of compound. However, the closest compounds to those of the present invention are believed to be the compounds disclosed in United Kingdom Patent Specification No. 2 077 264 and Japanese Pantent Application Kokai No. Sho. 59-175450, which compounds may be represented by the formulae (A) and (B), respectively:

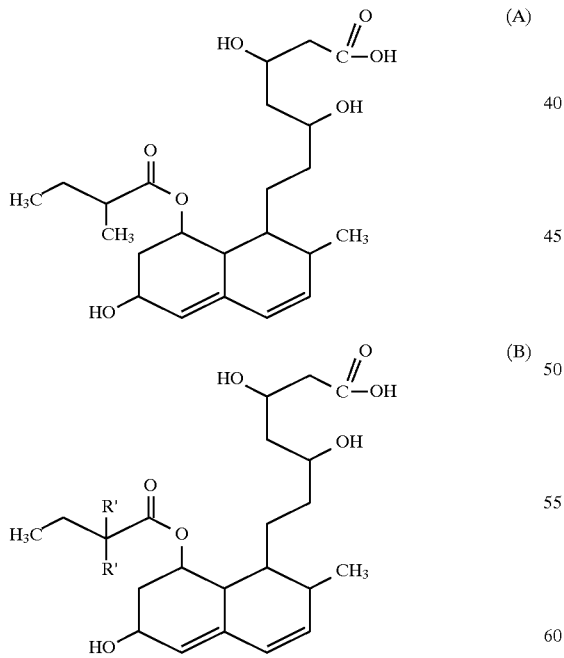

These prior art compounds, like the compounds of the present invention, have the ability to inhibit the biosynthesis of cholesterol, and can thus be used for the treatment and prophylaxis of the various diseases caused by hypercholesterolemia, such as atherosclerosis and various cardiac disorders.

BRIEF SUMMARY OF INVENTION

It is, therefore, an object of the present invention to provide a series of new hexahydronaphthalene derivatives.

It is a further, and more specific, object of the present invention to provide such compounds having the ability to inhibit the biosynthesis of cholesterol.

Other objects and advantages of the present invention will become apparent as the description proceeds.

Thus, the present invention provides compounds of formula (I):

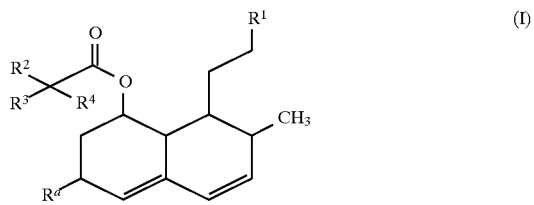

wherein $R^1$ represents a group of formula (II) or (III):

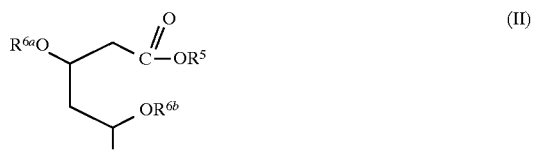

$R^2$ represents an alkyl group having from 1 to 6 carbon atoms, an alkenyl group having from 2 to 6 carbon atoms or an alkynyl group having from 2 to 6 carbon atoms;

$R^3$ and $R^4$ are independently selected from the group consisting of hydrogen atoms, alkyl groups having from 1 to 6 carbon atoms, alkenyl groups having from 2 to 6 carbon atoms and alkynyl groups having from 2 to 6 carbon atoms;

$R^5$ represents a hydrogen atom or a carboxy-protecting group;

$R^a$ represents a hydrogen atom or a group of formula $-OR^6$;

$R^6$, $R^{6a}$ and $R^{6b}$ are independently selected from the group consisting of hydrogen atoms, hydroxy-protecting groups, alkyl groups having from 1 to 6 carbon atoms, alkanesulfonyl groups having from 1 to 6 carbon atoms, halogenated alkanesulfonyl groups having from 1 to 6 carbon atoms and arylsulfonyl groups, in which the aryl part is an aromatic hydrocarbon ring which has from 6 to 14 ring carbon atoms and is unsubstituted or is substituted by at least one substituent selected from the group consisting of substituents α, defined below;

said substituents α are selected from the group consisting of halogen atoms, alkyl groups having from 1 to 6 carbon atoms, alkoxy groups having from 1 to 6 carbon atoms, carboxy groups, nitro groups, cyano groups, alkylenedioxy groups having from 1 to 4 carbon atoms, acylamino groups, alkoxycarbonyl groups having from 2 to 7 carbon atoms, and aryl groups;

PROVIDED THAT, when $R^2$ represents an ethyl group and $R^3$ represents a hydrogen atom, $R^4$ does not represent a methyl group, and, when $R^2$ represents an ethyl group and $R^3$ represents an alkyl group, $R^4$ does not also represent an alkyl group;

and pharmaceutically acceptable salts and esters thereof.

The invention also provides a pharmaceutical composition comprising an agent for inhibiting cholesterol biosynthesis in admixture with a pharmaceutically acceptable carrier or diluent, wherein said agent is selected from the group consisting of compounds of formula (I), as defined above, and pharmaceutically acceptable salts and esters thereof.

The invention still further provides a method of treating a mammal suffering from a disorder arising from a blood cholesterol imbalance, which comprises administering to said mammal an effective amount of an agent inhibiting cholesterol biosynthesis, wherein said agent is selected from the group consisting of compounds of formula (I), as defined above, and pharmaceutically acceptable salts and esters thereof.

The invention still further provides processes for the preparation of compounds of formula (I) and pharmaceutically acceptable salts and esters thereof, which are described in more detail hereafter.

DETAILED DESCRIPTION OF INVENTION

Included in the compounds of the present invention are those compounds of formulae (Ia) and (Ib):

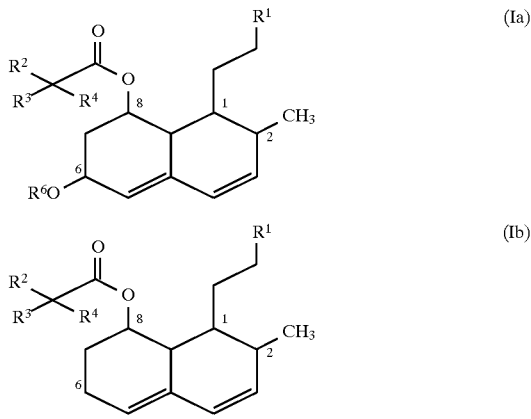

wherein $R^1$, $R^2$, $R^3$, $R^4$ and $R^6$ are as defined above. For the avoidance of doubt, the above two formulae also show a partial numbering system for the hexahydronaphthalene rings, as employed herein.

In the compounds of the present invention, where $R^2$, $R^3$, $R^4$, $R^6$, $R^{6a}$ and $R^{6b}$ represents an alkyl group, this may be a straight or branched chain alkyl group containing from 1 to 6 carbon atoms, preferably from 1 to 4 carbon atoms. Examples of such groups include the methyl, ethyl, propyl, isopropyl, butyl, isobutyl, sec-butyl, t-butyl, pentyl, isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, of which we prefer the methyl, ethyl, propyl, isopropyl, butyl and t-butyl groups. In the case of $R^2$, the methyl and ethyl groups are more preferred, the ethyl group being most preferred. In the case of $R^3$, the methyl, ethyl, propyl and isopropyl groups are more preferred, the ethyl and isopropyl groups being most preferred. In the case of $R^4$, the ethyl, propyl, isopropyl, butyl and t-butyl groups are more preferred, the ethyl and isopropyl groups being most preferred.

Where $R^2$, $R^3$ or $R^4$ represents an alkenyl group, this may be a straight or branched chain alkenyl group containing from 2 to 6 carbon atoms, preferably from 2 to 4 carbon atoms. Examples of such groups include the vinyl, 1-propenyl, allyl (i.e. 2-propenyl), 1-methyl-2-propenyl, 2-methyl-1-propenyl, 2-methyl-2-propenyl, 2-ethyl-2-propenyl, 1-butenyl, 2-butenyl, 1-methyl-2-butenyl, 2-methyl-2-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl groups, of which the vinyl, allyl and 3-butenyl groups are preferred, the allyl group being most preferred.

Where $R^2$, $R^3$ or $R^4$ represents an alkynyl group, this may be a straight or branched chain alkynyl group containing from 2 to 6 carbon atoms, preferably from 2 to 4 carbon atoms. Examples of such groups include the ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups, of which the 2-propynyl group is preferred.

The term "carboxy-protecting group", as used in the definition of $R^5$, signifies a protecting group capable of being cleaved by chemical methods (such as hydrogenolysis, hydrolysis, electrolysis or photolysis) to generate a free carboxy group, or a protecting group capable of being cleaved in vivo by biological methods such as hydrolysis.

Examples of carboxy-protecting groups which can be cleaved by chemical means include ester and other groups, such as:

alkyl groups having from 1 to 20 carbon atoms, more preferably from 1 to 6 carbon atoms, such as those exemplified above in relation to $R^2$ etc., and higher alkyl groups such as are well known in the art, for example the heptyl, octyl, nonyl, decyl, dodecyl, tridecyl, pentadecyl, octadecyl, nonadecyl and icosyl groups, but most preferably the methyl, ethyl and t-butyl groups;

halogenated alkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the or each aryl part is a carbocyclic aromatic group having from 6 to 14 carbon atoms, which may be substituted or unsubstituted and, if substituted, has at least one of substituents α defined and exemplified below; there may be 1, 2 or 3 such aryl substituents on the alkyl group; examples of such aralkyl groups include the benzyl, phenethyl, 1-phenylethyl, 3-phenylpropyl, 2-phenylpropyl, α-naphthylmethyl, β-naphthylmethyl, 2-(α-naphthyl)
ethyl, 2-(2-naphthyl)ethyl, benzhydryl (i.e.
diphenylmethyl), triphenylmethyl (i.e. trityl),
α-naphthyldiphenylmethyl, 4-methylbenzyl, 2,4,6-
trimethylbenzyl, 3,4,5-trimethylbenzyl,
4-methoxybenzyl, 4-methoxyphenyldiphenylmethyl,
2-nitrobenzyl, 4-nitrobenzyl, 3-nitrobenzyl,
4-chlorobenzyl, 4-bromobenzyl, 4-cyanobenzyl,
4-cyanophenyldiphenylmethyl, bis(o-nitrophenyl)
methyl, 9-anthrylmethyl and piperonyl groups;

alkenyl groups having from 2 to 6 carbon atoms, such as
the the vinyl, allyl, 2-methylallyl, 1-propenyl,
isopropenyl, 1-butenyl, 2-butenyl, 3-butenyl,
1-pentenyl, 2-pentenyl, 3-pentenyl, 4-pentenyl,
1-hexenyl, 2-hexenyl, 3-hexenyl, 4-hexenyl and
5-hexenyl groups, of which the vinyl, allyl,
2-methylallyl, 1-propenyl, isopropenyl and butenyl
groups are preferred, the allyl and 2-methylallyl groups
being most preferred.

substituted silylalkyl groups, in which the alkyl part is as
defined and exemplified above, and the silyl group has
up to 3 substituents selected from alkyl groups having
from 1 to 6 carbon atoms and phenyl groups which are
unsubstituted or have at least one substituent selected
from substituents α, defined and exemplified below, for
example a 2-trimethylsilylethyl group;

aryl groups having from 6 to 14 carbon atoms and
optionally substituted by one or more of substituents α,
defined and exemplified below, for example the phenyl,
α-naphthyl, β-naphthyl, indanyl and anthrenyl groups,
preferably the phenyl or indanyl group and more pref-
erably the phenyl group; any of these aryl groups may
be unsubstituted or substituted, and, if substituted,
preferably have at least one alkyl group having from 1
to 4 carbon atoms or acylamino group; examples of the
substituted groups include the tolyl and benzamidophe-
nyl groups;

phenacyl groups, which may be unsubstituted or have at
least one of substituents α defined and exemplified
below, for example the phenacyl group itself or the
p-bromophenacyl group; and cyclic and acyclic terpenyl groups, for example the
geranyl, neryl, linalyl, phytyl, menthyl (especially m-
and p-menthyl), thujyl, caryl, pinanyl, bornyl, norcaryl,
norpinanyl, norbornyl, menthenyl, camphenyl and nor-
bornenyl groups.

Examples of carboxy-protecting groups which are
capable of being cleaved in vivo by biological methods such
as hydrolysis include ester and other groups, such as:

alkoxyalkyl groups, in which the alkoxy and alkyl parts
each have from 1 to 5, preferably from 1 to 4, carbon
atoms, especially alkoxymethyl groups, and such
groups which have at least one, preferably from 1 to 5,
more preferably from 1 to 3, and most preferably 1,
substituents, preferably: lower alkoxymethyl groups
and other alkoxyalkyl groups (such as the
methoxymethyl, ethoxymethyl, propoxymethyl,
isopropoxymethyl, butoxymethyl and t-butoxymethyl
groups); lower alkoxy-substituted lower alkoxymethyl
groups (such as the 2-methoxyethoxymethyl group);
halogenated lower alkoxymethyl groups [such as the
2,2,2-trichloroethoxymethyl and bis(2-chloroethoxy)
methyl groups] and lower alkoxy-substituted ethyl and
higher alkyl groups (such as the 1-ethoxyethyl,
1-methyl-1-methoxyethyl and 1-isopropoxyethyl
groups);

other substituted ethyl groups, preferably: halogenated
ethyl groups (such as the 2,2,2-trichloroethyl group);
and arylselenyl-substituted ethyl groups, in which the
aryl part is as defined above, preferably a phenyl group
[such as the 2-(phenylselenyl)ethyl group];

aliphatic acyloxyalkyl groups, in which the acyl group is
preferably an alkanoyl group (which may be unsubsti-
tuted or may have at least one substituent selected from
the group consisting of amino groups, alkylamino
groups and dialkylamino groups), and more preferably
an alkanoyl group having from 2 to 6 carbon atoms, and
the alkyl part has from 1 to 6, and preferably from 1 to
4, carbon atoms such as the acetoxymethyl,
dimethylaminoacetoxymethyl, propionyloxymethyl,
butyryloxymethyl, isobutyryloxymethyl,
pivaloyloxymethyl, 1-pivaloyloxyethyl,
1-acetoxyethyl, 1-isobutyryloxyethyl,
1-pivaloyloxypropyl, 2-methyl-1-pivaloyloxypropyl,
2-pivaloyloxypropyl, 1-isobutyryloxyethyl,
1-isobutyryloxypropyl, 1-acetoxypropyl, 1-acetoxy-2-
methylpropyl, 1-propionyloxyethyl,
1-propionyloxypropyl, 2-acetoxypropyl and
1-butyryloxyethyl groups;

alkoxycarbonyloxyalkyl groups, especially
1-(alkoxycarbonyloxy)ethyl groups, in which the
alkoxy part has from 1 to 10, preferably from 1 to 6, and
more preferably from 1 to 4, carbon atoms, and the
alkyl part has from 1 to 6, preferably from 1 to 4,
carbon atoms, such as the methoxycarbonyloxymethyl,
ethoxycarbonyloxymethyl,
propoxycarbonyloxymethyl,
isopropoxycarbonyloxymethyl,
butoxycarbonyloxymethyl,
isobutoxycarbonyloxymethyl,
1-methoxycarbonyloxyethyl,
1-ethoxycarbonyloxyethyl,
1-propoxycarbonyloxyethyl, 1-
isopropoxycarbonyloxyethyl,
1-butoxycarbonyloxyethyl,
1-isobutoxycarbonyloxyethyl, 1-sec-
butoxycarbonyloxyethyl, 1-t-butoxycarbonyloxyethyl,
1-(1-ethylpropoxycarbonyloxy)ethyl and 1-(1,1-
dipropylbutoxycarbonyloxy)ethyl groups, and other
alkoxycarbonylalkyl groups, in which both the alkoxy
and alkyl groups have from 1 to 6, preferably from 1 to
4, carbon atoms, such as the 2-methyl-1-
(isopropoxycarbonyloxy)propyl,
2-(isopropoxycarbonyloxy)propyl,
isopropoxycarbonyloxymethyl,
t-butoxycarbonyloxymethyl, methoxycarbonyloxym-
ethyl and ethoxycarbonyloxymethyl groups;

cycloalkylcarbonyloxyalkyl and cycloalkyloxycarbony-
loxyalkyl groups, in which the cycloalkyl group has
from 3 to 10, preferably from 3 to 7, carbon atoms, is
mono- or poly-cyclic and is optionally substituted by at
least one (and preferably only one) alkyl group having
from 1 to 4 carbon atoms (e.g. selected from those alkyl
groups exemplified above) and the alkyl part has from
1 to 6, more preferably from 1 to 4, carbon atoms (e.g.
selected from those alkyl groups exemplified above)
and is most preferably methyl, ethyl or propyl, for
example the cyclohexyloxycarbonyloxymethyl,
1-methylcyclohexylcarbonyloxymethyl,
1-methylcyclohexyloxycarbonyloxymethyl,
cyclopentyloxycarbonyloxymethyl,
cyclopentylcarbonyloxymethyl,
1-cyclohexyloxycarbonyloxyethyl, 1-cyclohexylcarbonyloxyethyl,
1-cyclopentyloxycarbonyloxyethyl,
1-cyclopentylcarbonyloxyethyl,
1-cycloheptyloxycarbonyloxyethyl,
1-cycloheptylcarbonyloxyethyl,
1-methylcyclopentylcarbonyloxymethyl,
1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexyloxycarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl, 1-adamantylcarbonyloxyethyl and cyclohexyloxycarbonyloxy(cyclohexyl)methyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents α, defined and exemplified below] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and the phthalidyl group, which may be unsubstituted or may be substituted by at least one substituent selected from the group consisting of substituents α, defined and exemplified below, preferably an alkyl or alkoxy group, for example the phthalidyl, dimethylphthalidyl and dimethoxyphthalidyl groups;

any one of the alkyl groups exemplified above;

carboxyalkyl groups having from 2 to 7 carbon atoms, such as the carboxymethyl group; and amide-forming residues of an amino acid, such as phenylalanine.

Examples of substituents α, referred to above, include:

halogen atoms, such as the fluorine, chlorine, bromine and iodine atoms;

alkyl groups having from 1 to 6 carbon atoms, such as those exemplified above, particularly the methyl, ethyl and t-butyl groups;

alkoxy groups having from 1 to 6 carbon atoms, such as the methoxy, ethoxy, propoxy, isopropoxy, butoxy, isobutoxy, sec-butoxy, t-butoxy, pentyloxy, isopentyloxy, neopentyloxy, hexyloxy and isohexyloxy groups, of which we prefer those alkoxy groups having from 1 to 4 carbon atoms, preferably the methoxy, ethoxy, propoxy, isopropoxy, butoxy and isobutoxy groups, and most preferably the methoxy group;

carboxy groups, nitro groups and cyano groups;

alkylenedioxy groups having from 1 to 4 carbon atoms, such as the methylenedioxy group;

acylamino groups, including acylamino groups corresponding to the aliphatic and aromatic acyl groups exemplified hereafter in relation to the hydroxy-protecting groups, preferably an acetamido or benzamido group;

alkoxycarbonyl groups having from 2 to 7, preferably from 2 to 5, carbon atoms, such as the methoxycarbonyl, ethoxycarbonyl, propoxycarbonyl, isopropoxycarbonyl, butoxycarbonyl, isobutoxycarbonyl and t-butoxycarbonyl groups; and aryl groups, such as those exemplified above, save that any such aryl group which is included in substituents α is not further substituted by an aryl group.

In order to determine whether a protecting group is capable of being cleaved by biological means, a compound containing such a group, or a pharmaceutically acceptable salt thereof is administered by intravenous injection to a test animal, such as a rat or mouse, and the metabolic products subsequently recovered from the body fluids of the animal used are examined to determine whether the group has been cleaved. Of the protecting groups described above, those capable of being cleaved in vivo by biological methods such as hydrolysis are preferred. It will, of course, be appreciated that at least some of these groups which are capable of being cleaved in vivo by biological methods may also be cleaved by chemical means.

The term "hydroxy-protecting group", as used in the definitions of $R^6$, $R^{6a}$ and $R^{6b}$ signifies a protecting group capable of being cleaved by chemical methods (such as hydrogenolysis, hydrolysis, electrolysis or photolysis) to generate a free hydroxy group, or a protecting group capable of being cleaved in vivo by biological methods such as hydrolysis.

Examples of hydroxy-protecting groups which may be cleaved by chemical means include:

aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms, (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 6, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents α, defined and exemplified above, for example: unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 6, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 6, more preferably from 1 to 4, carbon atoms (such as the 4-anisoyl group); carboxy-substituted arylcarbonyl groups (such as the 2-carboxybenzoyl, 3-carboxybenzoyl and 4-carboxybenzoyl groups); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl)benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents α and oxygen atoms, preferably halkogen atoms and alkoxy groups; examples include: the tetrahydropyranyl groups, which may be substituted or unsubstituted, such as the tetrahydropyran-2-yl, 3-bromotetrahydropyran-2-yl and 4-methoxytetrahydropyran-4-yl groups; tetrahydrothiopyranyl groups, which may be substituted or unsubstituted, such as the tetrahydrothiopyran-2-yl and 4-methoxytetrahydrothiopyran-4-yl groups; tetrahydrofuranyl groups, which may be substituted or unsubstituted, such as the tetrahydrofuran-2-yl group; and tetrahydrothienyl groups, which may be substituted or unsubstituted, such as the tetrahydrothien-2-yl group;

tri-substituted silyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and tri-isopropylsilyl groups; and tri(lower alkyl)silyl groups in which one or two of the alkyl groups have been replaced by aryl groups, such as the diphenylmethylsilyl, diphenylbutylsilyl, diphenyl-t-butylsilyl, diphenylisopropylsilyl and phenyldiisopropylsilyl groups;

alkoxyalkyl groups, in which the alkoxy and alkyl parts each have from 1 to 6, preferably from 1 to 4, carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy) methyl groups] and lower alkoxy-substituted ethyl groups (such as the 1-ethoxyethyl, 1-methyl-1-methoxyethyl and 1-isopropoxyethyl groups);

other substituted ethyl groups, preferably: halogenated ethyl groups (such as the 2,2,2-trichloroethyl group); and arylselenyl-substituted ethyl groups, in which the aryl part is as defined above [such as the 2-(phenylselenyl)ethyl group];

aralkyl groups, preferably alkyl groups having from 1 to 4, more preferably from 1 to 3 and most preferably 1 or 2, carbon atoms which are substituted with from 1 to 3 aryl groups, as defined and exemplified above, which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl) methyl and piperonyl groups;

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups);

sulfo groups; and aralkyloxycarbonyl groups, in which the aralkyl part is as defined and exemplified above, and in which the aryl ring, if substituted, is substituted by at least one substituent selected from the group consisting of substituents α, defined and exemplified above, one or two lower alkoxy or nitro substituents, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Examples of hydroxy-protecting groups which are capable of being cleaved in vivo by biological methods such as hydrolysis include:

dioxolenylalkyl groups, aliphatic acyl groups and aromatic acyl groups, such as those exemplified above in relation to the carboxy-protecting groups;

the residue which forms a salt of a half-ester of a dicarboxylic acid, such as succinic acid;

the residue which forms a salt of a phosphate;

the residue of an ester of an amino acid; and carbonyloxyalkyloxycarbonyl groups, such as the pivaloyloxymethoxycarbonyl group.

Where $R^1$ represents a group of formula (II), the two groups represented by $R^{6a}$ and $R^{6b}$ may together form one of the following bidentate protecting groups:

a lower alkylidene group having from 1 to 4 carbon atoms, such as the methylidene, ethylidene or isopropylidene group;

an aralkylidene group, in which the aryl part may be as defined above and the alkylidene part has from 1 to 4 carbon atoms, such as the benzylidene group;

an alkoxyethylidene group, in which the alkoxy part has from 1 to 6, preferably from 1 to 4 carbon atoms, such as the methoxyethylidene or ethoxyethylidene group;

the oxomethylene group; and the thioxomethylene group.

Whether or not the protecting groups described above are capable of removal by cleaving by biological methods can be determined in the same way as described above in relation to the carboxy-protecting groups.

Of these hydroxy-protecting groups, we prefer the silyl group and protecting groups capable of being cleaved in vivo by biological methods.

Where $R^6$, $R^{6a}$ or $R^{6b}$ represents an alkyl group, this may be any of the alkyl groups exemplified above in relation to $R^2$ etc.

Where $R^6$, $R^{6a}$ or $R^{6b}$ represents an alkanesulfonyloxy group, this may be a straight or branched chain group having from 1 to 6 carbon atoms, for example the methanesulfonyloxy, ethanesulfonyloxy and propanesulfonyloxy groups.

Where $R^6$, $R^{6a}$ or $R^{6b}$ represents a halogenated alkanesulfonyloxy group, this may be any of the unsubstituted alkanesulfonyloxy groups listed above and is preferably a fluorinated alkanesulfonyloxy group, such as the trifluoromethanesulfonyloxy or pentafluoroethanesulfonyloxy group.

Where $R^6$, $R^{6a}$ or $R^{6b}$ represents an arylsulfonyloxy group, the aryl part may be as defined and exemplified above, and examples of such groups include the benzenesulfonyloxy and p-toluenesulfonyloxy groups.

Of these groups, we prefer the alkyl groups.

Those compounds of the present invention which contain a free carboxy group, for example those where $R^1$ represents a group of formula (II) and $R^5$ represents a hydrogen atom, can form salts. Examples of such salts include: salts with an alkali metal, such as sodium, potassium or lithium; salts with an alkaline earth metal, such as barium or calcium; salts with another metal, such as magnesium, aluminum, iron, zinc, copper, nickel or cobalt; ammonium salts; organic base salts, particularly salts with organic amines, such as a salt with triethylamine, diisopropylamine, cyclohexylamine, t-octylamine, dibenzylamine, morpholine, glucosamine, phenylglycine alkyl esters, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium or tris(hydroxymethyl)aminomethane; and salts with a basic amino acid, such as histidine, α,γ-diaminobutyric acid, lysine, arginine, ornithine, glutamic acid or aspartic acid.

Also, where the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

The compounds of the present invention may contain one or more asymmetric carbon atoms in their molecules, and, in such a case, can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formulae (I), (Ia) and (Ib) and pharmaceutically acceptable salts and esters thereof in which:

(A) $R^2$ represents an alkyl group having from 1 to 4 carbon atoms, an alkenyl group having from 2 to 4 carbon atoms or an alkynyl group having from 2 to 4 carbon atoms; and $R^3$ and $R^4$ are the same or different and each represents a hydrogen atom, an alkyl group having from 1 to 4 carbon atoms, an alkenyl group having from 2 to 4 carbon atoms or an alkynyl group having from 2 to 4 carbon atoms;

or (B) $R^2$ represents an alkyl group having from 1 to 4 carbon atoms, an alkenyl group having from 2 to 4 carbon atoms or an alkynyl group having from 2 to 4 carbon atoms;

$R^3$ represents an alkyl group having from 1 to 4 carbon atoms, an alkenyl group having from 2 to 4 carbon atoms or an alkynyl group having from 2 to 4 carbon atoms; and $R^4$ represents a hydrogen atom, an alkyl group having from 1 to 4 carbon atoms, an alkenyl group having from 2 to 4 carbon atoms or an alkynyl group having from 2 to 4 carbon atoms;

(C) $R^2$ represents an alkyl group having from 1 to 4 carbon atoms or an alkenyl group having from 2 to 4 carbon atoms;

$R^3$ represents an alkyl group having from 1 to 4 carbon atoms or an alkenyl group having from 2 to 4 carbon atoms; and $R^4$ represents a hydrogen atom, an alkyl group having from 1 to 4 carbon atoms or an alkenyl group having from 2 to 4 carbon atoms;

(D) $R^2$ represents an ethyl group;

$R^3$ represents an alkyl group having from 1 to 4 carbon atoms; and $R^4$ represents an alkyl group having from 2 to 4 carbon atoms;

(E) $R^2$ represents an ethyl group;

$R^3$ represents an alkyl group having from 1 to 3 carbon atoms; and $R^4$ represents an alkyl group having 2 or 3 carbon atoms;

(F) $R^1$ represents a group of formula (II), and more preferably, $R^2$, $R^3$ and $R^4$ are as defined in one of (A) to (E) above;

(G) $R^1$ represents a group of formula (II); and $R^6$, $R^{6a}$ and $R^{6b}$ represent hydrogen atoms;

and more preferably, $R^2$, $R^3$ and $R^4$ are as defined in one of (A) to (E) above;

(H) pharmaceutically acceptable salts of the compounds defined in (G) above;

(I) $R^5$ represents a hydrogen atom or a protecting group capable of being cleaved in vivo by biological methods;

(J) $R^6$, $R^{6a}$ and $R^{6b}$ each represents a hydrogen atom or a protecting group capable of being cleaved in vivo by biological methods such as hydrolysis; and (K) $R^5$ represents a hydrogen atom.

Specific examples of individual compounds of the present invention are given by the following formulae (I-1), (I-1a), (I-2) and (I-2a), in which the various symbols used are as defined in the corresponding one of Tables 1 and 2, that is Table 1 relates to formulae (I-1) and (I-1a), and Table 2 relates to formulae (I-2) and (I-2a). In the Tables, the following abbreviations are used for certain groups:

TABLE 1

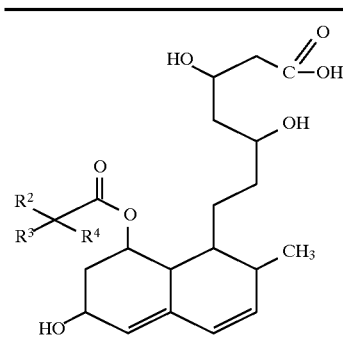

(I-1)

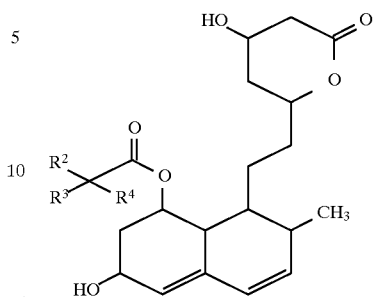

(I-1a)

TABLE 1-continued

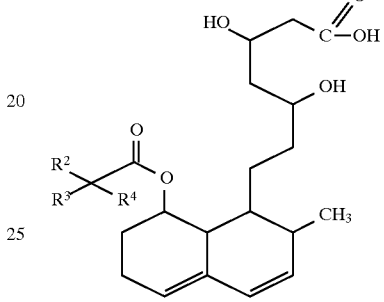

(I-2)

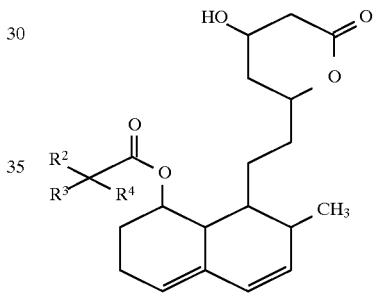

(I-2a)

| Cpd. No. | $R^2$ | $R^3$ | $R^4$ |
|---|---|---|---|
| 1-1 | Me | H | H |
| 1-2 | Et | H | H |
| 1-3 | Pr | H | H |
| 1-4 | iPr | H | H |
| 1-5 | Bu | H | H |
| 1-6 | iBu | H | H |
| 1-7 | tBu | H | H |
| 1-8 | —CH=CH$_2$ | H | H |
| 1-9 | All | H | H |
| 1-10 | —(CH$_2$)$_2$—CH=CH$_2$ | H | H |
| 1-11 | —CH$_2$—C≡CH | H | H |
| 1-12 | Me | H | Me |
| 1-13 | Pr | H | Me |
| 1-14 | iPr | H | Me |
| 1-15 | Bu | H | Me |
| 1-16 | iBu | H | Me |
| 1-17 | tBu | H | Me |
| 1-18 | —CH=CH$_2$ | H | Me |
| 1-19 | All | H | Me |
| 1-20 | —(CH$_2$)$_2$—CH=CH$_2$ | H | Me |
| 1-21 | —CH$_2$—C≡CH | H | Me |
| 1-22 | Et | H | Et |
| 1-23 | Pr | H | Et |
| 1-24 | iPr | H | Et |
| 1-25 | Bu | H | Et |
| 1-26 | iBu | H | Et |
| 1-27 | tBu | H | Et |
| 1-28 | —CH=CH$_2$ | H | Et |

TABLE 1-continued

| | | | |
|---|---|---|---|
| 1-29 | All | H | Et |
| 1-30 | —(CH₂)₂—CH=CH₂ | H | Et |
| 1-31 | —CH₂—C≡CH | H | Et |
| 1-32 | Pr | H | Pr |
| 1-33 | iPr | H | iPr |
| 1-34 | Bu | H | iPr |
| 1-35 | iBu | H | Pr |
| 1-36 | tBu | H | iPr |
| 1-37 | —CH=CH₂ | H | Pr |
| 1-38 | All | H | Pr |
| 1-39 | —(CH₂)₂—CH=CH₂ | H | iPr |
| 1-40 | —CH₂—C≡CH | H | Pr |
| 1-41 | Bu | H | Bu |
| 1-42 | iBu | H | iBu |
| 1-43 | tBu | H | Bu |
| 1-44 | —CH=CH₂ | H | iBu |
| 1-45 | All | H | Bu |
| 1-46 | —(CH₂)₂—CH=CH₂ | H | tBu |
| 1-47 | —CH₂—C≡CH | H | Bu |
| 1-48 | —CH=CH₂ | H | All |
| 1-49 | All | H | All |
| 1-50 | —(CH₂)₂—CH=CH₂ | H | All |
| 1-51 | —CH₂—C≡CH | H | All |
| 1-52 | Me | Me | Me |
| 1-53 | Et | Me | Me |
| 1-54 | Pr | Me | Me |
| 1-55 | iPr | Me | Me |
| 1-56 | Bu | Me | Me |
| 1-57 | iBu | Me | Me |
| 1-58 | tBu | Me | Me |
| 1-59 | —CH=CH₂ | Me | Me |
| 1-60 | All | Me | Me |
| 1-61 | —(CH₂)₂—CH=CH₂ | Me | Me |
| 1-62 | —CH₂—C≡CH | Me | Me |
| 1-63 | Pr | Me | Et |
| 1-64 | iPr | Me | Et |
| 1-65 | Et | Me | Et |
| 1-66 | Bu | Me | Et |
| 1-67 | iBu | Me | Et |
| 1-68 | tBu | Me | Et |
| 1-69 | —CH=CH₂ | Me | Et |
| 1-70 | All | Me | Et |
| 1-71 | —(CH₂)₂—CH=CH₂ | Me | Et |
| 1-72 | —CH₂—C≡CH | Me | Et |
| 1-73 | Pr | Me | Pr |
| 1-74 | iPr | Me | iPr |
| 1-75 | Bu | Me | Pr |
| 1-76 | iBu | Me | iPr |
| 1-77 | tBu | Me | Pr |
| 1-78 | —CH=CH₂ | Me | Pr |
| 1-79 | All | Me | Pr |
| 1-80 | —(CH₂)₂—CH=CH₂ | Me | Pr |
| 1-81 | —CH₂—C≡CH | Me | Pr |
| 1-82 | Bu | Me | Bu |
| 1-83 | iBu | Me | iBu |
| 1-84 | tBu | Me | tBu |
| 1-85 | —CH=CH₂ | Me | Bu |
| 1-86 | All | Me | Bu |
| 1-87 | —(CH₂)₂—CH=CH₂ | Me | Bu |
| 1-88 | —CH₂—C≡CH | Me | Bu |
| 1-89 | —CH=CH₂ | Me | All |
| 1-90 | All | Me | All |
| 1-91 | —(CH₂)₂—CH=CH₂ | Me | All |
| 1-92 | —CH₂—C≡CH | Me | All |
| 1-93 | Et | Et | Et |
| 1-94 | Pr | Et | Et |
| 1-95 | iPr | Et | Et |
| 1-96 | Bu | Et | Et |
| 1-97 | iBu | Et | Et |
| 1-98 | tBu | Et | Et |
| 1-99 | —CH=CH₂ | Et | Et |
| 1-100 | All | Et | Et |
| 1-101 | —(CH₂)₂—CH=CH₂ | Et | Et |
| 1-102 | —CH₂—C≡CH | Et | Et |
| 1-103 | Pr | Et | Pr |
| 1-104 | iPr | Et | iPr |
| 1-105 | Bu | Et | Pr |
| 1-106 | iBu | Et | iPr |
| 1-107 | tBu | Et | Pr |
| 1-108 | —CH=CH₂ | Et | Pr |
| 1-109 | All | Et | Pr |
| 1-110 | —(CH₂)₂—CH=CH₂ | Et | iPr |
| 1-111 | —CH₂—C≡CH | Et | Pr |
| 1-112 | Bu | Et | Bu |
| 1-113 | iBu | Et | iBu |
| 1-114 | tBu | Et | tBu |
| 1-115 | —CH=CH₂ | Et | Bu |
| 1-116 | All | Et | Bu |
| 1-117 | —(CH₂)₂—CH=CH₂ | Et | tBu |
| 1-118 | —CH₂—C≡CH | Et | Bu |
| 1-119 | —CH=CH₂ | Et | All |
| 1-120 | All | Et | All |
| 1-121 | —(CH₂)₂—CH=CH₂ | Et | All |
| 1-122 | —CH₂—C≡CH | Et | All |
| 1-123 | Pr | Pr | Pr |
| 1-124 | iPr | iPr | iPr |
| 1-125 | Bu | Pr | Pr |
| 1-126 | iBu | Pr | iPr |
| 1-127 | tBu | Pr | Pr |
| 1-128 | —CH=CH₂ | Pr | Pr |
| 1-129 | All | Pr | Pr |
| 1-130 | —(CH₂)₂—CH=CH₂ | Pr | Pr |
| 1-131 | —CH₂—C≡CH | Pr | Pr |
| 1-132 | Bu | Pr | Bu |
| 1-133 | iBu | Pr | iBu |
| 1-134 | tBu | Pr | Bu |
| 1-135 | —CH=CH₂ | Pr | Bu |
| 1-136 | All | Pr | Bu |
| 1-137 | —(CH₂)₂—CH=CH₂ | Pr | Bu |
| 1-138 | —CH₂—C≡CH | Pr | Bu |
| 1-139 | —CH=CH₂ | Pr | All |
| 1-140 | All | Pr | All |
| 1-141 | —(CH₂)₂—CH=CH₂ | Pr | All |
| 1-142 | —CH₂—C≡CH | Pr | All |
| 1-143 | Bu | Bu | Bu |
| 1-144 | iBu | iBu | iBu |
| 1-145 | tBu | Bu | Bu |
| 1-146 | —CH=CH₂ | Bu | Bu |
| 1-147 | All | Bu | Bu |
| 1-148 | —(CH₂)₂—CH=CH₂ | Bu | Bu |
| 1-149 | —CH₂—C≡CH | Bu | Bu |
| 1-150 | —CH=CH₂ | Bu | All |
| 1-151 | All | Bu | All |
| 1-152 | —(CH₂)₂—CH=CH₂ | Bu | All |
| 1-153 | —CH₂—C≡CH | Bu | All |
| 1-154 | —CH=CH₂ | All | All |
| 1-155 | All | All | All |
| 1-156 | —(CH₂)₂—CH=CH₂ | All | All |
| 1-157 | —CH₂—C≡CH | All | All |

All allyl
Bu butyl
iBu isobutyl
tBu t-butyl
Et ethyl
Me methyl
Pr propyl
iPr isopropyl

TABLE 2

| Cpd. No. | R² | R³ | R⁴ |
|---|---|---|---|
| 2-1 | Me | H | H |
| 2-2 | Et | H | H |
| 2-3 | Pr | H | H |
| 2-4 | iPr | H | H |
| 2-5 | Bu | H | H |
| 2-6 | iBu | H | H |
| 2-7 | tBu | H | H |
| 2-8 | —CH=CH₂ | H | H |
| 2-9 | All | H | H |
| 2-10 | —(CH₂)₂—CH=CH₂ | H | H |
| 2-11 | —CH₂—C≡CH | H | H |
| 2-12 | Me | H | Me |
| 2-13 | Pr | H | Me |
| 2-14 | iPr | H | Me |
| 2-15 | Bu | H | Me |
| 2-16 | iBu | H | Me |
| 2-17 | tBu | H | Me |
| 2-18 | —CH=CH₂ | H | Me |
| 2-19 | All | H | Me |
| 2-20 | —(CH₂)₂—CH=CH₂ | H | Me |
| 2-21 | —CH₂—C≡CH | H | Me |
| 2-22 | Et | H | Et |
| 2-23 | Pr | H | Et |
| 2-24 | iPr | H | Et |
| 2-25 | Bu | H | Et |
| 2-26 | iBu | H | Et |
| 2-27 | tBu | H | Et |
| 2-28 | —CH=CH₂ | H | Et |
| 2-29 | All | H | Et |
| 2-30 | —(CH₂)₂—CH=CH₂ | H | Et |
| 2-31 | —CH₂—C≡CH | H | Et |
| 2-32 | Pr | H | iPr |
| 2-33 | iPr | H | iPr |
| 2-34 | Bu | H | iPr |
| 2-35 | iBu | H | Pr |
| 2-36 | tBu | H | iPr |
| 2-37 | —CH=CH₂ | H | Pr |
| 2-38 | All | H | Pr |
| 2-39 | —(CH₂)₂—CH=CH₂ | H | iPr |
| 2-40 | —CH₂—C≡CH | H | Pr |
| 2-41 | Bu | H | Bu |
| 2-42 | iBu | H | iBu |
| 2-43 | tBu | H | Bu |
| 2-44 | —CH=CH₂ | H | iBu |
| 2-45 | All | H | Bu |
| 2-46 | —(CH₂)₂—CH=CH₂ | H | tBu |
| 2-47 | —CH₂—C≡CH | H | Bu |
| 2-48 | —CH=CH₂ | H | All |
| 2-49 | All | H | All |
| 2-50 | —(CH₂)₂—CH=CH₂ | H | All |
| 2-51 | —CH₂—C≡CH | H | All |
| 2-52 | Me | Me | Me |
| 2-53 | Et | Me | Me |
| 2-54 | Pr | Me | Me |
| 2-55 | iPr | Me | Me |
| 2-56 | Bu | Me | Me |
| 2-57 | iBu | Me | Me |
| 2-58 | tBu | Me | Me |
| 2-59 | —CH=CH₂ | Me | Me |
| 2-60 | All | Me | Me |
| 2-61 | —(CH₂)₂—CH=CH₂ | Me | Me |
| 2-62 | —CH₂—C≡CH | Me | Me |
| 2-63 | Pr | Me | Et |
| 2-64 | iPr | Me | Et |
| 2-65 | Et | Me | Et |
| 2-66 | Bu | Me | Et |
| 2-67 | iBu | Me | Et |
| 2-68 | tBu | Me | Et |
| 2-69 | —CH=CH₂ | Me | Et |
| 2-70 | All | Me | Et |
| 2-71 | —(CH₂)₂—CH=CH₂ | Me | Et |
| 2-72 | —CH₂—C≡CH | Me | Et |
| 2-73 | Pr | Me | Pr |
| 2-74 | iPr | Me | iPr |
| 2-75 | Bu | Me | Pr |
| 2-76 | iBu | Me | iPr |
| 2-77 | tBu | Me | Pr |
| 2-78 | —CH=CH₂ | Me | Pr |
| 2-79 | All | Me | Pr |
| 2-80 | —(CH₂)₂—CH=CH₂ | Me | Pr |
| 2-81 | —CH₂—C≡CH | Me | Pr |
| 2-82 | Bu | Me | Bu |
| 2-83 | iBu | Me | iBu |
| 2-84 | tBu | Me | tBu |
| 2-85 | —CH=CH₂ | Me | Bu |
| 2-86 | All | Me | Bu |
| 2-87 | —(CH₂)₂—CH=CH₂ | Me | Bu |
| 2-88 | —CH₂—C≡CH | Me | Bu |
| 2-89 | —CH=CH₂ | Me | All |
| 2-90 | All | Me | All |
| 2-91 | —(CH₂)₂—CH=CH₂ | Me | All |
| 2-92 | —CH₂—C≡CH | Me | All |
| 2-93 | Et | Et | Et |
| 2-94 | Pr | Et | Et |
| 2-95 | iPr | Et | Et |
| 2-96 | Bu | Et | Et |
| 2-97 | iBu | Et | Et |
| 2-98 | tBu | Et | Et |
| 2-99 | —CH=CH₂ | Et | Et |
| 2-100 | All | Et | Et |
| 2-101 | —(CH₂)₂—CH=CH₂ | Et | Et |
| 2-102 | —CH₂—C≡CH | Et | Et |
| 2-103 | Pr | Et | Pr |
| 2-104 | iPr | Et | iPr |
| 2-105 | Bu | Et | Pr |
| 2-106 | iBu | Et | iPr |
| 2-107 | tBu | Et | Pr |
| 2-108 | —CH=CH₂ | Et | Pr |
| 2-109 | All | Et | Pr |
| 2-110 | —(CH₂)₂—CH=CH₂ | Et | iPr |
| 2-111 | —CH₂—C≡CH | Et | Pr |
| 2-112 | Bu | Et | Bu |
| 2-113 | iBu | Et | iBu |
| 2-114 | tBu | Et | tBu |
| 2-115 | —CH=CH₂ | Et | Bu |
| 2-116 | All | Et | Bu |
| 2-117 | —(CH₂)₂—CH=CH₂ | Et | tBu |
| 2-118 | —CH₂—C≡H | Et | Bu |
| 2-119 | —CH=CH₂ | Et | All |
| 2-120 | All | Et | All |
| 2-121 | —(CH₂)₂—CH=CH₂ | Et | All |
| 2-122 | —CH₂—C≡CH | Et | All |
| 2-123 | Pr | Pr | Pr |
| 2-124 | iPr | iPr | iPr |
| 2-125 | Bu | Pr | Pr |
| 2-126 | iBu | Pr | iPr |
| 2-127 | tBu | Pr | Pr |
| 2-128 | —CH=CH₂ | Pr | Pr |
| 2-129 | All | Pr | Pr |
| 2-130 | —(CH₂)₂—CH=CH₂ | Pr | Pr |
| 2-131 | —CH₂—C≡CH | Pr | Pr |
| 2-132 | Bu | Pr | Bu |
| 2-133 | iBu | Pr | iBu |
| 2-134 | tBu | Pr | Bu |
| 2-135 | —CH=CH₂ | Pr | Bu |
| 2-136 | All | Pr | Bu |
| 2-137 | —(CH₂)₂—CH=CH₂ | Pr | Bu |
| 2-138 | —CH₂—C≡CH | Pr | Bu |
| 2-139 | —CH=CH₂ | Pr | All |
| 2-140 | All | Pr | All |
| 2-141 | —(CH₂)₂—CH=CH₂ | Pr | All |
| 2-142 | —CH₂—C≡CH | Pr | All |
| 2-143 | Bu | Bu | Bu |
| 2-144 | iBu | iBu | iBu |
| 2-145 | tBu | Bu | Bu |
| 2-146 | —CH=CH₂ | Bu | Bu |
| 2-147 | All | Bu | Bu |
| 2-148 | —(CH₂)₂—CH=CH₂ | Bu | Bu |
| 2-149 | —CH₂—C≡CH | Bu | Bu |
| 2-150 | —CH=CH₂ | Bu | All |
| 2-151 | All | Bu | All |
| 2-152 | —(CH₂)₂—CH=CH₂ | Bu | All |
| 2-153 | —CH₂—C≡CH | Bu | All |
| 2-154 | —CH=CH₂ | All | All |

TABLE 2-continued

| Cpd. No. | R² | R³ | R⁴ |
| --- | --- | --- | --- |
| 2-155 | All | All | All |
| 2-156 | —(CH₂)₂—CH=CH₂ | All | All |
| 2-157 | —CH₂—C≡CH | All | All |

Of the compounds listed above, preferred compounds are Compounds No. 1-4, 1-5, 1-6, 1-7, 1-9, 1-10, 1-13, 1-19, 1-20, 1-21, 1-22, 1-23, 1-25, 1-29, 1-30, 1-32, 1-33, 1-38, 1-39, 1-41, 1-45, 1-48, 1-49, 1-52, 1-54, 1-56, 1-57, 1-60, 1-63, 1-65, 1-66, 1-70, 1-71, 1-73, 1-74, 1-75, 1-79, 1-82, 1-86, 1-87, 1-90, 1-93, 1-94, 1-96, 1-97, 1-99, 1-100, 1-101, 1-102, 1-103, 1-105, 1-106, 1-108, 1-109, 1-112, 1-115, 1-116, 1-118, 1-120, 1-123, 1-125, 1-128, 1-129, 1-130, 1-135, 1-137, 1-139, 1-140, 1-141, 1-142, 1-146, 1-147, 1-151, 1-154, 1-155, 1-157, 2-4, 2-5, 2-6, 2-7, 2-9, 2-10, 2-13, 2-19, 2-20, 2-21, 2-22, 2-23, 2-25, 2-29, 2-30, 2-32, 2-33, 2-38, 2-39, 2-41, 2-45, 2-48, 2-49, 2-52, 2-54, 2-56, 2-57, 2-60, 2-63, 2-65, 2-66, 2-70, 2-71, 2-73, 2-74, 2-75, 2-79, 2-82, 2-86, 2-87, 2-90, 2-93, 2-94, 2-96, 2-97, 2-99, 2-100, 2-101, 2-102, 2-103, 2-105, 2-106, 2-108, 2-109, 2-112, 2-115, 2-116, 2-118, 2-120, 2-123, 2-125, 2-128, 2-129, 2-130, 2-135, 2-137, 2-139, 2-140, 2-141, 2-142, 2-146, 2-147, 2-151, 2-154, 2-155 and 2-157.

The more preferred compounds are Compounds No. 1-4, 1-5, 1-7, 1-13, 1-19, 1-22, 1-23, 1-25, 1-29, 1-32, 1-33, 1-38, 1-41, 1-45, 1-49, 1-52, 1-54, 1-56, 1-57, 1-60, 1-63, 1-65, 1-66, 1-70, 1-73, 1-74, 1-75, 1-79, 1-82, 1-87, 1-90, 1-93, 1-94, 1-96, 1-99, 1-100, 1-101, 1-102, 1-103, 1-105, 1-109, 1-112, 1-120, 1-155, 2-4, 2-5, 2-7, 2-13, 2-19, 2-22, 2-23, 2-25, 2-29, 2-32, 2-33, 2-38, 2-41, 2-45, 2-49, 2-52, 2-54, 2-56, 2-57, 2-60, 2-63, 2-65, 2-66, 2-70, 2-73, 2-74, 2-75, 2-79, 2-82, 2-87, 2-90, 2-93, 2-94, 2-96, 2-99, 2-100, 2-101, 2-102, 2-103, 2-105, 2-109, 2-112, 2-120 and 2-155.

The most preferred compounds are Compounds No.:

1-4. 3,5-dihydroxy-7-(6-hydroxy-2-methyl-8-isovaleryloxy-1,2,6,7,8,8a-hexahydro-1-naphthyl)heptanoic acid;

1-5. 3,5-dihydroxy-7-(6-hydroxy-2-methyl-8-hexanoyloxy-1,2,6,7,8,8a-hexahydro-1-naphthyl)heptanoic acid;

1-7. 3,5-dihydroxy-7-[6-hydroxy-2-methyl-8-(3,3-dimethylbutyryloxy)-1,2,6,7,8,8a-hexahydro-1-naphthyl]heptanoic acid;

1-13. 3,5-dihydroxy-7-[6-hydroxy-2-methyl-8-(2-methylpentanoyloxy)-1,2,6,7,8,8a-hexahydro-1-naphthyl]heptanoic acid;

1-22. 3,5-dihydroxy-7-[6-hydroxy-2-methyl-8-(2-ethylbutyryloxy)-1,2,6,7,8,8a-hexahydro-1-naphthyl]heptanoic acid;

1-32. 3,5-dihydroxy-7-[6-hydroxy-2-methyl-8-(2-propylpentanoyloxy)-1,2,6,7,8,8a-hexahydro-1-naphthyl]heptanoic acid;

1-33. 3,5-dihydroxy-7-[6-hydroxy-2-methyl-8-(2-isopropyl-3-methylbutyryloxy)-1,2,6,7,8,8a-hexahydro-1-naphthyl]heptanoic acid;

1-41. 3,5-dihydroxy-7-[6-hydroxy-2-methyl-8-(2-butylhexanoyloxy)-1,2,6,7,8,8a-hexahydro-1-naphthyl]heptanoic acid;

1-49. 3,5-dihydroxy-7-[6-hydroxy-2-methyl-8-(2-allyl-4-pentenoyloxy)-1,2,6,7,8,8a-hexahydro-1-naphthyl]heptanoic acid;

1-52. 3,5-dihydroxy-7-(6-hydroxy-2-methyl-8-pivaloyloxy-1,2,6,7,8,8a-hexahydro-1-naphthyl)heptanoic acid;

1-54. 3,5-dihydroxy-7-[6-hydroxy-2-methyl-8-(2,2-dimethylpentanoyloxy)-1,2,6,7,8,8a-hexahydro-1-naphthyl]heptanoic acid;

1-56. 3,5-dihydroxy-7-[6-hydroxy-2-methyl-8-(2,2-dimethylhexanoyloxy)-1,2,6,7,8,8a-hexahydro-1-naphthyl]heptanoic acid;

1-60. 3,5-dihydroxy-7-[6-hydroxy-2-methyl-8-(2,2-dimethyl-4-pentenoyloxy)-1,2,6,7,8,8a-hexahydro-1-naphthyl]heptanoic acid;

1-63. 3,5-dihydroxy-7-[6-hydroxy-2-methyl-8-(2-ethyl-2-methylpentanoyloxy)-1,2,6,7,8,8a-hexahydro-1-naphthyl]heptanoic acid;

1-65. 3,5-dihydroxy-7-[6-hydroxy-2-methyl-8-(2-ethyl-2-methylbutyryloxy)-1,2,6,7,8,8a-hexahydro-1-naphthyl]heptanoic acid;

1-73. 3,5-dihydroxy-7-[6-hydroxy-2-methyl-8-(2-methyl-2-propylpentanoyloxy)-1,2,6,7,8,8a-hexahydro-1-naphthyl]heptanoic acid;

1-90. 3,5-dihydroxy-7-[6-hydroxy-2-methyl-8-(2-allyl-2-methyl-4-pentenoyloxy)-1,2,6,7,8,8a-hexahydro-1-naphthyl]heptanoic acid;

1-93. 3,5-dihydroxy-7-[6-hydroxy-2-methyl-8-(2,2-diethylbutyryloxy)-1,2,6,7,8,8a-hexahydro-1-naphthyl]heptanoic acid;

1-94. 3,5-dihydroxy-7-[6-hydroxy-2-methyl-8-(2,2-diethylpentanoyloxy)-1,2,6,7,8,8a-hexahydro-1-naphthyl]heptanoic acid;

1-100. 3,5-dihydroxy-7-[6-hydroxy-2-methyl-8-(2,2-diethyl-4-pentenoyloxy)-1,2,6,7,8,8a-hexahydro-1-naphthyl]heptanoic acid;

1-120. 3,5-dihydroxy-7-[6-hydroxy-2-methyl-8-(2-allyl-2-ethyl-4-pentenoyloxy)-1,2,6,7,8,8a-hexahydro-1-naphthyl]heptanoic acid;

1-155. 3,5-dihydroxy-7-[6-hydroxy-2-methyl-8-(2,2-diallyl-4-pentenoyloxy)-1,2,6,7,8,8a-hexahydro-1-naphthyl]heptanoic acid;

2-4. 3,5-dihydroxy-7-(2-methyl-8-isovaleryloxy-1,2,6,7,8,8a-hexahydro-1-naphthyl)heptanoic acid;

2-5. 3,5-dihydroxy-7-(2-methyl-8-hexanoyloxy-1,2,6,7,8,8a-hexahydro-1-naphthyl)heptanoic acid;

2-7. 3,5-dihydroxy-7-[2-methyl-8-(3,3-dimethylbutyryloxy)-1,2,6,7,8,8a-hexahydro-1-naphthyl]heptanoic acid;

2-13. 3,5-dihydroxy-7-[2-methyl-8-(2-methylpentanoyloxy)-1,2,6,7,8,8a-hexahydro-1-naphthyl]heptanoic acid;

2-22. 3,5-dihydroxy-7-[2-methyl-8-(2-ethylbutyryloxy)-1,2,6,7,8,8a-hexahydro-1-naphthyl]heptanoic acid;

2-32. 3,5-dihydroxy-7-[2-methyl-8-(2-propylpentanoyloxy)-1,2,6,7,8,8a-hexahydro-1-naphthyl]heptanoic acid;

2-33. 3,5-dihydroxy-7-[2-methyl-8-(2-isopropyl-3-methylbutyryloxy)-1,2,6,7,8,8a-hexahydro-1-naphthyl]heptanoic acid;

2-41. 3,5-dihydroxy-7-[2-methyl-8-(2-butylhexanoyloxy)-1,2,6,7,8,8a-hexahydro-1-naphthyl]heptanoic acid;

2-49. 3,5-dihydroxy-7-[2-methyl-8-(2-allyl-4-pentenoyloxy)-1,2,6,7,8,8a-hexahydro-1-naphthyl]heptanoic acid;

2-52. 3,5-dihydroxy-7-(2-methyl-8-pivaloyloxy-1,2,6,7,8,8a-hexahydro-1-naphthyl)heptanoic acid;

2-54. 3,5-dihydroxy-7-[2-methyl-8-(2,2-dimethylpentanoyloxy)-1,2,6,7,8,8a-hexahydro-1-naphthyl]heptanoic acid;

2-56. 3,5-dihydroxy-7-[2-methyl-8-(2,2-dimethylhexanoyloxy)-1,2,6,7,8,8a-hexahydro-1-naphthyl]heptanoic acid;

2-60. 3,5-dihydroxy-7-[2-methyl-8-(2,2-dimethyl-4-pentenoyloxy)-1,2,6,7,8,8a-hexahydro-1-naphthyl]heptanoic acid;

2-63. 3,5-dihydroxy-7-[2-methyl-8-(2-ethyl-2-methylpentanoyloxy)-1,2,6,7,8,8a-hexahydro-1-naphthyl]heptanoic acid;

2-65. 3,5-dihydroxy-7-[2-methyl-8-(2-ethyl-2-methylbutyryloxy)-1,2,6,7,8,8a-hexahydro-1-naphthyl]heptanoic acid;

2-73. 3,5-dihydroxy-7-[2-methyl-2-(2-methyl-2-propylpentanoyloxy)-1,2,6,7,8,8a-hexahydro-1-naphthyl]heptanoic acid;

2-90. 3,5-dihydroxy-7-[2-methyl-8-(2-allyl-2-methyl-4-pentenoyloxy)-1,2,6,7,8,8a-hexahydro-1-naphthyl]heptanoic acid;

2-93. 3,5-dihydroxy-7-[2-methyl-8-(2,2-diethylbutyryloxy)-1,2,6,7,8,8a-hexahydro-1-naphthyl]heptanoic acid;

2-94. 3,5-dihydroxy-7-[2-methyl-8-(2,2-diethylpentanoyloxy)-1,2,6,7,8,8a-hexahydro-1-naphthyl]heptanoic acid;

2-100. 3,5-dihydroxy-7-[2-methyl-8-(2,2-diethyl-4-pentenoyloxy)-1,2,6,7,8,8a-hexahydro-1-naphthyl]heptanoic acid;

2-120. 3,5-dihydroxy-7-[2-methyl-8-(2-allyl-2-ethyl-4-pentenoyloxy)-1,2,6,7,8,8a-hexahydro-1-naphthyl]heptanoic acid;

2-155. 3,5-dihydroxy-7-[2-methyl-8-(2,2-diallyl-4-pentenoyloxy)-1,2,6,7,8,8a-hexahydro-1-naphthyl]heptanoic acid;

and the ring-closed lactones corresponding to the hydroxy-acids listed above;

and pharmaceutically acceptable salts and esters thereof.

The compounds of the present invention may be prepared by a variety of methods well known for the preparation of compounds of this type. For example, in general terms, they may be prepared by reacting a compound of formula (IV):

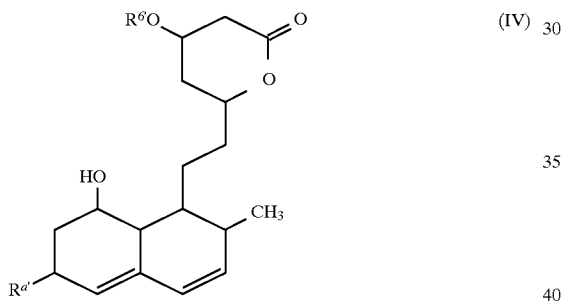

(IV)

(wherein $R^{a'}$ represents a hydrogen atom or a group of formula $R^{6'}O$—, and the symbols $R^{6'}$ each represents any of the groups represented by $R^6$ but may not represent a hydrogen atom) with a reactive compound containing the group $R^{6'}$, preferably with an acylating agent, to give a compound of formula (V):

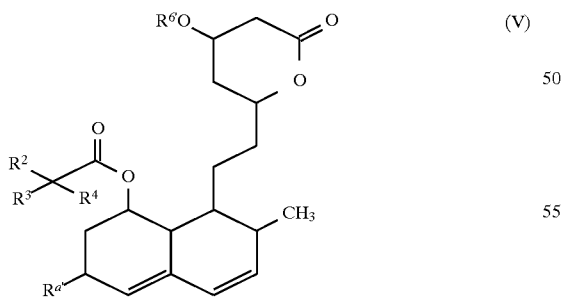

(V)

(wherein $R^2$, $R^3$, $R^4$ and $R^{6'}$ are as defined above), and, if necessary, removing protecting groups and, if necessary, subjecting the compound of formula (V) to ring-opening hydrolysis or solvolysis, and, if desired, where $R^a$ represents a hydrogen atom, introducing a group of formula $R^6O$— in place of $R^a$.

In more detail, the compounds of the present invention may be prepared as illustrated in the following Reaction Schemes A, B, C and D.

REACTION SCHEME A

Compounds of formula (Ia) may be prepared as illustrated in the following Reaction Scheme A.

In this method, the starting material, the compound of formula (VI), may be the known compound pravastatin, in which the hydroxy group at the 6-position is in the β-configuration. The stereochemistry of the corresponding groups at the 6-position is retained as the β-configuration throughout the whole of the reaction scheme. Alternatively, an epimeric isomer at the 6-position of pravastatin may be used as the starting material in Step A1, in which case it is possible to prepare the desired compounds of formulae (X), (XI) and (XII) in which the substituents at the 6-position are in the α-configuration. Although the stereochemistry at the 6- and other positions is not shown in the following formulae, the present invention envisages the use either of individual isolated isomers, e.g. pravastatin or its epimer, or mixtures of these isomers.

Reaction Scheme A:

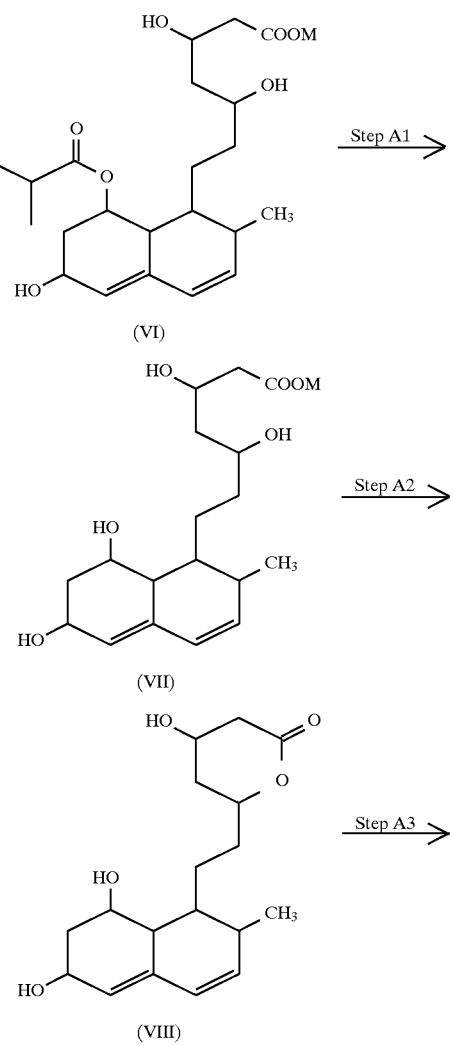

Reaction Scheme A:
-continued

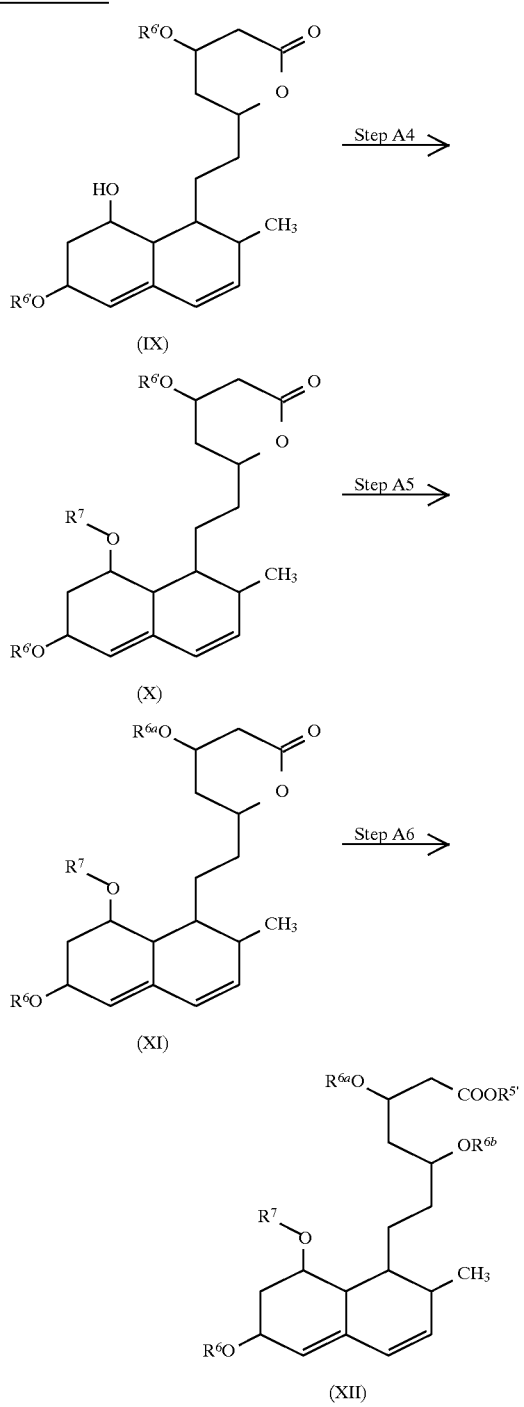

In the above formulae:

R⁵' represents a hydrogen atom, a carboxy-protecting group, as defined for R⁵ or the cationic portion of a salt;

R⁶' represents a hydroxy-protecting group, an alkyl group, an alkanesulfonyl group, a halogenated alkanesulfonyl group or an arylsulfonyl group, all as defined and exemplified above in relation to R⁶ etc.;

R⁷ represents a group of formula:

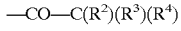

(wherein R², R³ and R⁴ are as defined above); and

M represents a hydrogen atom or the cationic portion of a salt.

Where R⁵' or M represents the cationic portion of a salt, this may be any of the cations exemplified previously in connection with the pharmaceutically acceptable salts.

Step A1

In Step A1 of this reaction scheme, a compound of formula (VII) is prepared by the hydrolysis of a compound of formula (VI) or a pharmaceutically acceptable salt thereof. The hydrolysis may be conducted by conventional means, for example using a base in a solvent to convert the ester side chain at the 8-position to a hydroxy group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water and organic solvents, such as: ethers, for example tetrahydrofuran, dioxane, dimethoxyethane or diethylene glycol dimethyl ether; alcohols, for example methanol, ethanol, propanol, isopropanol, butanol, isobutanol, t-butanol, isoamyl alcohol, diethylene glycol or ethylene glycol monomethyl ether; and mixtures of water with one or more of these organic solvents.

There is no particular limitation upon the nature of the base used, and any base commonly used as a base in conventional reactions may equally be used here. Examples of preferred bases include: inorganic bases, such as alkali metal carbonates (for example sodium carbonate, potassium carbonate or lithium carbonate), alkali metal hydrogencarbonates (for example sodium hydrogencarbonate, potassium hydrogencarbonate or lithium hydrogencarbonate), alkali metal hydroxides (for example sodium hydroxide, potassium hydroxide, barium hydroxide or lithium hydroxide), and alkali metal alkoxides (for example sodium methoxide, sodium ethoxide, potassium methoxide, potassium ethoxide, potassium t-butoxide or lithium methoxide).

Where an alkali metal carbonate, an alkali metal hydrogencarbonate or an alkali metal hydroxide is used as the base, the reaction is preferably carried out using one or more equivalents of the base per mole of the compound of formula (VI). Where an alkali metal alkoxide is used as the base, the reaction proceeds when more than a catalytic amount of the base is used.

The reaction can take place over a wide range of temperatures, and the precise reaction temperature is not critical to the invention. In general, we find it convenient to carry out the reaction either at a temperature of from −20° C. to 150° C., more preferably from 80° C. to 120° C., or at the temperature of the boiling point of the solvent used. The time required for the reaction may also vary widely, depending on many factors, notably the reaction temperature and the nature of the reagents, base and solvent employed. However, provided that the reaction is effected under the preferred conditions outlined above, a period of from 3 to 100 hours, more preferably from 24 to 60 hours, will usually suffice.

After completion of the reaction, the desired product of formula (VII) can be recovered from the reaction mixture by conventional means. For example, in one suitable recovery procedure: the reaction mixture is adequately neutralized; if insoluble materials exist, they are removed by filtration; water and a water-immiscible organic solvent, such as ethyl acetate, are added to the reaction mixture or to the filtrate;

and the product is extracted into the solvent; the extract is washed with water and dried, for example over anhydrous magnesium sulfate; and then the solvent is distilled off, leaving the desired product as the residue.

The compound of formula (VII) thus obtained is a salt of a hydroxy acid and, if necessary, it can be purified by conventional means, for example, by recrystallization, reprecipitation or the various chromatographic techniques. Examples of chromatographic techniques include: partition chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or with an alkylated silica gel (preferably high performance liquid chromatography); or a combination of these techniques; followed by eluting with a suitable eluting solvent.

Step A2

In this step, a lactone compound of formula (VIII) is prepared by reacting the salt of a hydroxy acid compound of formula (VII) with one or more equivalents of an acid to produce a free carboxylic acid and then subjecting the product to a ring closure reaction.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water and organic solvents, such as: ethers (for example tetrahydrofuran, dioxane, dimethoxyethane and diethylene glycol dimethyl ether); alcohols (for example methanol, ethanol, propanol, isopropanol, butanol, isobutanol, t-butanol, diethylene glycol and cyclohexanol); and mixtures of water and one or more of these organic solvents.

There is also no particular limitation upon the nature of the acid used in the first part of this step, and any catalyst conventionally used in this type of reaction may equally be used here. Examples of preferred acids include inorganic acids, such as hydrochloric acid, hydrobromic acid, sulfuric acid, perchloric acid or phosphoric acid.

The reaction can take place over a wide range of temperatures, and the precise reaction temperature is not critical to the invention. In general, we find it convenient to carry out the reaction at a temperature of from −20° C. to 50° C., more preferably at a temperature between 0° C. and about room temperature. The time required for the reaction may also vary widely, depending on many factors, notably the reaction temperature and the nature of the reagents, acid and solvent employed. However, provided that the reaction is effected under the preferred conditions outlined above, it may go to completion immediately after adding the acid; alternatively, a period of up to 2 hours, more preferably a period of up to 30 minutes may be allowed for the reaction.

After completion of the reaction, the desired product of this reaction can be recovered from the reaction mixture by conventional means. For example, in one suitable recovery procedure: the reaction mixture is adequately neutralized; if insoluble materials exist, they are removed by filtration; water and a water-immiscible organic solvent, such as ethyl acetate, are added to the reaction mixture or the filtrate and the product is extracted into the solvent; the extract is washed with water and dried, for example over anhydrous magnesium sulfate; and the solvent is distilled off, leaving the desired product as the residue. Alternatively, after completion of the reaction, the desired compound can be recovered by distilling off the solvent from the reaction mixture; mixing the residue with an organic solvent; filtering off insoluble materials; and distilling off the solvent. Examples of organic solvents which may be used in this recovery procedure include: aliphatic hydrocarbons, such as hexane, heptane, ligroin or petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, diethylene glycol or cyclohexanol; and ketones, such as acetone and methyl ethyl ketone.

The desired compound thus obtained can, if necessary, be purified by conventional means, for example, by recrystallization, reprecipitation or chromatographic techniques. Examples of suitable chromatographic techniques include: partition chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or with an alkylated silica gel (preferably high performance liquid chromatography); or a combination of these techniques; followed by eluting with a suitable eluting solvent.

Ring closing lactonization in the second part of the step causes the hydroxy acid to be converted to a lactone ring. The reaction can be conducted by a variety of methods, for example:

Method 1, which involves simply heating the corresponding hydroxy acid in a solvent;

Method 2, which involves treating the corresponding hydroxy acid with an esterifying agent in a solvent.

Method 1

The reaction is effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; and nitriles, such as acetonitrile or isobutyronitrile.

The reaction can take place over a wide range of temperatures, and the precise reaction temperature is not critical to the invention. In general, we find it convenient to carry out the reaction at a temperature of from 0° C. to the reflux temperature of the solvent used, more preferably from about room temperature to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 6 hours, more preferably from 30 minutes to 3 hours, will usually suffice.

The reaction can be accelerated by the use of an acid as a catalyst. There is no particular limitation upon the nature of the acid used, and any acid which can be used as an acid catalyst in conventional reactions may equally be used here. Examples of such acids include: organic acids, such as acetic acid, formic acid, oxalic acid, methanesulfonic acid, p-toluenesulfonic acid, trifluoroacetic acid or trifluoromethanesulfonic acid; and Lewis acids, such as boron trichloride, boron trifluoride or boron tribromide. Of these, we prefer the organic acids; more preferably the strong organic acids.

Method 2

The reaction of Method 2 is normally and preferably effected in the presence of a solvent. There is no particular restriction on the nature of the solvent to be employed, provided that it has no adverse effect on the reaction or on the reagents involved and that it can dissolve the reagents, at least to some extent. The solvent should, however, be anhydrous. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitriles, such as acetonitrile or isobutyronitrile; and amides, such as formamide, dimethylformamide, dimethylacetamide, N-methyl-2-pyridone, N-methylpyrrolidinone or hexamethylphosphoric triamide.

Examples of esterifying agent which may be used in Method 2 include: condensing agents, as exemplified below; alkyl haloformates, such as methyl chloroformate or ethyl chloroformate; and cyanophosphoric acid diesters, such as diethyl cyanophosphonate. Examples of condensing agents include: N-hydroxy derivatives, such as N-hydroxysuccinimide, 1-hydroxybenzotriazole and N-hydroxy-5-norbornen-2,3-dicarboximide; disulfide compounds, such as 2,2'-dipyridyl disulfide; succinic acid compounds, such as N,N'-disuccinimidyl carbonate; phosphinic chloride compounds, such as N,N'-bis(2-oxo-3-oxazolidinyl)phosphinic chloride; oxalate derivatives, such as N,N'-disuccinimidyl oxalate (DSO), N,N'-diphthalimide oxalate (DPO), N,N'-bis(norbornenylsuccinimidyl)oxalate (BNO), 1,1'-bis(benzotriazolyl)oxalate (BBTO), 1,1'-bis(6-chlorobenzotriazolyl)oxalate (BCTO) or 1,1'-bis(6-trifluoromethylbenzotriazolyl)oxalate (BTBO); triarylphosphines, such as triphenylphosphine; a combination of a di(lower alkyl) azodicarboxylate and a triarylphosphine, such as a combination of diethyl azodicarboxylate and triphenylphosphine; N-(lower alkyl)-5-arylisoxazolium-3'-sulfonates, such as N-ethyl-5-phenylisoxazolium-3'-sulfonate; carbodiimide derivatives including N',N'-dicycloalkylcarbodiimides, such as N',N'-dicyclohexylcarbodiimide (DCC) or 1-ethyl-3-(3-dimethylaminopropyl)carbodiimide (EDAPC); diheteroaryl diselenides, such as di-2-pyridyl diselenide; arylsulfonyl triazolides, such as p-nitrobenzenesulfonyl triazolide; 2-halo-1-(lower alkyl)pyridinium halides, such as 2-chloro-1-methylpyridinium iodide; diarylphosphoryl azides, such as diphenylphosphoryl azide (DPPA); imidazole derivatives, such as 1,1'-oxalyldiimidazole or N,N'-carbonyldiimidazole; benzotriazole derivatives, such as 1-hydroxybenzotriazole (HOBT); and dicarboximide derivatives, such as N-hydroxy-5-norbornene-2,3-dicarboximide (HONB). Of these, we prefer the diarylphosphoryl azides.

The reaction can take place over a wide range of temperatures, and the precise reaction temperature is not critical to the invention. In general, we find it convenient to carry out the reaction at a temperature of from −20° C. to 100° C., more preferably from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 8 hours, more preferably from 30 minutes to 4 hours, will usually suffice.

After completion of the reaction, the desired compound of formula (VIII) can be recovered from the reaction mixture by conventional means. For example, in one suitable recovery procedure: the reaction mixture is neutralized; if insoluble materials exist, they are removed by filtration; water and a water-immiscible organic solvent, such as ethyl acetate, are added to the filtrate or to the neutralized reaction mixture, and the product is extracted into the solvent; the extract is washed with water and dried, for example over anhydrous magnesium sulfate; and then the solvent is distilled off leaving the desired product as the residue.

The desired compound thus obtained can, if necessary, be further purified by conventional means, for example, recrystallization, reprecipitation or the various chromatographic techniques. Examples of suitable chromatographic techniques include: absorption chromatography through a carrier, such as silica gel, alumina or Florisil (containing magnesium-silica gel); partition chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or an alkylated silica gel (preferably high performance liquid chromatography); or an appropriate combination of these techniques; followed by elution with a suitable eluting solvent.

Step A3

In this step, a compound of formula (IX) is prepared by the selective protection of the two hydroxy groups other than the hydroxy group at the 8-position, of a compound of formula (VIII), with a group $R^{6'}$.

The protection can be effected by a variety of methods, depending, in part, on the nature of the selected protecting group, for example, the following Methods 1 to 3:

Method 1

This involves reacting a compound of formula (VIII) with a suitable amount, for example from 1 to 4 equivalents (more preferably from 2 to 3 equivalents) of a compound of formula: $R^{6'}$—X or a compound of formula: $R^{6'}$—O—$R^{6'}$ (wherein $R^{6'}$ is as defined above, but preferably represents an acyl group, and X represents a leaving group) in a solvent in the presence or absence of a base. In the above formulae, $R^{6'}$ is as defined above, but preferably represents a hydroxy-protecting group, more preferably a silyl group, and most preferably a t-butyldimethylsilyl group.

There is no particular limitation upon the nature of the leaving group, provided that it is a group capable of leaving as a nucleophilic residue, such as are well known in the art. Examples of preferred leaving groups include: halogen atoms, such as the chlorine, bromine and iodine atoms; lower alkoxycarbonyloxy groups, such as the methoxycarbonyloxy and ethoxycarbonyloxy groups; halogenated alkylcarbonyloxy groups, such as the chloroacetoxy, dichloroacetoxy, trichloroacetoxy and trifluoroacetoxy groups; lower alkanesulfonyloxy groups, such as the methanesulfonyloxy and ethanesulfonyloxy groups; lower haloalkanesulfonyloxy groups, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups. Of these, we prefer the halogen atoms, lower haloalkanesulfonyloxy groups and arylsulfonyloxy groups.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

There is no particular limitation upon the nature of the base used in Method 1, and any base which can be used in conventional reactions of this type may equally be used here. Examples of preferred bases include: organic bases, such as N-methylmorpholine, triethylamine, tributylamine, diisopropylethylamine, dicyclohexylamine, N-methylpiperidine, pyridine, 4-(1-pyrrolidinyl)pyridine, picoline, 4-(N,N-dimethylamino)pyridine, 2,6-di-t-butyl-4-methylpyridine, quinoline, N,N-dimethylaniline and N,N-diethylaniline. If desired, it is possible to use a catalytic amount of 4-(N,N-dimethylamino)pyridine, 4-(1-pyrrolidinyl)pyridine or a combination of other bases. In order to promote the reaction effectively, a quaternary ammonium salt (such as benzyltriethylammonium chloride or tetrabutylammonium chloride) or a crown ethers (such as dibenzo-18-crown-6) may be added to the reaction system.

The reaction can take place over a wide range of temperatures, and the precise reaction temperature is not critical to the invention. In general, we find it convenient to carry out the reaction at a temperature of from –20° C. to the reflux temperature of the solvent used, more preferably from 0° C. to the reflux temperature of the solvent used. The time required for the reaction may also vary widely, depending on many factors, notably the reaction temperature and the nature of the reagents, base and solvent employed. However, provided that the reaction is effected under the preferred conditions outlined above, a period of from 10 minutes to 3 days, more preferably from 1 to 6 hours, will usually suffice.

Method 2

This method comprises reacting a compound of formula (VIII) with a compound of formula: $R^{6'}$—OH (wherein $R^{6'}$ is as defined above and preferably represents an acyl group) in a solvent in the presence of an esterifying agent, such as those exemplified above in Method 2 of Step A2, and a catalytic amount of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

Examples of the bases which may be used in Method 2 are the same as those described for use in foregoing Method 1.

The reaction can take place over a wide range of temperatures, and the precise reaction temperature is not critical to the invention. In general, we find it convenient to carry out the reaction at a temperature of from –20° to 80° C., more preferably from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to one day, will usually suffice.

Method 3

This method comprises reacting a compound of formula (VIII) with a compound of formula: $R^{6'}$—OH (wherein $R^{6'}$ is as defined above and preferably represents an acyl group) in a solvent in the presence of halogenated phosphoric acid dialkyl ester, such as diethyl chlorophosphate, and a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

Examples of the bases which may be used in method 3 are the same as those described for use in foregoing Method 1.

The reaction can take place over a wide range of temperatures, and the precise reaction temperature is not critical to the invention. In general, we find it convenient to carry out the reaction at a temperature of from 0° C. to the reflux temperature of the solvent used, more preferably from about room temperature to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to one day, will usually suffice.

Where $R^{6'}$ represents a lower alkyl group, this may be introduced into the compound of formula (VIII) by conventional means, for example, by reacting the compound of formula (VIII) with a dialkyl sulfate, such as dimethyl sulfate or diethyl sulfate.

By utilizing protecting reagents having different reactivities, it is possible to prepare a compound having two hydroxy groups which are protected by different groups $R^{6'}$.

After completion of the reaction, the desired compound of formula (IX) can be recovered from the reaction mixture by conventional means. For example, in one suitable recovery procedure: the reaction mixture is neutralized; if insoluble materials exist, they are removed by filtration; water and a water-immiscible solvent, such as ethyl acetate, are added to the reaction mixture or the neutralized reaction mixture, and the product is extracted into the solvent; the extract is washed with water and dried, for example, over anhydrous magnesium sulfate; and then the solvent is distilled off, leaving the desired product.

The compound thus obtained may, if necessary, be purified by conventional means, for example, by recrystallization, reprecipitation or the various chromatographic techniques. Examples of suitable chromatographic techniques include: absorption column chromatography through a carrier, such as silica gel, alumina or Florisil (containing magnesium-silica gel); partition column chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or with an alkylated silica gel (preferably high performance liquid chromatographyl); or a combination of these techniques; followed by elution with a suitable eluting solvent.

Step A4

In this step, an ester compound of formula (X) is prepared by acylating a hydroxy group at the 8-position of a compound of formula (IX) with a group of $R^7$. The reaction is carried out following the procedure described in Step A3, using any one of the methods described below:

Method 1

This comprises reacting a compound of formula (IX) with a suitable amount, for example from 1 to 4 equivalents (more preferably from 2 to 3 equivalents) of a compound of formula: $R^7$—X or $R^7$—O—$R^7$ (wherein $R^7$ and X are as defined above) in a solvent in the presence or absence of a base.

Method 2

This comprises reacting a compound of formula (IX) with a compound of formula: $R^7$—OH (wherein $R^7$ is as defined above) in a solvent in the presence of an esterifying agent, such as those exemplified above in Method 2 of Step A2, and a catalytic amount of a base.

Method 3

This comprises reacting a compound of formula (IX) with a compound of formula: $R^7$—OH (wherein $R^7$ is as defined above) in a solvent in the presence of halogenated phosphoric acid diethyl ester, such as diethyl chlorophosphate and a base.

Step A5

In this step, a compound of formula (XI) is prepared by removing the hydroxy-protecting group represented by $R^{6'}$ from the compound of formula (X) and, if desired, then protecting some or all of the resulting free hydroxy groups with the same or different protecting groups, preferably ones capable of being cleaved in vivo by biological methods, such as hydrolysis.

The reaction conditions employed to remove the hydroxy-protecting group represented by $R^{6'}$ will vary, depending upon the nature of the protecting group but the reaction is generally carried out by means well-known in the art, for example as follows.

Removal with a fluoride anion or an organic acid

Where the hydroxy-protecting group is a silyl group, it can usually be eliminated by treating the protected compound with a compound capable of producing a fluoride anion, such as tetrabutylammonium fluoride or hydrofluoric acid, or by treating it with an organic acid, such as methanesulfonic acid, p-toluenesulfonic acid, trifluoroacetic acid or trifluoromethanesulfonic acid. Where a fluoride anion is employed as the deprotecting agent, the reaction can sometimes be accelerated by adding an organic acid, such as formic acid, acetic acid or propionic acid. This removal reaction has the advantage that side reactions are suppressed.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethyoxyethane and diethylene glycol dimethyl ether; and nitrites, such as acetonitrile and isobutyronitrile.

The reaction can take place over a wide range of temperatures, and the precise reaction temperature is not critical to the invention. In general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 2 to 24 hours will usually suffice.

Removal by reduction or oxidation

Where the hydroxy-protecting group is an aralkyl or aralkyloxycarbonyl group, it can preferably be removed by contacting the protected compound with a reducing agents (preferably by catalytic reduction employing hydrogen in the presence of a catalyst, for example at about room temperature) in a solvent or by using an oxidizing agent.

The reduction reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as ethanol and isopropanol; ethers, such as diethyl ether, tetrahydrofuran and dioxane; aromatic hydrocarbons, such as toluene, benzene and xylene; aliphatic hydrocarbons, such as hexane and cyclohexane; esters, such as ethyl acetate and propyl acetate; amides, such as formamide, dimethylformamide, dimethylacetamide, N-methyl-2-pyridone and hexamethylphosphoric triamide; aliphatic acids, such as formic acid and acetic acid; or water. A single one of these solvents or a mixture of two or more of them may be used. Of these, we prefer the alcohols, the aliphatic acids, a mixture of an alcohol and an ether, a mixture of an alcohol and water, or a mixture of an aliphatic acid and water.

There is no particular limitation upon the nature of the catalyst used, and any catalyst commonly used in catalytic reduction may equally be used here. Examples of preferred catalysts include: palladium-on-charcoal, palladium black, Raney nickel, platinum oxide, platinum black, rhodium-on-alumina, a combination of triphenylphosphine and rhodium chloride and palladium-on-barium sulfate.

The hydrogen pressure used in the reaction is not critical but the reaction is normally carried out at a pressure between ambient pressure and 10 atmospheres.

The reaction can take place over a wide range of temperatures, and the precise reaction temperature is not critical to the invention, although the preferred temperature may vary depending upon such factors as the nature of the reagents and the catalyst. In general, we find it convenient to carry out the reaction at a temperature of from 0° C. to 100° C., more preferably from 20° C. to 70° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 1 to 24 hours, will usually suffice.

In the case of the oxidation reaction, the reaction is likewise normally and preferably effected in the presence of a solvent. There is also no particular restriction on the nature of the solvent to be employed, provided that it has no adverse effect on the reaction or on the reagents involved and that it can dissolve the reagents, at least to some extent. Examples of suitable solvents include aqueous organic solvents. Examples of such organic solvents include: ketones, such as acetone; halogenated hydrocarbons, such as methylene chloride, chloroform and carbon tetrachloride; nitriles, such as acetonitrile; ethers, such as diethyl ether, tetrahydrofuran and dioxane; amides, such as dimethylformamide, dimethylacetamide and hexamethylphosphoric triamide; and sulfoxides, such as dimethyl sulfoxide.

There is no particular limitation upon the nature of the oxidizing agent used, and any oxidizing agent commonly used in conventional oxidation reactions of this type may equally be used here. Examples of preferred oxidizing agents include: potassium persulfate, sodium persulfate, ammonium cerium nitrate (CAN) and 2,3-dichloro-5,6-dicyano-p-benzoquinone (DDQ).

The reaction can take place over a wide range of temperatures, and the precise reaction temperature is not critical to the invention. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

Removal by treatment with an alkali metal

The protecting group can be eliminated by treatment with an alkali metal, such as lithium metal or sodium metal, in liquid ammonia or in an alcohol, such as methanol or ethanol, at a suitable temperature, for example a temperature of from −78° C. to −20° C.

Removal by treatment with aluminum chloride

It is also possible to remove the protecting group by contacting the protected compound with a mixture of aluminium chloride with sodium iodide or with an alkylsilyl halide, such as trimethylsilyl iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitrites, such as acetonitrile; and halogenated hydrocarbons, such as methylene chloride and chloroform. A single one of these solvents or a mixture of two or more of them may be used.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 3 days will usually suffice.

Where the reaction substrate contains a sulfur atom, it is preferred to use a mixture of aluminium chloride and sodium iodide.

Removal by treatment with a base

Where the hydroxy-protecting group is an aliphatic acyl, aromatic acyl or alkoxycarbonyl group, the protecting group can be removed by treating the protected compound with a base in a solvent.

There is no particular limitation upon the nature of the base used, provided that other parts of the compound are not affected when the protecting group is removed. Examples of preferred bases include: metal alkoxides, such as sodium methoxide; alkali metal carbonates, such as sodium carbonate, potassium carbonate and lithium carbonate; alkali metal hydroxides, such as sodium hydroxide, potassium hydroxide, lithium hydroxide and barium hydroxide; and ammonia, for example in the form of aqueous ammonia or of a mixture of concentrated ammonia and methanol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; organic solvents, for example, alcohols, such as ethanol and propanol; ethers, such as tetrahydrofuran and dioxane; or a mixture of water and any one or more of these organic solvents.

The reaction can take place over a wide range of temperatures, and the precise reaction temperature is not critical to the invention. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

Where the hydroxy-protecting group is an alkenyloxycarbonyl group, deprotection may also be accomplished by treatment with a base and the reaction conditions are similar to those employed when the hydroxy-protecting group is an aliphatic acyl, aromatic acyl or alkoxycarbonyl group.

Removal by treatment with an acid

Where the hydroxy-protecting group is an alkoxymethyl, tetrahydropyranyl, tetrahydrothiopyranyl, tetrahydrofuranyl, tetrahydrothienyl or substituted ethyl group, it can normally be removed by treating the protected compound with an acid.

There is no particular limitation upon the nature of the acid used, and any acid commonly used for this purpose, including Brönsted acids and Lewis acids, may equally be used here. Examples of preferred acids include: inorganic acids, such as hydrogen chloride; hydrochloric acid, sulfuric acid or nitric acid; Brönsted acids, including organic acids, such as acetic acid, trifluoroacetic acid, methanesulfonic acid or p-toluenesulfonic acid; Lewis acids, such as boron trifluoride; and strongly acidic cation resins such as Dowex-50W™.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as ethanol, propanol, isopropanol, butanol, isobutanol, t-butanol, isoamyl alcohol, diethylene glycol and cyclohexanol; ketones, such as acetone, methyl ethyl ketone, methyl isobutyl ketone, isophorone and cyclohexanone; or water. A single one of these solvents or a mixture of two or more of them may be used. Of these, we prefer the halogenated hydrocarbons, esters and ethers.

The reaction can take place over a wide range of temperatures, and the precise reaction temperature is not critical to the invention. In general, we find it convenient to carry out the reaction at a temperature of from −10° C. to 100° C., more preferably −5° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 30 minutes to 10 hours, will usually suffice.
Removal with palladium and triphenylphosphine or nickel tetracarbonyl Where the hydroxy-protecting group is an aryloxycarbonyl group, it can simply be removed by using a combination of palladium and triphenylphosphine or nickel tetracarbonyl, which has the advantage that side reactions are suppressed.
Introduction of a hydroxy-protecting group If desired, the resulting free hydroxy group may be subsequently protected with a protecting group, especially with a protecting group capable of being cleaved in vivo by biological methods, such as hydrolysis. This may be carried out using a corresponding reagent containing the desired protecting group following the procedure described in Step A3.

Where there is more than one hydroxy group to be protected, they can be protected with the same protecting group or with different protecting groups, for example:

(1) where two hydroxy groups are protected by different protecting groups each repesented by $R^{6'}$, each of these groups may be eliminated selectively and the resulting free hydroxy group may then be protected one at a time with appropriate protecting reagents to produce a compound having hydroxy groups protected by different groups $R^6$; or (2) two hydroxy groups are protected with different protecting groups represented by $R^6$ by utilizing the difference between the reactivities of the protecting reagents, as is well known in the art.

After completion of the reaction, the desired compound of formula (XI) can be recovered from the reaction mixture by conventional means. For example, in one suitable recovery procedure: the reaction mixture is neutralized; if insoluble materials exist, they are removed by filtration; water and a water-immiscible solvent, such as ethyl acetate, are added to the filtrate or the neutralized reaction mixture, and the product is extracted into the solvent; the extract is washed with water and dried, for example over anhydrous magnesium sulfate; and then the solvent is distilled off from the extract, leaving the desired product as the residue.

The desired compound thus obtained may, if necessary, be purified by conventional means, for example, recrystallization, reprecipitation or the various chromatographic techniques. Examples of suitable chromatographic techniques include: absorption column chromatography through a carrier such as silica gel, alumina or Florisil (containing magnesium and silica gel); partition column chromatography through an absorbent, such as Sephadex™ LH-20 (Pharmacia Inc.), Amberlite™ XAD-11 (Rohm and Haas Co.) or Diaion™ (Mitsubishi Kasei Corporation); liquid chromatography through a regular or reverse phase column packed with silica gel or with an alkylated silica gel (preferably high performance liquid chromatography); or a combination of these techniques; followed by elution with a suitable eluting solvent.

Step A6

In this step, a compound of formula (XII), which is a compound of the present invention, is prepared by hydrolysis or solvolysis of the lactone ring of the compound of formula (XI) to produce a salt of a carboxylic acid or a carboxylic acid ester. The reaction can, if desired, be conducted by:

(1) producing a free carboxylic acid;
(2) protecting some or all of the free hydroxy groups with the same or different protecting groups, preferably capable of being cleaved in vivo by biological methods, such as hydrolysis;
(3) protecting the resulting carboxy group with a protecting group, preferably one capable of being cleaved in vivo by biological methods, such as hydrolysis, or producing another salt of the carboxylic acid; and/or
(4) if desired, subjecting the carboxylic acid compound to ring-closure again to produce a lactone compound.

The preparation of the salt of a carboxylic acid may be effected by a conventional hydrolysis reaction using a base, preferably from 1 to 2 moles of the base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water or a mixture of water with one or more organic solvents, for example: ethers, such as tetrahydrofuran, dioxane or diethylene glycol dimethyl ether; alcohols, such as ethanol, propanol, isopropanol, butanol or isobutanol; ketones, such as acetone or methyl ethyl ketone; nitriles, such as acetonitrile or isobutyronitrile; and amides, such as formamide, dimethylformamide, dimethylacetamide, N-methyl-2-pyrolidone, N-methylpyrrolidinone or hexamethylphosphoric triamide).

There is also no particular limitation upon the nature of the base used, and any base commonly used in conventional reactions may equally be used here. Examples of preferred bases include: alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydroxides, such as sodium hydroxide, potassium hydroxide, calcium hydroxide, barium hydroxide or lithium hydroxide; and alkali metal alkoxides, such as sodium methoxide, sodium ethoxide, potassium methoxide, potassium ethoxide, potassium t-butoxide or lithium methoxide.

The reaction will take place over a wide range of temperatures, and the precise reaction temperature chosen is not critical to the invention. In general, we find it convenient to carry out the reaction at a temperature in the range of from −10° C. to 100° C., more preferably from 0° C. to about room temperature. The time required for the reaction may likewise vary widely, depending on many factors, notably the reaction temperature, the base used and the nature of the reagents. However, in most cases, a period of from 30 minutes to 10 hours, more preferably from 1 to 5 hours, will normally suffice.

The reaction for preparing the carboxylic acid ester can be effected by solvolysis in the presence of an acid catalyst and a solvent containing an alcohol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitriles, such as acetonitrile or isobutyronitrile; and amides, such as formamide, dimethylformamide, dimethylacetamide, N-methyl-2-pyrrolidone, N-methylpyrrolidinone or hexamethylphosphoric triamide. However, we prefer to use as the solvent the alcohol which corresponds to the ester residue which it is desired to introduce, by itself.

There is likewise no particular limitation upon the nature of the acid catalyst used, and any acid commonly used as a catalyst in conventional reactions may equally be used here. Examples of preferred acid catalysts include: inorganic acids, such as hydrochloric acid, hydrobromic acid, sulfuric acid, perchloric acid or phosphoric acid; Brönsted acids, for example, organic acids, including carboxylic acids (such as acetic acid, oxalic acid, formic acid and trifluoroacetic acid) and sulfonic acids (such as methanesulfonic acid, p-toluenesulfonic acid and trifluoromethanesulfonic acid); Lewis acids, such as boron trichloride, boron trifluoride or boron tribromide; and acidic ion-exchange resins. Of these, we prefer the organic acids, and more preferably strong organic acids.

The reaction will take place over a wide range of temperatures, and the precise reaction temperature chosen is not critical to the invention. In general, we find it convenient to carry out the reaction at a temperature in the range of from 0° C. to the boiling point of the solvent used, more preferably from 50° C. to the boiling point of the solvent used. The time required for the reaction may likewise vary widely, depending on many factors, notably the reaction temperature and the nature of the reagents and the solvent used. However, in most cases, a period of from 10 minutes to 6 days, more preferably from 30 minutes to 3 days, will normally suffice.

After completion of the reaction, the desired compound can be recovered from the reaction mixture by conventional means. For example, where the reaction is carried out using acidic ion-exchange resin as the acid catalyst, a suitable recovery procedure comprises: filtering the reaction mixture, and then removing the solvent by distillation from the filtrate, leaving the desired product as the residue. Where the reaction is carried out using another acid as the acid catalyst, a suitable recovery procedure comprises: neutralizing the reaction mixture; if insoluble materials exist, removing them by filtration; adding water and a water-immiscible solvent, such as ethyl acetate, to the neutralized reaction mixture or to the filtrate, and extracting the product into the solvent; washing the extract with water and drying it, for example over anhydrous magnesium sulfate; and then removing the solvent by distillation, leaving the product as the residue.

The desired product thus obtained, if necessary, is purified by conventional means, for example, by recrystallization, reprecipitation or the various chromatographic techniques. Exampes of such chromatographic techniques include: partition column chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); liquid chromatography through a regular or reverse phase column packed with silica gel or with an alkylated silica gel (preferably high performance liquid chromatography); or a suitable combination of these techniques; followed by elution with a suitable eluting solvent.

Preferably, a free carboxylic acid is prepared by adjusting the pH of the filtrate containing a salt of carboxylic acid obtained above to less than pH 5, preferably to a pH of from 3 to 4, by adding a suitable acid.

There is no particular limitation upon the type of the acid used, and any organic acid or mineral acid may be used, provided that it has no adverse effect upon the desired compound. Examples of preferred acids include: inorganic acids, such as hydrochloric acid, hydrobromic acid, sulfuric acid, perchloric acid or phosphoric acid; Brönsted acids including organic acids, such as acetic acid, formic acid, oxalic acid, methanesulfonic acid, p-toluenesulfonic acid, trifluoroacetic acid or trifluoromethanesulfonic acid; and acidic ion-exchange resins.

The free carboxylic acid compound thus obtained may be recovered and purified by conventional means, for example, by extraction, washing, drying or the like and then can be used in the following reactions.

The hydroxy group of the resulting compound (which contains a carboxylic acid salt group, a carboxylic acid ester group or a free carboxylic acid group in its molecule) can be protected, preferably by a protecting group capable of being cleaved in vivo by biological methods, such as hydrolysis. The reaction conditions employed for introducing this protecting group are similar to those employed in Step A5.

Where the product is a compound of formula (II) containing two free hydroxy groups, the hydroxy groups can be protected simultaneously by a diol-protecting group, such as an isopropylidene, benzylidene or ethylidene group, by reacting the compound with a suitable reagent, in the presence of an acid catalyst.

There is no particular limitation upon the nature of the reagent used to introduce the diol protecting group, and any such reagent commonly used in the protection of a diol group may equally be used here. Examples of preferred reagents include: aldehyde derivatives, such as benzaldehyde; ketone derivatives, such as acetone; and dimethoxy compounds, such as 2,2-dimethoxypropane or dimethoxybenzyl.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; ethers, such as dioxane or tetrahydrofuran; hydrocarbons, such as hexane or pentane; aromatic hydrocarbons, such as benzene or toluene; esters, such as ethyl acetate; and polar solvents, such as dimethylformamide or acetone.

There is no particular limitation upon the nature of the acid catalyst used, and any acid commonly used as a catalyst in conventional reactions of this type may equally be used here. Examples of preferred acid catalysts include: organic acids, such as p-toluenesulfonic acid, camphorsulfonic acid and pyridinium p-toluenesulfonate; and inorganic acids, such as hydrochloric acid.

The reaction will take place over a wide range of temperatures, and the precise reaction temperature chosen is not critical to the invention, although the preferred temperature will vary, depending upon the nature of the acid catalyst and starting compound used. However, in general, we find it convenient to carry out the reaction at a temperature in the range of from 0° C. to 100° C. The time required for the reaction may likewise vary widely, depending on many factors, notably the reaction temperature and the nature of the reagents. However, in most cases, a period of from 0.1 to 24 hours will normally suffice.

Where the protecting group capable of being cleaved in vivo by biological methods used as the carboxy-protecting group is an alkyl or analogous group, the compound containing a carboxylic acid salt group or a free carboxylic acid group can be protected by the following methods:

Method 1

In this method, the compound to be protected is reacted with a compound of formula $R^{5''}$—X' (wherein $R^{5''}$ represents a protecting group capable of being cleaved in vivo by biological methods, included in the definition of $R^5$, and X' represents a group or atom capable of leaving as a nucleophilic residue). Examples of groups and atoms capable of leaving as a nucleophilic residue include: halogen atoms, such as the chlorine, bromine and iodine atoms; lower alkanesulfonyloxy groups, such as the methanesulfonyloxy and ethanesulfonyloxy groups; haloalkanesulfonyloxy groups, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups. Examples of such compounds include: aliphatic acyloxymethyl halides, such as acetoxymethyl chloride, pivaloyloxymethyl bromide and pivaloyloxymethyl chloride; lower alkoxycarbonyloxyalkyl halides, such as ethoxycarbonyloxymethyl chloride, isopropoxycarbonyloxymethyl chloride, 1-(ethoxycarbonyloxy)ethyl chloride and 1-(ethoxycarbonyloxy)ethyl iodide; phthalidyl halides; and (5-methyl-2-oxo-5-methyl-1,3-dioxolen-4-yl)methyl halides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

The reaction is also effected in the presence of a base. There is no particular limitation upon the nature of the base used, and any base commonly used in conventional reactions of this type may equally be used here. Examples of preferred bases include: alkali metal carbonates, such as sodium carbonate, potassium carbonate and lithium carbonate; alkali metal hydrogencarbonates, such as sodium hydrogencarbonate, potassium hydrogencarbonate and lithium hydrogencarbonate; alkali metal hydrides, such as lithium hydride, sodium hydride and potassium hydride; alkali metal hydroxides, such as sodium hydroxide, potassium hydroxide, barium hydroxide and lithium hydroxide; alkali metal fluorides, such as sodium fluoride and potassium fluoride; alkali metal alkoxides, such as sodium methoxide, sodium ethoxide, potassium methoxide, potassium ethoxide, potassium t-butoxide and lithium methoxide; alkali metal alkylthiolates, such as sodium methylthiolate and sodium ethylthiolate; organic bases, such as N-methylmorpholine, triethylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]nona-5-ene, 1,4-diazabicyclo[2.2.2]octane (DABCO) and 1,8-diazabicyclo[5.4.0]undec-7-ene (DBU); and organic metal bases, such as butyllithium, lithium diisopropylamide and lithium bis(trimethylsilyl)amide.

The reaction will take place over a wide range of temperatures, and the precise reaction temperature chosen is not critical to the invention. In general, we find it convenient to carry out the reaction at a temperature in the range of from −20° C. to 120° C., more preferably from 0° C. to 80° C. The time required for the reaction may likewise vary widely, depending on many factors, notably the reaction temperature and the nature of the reagents. However, in most cases, a period of from 0.5 to 10 hours will normally suffice.

Method 2

This method comprises reacting the unprotected compound with a compound of formula $R^{5'}$—OH (wherein $R^{5'}$ is as defined above) in a solvent in the presence of an esterifying agent and a catalytic amount of a base. The reaction is carried out following the procedure described in Method 2 of Step A3.

Method 3

This method comprises reacting the unprotected compound with a compound of formula $R^{5'}$—OH (wherein $R^{5'}$ is as defined above) in a solvent in the presence of a halogenated phosphoric acid diethyl ester, such as diethyl chlorophosphate, and a base. The reaction is carried out following the procedure described in Method 3 of Step A3.

Method 4

This method may be used where the protecting group is a lower alkyl group and comprises reacting the unprotected compound with the corresponding alcohol used as a reagent, such as methanol, ethanol, propanol and butanol in a solvent. There is no particular limitation upon the nature of the solvent used, provided that it has no adverse effect upon the reaction and that it can dissolve a starting material, at least to some extent. Examples of preferred solvents include: the same alcohols as used as the reagent; aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide. Of these, we prefer to use the same alcohols as are used as the reagent. The reaction is effected in the presence of an acid catalyst. There is no particular limitation upon the nature of the acid catalyst used, and any acid commonly used as a catalyst in conventional reactions of this type may equally be used here. Examples of preferred acid catalyst include: inorganic acids, such as hydrochloric acid, hydrobromic acid, sulfuric acid, perchloric acid and phosphoric acid; Brönsted acids including organic acids, such as acetic acid, formic acid, oxalic acid, methanesulfonic acid, p-toluenesulfonic acid, trifluoroacetic acid and trifluoromethanesulfonic acid; Lewis acids, such as boron trichloride, boron trifluoride and boron tribromide; and acidic ion-exchange resins.

The reaction will take place over a wide range of temperatures, and the precise reaction temperature chosen is not critical to the invention. In general, we find it convenient to carry out the reaction at a temperature in the range of from 0° C. to 100° C., more preferably from 20° C. to 60° C. The time required for the reaction may likewise vary widely, depending on many factors, notably the reaction temperature and the nature of the reagents. However, in most cases, a period of from 1 to 24 hours will normally suffice.

Method 5

This method comprises reacting the unprotected carboxylic acid compound with either:

(i) a halogenating agent, for example phosphorus pentachloride, thionyl chloride or oxalyl chloride, at a suitable temperature, for example about room temperature, for a suitable period, for example a period of from 30 minutes to 5 hours, to produce the corresponding acid halide, or (ii) a chloroformate, such as methyl chloroformate or ethyl chloroformate, in the presence of an organic amine (such as triethylamine), which may be carried out at a similar temperature and for a similar time to those in (i) above, to produce the corresponding acid anhydride;

followed by treating the resulting acid anhydride or acid halide with a suitable alcohol or alkali metal alkoxide to give the desired ester. To prepare the t-butyl ester, the use of potassium t-butoxide is preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride and chloroform; esters, such as ethyl acetate and propyl acetate; ethers, such as diethyl ether, tetrahydrofuran, dioxane and dimethoxyethane; and nitrites, such as acetonitrile. It is also effected in the presence of a base, the nature of which is not critical, for example triethylamine. The reaction can take place over a wide range of temperatures, and the precise reaction temperature is not critical to the invention. In general, we find it convenient to carry out the reaction at a temperature of from −10° C. to 150° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 15 hours, more preferably from 30 minutes to 10 hours, will usually suffice.

Method 6

This method comprises reacting the unprotected free carboxylic acid compound with a diazoalkane, such as diazomethane or diazoethane (generally an ethereal solution of the diazoalkane) at a suitable temperature, for example about room temperature, but, if necessary, the reaction is carried out with heating.

Alternatively, a carboxylic acid ester may be used as the starting compound, in which case, the desired compound can be prepared by conventional means, that is by transesterification with a compound of formula $R^{5'}$—OH, wherein $R^{5'}$ is as defined above.

Where the carboxy-protecting group capable of being cleaved in vivo by biological methods is an amide-type group, the protecting reaction may be accomplished by:

Method 7

This method comprises converting a salt of the carboxylic acid or the free carboxylic acid, which may have been prepared as described above, to an acid halide or acid anhydride following the procedure described in Method 5, and then reacting the acid halide or acid anhydride with the corresponding base, for example gaseous ammonia or dimethylamine.

Method 8

This method comprises subjecting a carboxylic acid ester, which may have been prepared as described above in Methods 1 to 6, to a conventional ester-amide interchange reaction.

Preparation of salts

Reactions which produce a salt of the carboxylic acid may be carried out as follows:

(1) Metal salts of carboxylic acids

The desired salt can be prepared by contacting a free carboxylic acid with a suitable metal compound, for example from a metal hydroxide or a metal carbonate, in an aqueous solvent.

Examples of preferred aqueous solvents include water itself or a mixture of water and an organic solvent such as: an alcohol, for example methanol or ethanol; or a ketone, for example acetone. We especially prefer to use a mixture of water and a hydrophilic organic solvent.

In general, the reaction is preferably carried out at about room temperature or, if necessary, it may optionally be conducted with heating.

(2) Amine salts of carboxylic acids

The desired salt can be prepared by contacting a free carboxylic acid with a suitable amine in an aqueous solvent.

Examples of preferred aqueous solvents include water itself or a mixture of water and an organic solvent such as: an alcohol, for example methanol or ethanol; an ether, for example tetrahydrofuran; or a nitrile, for example acetonitrile. Of these, we particularly prefer aqueous acetone.

In general, the reaction is preferably carried out in the pH range of from 7.0 to 8.5 at a temperature below room temperature, particularly at a temperature from 5° C. to 10° C. It goes immediately to completion.

Alternatively, the desired salt can be prepared by a salt-amine inter-exchange reaction, that is, by dissolving a metal salt of carboxylic acid, which may have been prepared as described in (1) above, in an aqueous solvent and then adding a mineral acid salt of the desired amine (for example a salt of hydrohalic acid, such as the hydrochloride). The reaction may be effected under the same conditions as described above.

(3) Amino acid salts of carboxylic acids

The desired salt can be prepared by contacting a free carboxylic acid with the desired amino acid in an aqueous solvent.

Examples of preferred aqueous solvents include water itself or a mixture of water and an organic solvent such as: an alcohol, for example methanol or ethanol; or an ether, such as tetrahydrofuran.

The reaction is normally carried out with heating, preferably at a temperature of from 50° C. to 60° C.

Preparation of a lactone

The desired lactone compound can be prepared by contacting the carboxylic acid compound prepared as described above with a catalytic amount of an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; ethers, such as tetrahydrofuran, dioxane, dimethoxyethane and diethylene glycol dimethyl ether; ketones, such as acetone and methyl ethyl ketone; nitriles, such as acetonitrile and isobutyronitrile; amides, such as formamide, dimethylformamide, dimethylacetamide, N-methyl-2-pyrrolidone and hexamethylphosphoric triamide; sulfoxides, such as dimethylsulfoxide and sulfolane; or a mixture of one or more of these organic solvents with water.

There is no particular limitation upon the nature of the acid catalyst used, and any acid catalyst commonly used in conventional reactions of this type may equally be used here. Examples of preferred acid catalysts include: inorganic acids, such as hydrochloric acid, hydrobromic acid, sulfuric acid, perchloric acid and phosphoric acid; Brönsted acids including organic acids, such as acetic acid, formic acid, oxalic acid, methanesulfonic acid, p-toluenesulfonic acid, trifluoroacetic acid and trifluoromethanesulfonic acid; Lewis acids, such as zinc chloride, tin tetrachloride, boron trichloride, boron trifluoride and boron tribromide; and acidic ion-exchange resins. Of these, we prefer the inorganic acids.

The reaction can take place over a wide range of temperatures, and the precise reaction temperature is not critical to the invention. In general, we find it convenient to carry out the reaction at a temperature of from −20° C. to 170° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to one day will usually suffice.

After completion of the reaction, the resulting compound of formula (XII) can be recovered and purified by any suitable combination of various kinds of recovery and purification methods, such as those described and exemplified above, notably the various chromatography techniques. Examples of such techniques include: partition column chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); ion-exchange chromatography; gel filtration through a Sephadex column; liquid chromatography through a regular or reverse phase column packed with silica gel or with an alkylated silica gel (preferably high performance liquid chromatography); or any suitable combination of these chromatographic methods; The desired compound may then be eluted with a suitable eluting solvent. Otherwise the product may effectively be extracted with an organic solvent, such as diethyl ether, ethyl acetate or chloroform.

Where the desired compound obtained in the steps described above is produced as a mixture of stereoisomers and the resolution of individual isomers is required, each of the isomers can be separated and purified by conventional methods described above at the end of each reaction or at any desired time after completion of each reaction.

REACTION SCHEME B

An alternative method of preparing compound of the present invention is shown in Reaction Scheme B:

Reaction Scheme B:

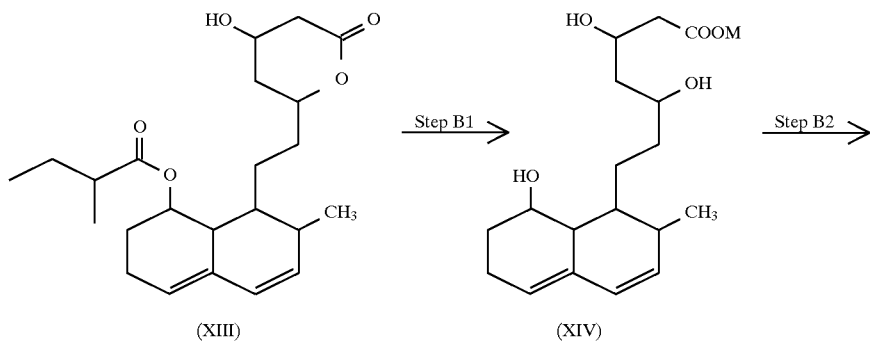

Reaction Scheme B:

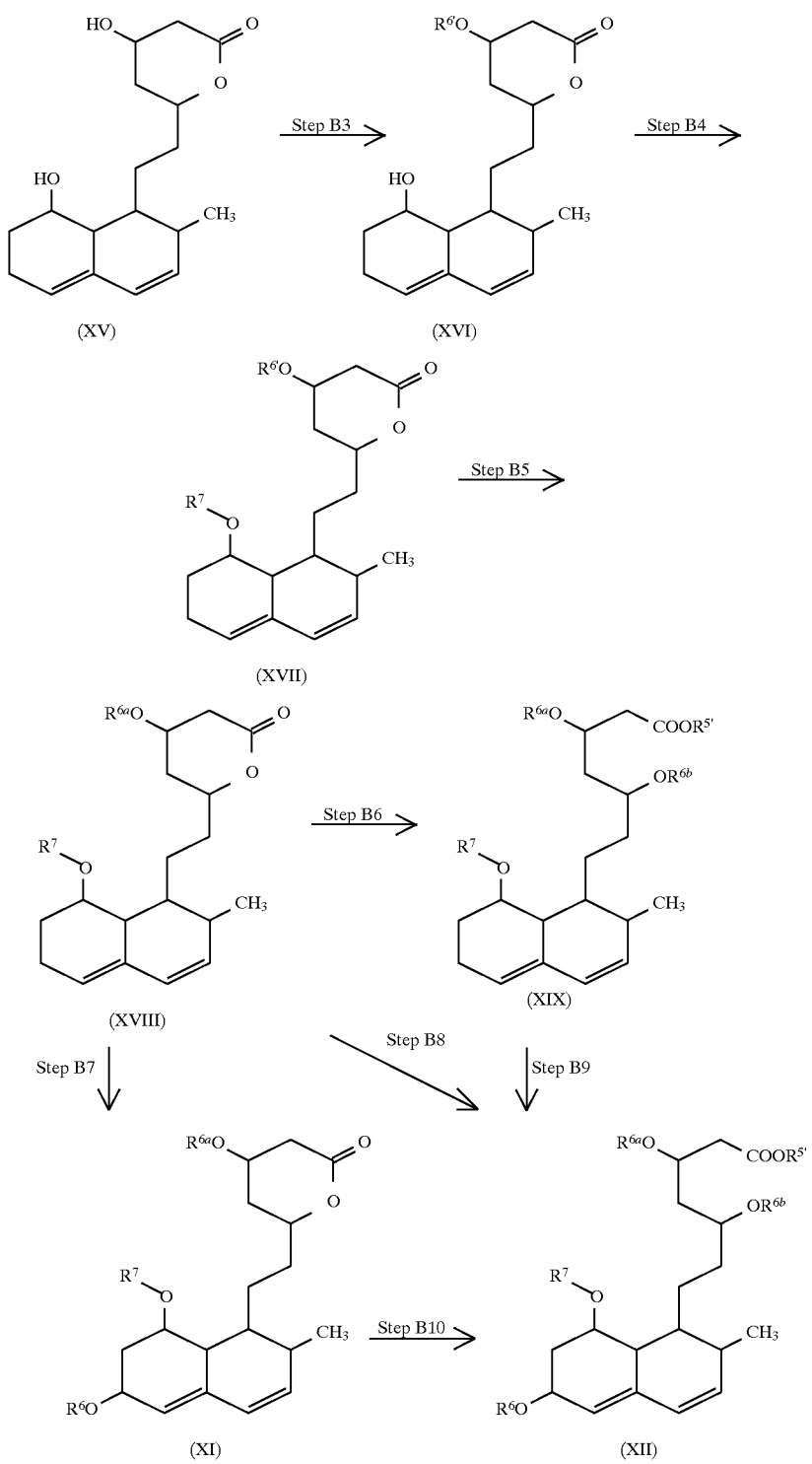

In the above formulae, $R^{5'}$, $R^6$, $R^{6a}$, $R^{6b}$, $R^{6'}$ and $R^7$ are as defined above.

Reaction Scheme B provides a method of preparing compounds of formulae (XVIII) and (XIX), which are compounds of the present invention, and an alternative method of preparing compounds of formulae (XI) and (XII), which are also compounds of the present invention.

Step B1

In this Step, a compound of formula (XIV) is prepared by hydrolysis of the ester side chain at the 8-position of a starting compound of formula (XIII), using a base in a solvent. This reaction is essentially the same as that described in Step A1 of Reaction Scheme A, and may be carried out using the same reagents and reaction conditions.

Step B2

In this Step, a lactone compound of formula (XV) is prepared by neutralizing the salt of a hydroxy acid of formula (XIV), preferably in a solvent with one or more equivalents of an acid, and then ring-closing the resulting free acid. This reaction is essentially the same as that described in Step A2 of Reaction Scheme A, and may be carried out using the same reagents and reaction conditions.

Step B3

In this Step, a compound of formula (XVI) is prepared by selectively protecting a hydroxy group other than the hydroxy group at the 8-position, of the compound of formula (XV), with a group $R^{6'}$. This reaction is essentially the same as that described in Step A3 of Reaction Scheme A, and may be carried out using the same reagents and reaction conditions.

Step B4

In this Step, a compound of formula (XVII) is prepared by acylating the hydroxy group at the 8-position of the compound of formula (XVI) with a group $R^7$. This reaction is essentially the same as that described in Step A4 of Reaction Scheme A, and may be carried out using the same reagents and reaction conditions.

Step B5

In This Step, a compound of formula (XVIII), which is a compound of the present invention, is prepared by eliminating the hydroxy-protecting group represented by $R^{6'}$ of the compound of formula (XVII) and then, if desired, protecting the resulting hydroxy group with another protecting group, preferably one capable of being cleaved in vivo by biological methods, such as hydrolysis. This reaction is essentially the same as that described in Step A5 of Reaction Scheme A, and may be carried out using the same reagents and reaction conditions.

Step B6

In this Step, a compound of formula (XIX) is prepared by hydrolysis or solvolysis of a lactone ring in a compound of formula (XVIII), to produce a salt of a carboxylic acid or a carboxylic acid ester and then, if desired, subjecting the product to any of following reactions:
(1) producing a free carboxylic acid;
(2) protecting some or all of the free hydroxy groups with protecting groups, preferably ones capable of being cleaved in vivo by biological methods, such as hydrolysis;
(3) protecting the resulting carboxy group with a protecting group, preferably one capable of being cleaved in vivo by biological methods, such as hydrolysis, or producing other salts of the carboxylic acid; and/or
(4) if desired, producing again a lactone compound by ring-closure. The reaction is carried out following the procedure described in Step 6.

Steps B7, B8 and B9

In these Steps, compounds of formulae (XI) and (XII) are prepared by introducing stereospecifically a hydroxy group into the 6-position of the carboxylic acid compound of formula (XIX), a pharmaceutically acceptable salt or ester thereof, or a lactone compound of formula (XVIII) by enzymatic hydrolysis. This may be carried out using the procedure described hereafter under the heading "Preparation by Biological Methods". Subsequently, if desired, the following reactions may be conducted:
(1) hydrolysis or solvolysis;
(2) production of a free carboxylic acid;
(3) protecting some or all of the free hydroxy groups with protecting groups, preferably ones capable of being cleaved in vivo by biological methods, such as hydrolysis, which groups may be the same as each other or they may be different from each other;
(4) protecting the resulting carboxy group with a protecting group which is preferably capable of being cleaved in viva by biological methods, such as hydrolysis, or producing other salts of a carboxylic acid; and/or
(5) ring-closing again to produce a lactone compound.

These reactions are essentially the same as those described in Step A6 of Reaction Scheme A, and may be carried out using the same reagents and reaction conditions.

REACTION SCHEME C

This provides an alternative method of preparing the compound of formula (XI) used as an intermediate in Reaction Scheme A and the compound of formula (XVIII) used as an intermediate in Reaction Scheme B.

Reaction Scheme C:

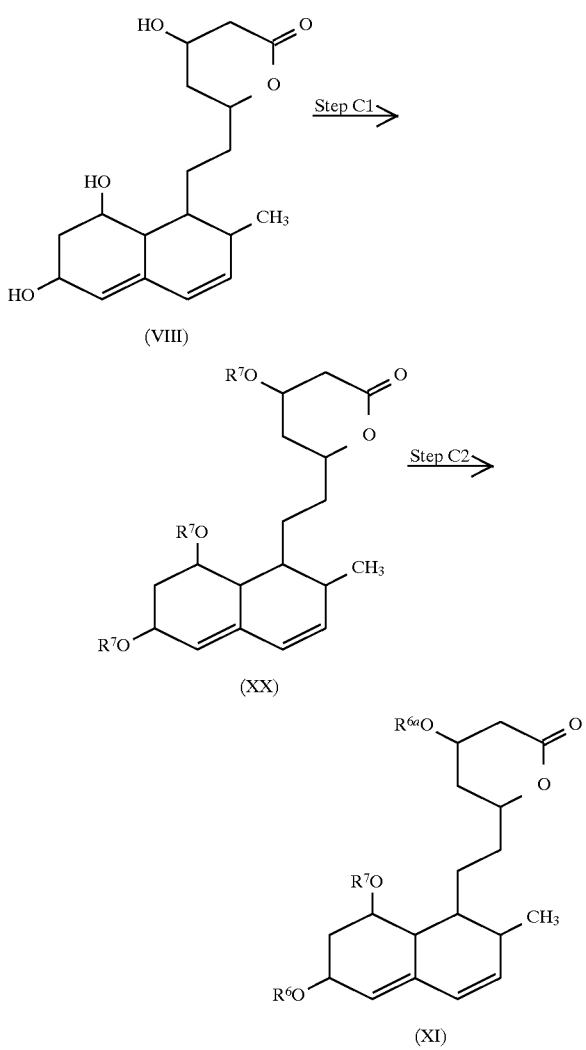

Reaction Scheme C:

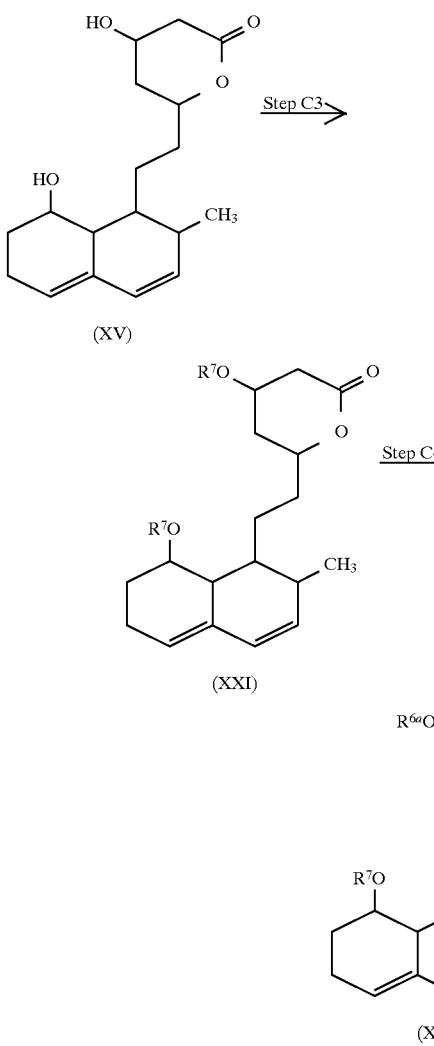

In the above formulae, $R^6$, $R^{6a}$ and $R^7$ are as defined above.

The compounds of formulae (XI) and (XVIII) used as intermediates can be prepared by acylating all of the hydroxy groups in a compound of formula (VIII) or (XV) with a group of $R^7$ to produce a compound of formula (XX) or (XXI), respectively. This reaction is essentially the same as that described in Step A4 of Reaction Scheme A, and may be carried out using the same reagents and reaction conditions. One or two protecting groups other than the acylated hydroxy group at the 8-position are then removed selectively following the procedure described in British Patent Specification No. 2,255,974 A, after which, if desired, either or both of the deprotected groups are protected by a protecting group, preferably one capable of being cleaved in vivo by biological methods such as hydrolysis, which groups may be the same as each other or different from each other. This reaction is essentially the same as that described in Step A5 of Reaction Scheme A, and may be carried out using the same reagents and reaction conditions.

REACTION SCHEME D

This provides an alternative method of preparing the compounds of formulae (I') and (XXII) by fermentation.

Reaction Scheme D:

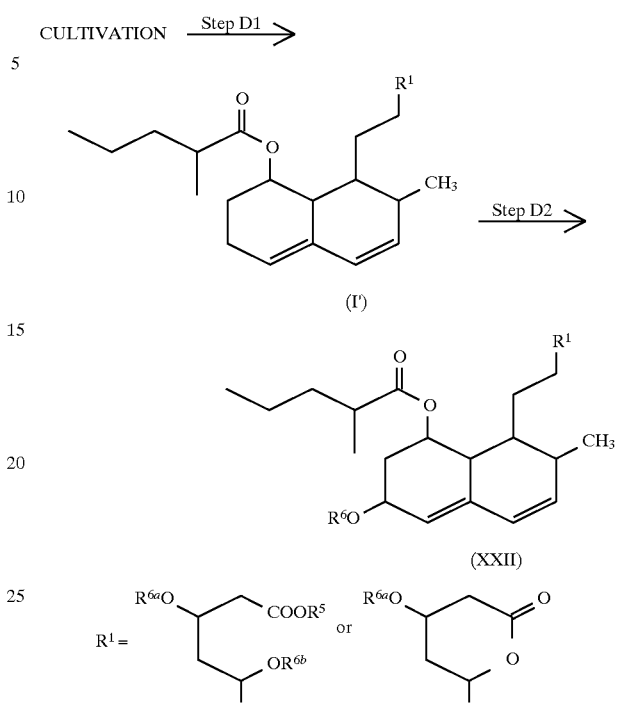

In the above formulae, $R^5$, $R^6$, $R^{6a}$ and $R^{6b}$ are as defined above.

In Step D1, a compound of formula (I'), which is a compound of the present invention, is prepared by incubating a microorganism capable of producing the said compound, which belongs to the genus Penicillium. This may be carried out using the procedure described hereafter under the heading "Preparation by Biological Methods".

If desired, one or more of the following reactions are then carried out:
(1) hydrolysis or solvolysis:
(2) production of a free carboxylic acid:
(3) protecting some or all of the free hydroxy groups with protecting groups, preferably ones capable of being cleaved in vivo by biological methods, such as hydrolysis, which groups ray be the same as each other or they may be different from each other;
(4) protecting the resulting carboxy group with a protecting group which is preferably capable of being cleaved in vivo by biological methods, such as hydrolysis, or producing other salts of a carboxylic acid; and/or
(5) if desired, ring-closing again to produce a lactone compound.

The compound of formula (XIII) used as a starting material in Reaction Scheme B can be prepared chemically following the procedure described in any one of the following literature references:
(1) D. J. Clive et al., J. Am. Chem. Soc., 112, 3018 (1990);
(2) C. T. Hsu et al., J. Am. Chem. Soc., 105, 593 (1983);
(3) N. N. Girotra et al., Tetrahedron Lett., 23, 5501 (1982); ibid., 24, 3687(1983) and ibid., 25, 5371 (1984);
(4) M. Hirama et al., J. Am. Chem. Soc., 104, 4251 (1982);
(5) P. A. Grieco et al., J. Am. Chem. Soc., 108, 5908 (1986);
(6) T. Rosen et al., J. Am. Chem. Soc., 107, 3731 (1985);
(7) G. E. Keck et al., J. Org. Chem. 51, 2487 (1986);
(8) A. P. Kozikowski et al., J. Org. Chem., 52, 3541 (1987);
(9) S. J. Danishefsky et al., J. Am. Chem. Soc., 111, 2599 (1989);

Following the procedures described in Japanese Patent Publication No. Sho 56-12114 and Japanese Patent Application Kokai No. Sho 51-136885, the starting compounds of formulae (XIII) and (XV) employed in Reaction Schemes B and C may be prepared microbiologically. In Step D1 of Reaction Scheme D, both compounds may simultaneously be prepared.

Pravastatin, which may be used as a starting material, can be prepared enzymatically by stereo-selective hydroxylation of a compound of formula (XIII) at the 6-position to produce a compound having a 6β-hydroxy group following the procedure disclosed in Japanese Patent Publication No. 61-13699 or in Steps B7, B8 and B9.

An epimer at the 6-position of pravastatin, that is, a compound having the 6-hydroxy group in the α-configuration, can also be used as a starting material in Step A1. This starting compound can be prepared by stereoselective hydroxylation at the 6-position of a compound of formula (XIII) in a similar manner to the synthesis of pravastatin, following the procedure disclosed in Japanese Patent Publication No. Sho 61-13699 or as described in Steps B7, B8 and B9.

The carboxylic acid of formula $R^7$—OH, which is used as a starting material in the process of the present invention, can easily be prepared by known methods, for example, the method reported by P. E. Pfeffer, J. Org. Chem., 37, 451 (1972).

PREPARATION BY BIOLOGICAL METHODS

Certain of the compounds of the present invention may also be prepared by biological methods, as described in more detail below.

Preparation of compounds of formula (I')

For example, those compounds of formula (IV) which have a 2-methylpentanoyloxy group at the 8-position, that is to say compounds of formula (I'):

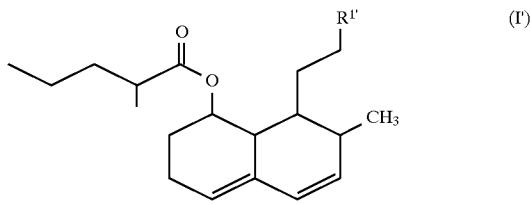

where $R^{1'}$ represents a group of formula (II') or (III'):

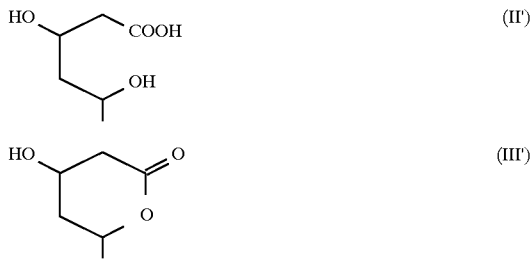

may be prepared by cultivating a microorganism of the genus Penicillium in a nutrient medium therefor and separating said compound of formula (I') from the nutrient medium. This method also forms a part of the present invention.

There is no particular limitation upon the species of microorganism used to produce the compound of formula (I'), provided that it belongs to the genus Penicillium and has the ability to produce a compound of formula (I'). An example of a strain of microorganism capable of producing a compound of formula (I') is *Penicillium citrinum* Thom SANK 13380 which belongs to the genus Penicillium and has been deposited under the terms of the Budapest Treaty at the Fermentation Research Institute, Agency of Industrial Science & Technology, Ministry of International Trade and Industry, Tokyo, Japan, under the Accession Number FERM BP-4129: Date of Deposition, 22nd Dec., 1992.

The mycological properties of Strain SANK 13380 are as follows.

Colonies on Czapek yeast autolysate agar (CYA) medium were 1.8 cm in diameter after growth for 7 days at 25° C. The surface colors were white (1A1) to light yellow (2A4), and the surface was covered with white, floccose aerial hyphae. The reverse was colored white (1A1) to light yellow (2A4), and radial creases were observed. Neither exudates nor soluble pigments were found.

Colonies on malt extract agar (MEA) medium were 1.3 cm in diameter (after growth at 25° C. for 7 days). The surface was colored pale yellow (2A3), and the surface appearance varied from velvety to powdery. The reverse was colored brownish orange (7C7).

Colonies on 25% w/v glycerol nitrate agar (G25N) medium were 1.6 cm in diameter (after growth at 25° C. for 7 days). The surface colors ranged from white (1A1) to yellowish white (1A2), and the surface was covered with floccose hyphae. The reverse was colored pale yellow (2A3).

No growth was observed on any of these media at 5° C. or 37° C.

The surfaces of conidiophores are smooth, and biverticillate. Metulae are cylindrical with slightly vesiculate, and 9–15×3–4 μm in size. Phialides are ampulliform, and 8–10× 3–4 μm in size. Conidia are globose, and the surfaces are smooth to slightly rough, 2.5 to 4 μm in diameter.

On comparing these properties with those of known species, the properties of this strain were found to accord with those of *Penicillium citrinum* Thom described by J. I. Pitt in "The genus Penicillium and its teleomorphic states, Eupenicillium and Talaromyces", p 634, Academic Press (1979). Accordingly, this strain was identified as *Penicillium citrinum* Thom.

The description of the color tones follows the guidelines of A. Kornerup and H. H. Wansher in "Methuen Handbook of Colour", 3rd Ed. (1978) Published by Eyre Methuen (London).

It will be appreciated that SANK 13380, or any other strain capable of producing a compound of formula (I'), may be sub-cultured or biotechnologically altered or modified to produce an organism with different characteristics. The only requirement is that the resulting organism be capable of producing the required compound. Alterations may occur naturally or artificially, by induction, for example by ultraviolet radiation, high frequency waves, radiation and chemical mutagens.

Such alterations and modifications may take any desired form, or may be consequent on such considerations as, for example, culture conditions. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in Penicillium spp. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring Penicillium plasmid and inserting a desired gene or genes from another source. Natural plasmids may also be modified in any other manner that may be considered desirable.

Any such modified strain may be employed in the process of the present invention, provided only that the strain is capable of producing a compound of formula (VI), a matter which can readily be ascertained by simple and routine experimentation.

In order to obtain a compound of formula (VI) from a culture of a suitable microorganism, the microorganism should be fermented in a suitable medium. Such media are generally well known in the art, and will frequently be of a type commonly used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism.

Suitable carbon sources include any carbon-containing material which is assimilable by the microorganism, for example: carbohydrates, such as glucose, fructose, maltose, lactose, sucrose, starch, mannitol, dextrin, glycerin, thick malt syrup, molasses, blackstrap molasses, oat powder, rye powder, corn starch, potato, corn powder, soybean powder, or malt extract; oils or fats, such as soybean oil, cotton seed oil, olive oil, cod-liver oil, or lard oil; organic acids, such as citric acid, sodium ascorbate, malic acid, acetic acid, fumaric acid, tartaric acid, succinic acid or gluconic acid; alcohols, such as methanol, ethanol, propanol, isopropanol, butanol, isobutanol, or t-butanol; and amino acids, such as glutamic acid. These substances can be used alone or a mixture of any two or more of them may be used. Typical amounts will be in a range from about 1 to 10% w/v of the amount of medium, although the amount may be varied as desired and in accordance with the desired result.

Suitable nitrogen sources include any nitrogen-containing material which is assimilable by the microorganism, for example any substance containing a protein, or other readily assimilable source of nitrogen. Representative examples of nitrogen sources are: organic nitrogen sources from animals and plants, and may be extracts from such natural sources as soybean meal, wheat bran, wheat germ, peanut meal, cottonseed meal, cottonseed oil, soy protein isolate, casamino acid, casein hydrolysate, fermamine, fish meal, corn steep liquor, peptone, meat extract, yeast, yeast autolysate, yeast extract, malt extract and urea; amino acids, such as aspartic acid, glutamine, cystine, or alanine; ammonium salts, such as ammonium sulfate, ammonium nitrate, ammonium chloride or ammonium phosphate; and inorganic nitrogen compounds, such as sodium nitrate or potassium nitrate. As with the carbon source, these may be employed alone or in any combination. Suitable amounts are typically within a range from about 0.2 to 6% w/v of the amount of medium.

Suitable nutrient inorganic salts are those which provide trace elements as well as the major constituent of the salt. Preferably, salts should provide such ions as sodium, potassium, magnesium, ammonium, calcium, phosphate, sulfate, chloride, or carbonate in an assimilable form, and preferably such trace metals as molybdenum, boron, copper, cobalt, manganese and iron. Examples of suitable compounds include: sodium chloride, manganese chloride, cobalt chloride, potassium chloride, calcium chloride, calcium carbonate, aluminum potassium sulfate, manganese sulfate, cupric sulfate, cobalt sulfate, zinc sulfate, ferrous sulfate, magnesium sulfate, monopotassium phosphate, dipotassium phosphate, disodium phosphate, or ammonium molybdate. In addition, any other additives necessary for the growth of the microorganism and for promoting the formation of a compound of formula (I') may be used in any suitable combination.

Addition of a sulfur compound assimilable by the microorganism from the medium may sometimes elevate production of the desired compound. Suitable sulfur compounds include inorganic sulfur compounds including: sulfates, such as zinc sulfate, cupric sulfate, ferrous sulfate or ammonium sulfate; thiosulfates, such as ammonium thiosulfate; and sulfites, such as ammonium sulfite; or organic sulfur compounds including: sulfur-containing amino acids, such as cystine, cystein, or L-thiazoline-4-carboxylic acid; heavy metal sulfate compounds, such as ferrous sulfate or cupric sulfate: vitamins, such as vitamin $B_1$ or biotin; and bacterial growth promoting factors, such as thiamine.

An antifoaming agent such as a silicone oil, a polyalkylene glycol ether, a vegetable oil, or suitable surfactant may be added to the medium. Such addition may be particularly appropriate when the microorganism is fermented as a liquid culture.

It is preferred that the pH of the culture medium for the cultivation of Penicillium citrinum Thom SANK 13380, when used for the production of a compound of formula (I'), should be maintained in the region of pH 5.0 to pH 8.0, more preferably from pH 6.0 to pH 7.0, although the only requirement is that the pH should not prevent growth of the microorganism, or adversely irreversibly affect the quality of the final product.

Penicillium citrinum Thom SANK 13380 will, in general, grow at temperatures ranging from 15° C. to 35° C., and grow well at from 22° C. to 30° C. Other temperatures not falling within these ranges may be applicable where a strain has been developed which can grow at lower or higher temperatures, or for other special purposes, as is well known in the art. For the production of a compound of formula (I'), a preferable temperature is in the range of from 15' C. to 35' C., more preferably between 22° C. and 26° C., and most preferably about 24° C.

There is no particular restriction on the culture technique used for the preparation of the compound of formula (I'), and any culture method commonly used for bacterial growth may equally be used here. However, the compound of formula (I') is ideally obtained by aerobic culture, and any suitable aerobic culture techniques, such as, for example, solid culture, stirring culture, stationary culture, shaking culture or aeration-agitation culture may be employed.

If the culture is conducted on a small scale, then a shaking culture fermented for several days at from 20° C. to 30° C., more preferably about 24° C., is generally preferred.

To start a fermentative culture, a preferred technique employs an initial inoculum prepared in one or two steps, for example, in an Erlenmeyer flask, which is preferably provided with baffles (a water flow controlling wall). A carbon source and a nitrogen source may be used in combination for the culture medium. The seed flask is shaken in a thermostatic incubator at a suitable temperature, for example from 20° to 30° C., more preferably from 22° C. to 26° C., and most preferably at about 24° C., for a suitable period, normally from 2 to 7 days, or until sufficient growth is observed, preferably from 3 to 5 days. The resulting seed culture may then be used to inoculate a second seed culture, or a production culture. If a second seeding is conducted, this may be performed in a similar manner, and partly used for inoculation to the production medium. The flask into which the seed culture is inoculated is shaken for a suitable period, for example from 2 to 7 days, or until maximal production is obtained, at a suitable temperature, for example 24° C. When incubation is complete, the contents of the flask may be collected by centrifugation or filtration.

If the culture is to be performed on a large scale, cultivation in a suitable aeration-agitation fermenter may be preferable. In this procedure, the nutrient medium can be prepared in a fermenter. The medium is first sterilized at a suitably high temperature, for example about 120° C., after which it is cooled and seeded with an inoculum previously grown on a sterilized medium. The culture is preferably performed at a temperature from 20° C. to 26° C., more preferably from 22° C. to 24° C., with stirring and aeration. This procedure is suitable for obtaining a large amount of the compound.

The amount of the compound of formula (I') produced by the culture with the passage of time can be monitored by sampling and assessing the content of the compound of formula (I') by, for example, high performance liquid chromatography. The compound of formula (I') can exist in both the lactone and hydroxy forms, and will usually be produced as a mixture of these forms. It is possible to determine the amounts of each form at the same time. In general, the amount of the compound of formula (I') produced reaches a maximum after a period of time of between 72 hours and 300 hours.

The compound of formula (I') produced by the culture exists both in the culture filtrate and in the bacterial cells. It can exist in either the hydroxy-acid form or the lactone form, each of which can change to the other. In addition, the hydroxy-acid form can form a corresponding salt, which will be stable.

Therefore, the compound of formula (I') can be extracted and collected directly by using this property in combination with other properties, for example, as follows.

Method 1

The bacterial cells and other solid materials in the medium are centrifuged or filtered using a filter aid such as diatomaceous earth to separate it into the supernatant and bacterial cells.

(1) Supernatant

The lactone ring in the lactone form of the molecule of the compound of formula (I') existing in the supernatant is hydrolyzed under alkaline conditions (preferably at pH 12 or higher) whereby it opens and all of the compound of formula (I') is converted into the hydroxy-acid salt form. The salt is then converted into the corresponding free hydroxy-acid by careful acidification; and then the compound of formula (I') is obtained from this mixture as the free hydroxy-acid by extraction with a water-immiscible organic solvent, for example: an aliphatic hydrocarbon, such as hexane or heptane; an aromatic hydrocarbon, such as benzene, toluene or xylene; a halogenated hydrocarbon, such as methylene chloride, chloroform, carbon tetrachloride, dichloroethane, chlorobenzene or dichlorobenzene; an ether, such as diethyl ether or diisopropyl ether; or an ester, such as ethyl formate, ethyl acetate, propyl acetate, butyl acetate or diethyl carbonate. A single one of these solvents or a mixture of any two or more of them may be used.

(2) Bacterial cells

The bacterial cells are mixed with a water-miscible organic solvent, for example: an alcohol, such as methanol or ethanol; a ketone, such as acetone; a nitrile, such as acetonitrile or isobutyronitrile; an amide, such as dimethylformamide, dimethylacetamide, N-methyl-2-pyrrolidone, N-methylpyrrolidinone or hexamethylphosphoric triamide. The final concentration of bacterial cells in the resulting mixture is preferably from 50% to 90%. The resulting mixture is preferably then treated in a similar manner to that described above for the supernatant, to obtain the free hydroxy-acid.

Method 2

The culture medium is treated under alkaline conditions (preferably at pH 12 or higher), with heating or at room temperature, to disrupt the cells, and to hydrolyze and to open the lactone ring in the molecule. At that time, all of the compound of formula (I') is converted into its hydroxy-acid salt form. The compound of formula (I') in the free hydroxy-acid form is obtained after conversion of the salt form into its corresponding free hydroxy-acid form by a similar treatment to that described above for the supernatant in Method 1.

The resulting free hydroxy-acid form can be dissolved in the form of a salt in an aqueous solution of an alkali metal base, for example, an alkali metal hydroxide such as sodium hydroxide. Furthermore, the free hydroxy-acid form can be converted into a salt which is easily obtainable and most stable.

Alternatively, the resultant free hydroxy-acid form can be converted into its lactone form by dehydration with heating or by ring closure in an organic solvent.

Isolation and purification of the free hydroxy-acid, hydroxy-acid salt and lactone forms thus obtained can be effected by conventional means commonly used for the isolation and purification of organic compounds. Examples of such methods include a method using a synthetic adsorbent, such as partition chromatography using a carrier, Sephadex LH-20 (trade mark for a product of Pharmacia), Amberlite XAD-11 (trade mark for a product of Rohm and Haas) or Diaion HP-20 (trade mark for a product of Mitsubishi Chem. Ind.). Alternatively, it may be isolated and purified using ordinary phase or reverse phase column chromatography using silica gel or alkylated silica gel (preferably high performance liquid chromatography), followed by elution with a suitable solvent.

The lactone form can be also purified by adsorption column chromatography using a carrier such as silica gel, alumina, or Florisil (a trade mark for a carrier of magnesium—silica gel type).

Examples of solvents which may be employed as the eluent include: aliphatic hydrocarbons, such as hexane, heptane, ligroin or petroleum ether; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; and ethers, such as diethyl ether, diisopropyl ether, tetrahydrofuran, dioxane, dimethoxyethane or diethylene glycol dimethyl ether.

Alternatively, it can be obtained by passing the extracted solution through a column using an adsorbent to remove impurities; or by adsorption of the free hydroxy-acid form on such a column, followed by elution with an aqueous alcohol, such as aqueous methanol, aqueous ethanol, aqueous butanol or aqueous isopropanol, or an aqueous ketone, such as aqueous acetone. Suitable adsorbing agent which may be employed include active carbon, or an adsorbing resin such as Amberlite XASD-2, XAD-4 (trade mark for a product of Rohm and Haas) or Diaion HP-10, HP-20, CHP-20, HP-50 (trade mark for a product of Mitsubishi Chem. Ind.).

The free hydroxy-acid and the salt of the hydroxy-acid can be converted into each other by conventional means, and purified in any desired form.

Hydroxylation of a compound of formula (Ib) to a compound of formula (Ia)

A compound of formula (Ib):

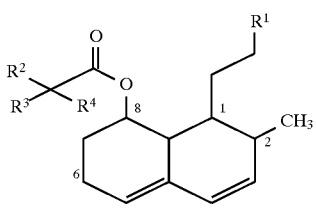

(Ib)

in which $R^1$ is as defined above or a corresponding compound in which reactive groups are protected may be converted to a compound of formula (Ia):

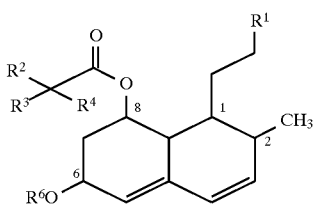

(Ia)

in which $R^1$ is as defined above or a corresponding compound in which reactive groups are protected by means of a hydrolyzing enzyme.

The hydrolyzing enzyme may be derived from a microorganism of a genus selected from the group consisting of Amycolata, Nocardia, Syncephalastrum, Mucor, Rhizopus, Zygorynchus, Circinella, Actinomucor, Gongronella, Phycomyces, Absidia, Cunninghamella, Mortierella, Pychnoporus (old genus name: Trametes), Streptomyces and Rhizoctonia.

This hydrolysis may be effected by any of the following methods:

Method 1: which comprises adding a compound of formula (Ib) to a broth in the course of the cultivation of converting microorganisms, and then continuing the cultivation;

Method 2: which comprises contacting a compound of formula (Ib) with cultured cells collected from a culture broth of the said microorganism; or Method 3: which comprises contacting a compound of formula (Ib) with a cell-free extract prepared from the said microorganism.

In any of these methods, the microorganism is cultivated under conditions suitable to maximize production and efficacy of the enzyme in a suitable culture medium. The composition of the medium may be as described above in connection with the cultivation of microorganisms of the genus Penicillium.

There is no particular limitation upon the species of the microorganism used, provided that it is a microorganism capable of introducing a hydroxy group at the 6-position of the compound of formula (Ib). Examples of such microorganisms include:

fungi of the class Zygomycetes: genera Syncephalastrum, Mucor, Rhizopus, Zygorynchus, Circinella, Actinomucor, Gongronella, Phycomyces, Absidia, Cunninghamella and Mortierella;

fungi of other classes than Zygomycetes: genera Pychnoporus (former genus name: Trametes) and Rhizoctonia;

actinomycetes: genera Amycolata, Nocardia and Streptomyces; preferably strains belonging to the genus Syncephalastrum, including:
Syncephalastrum racemosum (Cohn) Schroeter SANK 41872 (FERM BP-4107); Syncephalastrum nigricans Vuillemin SANK 42372, IFO 4814 (FERM BP-4106); Syncephalastrum nigricans SANK 42172 (FERM P-6041); Syncephalastrum nigricans SANK 42272 (FERM P-6042); and Syncephalastrum racemosum IFO 4828;

strains belonging to the genus Mucor, including:
Mucor hiemalis Wehmer SANK 36372, IFO 5834 (FERM BP-4108); Mucor hiemalis f. hiemalis IFO 5303; Mucor hiemalis f. hiemalis IFO 8567; Mucor hiemalis f. hiemalis IFO 8449; Mucor hiemalis f. hiemalis IFO 8448; Mucor hiemalis f. hiemalis IFO 8565; Mucor hiemalis f. hiemalis CBS 117.08; Mucor hiemalis f. hiemalis CBS 109.19; Mucor hiemalis f. hiemalis CBS 200.28; Mucor hiemalis f. hiemalis CBS 242.35; Mucor hiemalis, f. hiemalis CBS 110.19; Mucor hiemalis f. hiemalis CBS 201.65; Mucor bacilliformis NRRL 2346; Mucor circinelloides f. circinelloides IFO 4554; Mucor circinelloides f. circinelloides IFO 5775; Mucor hiemalis f. corticolus SANK 34572 (FERM P-5913); Mucor dimorphosporus IFO 4556; Mucor fragillis CBS 23635; Mucor genevesis IFO 4585; Mucor globosus SANK 35472 (FERM P-5915); and Mucor circinelloides f. griseocyanus IFO 4563;

strains belonging to the genus Rhizopus, including:
Rhizopus chinensis IFO 4772; Rhizopus circinans ATCC 1225; and Rhizopus arrhizus ATCC 11145;

strains belonging to the genus Zygorynchus, including:
Zygorynchus moelleriIFO 4833;

strains belonging to the genus Circinella, including:
Circinella muscae IFO 4457; Circinella umbellata IFO 4452; and Circinella umbellata IFO 5842;

strains belonging to the genus Actinomucor, including:
Actinomucor elegans ATCC 6476;

strains belonging to the genus Gongronella, including:
Gongronella butleri IFO 8080;

strains belonging to the genus Phycomyces, including:
Phycomyces blakesleeanus SANK 45172 (FERM P-5914);

strains belonging to the genus Absidia, including:
Absidia coerulea IFO 4423; and Absidia glauca var. paradoxa IFO 4431;

strains belonging to the genus Cunninghamella, including:
Cunninghamella echinulata IFO 4445; Cunninghamella echinulata IFO 4444; and Cunninghamella echinulata ATCC 9244;

strains belonging to the genus Mortierella, including:
Mortierella isabellina IFO 6739;

strains belonging to the genus Amycolata, including:
Amycolata autotrophica SANK 62981 (FERM BP-4105); Amycolata autotrophica SANK 62781 (FERM P-6181); Amycolata autotrophica subsp. canberrica subsp. nov SANK 62881 (FERM P-6182); and Amycolata autotrophica IFO 12743;

strains belonging to the genus Nocardia, including:
Nocardia asteroides IFO 3424; Nocardia farcinica ATCC 3318; and Nocardia coeliaca ATCC 17040;

strains belonging to the genus Pychnoporus, including:
Pycnoporus coccineus SANK 11280 (FERM P-5916);

strains belonging to the genus Streptomyces, including:
Streptomyces carbophilus SANK 62585 (FERM BP-4128);

*Streptomyces roseochromogenus* IFO 3363; *Streptomyces roseochromogenus* IFO 3411; and *Streptomyces halstedii* IFO 3199;

strains belonging to the genus Rhizoctonia, including:

*Rhizoctonia solani* SANK 22972 (FERM P-5917).

Of these, the most preferred microorganisms are:

*Amycolata autotrophica* SANK 62981 (FERM BP-4105);

*Syncephalastrum racemosum* (Cohn) Schroeter SANK 41872 (FERM BP-4107);

*Syncephalastrum nigricans* Vuillemin SANK 42372 (FERM BP-4106);

*Mucor hiemalis* Wehmer SANK 36372 (FERM BP-4108); and

*Streptomyces carbophilus* SANK 62585 (FERM BP-4128).

The microorganisms described above have been deposited in the culture collection of the Fermentation Research Institute, Agency of Industrial Science and Technology, the Ministry of International Trade and Industry or are available from official agencies (IFO, CBS, NRRL and ATCC) without restriction as to availability. The following Examples using the foregoing more preferred fungi are provided in order that the present invention may be more fully understood.

It will be appreciated that the strains mentioned above, or any other strain capable of similar activity, may be subcultured or biotechnologically altered or modified to produce an organism with different characteristics. The only requirement is that the resulting organism be capable of producing the required compound. Alterations may occur naturally or artificially, by induction.

Such alterations and modifications may take any desired form, or may be consequent on such considerations as culture conditions, for example. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in species of which the above are strains. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring plasmid and inserting a desired gene or genes from another source. Natural plasmids may also be modified in any other manner that may be considered desirable.

Any such modified strain may be employed in the process of the present invention, provided only that the strain is capable of the required activity, a matter which can readily be ascertained by simple and routine experimentation.

The mycological properties of these strains are as follows.
Mycological properties of *Amycolata autotrophica* SANK 62981

According to the methods of Shirling and Gottlieb [International Journal of Systematic Bacteriology 16, 313–340 (1968)] and of S. A. Waksman [The Actinomycetes], the strain was observed throughout 14 days.

(1) Morphological characteristics

The shape of the top of aerial hyphae: Rectus-flexibilis

The mode of hyphal branching: Simple branching

Hyphal division: Observable

Surface structure of arthrospores: Smooth

Other organs: None (2) Properties on various kinds of media for classification

The strain grows well on any of the media tested.

Strain SANK 62981 grows showing a light brownish white to pale yellowish orange color. As cultivation progresses, light brown to violet spots are observed.

On other media than yeast extract—malt extract agar medium, the formation of light brownish grey aerial hyphae is observed.

No formation of soluble pigment is observed.

TABLE 3

Properties after culture for 14 days at 28° C. on various kinds of media

| Medium | Item | SANK 62981 |
|---|---|---|
| Yeast extract - malt extract agar (ISP 2) | G | Very good, brownish white (2-9-8) to grayish red-brown (4-3-5) |
|  | AM | Trace, white |
|  | R | Brownish white (2-9-8) to grayish red brown (4-3-5) |
|  | SP | Not produced |
| Oatmeal agar (ISP 3) | G | Very good, dark reddish brown (4-3-4) |
|  | AM | Ordinary, pale pink (2-8-4) |
|  | R | Brownish violet (3-3-2) |
|  | SP | Not produced |
| Inorganic salt-starch agar (ISP 4) | G | Very good, brownish violet (3-3-2) |
|  | AM | Good, light brownish gray (2-8-2) |
|  | R | Dark reddish brown (4-3-4) |
|  | SP | Not produced |
| Glycerine - aspargine agar (ISP S) | G | Very good, pale brown (2-9-9) to brownish violet (3-3-2) |
|  | AM | Abundant, white |
|  | R | Pale yellowish orange (2-9-9) to grayish red brown (4-3-6) |
|  | SP | Not produced |
| Tyrosine agar (ISP 7) | G | Good, grayish brown (4-6-6) |
|  | AM | Trace, white |
|  | R | Pale yellowish orange (2-9-9) to brownish violet (3-3-2) |
|  | SP | Not produced |
| Sucrose nitrate agar | G | Not so good, pale yellowish orange (2-9-9) |
|  | AM | Ordinary, white |
|  | R | Pale yellowish orange (2-9-9) |
|  | SP | Not produced |
| Glucose - asparagine agar | G | Very good, pale yellowish orange (2-9-9) to brownish violet (3-3-2) |
|  | AM | Ordinary, white |
|  | R | Pale yellowish orange (2-9-9) to grayish red brown (4-3-6) |
|  | SP | Not produced |
| Nutrient agar | G | Good, pale yellowish orange (2-9-9) |
|  | AM | Trace, white |
|  | R | Pale yellowish orange (2-9-9) |
|  | SP | Not produced |

TABLE 3-continued

Properties after culture for 14 days at 28° C. on various kinds of media

| Medium | Item | SANK 62981 |
| --- | --- | --- |
| Water agar | G | Not so good, pale yellowish orange (2-9-9) |
| | AM | Ordinary, white Pale yellowish orange (2-9-9) |
| | SP | Not produced |
| Potato extract - carrot extract agar | G | Not so good, pale yellowish orange (2-9-9) |
| | AM | Ordinary, white |
| | R | Pale yellowish orange (2-9-9) |
| | SP | Not produced |

In the table, G, AM, R and SP mean growth, aerial mycelium, reverse and soluble pigment respectively.

The color tones are indicated in the above Table according to the Color Tip Numbers described in [Standard Color Table] published by Nihon Shikisai Kenkyujo.

(3) Physiological properties

Reduction of nitrate: Positive

Hydrolysis of starch: Negative

Formation of melanoid pigment: Negative

Determined on the following 3 media:

Medium 1: Tryptone.yeast extract broth (ISP 1) Medium 2: Peptone.yeast extract.iron agar (ISP 6)

Medium 3: Tyrosine agar (ISP 7)

(4) Assimilability of various kinds of carbon sources

By using Pridham-Gottlieb agar medium (ISP 9) assimilation of carbon sources was examined and judged after culture for 14 days at 28° C.

In the following table:

+means assimilation,

±means a little assimilation and

−means no assimilation.

D-Glucose: +

L-Arabinose: +

D-Xylose: +

D-Fructose: +

L-Rhamnose: ±

Inositol: +

Sucrose: −

Raffinose:−

D-Mannitol: +

Control: −

(5) Intracellular components

According to the methods of B. Becker et al. [Applied Microbiology 12, 236 (1965)], and M. P. Lechevalier et al. [The Actinomycetales by H. Prauser, p. 311 (1970)], the acid hydrolysates of the cells of these strains were analyzed by paper chromatography. In the cell walls, meso-2,6-diaminopimelic acid was found, and arabinose and galactose were noted as sugar components of the bacterial cells, from which the bacterial components were confirmed to be type IV-A.

No mycolic acid was found.

On the basis of these results, strain SANK 62981 was determined to belong to the species *Amycolata autotrophica*.

However, as the vegetative growth of the strain of SANK 62981 reveals a color tone like amethyst, it is concluded that the species is a subspecies of *Amycolata autotrophica*.

This strain has been deposited under the conditions of the Budapest Treaty in the permanent culture collection of the Fermentation Research Institute, Agency of Industrial Science & Technology, Ministry of International Trade and Industry, Japan, under the Accession Number FERM BP-4105.

This strain was identified according to the standard of the International Streptomyces Project; [Bergey's Manual of Determinative Bacteriology, 8th Ed.]; [The Actinomycetes, Vol. 2] by S. A. Waksman; and recent reports about Actinomycetes. The genus Amycolata was hitherto classified as part of the genus Nocardia. However, because of differences in the components of bacterial cells, Amycolata is now thought to be an independent genus from Nocardia, and each forms a new genus [International Journal of Systematic Bacteriology 36, 29 (1986)].

Mycological properties of *Syncephalastrum racemosum* (Cohn) Schroeter SANK 41872

This strain was obtained by transfer from a strain deposited at the IFO under the accession number IFO 4814. It was redeposited at the Fermentation Research Institute, Agency of Industrial Science and Technology, the Ministry of International Trade and Industry and assigned the accession number FERM BP-4107.

Mycological properties of *Syncephalastrum nigricans* Vuillemin SANK 42372

Vegetative hyphae develop well and grow rapidly.

Sporangiophores stand vertically from the hyphae, are pale brown in color with rhizoid and irregular branches, and form septa.

Lateral branches sometimes curve sharply.

At the tops of the main axis and lateral branches, vesicles are formed. Vesicles are sub-spherical or oval, sometimes elliptical in shape, and those formed at the top of the main axis are 28 $\mu$m to 50 $\mu$m in diameter, and those formed at the top of the lateral branches are 15 $\mu$m to 25 $\mu$m in diameter.

Many merosporangia are formed on the whole surface. Sporangiophores are single rod or finger-like in shape, and frequently from 5 to 10 spores are formed in a line.

Spores are almost colorless with smooth surfaces, unicellular and sub-spherical to oval in shape, from 3.5 $\mu$m to 6.5 $\mu$m in diameter.

No zygospores are observable.

Comparing these properties with those of known strains, the properties of this strain accorded well with those of *Syncephalastrum nigricans* Vuillemin described in "An Illustrated Book of Fungi" Edited by Keisuke Tsubaki & Shun-ichi Udagawa, Kodansha; p.303–304 (1978).

This strain has been deposited under the conditions of the Budapest Treaty at the Fermentation Research Institute, Agency of Industrial Science & Technology, Ministry of International Trade and Industry under the Accession Number FERM BP-4106.

Mycological properties of *Mucol hiemalis* Wehmer SANK 36372

This strain was obtained by transfer from a strain deposited at the IFO under the accession number IFO 5834. It was redeposited at the Fermentation Research Institute, Agency of Industrial Science and Technology, the Ministry of International Trade and Industry and assigned the Accession number FERM BP-4108.

Mycological properties of *Streptomyces carbophilus* SANK 62585

(1) Morphological characteristics

The morphology of the strain was observed under a microscope after 14 days cultivation at 28° C. on a medium prescribed by International Streptomyces Project (ISP).

Substrate hyphae elongated well and branched and aerial mycelia branched simply. Sporangiophores were straight or curved or sometimes formed spirals and the spore surface was smooth.

No special organs such as whirls, sclerotia, fragmentation of substrate hyphae or sporangia were observed.

(2) Properties on various kinds of media for classification

The properties of strain SANK 62585 were determined on various media after 14 days incubation at 28° C. The results are shown in Table 4.

TABLE 4

| Medium | Item | Properties of strain SANK 62585 |
|---|---|---|
| Yeast extract - malt extract agar (ISP 2) | G: | Very good, yellowish brown (6-7-9) |
| | AM: | Very abundant, powdery, light olive gray (2-8-11) |
| | R: | Yellowish brown (6-5-9) |
| | SP: | Not produced |
| Oatmeal agar (ISP 3) | G: | Very good, grayish yellow brown (4-5-9) |
| | AM: | Very abundant, powdery, light olive gray (2-8-12) |
| | R: | Dark brownish gray (2-3-9) |
| | SP: | Not produced |
| Inorganic salt-starch agar (ISP 4) | G: | Very good, brownish gray (2-6-9) |
| | AM: | Abundant, powdery, yellowish gray (1-9-10) to light olive gray (2-8-12) |
| | R: | Pale brown (2-8-9) to brownish gray (2-4-9) |
| | SP: | Not produced |
| Glycerine-asparagine agar (ISP S) | G: | Not so good, pale yellowish brown (2-7-9) |
| | AM: | Moderate, powdery, grayish white (N-9) |
| | R: | Pale yellowish brown (4-8-9) |
| | SP: | Not produced |
| Tyrosine agar (ISP 7) | G: | Good, dark yellowish brown (4-4-9) |
| | AM: | Very abundant, powdery, yellowish gray (1-9-10) to light olive gray (2-8-11) |
| | R: | Dark brownish gray (2-3-9) |
| | SP: | Not produced |
| Sucrose-nitrate agar | G: | Not so good, pale yellowish orange (2-9-9) |
| | AM: | Moderate, powdery, grayish white (N-9) |
| | R: | Pale yellowish orange (2-9-9) |
| | SP: | Not Produced |
| Glucose-asparagine agar | G: | Not so good, yellowish gray (2-5-9) to brownish gray (1-9-10) |
| | AM: | Poor, grayish white (N-9) |
| | R: | Yellowish gray (2-5-9) to brownish gray (1-9-10) |
| | SP: | Not produced |
| Nutrient agar (Difco) | G: | Not so good, light olive gray (4-8-10) |
| | AM: | None |
| | R: | Light olive gray (4-8-10) |
| | SP: | Not produced |
| Peptone - yeast extract - iron agar (ISP 6) | G: | Good, yellowish brown (4-6-9) |
| | AM: | None |
| | R: | Yellowish brown (4-6-9) |
| | SP: | Not produced |
| Potato extract-carrot extract agar | G: | Poor, yellowish gray (1-9-10) to dark orange (6-8-6) |
| | AM: | Moderate, powdery, pale yellowish orange (2-9-9) |
| | R: | Pale brown (3-8-6) |
| | SP: | Not produced |

In the above Table, the abbreviations used are as defined in Table 3.

The color tones are indicated in the above Table according to the Color Tip Numbers described in [Standard Color Table] published by Nihon Shikisai Kenkyujo.

(3) Physiological properties

Hydrolysis of starch: positive

Liquefaction of gelatin: negative

Reduction of nitrate: positive

Coagulation of milk: positive

Peptonization of milk: positive

Temperature range for growth (Medium 1): 4°–45° C.

Temperature range for optimum growth (Medium 1): 15°–35° C.

Production of melanoid pigments (Medium 2): negative (Medium 3): pseudo-positive (Melanoid pigment is sometimes produced in the latter period of incubation.)

(Medium 4): negative

The media used in the above tests were:

Medium 1: Yeast malt agar (ISP 2)

Medium 2: Tryptone-yeast extract broth (ISP 1)

Medium 3: Peptone-yeast extract-iron agar (ISP 6)

Medium 4: Tyrosine agar (ISP 7)

(4) Assimilability of carbon sources

Assimilability of the carbon source which was utilized in Pridham-Gottlieb basal agar (ISP 9) medium was examined by adding D-glucose, L-arabinose, D-xylose, inositol, D-mannitol, D-fructose, L-rhamnose, sucrose, raffinose, cellobiose or trehalose. Fermentation employing this microorganism was conducted at a temperature of 28° C. for 14 days. As the strain grew well in the control medium without the addition of any carbon source, the assimilability of carbon sources remains to be determined. However, the vegetative growth of this strain in media containing D-glucose, D-xylose, inositol, raffinose, cellobiose or trehalose was far superior to that in the control medium.

(5) Intracellular components

The cell wall components of the strain SANK 62585 was analyzed following the method described by B. Becker et al. [Applied Microbiology, 12, 421–423 (1964)]. L,L-Diaminopimelic acid and glycine were detected. The cell walls of this strain were thus confirmed to be cell wall type 1. The sugar components of the whole cell were analyzed following the method described by M. P. Lechevalier et al. [Journal of Laboratory and Clinical Medicine, 71, 934 (1968)], but no characteristic patterns were found.

On the basis of the foregoing data, it is evident that SANK 62585 belongs to the genus Streptomyces, one of the genera of actinomycetes.

Identification of the strain SANK 62585 was made according to the standard of ISP (The International Streptomyces Project), Bergey's Mannual of Determinative Bacteriology (the 8th edition), S. A. Waksman: The Actinomycetes and recent literature on Actinomycetes. A careful comparison of the foregoing data with published descriptions of known microorganisms reveals significant differences which indicate that SANK 62585 should be classified as a new species belonging to the genus Streptomyces. On this basis, it was designated *Streptomyces carbophilus*. The strain has been deposited in the permanent culture collection of the Fermentation Research Institute, Agency of Industrial Science and Technology, the Ministry of International Trade and Industry, and has been assigned the Accession number FERM BP-4128.

There is no particular limitation upon the method of cultivation employed for the growth of the converting microorganism, and any method commonly used for cultivating microorganisms may equally be used here. Examples of such methods include: solid culture, stationary culture, shaking culture, agitating culture and aerating culture. Of these, an aerobic culture method is preferred, that is, agitating culture, shaking culture or aerating culture, more preferably shaking culture.

Fermentation for industrial purposes is preferably carried out by agitating culture with forced aeration.

The pH of the nutrient medium for the growth of the converting microorganism is normally in the range of from pH 5.0 to 8.0, preferably from pH 6.0 to 7.0.

The fermentation employing the converting microorganism is preferably conducted at temperature ranging from 15° to 35° C., more preferably from 26° to 30° C., and most preferably at 28° C.

Method 1

This method of conducting the enzymatic hydrolysis is effected by incubating a strain of the converting microorganism and by adding a compound of formula (Ib) in the course of the fermentation.

The time at which the compound is added may vary, depending upon the optimum cultivating conditions for the converting microorganism employed, particularly upon the culture apparatus, the composition of the medium, the culture temperature and other conditions, it is preferred to added the compound of formula (Ib) when the hydroxylating ability of the converting microorganism begins to rise. In general, the point of time from 1 to 3 days after begining the incubation of the converting microorganism is preferred.

The amount of the compound of formula (Ib) to be added is normally in a range of from 0.01 to 5.0%, more preferably from 0.025 to 2.0%, based on the volume of the medium.

The time required for the incubation may vary widely, depending upon many factors, including the cultivation conditions and the nature of the microorganism, but, in general, a period of from 3 to 5 days after the addition of the compound of formula (Ib) is appropriate.

Method 2

This method is conducted by incubating the converting microorganism in the presence of a small amount of substrate following the procedure of Method 1, until the hydroxylation by the microorganism reaches to maximum productivity.

The hydroxylating ability will vary, depending upon the type of culture medium, the fermentation temperature and other conditions, but it generally reaches a maximum between 4 and 5 days after beginning of the culture. The culture is normally terminated at this time.

The cells are then collected by subjecting the culture broth to centrifugation, filtration or the like. It is preferred that the cells thus collected should be washed before use with physiological saline or with an appropriate a buffer solution.

The compound of formula (Ib) is usually contacted with the cells thus obtained in an aqueous solvent, for example, a phosphate buffer of pH 5 to 9.

The hydrolysis reaction is preferably carried out at a temperature of from 20° to 45° C., more preferably from 25° to 35° C.

The concentration of the compound of formula (Ib) is preferably in a range of from 0.01 to 5.0% based on the volume of the medium.

The time required for the reaction will vary, depending upon many factors, such as the concentration of the compound of formula (Ib), the reaction temperature and other conditions, but the reaction is normally complete within a period of from 1 to 5 days.

Method 3

In this method, a cell-free extract is prepared by disrupting the cells, which may be achieved by physical or chemical means, for example, by grinding or ultrasonic treatment, to make a suspension containing the cellular components, including the enzyme. Alternatively, it may be effected by treating the cells with an organic solvent, a surface active agent or an enzyme to make a cell-free extract. The cells may be obtained as described in Method 2. The extract then is contacted with the compound of formula (Ib).

The conditions employed for contacting the cell-free extract with the compound of formula (Ib) are similar to those described in Method 2.

According to the methods described above, a suitable substrate (a hydroxy-acid or a lactone compound) is reacted with the converting microorganism or with a cell-free enzyme-containing extract thereof to introduce stereoselectively a hydroxy group into the 6-position of the substrate. The desired compounds having a 6β-hydroxy group can be prepared selectively by using an appropriate combination, for example:

(1) a lactone compound and a strain of *Mucor hiemalis* Wehmer;
(2) a hydroxy-acid compound and a strain of *Streptomyces carbophilus*; or
(3) a hydroxy-acid compound and a strain of *Amycolata autotrophica*.

The desired compounds having a 6α-hydroxy group can be prepared by using an appropriate combination, for example:

(1) a lactone compound and a strain of *Syncephalastrum nigricans* Vuillemin; or
(2) a lactone compound and a strain of *Syncephalastrum racemosum* (Cohn) Schroeter.

The products prepared by the above methods of the present invention are found in the broth filtrate and mycelia at the end of the fermentation. The compound of the present invention exists in the form of either the hydroxy-acid or the lactone and the forms are interconvertable with each other. An important advantage of a hydroxy-acid compound that it can form a stable salt.

Accordingly the extraction and recovery of the desired product from the whole fermentation broth can, for example, be carried out by the following Method 1 or Method 2.

Method 1

The whole fermentation broth is centrifuged or filtered using a filter aid, such as diatomaceous earth, to separate the supernatant from the mycelia and other solid materials. These are then treated as follows:

(1) Supernatant

When the supernatant contains a lactone compound, it is subjected to hydrolysis under alkaline conditions (preferably at a pH 12 or more) in order to open the lactone ring. The hydrolyzate is then acidified carefully to produce a free hydroxy-acid. This acidified hydrolyzate or the supernatant containing a free hydroxy-acid is then extracted with a water-immiscible organic solvent, and the solvent is removed from the extract, for example by distillation under reduced pressure. Examples of suitable water-immiscible organic solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether or diisopropyl ether; esters, such as ethyl formate, ethyl acetate, propyl acetate, butyl acetate or diethyl carbonate; and mixtures of any two or more of the above solvents.

(2) Mycelium

The mycelial cake is mixed with a water-imiscible organic solvent such that the final concentration of the cake is 50 to 90% by volume of the mixture. The resulting mixture is then treated in a similar manner to that described above for the treatment of the supernatant. Examples of suitable water-immiscible organic solvents include: alcohols, such as methanol or ethanol; ketones, such as acetone; nitriles, such as acetonitrile or isobutyronitrile; and amides, such as formamide, dimethylformamide, dimethylacetamide, N-methyl-2-pyrrolidone, N-methypyrrolidinone or hexamethylphosphoric triamide.

Method 2

The fermentation broth is hydrolyzed under alkaline conditions (preferably at pH 12 or more), either with heating or at room temperature, to open the lactone ring at the same time as destroying the mycelia. The whole of the active compounds in the broth are forcedly converted to a salt of the hydroxy-acid compound and the desired free hydroxy-acid may be recovered from the mixture by similar treatment to that described above for the supernatant.

The free hydroxy-acid compound thus obtained can, if desired, be dissolved in an aqueous solution of an alkali metal salt or an alkali metal hydroxide, such as sodium hydroxide, to form a corresponding salt, following the procedure described in Step 6. The hydroxy-acid may then be recovered conveniently in the form of its most stable salt.

Alternatively, in order to recover the desired compound, the free hydroxy-acid compound thus obtained is dehydrated by heating in an organic solvent to produce a compound having a lactone ring, following the procedure described in Step 6.

A mixture consisting of compounds including the free hydroxy-acid, one or more salts of the hydroxy-acid and the lactone compound can normally be separated and recovered by conventional means used in organic chemistry. For example, they may be separated and recovered by the various chromatographic techniques, including: partition column chromatography through a synthetic absorbent such as Sephadex LH-20™ (Pharmacia Inc.), Amberlite™ XAD-11 (Rohm and Haas Co.) or Diaion™ HP-20 (Mitsubishi Kasei Corporation); liquid chromatography through a regular or reverse phase column packed with silica gel or with an alkylated silica gel (preferably high speed liquid chromatography); or an appropriate combination of these techniques; after which the compound may be obtained by eluting with a suitable eluting solvent.

A lactone compound can also be purified by absorption column chromatography through a carrier such as silica gel, alumina or Florisil (containing magnesium and silica gel).

Examples of the preferred solvents used for the elution include: aliphatic hydrocarbons, such as hexane, heptane, ligroin or petreum ethers; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; and ethers, such as diethyl ether, diisopropyl ether, tetrahydrofuran, dioxane, dimethoxyethane or diethylene glycol dimethyl ether.

Alternatively the extract may be purified by absorption column chromatography to remove inpurities. The desired hydroxy-acid compound can be obtained by absorbing it in an absorption column and then eluting it with an eluting solvent, for example: an aqueous alcohol, such as aqueous methanol, aqueous ethanol, aqueous propanol or aqueous isopropanol; or an aqueous ketone, such as aqueous acetone. Examples of such absorbents include: active charcoal; or an absorption resin, such as Amberlite™ XAD-2 or XAD-4 (Rohm and Haas Co.); or Diaion™ HP-10, HP-20, CHP-20 or HP-50 (Mitsubishi Kasei Corporation).

For the purpose of purification, the desired compound can be utilized in the form of either the free hydroxy-acid or a salt of the hydroxy-acid because both forms are mutually interconvertable following the procedure described in Step 6.

BIOLOGICAL ACTIVITY

The compounds of the present invention have a marked ability to reduce the levels of serum cholesterol. Specifically, the compounds inhibit the biosynthesis of chlolesterol in an enzyme system or a culture cell system separated from an experimental animal by inhibiting 3-hydroxy-3-methylglutaryl-CoA reductase (HMG-CoA), the rate limiting enzyme of sterol biosynthesis, by competing with the HMG-CoA. This demonstrates that the compounds will exhibit a powerful serum cholesterol reducing effect when employed in the treatment of humans and other animals.

Experiment 1

Determination of HMG-CoA reductase inhibitory activity

The ability of the preferred test compounds to inhibit the activity of HMG-CoA reductase was determined by the method of Koga et al. [Eur. J. Biochem. 209, 315–319 (1992)], the improved procedure of Kuroda et al. [Biochem. Biophys, Acta, 485, 70–81 (1977)] which a modification of the method of Shapiro et al. [Anal. Biochem. 31, 383–390, (1969)].

A solution of 5 $\mu$l of the preferred test compound dissolved in distilled water was added to 45 $\mu$l of a reaction mixture containing 100 mM of a potassium phosphate buffer (pH7.4), 0.2 mM of [$^{14}$C]HMG-CoA, 10 mM of ethylenediaminetetraacetic acid disodium salt, 10 mM of dithiothreitol, 10 mM of NADPH (=reduced nicotinamide adenine dinucleotide phosphate) and an enzyme solution (rat liver microsomal fraction). The concentrations are expressed in terms of the final 50 $\mu$l of assay mixture. The resulting mixture was incubated for 15 minutes at 37° C. The reaction was then terminated by adding 10 $\mu$l of 2N aqueous hydrochloric acid, to lactonize the [$^{14}$C]mevalonate produced. After 15 minutes incubation, 1 ml of a 1:1 by volume aqueous suspension of Biorex-5 was added and the tubes were vigorously mixed using a Vortex mixer. The mixture was then centrifuged at 3,000×g for 10 minutes at 4° C. The supernatant (400 $\mu$l) was mixed with 4.5 ml of Optiflow™ in scintillation vials and the activity of the [$^{14}$C] mevalonolactone was determined by a liquid scintillation counter.

The results are shown in the following Table 5.

Experiment 2

Detemination of inhibitory activity against sterol synsthesis in mouse liver

Sterol synthesis in the liver in mice was measured by the method of Koga et al. [Biochem. Biophys. Acta, 1045, 115–120, (1990)].

15 $\mu$l of [$^{14}$C]acetate was intraperitoneally injected into each mouse. One hour later, the animal was sacrificed by decapitation and the liver was excised. Sterol synthesis in the liver was measured by the incorporation of [$^{14}$C]activity into the digitonin-precipitable sterols. The preferred test compounds dissolved in 1% Tween 80 were administered orally to the mice 2 hours before the injection of [$^{14}$C] acetate.

The sterol synthesis activity in a control animal receiving only a 1% Tween 80 solution was defined as 100%. The relative inhibition of sterol synthesis in the liver in mice which received different doses of test compound was determined, and ED$_{50}$ (mg/kg) values (the dose required to inhibit sterol synsthesis in the liver by 50%) were calculated.

The results are shown in the following Table 5.

TABLE 5

| Test Cpd. | HMG-CoA Reductase inhibitory activity IC$_{50}$ (nM) | Sterol-synthesis inhibitory activity ED$_{50}$ (mg/kg) |
| --- | --- | --- |
| Example 50 | 35.5 | 0.15 |
| Example 51 | 33.8 | 0.063 |
| Example 52 | 32.3 | 0.054 |
| Example 64 | 34.4 | 0.13 |
| Example 65 | 36.6 | 0.19 |
| Example 67 | 32.1 | 0.048 |
| Example 69 | 32.9 | 0.028 |
| Prior art cpd. | 44.9 | 0.58 |

The prior art compound employed was the compound of Example 4 described in Japanese Patent Publication No. Hei 3-33698, which is the sodium salt of the carboxylic acid form of the following formula (XXIII):

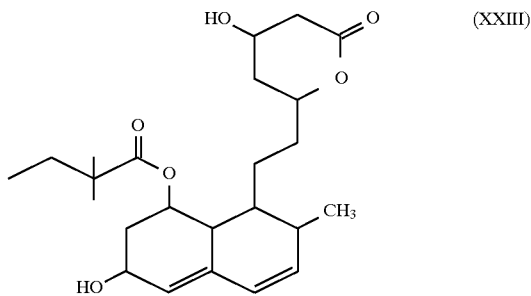

As can clearly be seen from the test results given above, the compounds of the present invention compete with 3-hydroxy-3-methylglutaryl-CoA, which is responsible for the rate-determining step of cholesterol biosynthesis in the the enzyme system separated from laboratory animals or in the liver of mouse. Accordingly the activity of 3-hydroxy-3-methylglutaryl-CoA reductase is inhibited and cholesterol biosynthesis is prevented.

The compounds of the present invention reveal strong cholesterol lowering activity in the blood serum of animals. In addition, their toxicity is very low. Consequently they are useful as a medicament for the treatment of hyperlipemia and the prophylaxis of arteriosclerosis, and also as antifungal or antineoplastic agents.

For this purposes, the compounds of formulae (I) and (IV) can be administered orally in the form of tablets, capsules, granules, powders or syrups, or parenterally by intravenous injection, suppositories or the like. These pharmaceutical formulations can be prepared by mixing the compounds of the present invention with one or more adjuvants, such as excipients (e.g. organic excipients including sugar derivatives, such as lactose, sucrose, glucose, mannitol or sorbitol; starch derivatives, such as cornstarch, mashed potato, α-starch, dextrine or carboxymethyl starch; cellulose derivatives, such as crystalline cellulose, low hydroxypropyl-substituted cellulose, hydroxypropylmethyl cellulose, carboxymethyl cellulose, carboxymethyl cellulose calcium or internally bridged carboxymethyl cellulose sodium; gum arabic; dextran; and Pullulan; inorganic excipients including silicates, such as light silicic acid anhydride, synthetic aluminum silicate or magnesium meta-silicic acid aluminate; phosphates, such as calcium phosphate; carbonates, such as calcium carbonate; and sulfates, such as calcium sulfate); lubricants (e.g. metal stearates, such as stearic acid, calcium stearate or magnesium stearate; talc; colloidal silica; waxes, such as bees wax or spermaceti; boric acid; adipic acid; sulfates, such as sodium sulfate; glycol; fumaric acid; sodium benzoate; DL-leucine; sodium salts of aliphatic acids; lauryl sulfates, such as sodium laurylsulfate or magnesium laurylsulfate; silicates, such as silicic acid anhydride or silicic acid hydrate; and the foregoing starch derivatives); binders (e.g. polyvinyl pyridone, Macrogol; and similar compounds to the excipients described above); disintegrating agents (e.g. similar compounds to the excipients described above; and chemically modified starch-celluloses, such as Crosscarmelose sodium, sodium carboxymethyl starch or bridged polyvinyl pyrrolidone); stabilizers (e.g. p-hydroxybenzoates, such as methylparaben or propylparaben; alcohols, such as chlorobutanol, benzyl alcohol or phenylethyl alcohol; benzalkonium chloride; phenols, such as phenol or cresol; thimerosal; dehydroacetic acid; and sorbic acid); corrigents (e.g. sweeteners, vinegar or perfums, such as those conventionally used); diluents and the like.

The dose varies depending upon the condition and age of the patient and upon the route and type of administration but, for example, the compounds of the present invention can be administered orally in a daily dose of from 0.01 to 1000 mg/kg body weight (preferably 0.05 to 200 mg/kg body weight), either as a single dose or as divided doses.

The preparation of certain of the compounds of the invention is further illustrated by the following Examples. The subsequent Preparations, as well as Examples A and B, illustrate the preparation of certain of the starting materials used in these Examples.

These Examples include the preparation of representative compounds of the invention by direct isolation from microorganisms. The processes described in these Examples are purely illustrative, and these may be modified, for example on the basis of the properties of the desired compound, in order to recover the desired compound.

EXAMPLE A (4R,6R)-6-{2-[(1S,2S,6S,8S,8aR)-1,2,6,7,8,8a-Hexahydro-6,8-dihydroxy-2-methyl-1-naphthyl]ethyl}tetrahydro-4-hydroxy-2H-pyran-2-one

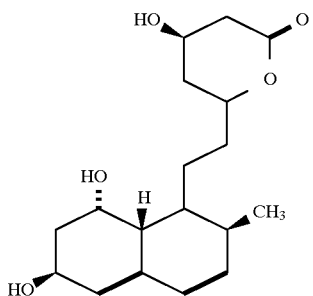

A-(1) Sodium (3R,5R)-3,5-dihydroxy-7-[(1S,2S,6S,8S,8aR)-6,8-dihydroxy-2-methyl-1,2,6,7,8,8a-hexahydro-1-naphthyl]heptanoate 50 ml (0.24 mol) of a 28% w/v solution of sodium methoxide in methanol were added to a solution of 100 g (0.31 mol) of (3R,5R)-3,5-dihydroxy-7-[(1S,2S,6S,8S,8aR)-6-hydroxy-2-methyl-8-[(S)-2-methyl-butyryloxy]-1,2,6,7,8,8a-hexahydro-1-naphthyl]heptanoate (pravastatin: prepared as described in U.S. Pat. No. 4,346,227) in 900 ml of methanol, and the resulting mixture was heated under reflux for 60 hours. At the end of this time, the mixture was cooled to room temperature, and the methanol was then removed from the reaction mixture by distillation under reduced pressure. The resulting residue was washed with 200 ml of hexane and then dried in vacuo to give 120 g of the title compound.

A-(2) (3R,5R)-3,5-Dihydroxy-7-[(1S,2S,6S,8S,8aR)-6,8-dihydroxy-2-methyl-1,2,6,7,8,8a-hexahydro-1-naphthyl]heptanoic acid The whole of the sodium (3R,5R)-3,5-dihydroxy-7-[(1S,2S,6S,8S,8$_a$R)-6,8-dihydroxy-2-methyl-1,2,6,7,8,8a-hexahydro-1-naphthyl]heptanoate prepared as described in Step 1, above, was dissolved directly and without further purification in 300 ml of water. The pH of the solution was adjusted to pH 4.0 by the addition of a 35% w/v aqueous hydrogen chloride solution. The water was then removed from the mixture by distillation under reduced pressure. The residue was dried in vacuo, after which the dried residue was dissolved in 300 ml of ethanol. Sodium chloride formed during the reaction was then removed by filtration, after which the resulting filtrate was concentrated by evaporation under reduced pressure. The residue obtained was dried to give 94 g of the title compound.

A-(3) (4R,6R)-6-{2-[(1S,2S,6S,8S,8aR)-1,2,6,7,8,8a-Hexahydro-6,8-dihydroxy-2-methyl-1-naphthyl]ethyl}tetrahydro-4-hydroxy-2H-pyran-2-one The whole of the crude (3R,5R)-3,5-dihydroxy-7-[(1S,2S,6S,8S,8aR)-6,8-dihydroxy-2-methyl-1,2,6,7,8,8a-hexahydro-1-naphthyl]heptanoic acid, prepared as described in Step 2, above, was mixed with 1000 ml of tetrahydrofuran. 38 ml (0.27 mol) of triethylamine were then added to the mixture, followed by 38 ml (0.25 mol) of diethyl cyanophosphonate, whilst ice-cooling and stirring. The resulting mixture was then stirred at room temperature for 1.5 hours. At the end of this time, the tetrahydrofuran was removed from the reaction mixture by distillation under reduced pressure and the residue was triturated with a mixture of diethyl ether and ethanol to stimulate crystallization. The resulting crystals were collected by filtration to provide 47.7 g of the title compound. This was then recrystallized from a mixture of ethyl acetate and ethanol to produce colorless plates melting at between 161° and 163° C.

Nuclear Magnetic Resonance Spectrum: (270 MHz, hexadeuterated dimethyl sulfoxide) δ ppm: 0.82 (3H, doublet, J=6.8 Hz); 4.07–4.15 (2H, multiplet); 4.29 (1H, doublet, J=4.4 Hz, interchangeable with D$_2$O); 4.23–4.35 (1H, multiplet); 4.52 (1H, doublet, J=6.4 Hz, interchangeable with D$_2$O); 4.51–4.62 (1H, multiplet); 5.15 (1H, doublet, J=2.9 Hz, interchangeable with D$_2$O); 5.40 (1H, broad singlet); 5.84 (1H, doublet of doublets, J=6.2 & 9.8 Hz); 5.90 (1H, doublet, J=9.8 Hz).

Elemental Analysis:

Calculated for $C_{18}H_{26}O_5$: C: 67.06%; H: 8.13%; Found: C: 66.81%; H: 8.37%.

Infrared Absorption Spectrum (KBr) $\nu_{max}$ cm$^{-1}$: 3436, 3339, 3222, 1730, 1260, 1217, 1042.

Mass Spectrum (m/e): 322 (M$^+$), 304, 286, 268.

$[\alpha]_D^{25}$ +188.6° (c=0.59, ethanol).

EXAMPLE B (4R,6R)-6-{2-[(1S,2S,6S,8S,8aR)-1,2,6,7,8,8a-Hexahydro-6-t-butyldimethylsilyloxy-8-hydroxy-2-methyl-1-naphthyl]ethyl}tetrahydro-4-t-butyldimethylsilyloxy-2H-pyran-2-one

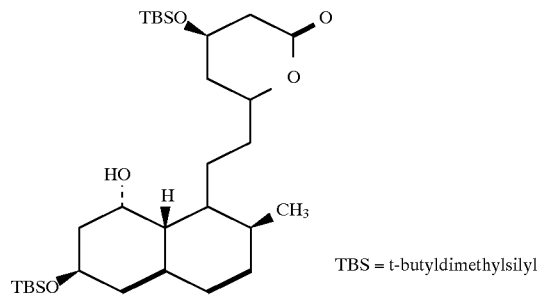

TBS = t-butyldimethylsilyl

A solution of 9.04 g (60.0 mmol) of t-butyldimethylsilyl chloride in 35 ml of dimethylformamide was added dropwise to a solution of 9.65 g (30.0 mmol) of (4R,6R)-6-{2-[(1,2S,6S,8S,8aR)-1,2,6,7,8,8a-hexahydro-6,8-dihydroxy-2-methyl-1-naphthyl]ethyl}tetrahydro-4-hydroxy-2H-pyran-2-one [prepared as described in Example A, above] and 6.12 g (90.0 mmol) of imidazole in 45 ml of dimethylformamide, whilst ice-cooling and stirring. The resulting mixture was then stirred at room temperature for 5 hours, after which the solvent was removed by distillation under reduced pressure. The resulting residue was dissolved in 500 ml of ethyl acetate, and the solution was then washed first with water and then with a saturated aqueous solution of sodium chloride. The solution was then dried over anhydrous magnesium sulfate, after which the solution was filtered. The resulting filtrate was then concentrated by evaporation under reduced pressure. The concentrate was purified by flash column chromatography through silica gel using a gradient elution method, with mixtures of hexane and ethyl acetate ranging from 2:1 to 1:1 by volume as the eluent, to provide 13.3 g of the title compound as a colorless solid. This was then recrystallized from diisopropyl ether to produce colorless needles, melting at between 132° and 134° C.

Elemental Analysis:

Calculated for $C_{30}H_{54}O_5Si_2$: C: 65.40; H: 9.88; Found: C: 65.29; H: 9.96.

Nuclear Magnetic Resonance Spectrum: (270 MHz, hexadeuterated dimethyl sulfoxide) δ ppm: 0.79–0.92 (21H, multiplet); 4.07–4.15 (1H, multiplet); 4.27–4.34 (1H, multiplet); 4.38 (1H, doublet, J=3.9 Hz, interchangeable with D$_2$O); 4.48–4.60 (2H, multiplet); 5.33 (1H, broad singlet); 5.82 (1H, doublet of doublets, J=6.2 & 9.8 Hz); 5.92 (1H, doublet, J=9.8 Hz).

Infrared Absorption Spectrum (KBr) $\nu_{max}$ cm$^{-1}$: 3497, 2956, 2929, 2857, 1736, 1711, 1361, 1257, 1071, 837.

Mass Spectrum (m/e): 550 (M$^+$), 532, 493, 475, 343, 275

$[\alpha]_D^{25}$ +89.7° (c=0.50, acetone).

The following Examples 1 to 23 describe the preparation of compounds of the following formula:

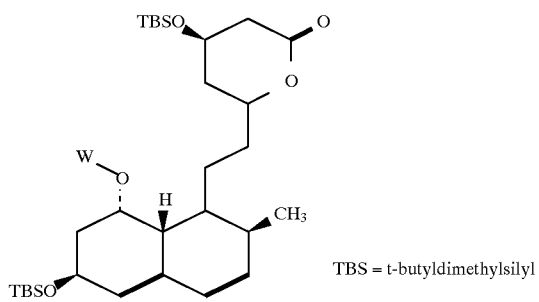

TBS = t-butyldimethylsilyl i.e. compounds of formula (I) in which $R^1$ represents a group of formula (III) and $R^6$ represents a t-butyldimethylsilyl group. Each group W, as defined in the following Examples, is attached to the formula shown above via the bond marked Z.

EXAMPLE 1

(4R,6R)-6-{2-[(1S,2S,6S,8S,8aR)-1,2,6,7,8,8a-Hexahydro-6-t-butyldimethylsilyloxy-8-(3,3-dimethylbutyryloxy)-2-methyl-1-naphthyl]ethyl}tetrahydro-4-t-butyldimethylsilyloxy-2H-pyran-2-one

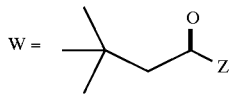

0.46 ml (3.6 mmol) of 3,3-dimethylbutyric acid, 741 mg (3.6 mmol) of dicyclohexyl carbodiimide and 13 mg (0.09 mmol) of 4-(1-pyrrolidinyl)pyridine were added to a solution of 1.00 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] in 15 ml of methylene chloride, whilst ice-cooling. The resulting mixture was stirred at the same temperature for 30 minutes and then stirred at room temperature for a further 19 hours. At the end of this time, the solvent was removed by distillation under reduced pressure and the resulting residue was mixed with 20 ml of diethyl ether. Any insoluble material was removed by filtration and then washed twice with diethyl ether, using 5 ml for each washing. The filtrate and the washings were then combined and the solvent was removed by distillation under reduced pressure. The resulting residue was purified by flash column chromatography through silica gel, using a 4:1 by volume mixture of hexane and ethyl acetate as the eluent, to give 555 mg (47% yield) of the title compound.

Nuclear Magnetic Resonance Spectrum (270 MHz, CDCl$_3$) δ ppm: 2.20 (2H, singlet); 4.24–4.32 (1H, multiplet); 4.39–4.48 (1H, multiplet); 4.53–4.65 (1H, multiplet); 5.37 (1H, broad singlet); 5.45 (1H, broad singlet); 5.84 (1H, doublet of doublets, J=9.8 & 5.9 Hz); 5.99 (1H, doublet, J=9.8 Hz).

Infrared Absorption Spectrum (CHCl$_3$) $v_{max}$ cm$^{-1}$: 2950, 1800, 1250, 1080, 840.

Mass Spectrum (m/e): 648 (M$^+$), 633, 591, 532, 475.

$[α]_D^{25}$ +87.5° (c=0.63, acetone).

EXAMPLE 2

(4R,6R)-6-{2-[(1S,2S,6S,8S,8aR)-1,2,6,7,8,8a-Hexahydro-6-t-butyldimethylsilyloxy-8-(2-ethylbutyryloxy)-2-methyl-1-naphthyl]ethyl}tetrahydro-4-t-butyldimethylsilyloxy-2H-pyran-2-one

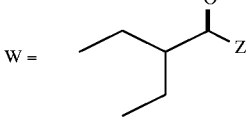

1.26 ml (9.1 mmol) of triethylamine, 15 mg (0.1 mmol) of 4-(1-pyrrolidinyl)pyridine and 0.63 ml (2.73 mmol) of 2-ethylbutyric anhydride were added to a solution of 1.00 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] in 10 ml of methylene chloride, whilst ice-cooling. The resulting mixture was stirred at room temperature for 3 days. At the end of this time, the reaction mixture was diluted with 50 ml of ethyl acetate and the diluted mixture was then washed with 20 ml of water, a 10% w/v aqueous solution of citric acid, 20 ml of a saturated aqueous solution of sodium hydrogencarbonate and 20 ml of a saturated aqueous solution of sodium chloride, in that order. The washed mixture was then dried over anhydrous magnesium sulfate, after which the mixture was filtered. The filtrate thus obtained was concentrated by evaporation under reduced pressure, and the resulting concentrate was purified by flash column chromatography through silica gel, using a 5:1 by volume mixture of hexane and ethyl acetate as the eluent, to give 1.04 g (88% yield) of the title compound.

Nuclear Magnetic Resonance Spectrum (270 MHz, CDCl$_3$) δ ppm: 4.24–4.32 (1H, multiplet); 4.37–4.49 (1H, multiplet); 4.51–4.62 (1H, multiplet); 5.42 (1H, broad singlet); 5.47 (1H, broad singlet); 5.84 (1H, doublet of doublets, J=9.8 & 5.9 Hz); 5.98 (1H, doublet, J=9.8 Hz).

Infrared Absorption Spectrum (CHCl$_3$) $v_{max}$ cm$^{-1}$: 2950, 1720, 1250, 1080, 840.

Mass Spectrum (m/e): 648 (M$^+$), 633, 591, 532, 475.

$[α]_D^{25}$ +102.2° (c=0.78, acetone).

EXAMPLE 3

(4R,6R)-6-{2-[(1S,2S,6S,8S,8aR)-1,2,6,7,8,8a-Hexahydro-6-t-butyldimethylsilyloxy-8-[(S)-2-methylvaleryloxy]-2-methyl-1-naphthyl]ethyl}tetrahydro-4-t-butyldimethylsilyloxy-2H-pyran-2-one

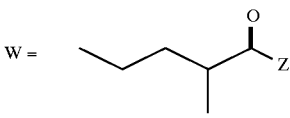

690 mg (6.8 mmol) of triethylamine and 713 mg (4.1 mmol) of diethyl chlorophosphate were added to a solution of 400 mg (3.4 mmol) of (S)-2-methylvaleric acid in 15 ml of dry benzene, and the resulting mixture was stirred at room temperature for one hour. 1.58 g (2.9 mmol) of (4R,6R)-6-

{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 250 mg (1.7 mmol) of 4-(1-pyrrolidinyl)pyridine were then added to the mixture. The mixture was then stirred at room temperature for 24 hours, after which the mixture was diluted with 20 ml of benzene. The diluted mixture was then washed with 20 ml of water, 20 ml of a 10% w/v aqueous solution of citric acid, a saturated aqueous solution of sodium hydrogencarbonate and a saturated aqueous solution of sodium chloride, in that order. The organic layer was dried over anhydrous magnesium sulfate, and the solvent was removed by distillation under reduced pressure. The resulting residue was purified by flash column chromatography through silica gel, using a 6:1 by volume mixture of hexane and ethyl acetate as the eluent, to give 1.38 g (74% yield) of the title compound.

Nuclear Magnetic Resonance Spectrum (400 MHz, $CDCl_3$) δ ppm: 1.11 (3H, doublet, J=7.1 Hz); 4.27–4.30 (1H, multiplet); 4.40–4.44 (1H, multiplet); 4.55–4.61 (1H, multiplet); 5.36 (1H, broad singlet); 5.48 (1H, broad singlet); 5.85 (1H, doublet of doublets, J=9.7 & 5.9 Hz); 5.99 (1H, doublet, J=9.7 Hz).

Infrared Absorption Spectrum ($CHCl_3$) $v_{max}$ $cm^{-1}$: 2950, 1720, 1250, 1080, 840.

Mass Spectrum (m/e): 648 ($M^+$), 591, 532, 475.

$[\alpha]_D^{25}$ +88.3° (c=0.30, acetone).

EXAMPLE 4

(4R,6R)-6-{2-[(1S,2S,6S,8S,8aR)-1 2,6,7,8,8a-Hexahydro-6-t-butyldimethylsilyloxy-8-(2-propylvaleryloxy)-2-methyl-1-naphthyl]ethyl}tetrahydro-4-t-butyldimethylsilyloxy-2H-pyran-2-one

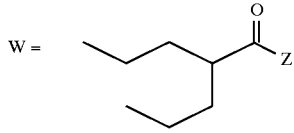

15 mg (0.1 mmol) of 4-(1-pyrrolidinyl)pyridine and 592 mg (3.6 mmol) of 2-propylvaleryl chloride were added to a solution of 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] in 5 ml of dry pyridine, whilst ice-cooling, and the resulting mixture was stirred at 70° C. for 3 hours. At the end of this time, the reaction mixture was diluted with 100 ml of ethyl acetate, and the diluted mixture was then washed with 100 ml of water, 100 ml of a 10% w/v aqueous solution of hydrogen chloride, a saturated aqueous solution of sodium hydrogencarbonate and a saturated aqueous solution of sodium chloride, in that order. The organic layer was then dried over anhydrous magnesium sulfate, after which this layer was removed by filtration. The resulting filtrate was concentrated by evaporation under reduced pressure and the residue obtained was purified by flash column chromatography through silica gel, using a 5:1 by volume mixture of hexane and ethyl acetate as the eluent, to give 1.15 g (93% yield) of the title compound.

Nuclear Magnetic Resonance Spectrum (270 MHz, $CDCl_3$) δ ppm: 4.25–4.31 (1H, multiplet); 4.36–4.48 (1H, multiplet); 4.51–4.62 (1H, multiplet); 5.40 (1H, broad singlet); 5.47 (1H, broad singlet); 5.85 (1H, doublet of doublets, J=9.8 & 5.9 Hz); 5.99 (1H, doublet, J=9.8 Hz).

Infrared Absorption Spectrum ($CHCl_3$) $v_{max}$ $cm^{-1}$: 2950, 1720, 1250, 840.

Mass Spectrum (m/e): 676 ($M^+$), 621, 549, 532, 475.

$[\alpha]_D^{25}$ +97.5° (c=0.40, acetone).

EXAMPLE 5

(4R,6R)-6-{2-[(1S,2S,6S,8S,8aR)-1,2,6,7,8,8a-Hexahydro-6-t-butyldimethylsilyloxy-8-(2-ethyl-2-methylbutyryloxy)-2-methyl-1-naphthyl]ethyl}tetrahydro-4-t-butyldimethylsilyloxy-2H-pyran-2-one

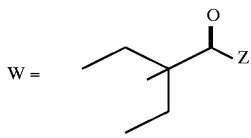

0.76 ml (5.4 mmol) of triethylamine, 807 mg (5.4 mmol) of 4-(1-pyrrolidinyl)pyridine and 674 mg (4.5 mmol) of 2-ethyl-2-methylbutyryl chloride were added to a solution of 500 mg (0.91 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] in 10 ml of benzene and the resulting mixture was heated under reflux for 5 hours. At the end of this time, the reaction mixture was diluted with 50 ml of ethyl acetate. The diluted mixture was then washed with 30 ml of water, 30 ml of a 10% w/v aqueous solution of citric acid, a saturated aqueous solution of sodium hydrogencarbonate and a saturated aqueous solution of sodium chloride, in that order. The organic phase was then dried over anhydrous magnesium sulfate, after which this phase was filtered. The filtrate was concentrated by evaporation under reduced pressure and the concentrate was purified by flash column chromatography through silica gel, using a 5:1 by volume mixture of hexane and ethyl acetate as the eluent, to give 601 mg (100% yield) of the title compound.

Nuclear Magnetic Resonance Spectrum (270 MHz, $CDCl_3$) δ ppm: 1.07 (3H, singlet); 4.23–4.32 (1H, multiplet); 4.37–4.48 (1H, multiplet); 4.51–4.64 (1H, multiplet); 5.35 (1H, broad singlet); 5.46 (1H, broad singlet); 5.84 (1H, doublet of doublets, J=9.8 & 5.9 Hz); 5.98 (1H, doublet, J=9.8 Hz).

Infrared Absorption Spectrum ($CHCl_3$) $v_{max}$ $cm^{-1}$: 2950, 1720, 1250, 1180, 840.

Mass Spectrum (m/e): 662 ($M^+$), 647, 605, 549, 532.

$[\alpha]_D^{25}$ +93.7° (c=0.51, acetone).

EXAMPLE 6

(4R,6R)-6-{2-[(1S,2S,6S,8S,8aR)-1,2,6,7,8,8a-Hexahydro-6-t-butyldimethylsilyloxy-8-(2,2-diethylbutyryloxy)-2-methyl-1-naphthyl]ethyl}tetrahydro-4-t-butyldimethylsilyloxy-2H-pyran-2-one

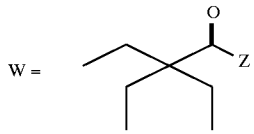

1.48 g (9.1 mmol) of 2,2-diethylbutyryl chloride were added to a solution of 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] 1.67 g (11.3 mmol) of 4-(1-pyrrolidinyl)pyridine and 1.0 ml (7.1 mmol) of triethylamine in 10 ml of toluene, and the resulting mixture was heated under reflux for 10 hours. At the end of this time the reaction mixture was worked-up following a procedure similar to that described in Example 5, above, to give 1.09 g (89% yield) of the title compound.

Nuclear Magnetic Resonance Spectrum (360 MHz, CDCl$_3$) δ ppm: 0.96 (9H, triplet, J=7.7 Hz); 1.22–1.29 (1H, multiplet); 1.41–1.47 (2H, multiplet); 4.26–4.29 (1H, multiplet); 4.42–4.45 (1H, multiplet); 4.53–4.60 (1H, multiplet); 5.39 (1H, broad singlet); 5.46 (1H, broad singlet); 5.85 (1H, doublet of doublets, J=9.7 & 5.9 Hz); 5.99 (1H, doublet, J=9.7 Hz).

Infrared Absorption Spectrum (CHCl$_3$) ν$_{max}$ cm$^{-1}$: 2950, 1715, 1260, 840.

Mass Spectrum (m/e): 676 (M$^+$), 661, 619, 532, 475, 400.
[α]$_D^{25}$ +80.2° (c=0.59, acetone).

EXAMPLE 7

(4R,6R)-6-{2-[(1S,2S,6S,8S,8aR)-1,2,6,7,8,8a-Hexahydro-6-t-butyldimethylsilyloxy-8-(2,2-dimethyl-4-pentenoyloxy)-2-methyl-1-naphthyl]ethyl}tetrahydro-4-t-butyldimethylsilyloxy-2H-pyran-2-one

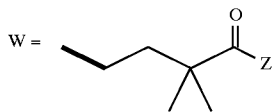

A procedure similar to that described in Example 3, above, was followed, but using 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 466 mg (3.6 mmol) of 2,2-dimethyl-4-pentenoic acid, to provide 231 mg of the title compound.

Nuclear Magnetic Resonance Spectrum (270 MHz, CDCl$_3$) δ ppm: 1.41 (6H, singlet); 2.26 (2H, doublet, J=7.3 Hz); 4.25–4.33 (1H, multiplet); 4.38–4.47 (1H, multiplet); 5.00–5.10 (2H, multiplet); 5.34 (1H, broad singlet); 5.45 (1H, broad singlet); 5.60–5.76 (1H, multiplet); 5.83 (1H, doublet of doublets, J=9.8 & 5.9 Hz); 5.97 (1H, doublet, J=9.8 Hz).

Infrared Absorption Spectrum (CHCl$_3$) ν$_{max}$ cm$^{-1}$: 2950, 1720, 1250, 1180, 840.

Mass Spectrum (m/e): 645 (M$^+$–15), 603, 535, 517, 475.
[α]$_D^{25}$ +87.2° (c=0.36, acetone).

EXAMPLE 8

(4R,6R)-6-{2-[(1S,2S,6S,8S,8aR)-1,2,6,7,8,8a-Hexahydro-6-t-butyldimethylsilyloxy-8-(2-allyl-4-pentenoyloxy)-2-methyl-1-naphthyl]ethyl}tetrahydro-4-t-butyldimethylsilyloxy-2H-pyran-2-one

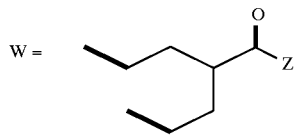

A procedure similar to that described in Example 3, above, was followed, but using 1.10 g (2.0 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 560 mg (4.0 mmol) of 2-allyl-4-pentenoic acid, to provide 1.02 g of the title compound.

Nuclear Magnetic Resonance Spectrum (270 MHz, CDCl$_3$) δ ppm: 4.26–4.31 (1H, multiplet); 4.40–4.46 (1H, multiplet); 4.52–4.62 (1H, multiplet); 4.98–5.11 (4H, multiplet); 5.40 (1H, broad singlet); 5.47 (1H, broad singlet); 5.63–5.80 (2H, multiplet); 5.85 (1H, doublet of doublets, J=9.8 & 5.9 Hz); 5.99 (1H, doublet, J=9.8 Hz).

Infrared Absorption Spectrum (CHCl$_3$) ν$_{max}$ cm$^{-1}$: 2950, 1720, 1250, 1080, 840.

Mass Spectrum (m/e): 672 (M$^+$), 615, 532, 475.
[α]$_D^{25}$ +85.2° (c=0.42, acetone).

EXAMPLE 9

(4R,6R)-6-{2-[(1S,2S,6S,8S,8aR)-1,2,6,7,8,8a-Hexahydro-6-t-butyldimethylsilyloxy-8-(2-butylhexanoyloxy)-2-methyl-1-naphthyl]ethyl}tetrahydro-4-t-butyldimethylsilyloxy-2H-pyran-2-one

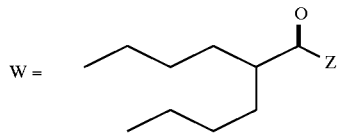

A procedure similar to that described in Example 3, above, was followed, but using 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 627 mg (3.6 mmol) of 2-butylhexanoic acid, to provide 797 mg of the title compound.

Nuclear Magnetic Resonance Spectrum (270 MHz, CDCl$_3$) δ ppm: 4.25–4.26 (1H, multiplet); 4.39–4.48 (1H, multiplet); 4.52–4.63 (1H, multiplet); 5.42 (1H, broad singlet); 5.48 (1H, broad singlet); 5.86 (1H, doublet of doublets, J=9.8 & 5.9 Hz); 6.00 (1H, doublet, J=9.8 Hz).

Infrared Absorption Spectrum (CHCl₃) $v_{max}$ cm⁻¹: 2950, 1850, 1720, 1460, 1250.

Mass Spectrum (m/e): 689 (M⁺−15), 647, 549, 532.

$[\alpha]_D^{25}$ +64.8° (c=0.27, acetone).

EXAMPLE 10

(4R,6R)-6-{2-[(1S,2S,6S,8S,8aR)-1,2,6,7,8,8a-Hexahydro-6-t-butyldimethylsilyloxy-8-hexanoyloxy-2-methyl-1-naphthyl]ethyl}tetrahydro-4-t-butyldimethylsilyloxy-2H-pyran-2-one

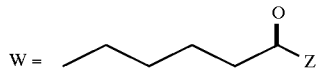

A procedure similar to that described in Example 3, above, was followed, but using 1.0 g (1.8 mmol) of (4R, 6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 423 mg (3.6 mmol) of hexanoic acid, to provide 364 mg of the title compound.

Nuclear Magnetic Resonance Spectrum (270 MHz, CDCl₃) δ ppm: 4.25–4.32 (1H, multiplet); 4.39–4.46 (1H, multiplet); 4.55–4.65 (1H, multiplet); 5.38 (1H, broad singlet); 5.48 (1H, broad singlet); 5.85 (1H, doublet of doublets, J=9.8 & 5.9 Hz); 6.00 (1H, doublet, J=9.8 Hz).

Infrared Absorption Spectrum (CHCl₃) $v_{max}$ cm⁻¹: 2950, 1720, 1250, 1180, 840.

Mass Spectrum (m/e): 591 (M⁺−57), 532, 517, 475.

$[\alpha]_D^{25}$ +76.5° (c=0.46, acetone).

EXAMPLE 11

(4R,6R)-6-{2-[(1S,2S,6S,8S,8aR)-1,2,6,7,8,8a-Hexahydro-6-t-butyldimethylsilyloxy-8-isovaleryloxy-2-methyl-1-naphthyl]ethyl}tetrahydro-4-t-butyldimethylsilyloxy-2H-pyran-2-one

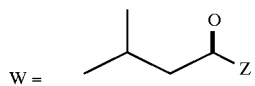

A procedure similar to that described in Example 4, above, was followed, but using 1.10 g (2.0 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example 3, above] and 361 mg (3.0 mmol) of isovaleryl chloride, to provide 1.14 g of the title compound.

Nuclear Magnetic Resonance Spectrum (270 MHz, CDCl₃) δ ppm: 0.94 (6H, doublet, J=6.4 Hz); 4.27–4.29 (1H, multiplet); 4.40–4.50 (1H, multiplet); 4.55–4.65 (1H, multiplet); 5.39 (1H, broad singlet); 5.48 (1H, broad singlet); 5.85 (1H, doublet of doublets, J=9.8 & 5.9 Hz); 5.98 (1H, doublet, J=9.8 Hz).

Infrared Absorption Spectrum (CHCl₃) $v_{max}$ cm⁻¹: 2875, 1725, 1225, 1080, 840.

Mass Spectrum (m/e): 634 (M⁺), 577, 532, 475.

$[\alpha]_D^{25}$ +100.0° (c=0.43, acetone).

EXAMPLE 12

(4R,6R)-6-{2-[(1S,2S,6S,8S,8aR)-1,2,6,7,8,8a-Hexahydro-6-t-butyldimethylsilyloxy-8-pivaloyloxy-2-methyl-1-naphthyl]ethyl}tetrahydro-4-t-butyldimethylsilyloxy-2H-pyran-2-one

A procedure similar to that described in Example 4, above, was followed, but using 1.10 g (2.0 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 486 mg (4.0 mmol) of pivaloyl chloride, to provide 594 mg of the title compound.

Nuclear Magnetic Resonance Spectrum (270 MHz, CDCl₃) δ ppm: 1.17 (9H, singlet); 4.27–4.31 (1H, multiplet); 4.40–4.44 (1H, multiplet); 4.56–4.63 (1H, multiplet); 5.32 (1H, broad singlet); 5.48 (1H, broad singlet); 5.84 (1H, doublet of doublets, J=9.7 & 5.9 Hz); 5.98 (1H, doublet, J=9.7 Hz).

Infrared Absorption Spectrum (CHCl₃) $v_{max}$ cm⁻¹: 2950, 1720, 1255, 1080, 840.

Mass Spectrum (m/e): 634 (M⁺), 577, 532, 475, 343.

$[\alpha]_D^{25}$ +89.1° (c=0.45, acetone).

EXAMPLE 13

(4R,6R)-6-{2-[(1S,2S,6S,8S,8aR)-1,2,6,7,8,8a-Hexahydro-6-t-butyldimethylsilyloxy-8-(2,2-dimethylvaleryloxy)-2-methyl-1-naphthyl]ethyl}tetrahydro-4-t-butyldimethylsilyloxy-2H-pyran-2-one

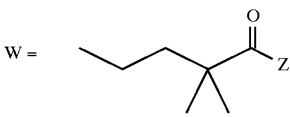

A procedure similar to that described in Example 4, above, was followed, but using 2.0 g (3.6 mmol) of (4R, 6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 2.16 g (14.5 mmol) of 2,2-dimethylpentanoyl chloride, to provide 1.31 g of the title compound.

Nuclear Magnetic Resonance Spectrum (270 MHz, CDCl₃) δ ppm: 1.13 (6H, singlet); 4.25–4.32 (1H, multiplet); 4.36–4.46 (1H, multiplet); 4.52–4.64 (1H, multiplet); 5.32 (1H, broad singlet); 5.45 (1H, broad singlet); 5.83 (1H, doublet of doublets, J=9.8 & 5.9 Hz); 5.98 (1H, doublet, J=9.8 Hz).

Infrared Absorption Spectrum (CHCL₃) $v_{max}$ cm⁻¹: 2950, 1720, 1250, 1080, 840.

Mass Spectrum (m/e): 662, 647, 605, 532, 475.

$[\alpha]_D^{25}$ +93.6° (c=0.78, acetone).

EXAMPLE 14

(4R,6R)-6-{2-[(1S,2S,6S,8S,8aR)-1,2,6,7,8,8a-Hexahydro-6--butyldimethylsilyloxy-8-(2-allyl-2-methyl-4-pentenoyloxy)-2-methyl-1-naphthyl]ethyl}tetrahydro-4-t-butyldimethylsilyloxy-2H-pyran-2-one

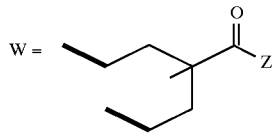

A procedure similar to that described in Example 4, above, was followed, but using 2.0 g (3.6 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 1.26 g (7.3 mmol) of 2-allyl-2-methyl-4-pentenoyl chloride, to provide 2.13 g of the title compound.

Nuclear Magnetic Resonance Spectrum (270 MHz, $CDCl_3$) δ ppm: 1.08 (3H, singlet); 4.28–4.31 (1H, multiplet); 4.41–4.45 (1H, multiplet); 4.56–4.60 (1H, multiplet); 5.04–5.08 (4H, multiplet); 5.38 (1H, broad singlet); 5.46 (1H, broad singlet); 5.62–5.72 (2H, multiplet); 5.85 (1H, doublet of doublets, J=9.7 & 5.9 Hz); 5.98 (1H, doublet, J=9.7 Hz).

Infrared Absorption Spectrum ($CHCl_3$) $v_{max}$ cm$^{-1}$: 2950, 1720, 1250, 1080, 835.

Mass Spectrum (m/e): 686 (M$^+$), 629, 532, 475.

$[\alpha]_D^{25}$ +105.0° (c=0.43, acetone).

EXAMPLE 15

(4R,6R)-6-{2-[(1S,2S,6S,8S,8aR)-1,2,6,7,8,8a-Hexahydro-6-t-butyldimethylsilyloxy-8-(2-methyl-2-propylvaleryloxy)-2-methyl-1-naphthyl]ethyl}tetrahydro-4-t-butyldimethylsilyloxy-2H-pyran-2-one

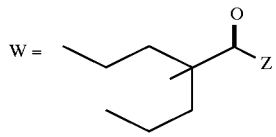

A procedure similar to that described in Example 4, above, was followed, but using 2.0 g (3.6 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 1.92 g (10.9 mmol) of 2-methyl-2-propylvaleryl chloride, to provide 1.05 g of the title compound.

Nuclear Magnetic Resonance Spectrum (270 MHz, $CDCl_3$) δ ppm: 1.08 (3H, singlet); 4.26–4.32 (1H, multiplet); 4.38–4.45 (1H, multiplet); 4.53–4.60 (1H, multiplet); 5.45 (1H, broad singlet); 5.47 (1H, broad singlet); 5.85 (1H, doublet of doublets, J=9.7 & 5.9 Hz); 5.98 (1H, doublet, J=9.7 Hz).

Infrared Absorption Spectrum ($CHCl_3$) $v_{max}$ cm$^-$: 2950, 1720, 1250, 1180, 840.

Mass Spectrum (m/e): 690 (M$^+$), 675, 633, 549, 532.

$[\alpha]_D^{25}$ +97.5° (c=0.52, acetone).

EXAMPLE 16

(4R,6R)-6-{2-[(1S,2S,6S,8S,8aR)-1,2,6,7,8,8a-Hexahydro-6-t-butyldimethylsilyloxy-8-(2,2-diethylvaleryloxy)-2-methyl-1-naphthyl]ethyl}tetrahydro-4-t-butyldimethylsilyloxy-2H-pyran-2-one

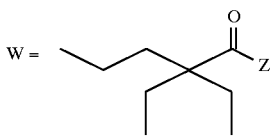

A procedure similar to that described in Example 4, above, was followed, but using 2.0 g (3.6 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above) and 1.29 g (7.3 mmol) of 2,2-diethylvaleryl chloride, to provide 188 mg of the title compound.

Nuclear Magnetic Resonance Spectrum (270 MHz, $CDCl_3$) δ ppm: 4.20–4.25 (1H, multiplet); 4.33–4.37 (1H, multiplet); 4.46–4.53 (1H, multiplet); 5.32 (1H, broad singlet); 5.39 (1H, broad singlet); 5.79 (1H, doublet of doublets, J=9.7 & 5.8 Hz); 5.92 (1H, doublet, J=9.7 Hz).

Infrared Absorption Spectrum ($CHCl_3$) $v_{max}$ cm$^{-1}$: 2950, 1720, 1250, 1080.

Mass Spectrum (m/e): 690 (M$^+$), 675, 633, 568, 532.

$[\alpha]_D^{25}$ +95° (c=0.49, acetone).

EXAMPLE 17

(4R,6R)-6-{2-[(1S,2S,6S,8S,8aR)-1,2,6,7,8,8a-Hexahydro-6-t-butyldimethylsilyloxy-8-(2-isopropyl-3-methylbutyryloxy)-2-methyl-1-naphthyl]ethyl}tetrahydro-4-t-butyldimethylsilyloxy-2H-pyran-2-one

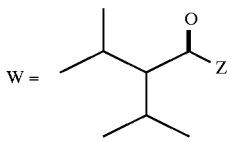

A procedure similar to that described in Example 4, above, was followed, but using 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 888 mg (5.5 mmol) of 2-isopropyl-3-methylbutyryl chloride, to provide 198 mg of the title compound.

Nuclear Magnetic Resonance Spectrum (270 MHz, $CDCl_3$) δ ppm: 4.26–4.32 (1H, multiplet); 4.45–4.60 (2H, multiplet); 5.45 (2H, broad singlet); 5.85 (1H, doublet of doublets, J=9.7 & 6.0 Hz); 5.99 (1H, doublet, J=9.7 Hz).

Infrared Absorption Spectrum ($CHCl_3$) $v_{max}$ cm$^{-1}$: 2950, 1720, 1250, 1180, 840.

Mass Spectrum (m/e): 676 (M$^+$), 661, 619, 568, 532.

$[\alpha]_D^{25}$ +95.0° (c=0.36, acetone).

EXAMPLE 18

(4R,6R)-6-{2-[(1S,2S,6S,8S,8aR)-1,2,6,7,8,8a-Hexahydro-6-t-butyldimethylsilyloxy-8-(2,2-diethyl-4-pentenoyloxy)-2-methyl-1-naphthyl]ethyl}tetrahydro-4-t-butyldimethylsilyloxy-2H-pyran-2-one

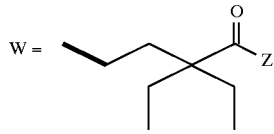

A procedure similar to that described in Example 6, above, was followed, but using 2.0 g (3.6 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one (prepared as described in Example B, above] and 3.17 g (18.1 mmol) of 2,2-diethyl-4-pentenoyl chloride, to provide 1.95 g of the title compound.

Nuclear Magnetic Resonance Spectrum (270 MHz, CDCl$_3$) δ ppm: 4.22–4.33 (1H, multiplet); 4.38–4.47 (1H, multiplet); 4.52–4.62 (1H, multiplet); 5.00–5.14 (2H, multiplet); 5.41 (1H, broad singlet); 5.46 (1H, broad singlet); 5.54–5.72 (1H, multiplet); 5.85 (1H, doublet of doublets, J=9.7 & 5.9 Hz); 5.99 (1H, doublet, J=9.7 Hz).

Infrared Absorption Spectrum (CHCl$_3$) $v_{max}$ cm$^{-1}$: 2950, 1720, 1250, 1080, 840.

Mass Spectrum (m/e): 688 (M$^+$), 631, 623, 568, 532.

$[α]_D^{25}$ +79.3° (c=0.29, acetone).

EXAMPLE 19

(4R,6R)-6-{2-[(1S,2S,6S,8S,8aR)-1,2,6,7,8,8a-Hexahydro-6-t-butyldimethylsilyloxy-8-(2-allyl-2-ethyl-4-pentenoyloxy)-2-methyl-1-naphthyl]ethyl}tetrahydro-4-t-butyldimethylsilyloxy-2H-pyran-2-one

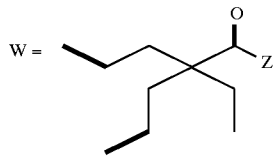

A procedure similar to that described in Example 6, above, was followed, but using 1.65 g (3.0 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 2.80 g (15.0 mmol) of 2-allyl-2-ethyl-4-pentenoyl chloride, to provide 1.63 g of the title compound.

Nuclear Magnetic Resonance Spectrum (270 MHz, CDCl$_3$) δ ppm: 0.81 (3H, triplet, J=7.4 Hz); 4.17–4.29 (1H, multiplet); 4.41–4.45 (1H, multiplet); 4.54–4.60 (1H, multiplet); 5.04–5.12 (4H, multiplet); 5.42 (1H, broad singlet); 5.46 (1H, broad singlet); 5.60–5.69 (2H, multiplet); 5.85 (1H, doublet of doublets, J=9.7 & 5.9 Hz); 5.98 (1H, doublet, J=9.7 Hz).

Infrared Absorption Spectrum (CHCl$_3$) $v_{max}$ cm$^{-1}$: 2950, 1720, 1255, 1080, 840.

Mass Spectrum (m/e): 700 (M$^+$), 643, 532, 475, 400.

$[α]_D^{25}$ +89.3° (c=0.56, acetone).

EXAMPLE 20

(4R,6R)-6-{2-[(1S,2S,6S,8S,8-aR)-1,2,6,7,8,8a-Hexahydro-6-t-butyldimethylsilyloxy-8-(2,2-diallyl-4-pentenoyloxy)-2-methyl-1-naphthyl]ethyl}tetrahydro-4-t-butyldimethylsilyloxy-2H-pyran-2-one

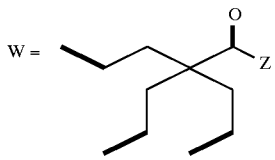

A procedure similar to that described in Example 6, above, was followed, but using 1.10 g (2.0 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example 3, above] and 584 mg (2.9 mmol) of 2,2-diallyl-4-pentenoyl chloride, to provide 585 mg of the title compound.

Nuclear Magnetic Resonance Spectrum (270 MHz, CDCl$_3$) δ ppm: 2.29 (3H, doublet, J=7.2 Hz); 2.38 (3H, doublet, J=7.2 Hz); 4.28–4.30 (1H, multiplet); 4.41–4.45 (1H, multiplet); 4.54–4.61 (1H, multiplet); 5.03–5.16 (6H, multiplet); 5.43 (1H, broad singlet); 5.45 (1H, broad singlet); 5.53–5.80 (3H, multiplet); 5.85 (1H, doublet of doublets, J=9.7 & 5.9 Hz); 5.98 (1H, doublet, J=9.7 Hz).

Infrared Absorption Spectrum (CHCl$_3$) $v_{max}$ cm$^{-1}$: 2950, 1720, 1250, 1080, 835.

Mass Spectrum (m/e): 712 (M$^+$), 655, 532, 475, 343.

EXAMPLE 21

(4R,6R)-6-{2-[(1S,2S,6S,8S,8aR)-1,2,6,7,8,8a-Hexahydro-6-t-butyldimethylsilyloxy-8-(2-ethyl-2-methylvaleryloxy)-2-methyl-1-naphthyl]ethyl}tetrahydro-4-t-butyldimethylsilyloxy-2H-pyran-2-one

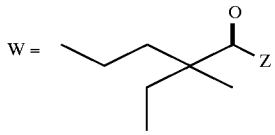

A procedure similar to that described in Example 6, above, was followed, but using 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 1.18 g (7.3 mmol) of 2-ethyl-2-methylvaleryl chloride, to provide 956 mg of the title compound.

Nuclear Magnetic Resonance Spectrum (270 MHz, CDCl$_3$) δ ppm: 4.27–4.30 (1H, multiplet); 4.40–4.44 (1H, multiplet); 4.54–4.58 (1H, multiplet); 5.36 (1H, broad singlet); 5.46 (1H, broad singlet); 5.85 (1H, doublet of doublets, J=9.7 & 5.9 Hz); 5.98 (1H, doublet, J=9.7 Hz).

Infrared Absorption Spectrum (CHCl$_3$) $v_{max}$ cm$^{-1}$: 2950, 1720, 1250, 1080, 840.

Mass Spectrum (m/e): 676 (M⁺), 619, 591, 532, 475.

$[\alpha]_D^{25}$ +93.2° (c=0.22, acetone).

By use of stereospecific starting materials, i.e. (2S)- or (2R)-2-ethyl-2-methylvaleryl chloride, the corresponding stereoisomers of the title compound may be produced, for example as shown in Example 22. Either of the two stereoisomers obtained in this manner may then be used as a starting compound in Example 43.

EXAMPLE 22

(4R,6R)-6-{2-[(1S,2S,6S,8S,8aR)-1,2,6,7,8,8a-Hexahydro-6-t-butyldimethylsilyloxy-8-[(2S)-2-ethyl-2-methylvaleryloxy]-2-methyl-1-naphthyl]ethyl}tetrahydro-4-t-butyldimethylsilyloxy-2H-pyran-2-one

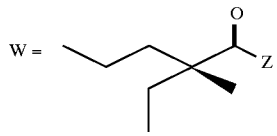

121 μl (1.66 mmol) of thionyl chloride were added to 60 mg (0.42 mmol) of (−)-(2S)-2-ethyl-2-methylpentanoic acid [prepared as described in Preparation 16], and the resulting mixture was heated at 100° C. for one hour. At the end of this time, the mixture was concentrated by evaporation under reduced pressure. The whole of the (−)-(2S)-2-ethyl-2-methylvaleryl chloride obtained in this manner was added, directly and without purification, to a solution of 458 mg (0.83 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], 203 mg (1.66 mmol) of 4-(N,N-dimethylamino)pyridine, a catalytic amount (20 mg) of 4-dimethylaminopyridine and 232 μl of triethylamine in 2.5 ml of toluene, and the resulting mixture was heated under reflux for 24 hours. At the end of this time, the reaction mixture was cooled to room temperature and then mixed with 10 ml of a 10% w/v aqueous solution of hydrogen chloride. The aqueous mixture was extracted three times, each time with 20 ml of ethyl acetate. The combined extracts were then washed with a saturated aqueous solution of sodium chloride, after which the washed solution was dried over anhydrous sodium sulfate. The solvent was then removed by distillation under reduced pressure, and the resulting pale-yellow oily residue was purified by flash column chromatography through silica gel, using a 5:1 by volume mixture of hexane and ethyl acetate as the eluent, to give 88 mg (31% yield) of the title compound as a foam-like substance.

Nuclear Magnetic Resonance Spectrum (270 MHz, CDCl₃) δ ppm: 4.27–4.30 (1H, multiplet); 4.40–4.44 (1H, multiplet); 4.54–4.58 (1H, multiplet); 5.36 (1H, broad singlet); 5.46 (1H, broad singlet); 5.85 (1H, doublet of doublets, J=9.7 & 5.9 Hz); 5.98 (1H, doublet, J=9.7 Hz).

Infrared Absorption Spectrum (CHCl₃) $\nu_{max}$ cm⁻¹: 2950, 1720, 1250, 1080, 840.

Mass Spectrum (m/e): 676 (M⁺).

$[\alpha]_D^{25}$ +85.2° (c=0.46, acetone).

EXAMPLE 23

(4R,6R)-6-{2-[(1S,2S,6S,8S,8aR)-1,2,6,7,8,8a-Hexahydro-6-t-butyldimethylsilyloxy-8-(2,2-dimethylhexanoyloxy)-2-methyl-1-naphthyl]ethyl}tetrahydro-4-t-butyldimethylsilyloxy-2H-pyran-2-one

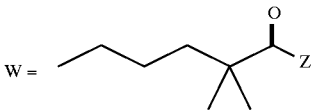

A procedure similar to that described in Example 6, above, was followed, but using 1.10 g (2.0 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] and 1.63 g (10.0 mmol) of 2,2-dimethylhexanoyl chloride, to provide 1.22 g of the title compound.

Nuclear Magnetic Resonance Spectrum (400 MHz, CDCl₃) δ ppm: 1.20 (6H, singlet); 4.27–4.30 (1H, multiplet); 4.40–4.44 (1H, multiplet); 4.55–4.61 (1H, multiplet); 5.34 (1H, broad singlet); 5.47 (1H, broad singlet); 5.84 (1H, doublet of doublets, J=9.6 & 5.9 Hz); 5.98 (1H, doublet, J=9.6 Hz).

Infrared Absorption Spectrum (CHCl₃) $\nu_{max}$ cm⁻¹: 2950, 1720, 1250, 1080, 835.

Mass Spectrum (m/e): 676 (M⁺), 619, 532, 475, 343.

$[\alpha]_D^{25}$ +86.9° (c=0.58, acetone).

Each of the following Examples 24 to 46, describes the preparation of compounds of the following formula:

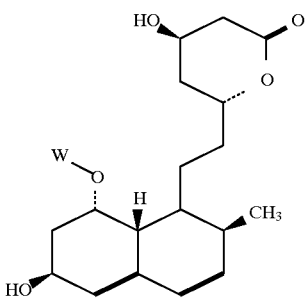

i.e. compounds of formula (I) in which R¹ represents a group of formula (III) and R⁶ represents a hydrogen atom. Each group W, as defined in the following Examples, is attached to the formula shown above via the bond marked Z.

EXAMPLE 24

(4R,6R)-6-{2-[(1S,2S,6S,8S,8aR)-1,2,6,7,8,8a-Hexahydro-6-hydroxy-8-(2-ethyl-2-methylbutyryloxy)-2-methyl-1-naphthyl]ethyl}tetrahydro-4-hydroxy-2H-pyran-2-one

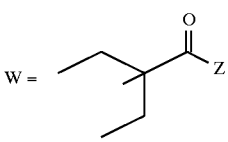

A solution of 600 mg (0.9 mmol) of (4R,6R)-6-{2-[(1S,2S,6S,8S,8aR)-1,2,6,7,8,8a-hexahydro-6-t- butyldimethylsilyloxy-8-(2-ethyl-2-methylbutyryloxy)-2-methyl-1-naphthyl]ethyl}tetrahydro-4-t-butyldimethylsilyloxy-2H-pyran-2-one [prepared as described in Example 5, above] in 2 ml of tetrahydrofuran was added to a mixture of 12.7 ml of a 1M tetrahydrofuran solution of tetrabutylammonium fluoride and 1.27 ml of acetic acid, and the resulting mixture was stirred at room temperature for 15 hours. At the end of this time, the tetrahydrofuran was removed from the reaction mixture by distillation under reduced pressure. The residue was then diluted with 50 ml of ethyl acetate and the diluted solution was washed twice with 50 ml each time of water, three times with 30 ml each time of a saturated aqueous solution of sodium hydrogencarbonate and once with a saturated aqueous solution of sodium chloride, in that order. The organic layer was then dried over anhydrous magnesium sulfate and removed from the mixture by filtration, after which the solvent was removed by distillation under reduced pressure. The residue was purified by flash column chromatography through silica gel, using ethyl acetate as the eluent, to give 387 mg (98% yield) of the title compound as a colorless solid. This compound was recrystallized from a mixture of hexane and ethyl acetate to produce the title compound as colorless prisms, melting at between 152° and 154° C.

Elemental Analysis: Calculated for $C_{25}H_{38}O_6$: C: 69.10%; H: 8.81%; Found: C: 68.83%; H: 8.70%.

Nuclear Magnetic Resonance Spectrum (270 MHz, CDCl$_3$) δ ppm: 0.81 (3H, triplet, J=7.3 Hz); 0.82 (3H, triplet, J=7.3 Hz); 0.90 (3H, doublet, J=7.3 Hz); 1.06 (3H, singlet); 4.33–4.44 (2H, multiplet); 4.54–4.65 (1H, multiplet); 5.04 (1H, broad singlet); 5.37 (1H, broad singlet); 5.89 (1H, doublet of doublets, J=5.9 & 9.8 Hz); 6.00 (1H, doublet, J=9.8 Hz).

Infrared Absorption Spectrum (CHCl$_3$) $\nu_{max}$ cm$^{-1}$: 3450, 2950, 1720, 1150.

Mass Spectrum (m/e) 434 (M$^+$), 416, 304, 286.

$[\alpha]_D^{25}$ +175.4° (c=0.54, acetone).

EXAMPLE 25

(4R,6R)-6-{2-[(1S,2S,6S,8S,8aR)-1,2,6,7,8,8a-Hexahydro-6-hydroxy-8-(2-ethylbutyryloxy)-2-methyl-1-naphthyl]ethyl}tetrahydro-4-hydroxy-2H-pyran-2-one

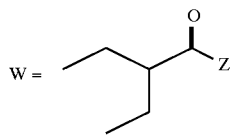

A procedure similar to that described in Example 24, above, was followed, but using 1.0 g (1.6 mmol) of (4R,6R)-6-{2-[(1S,2S,6S,8S,8aR)-1,2,6,7,8,8a-hexahydro-6-t-butyldimethylsilyloxy-8-(2-ethylbutyryloxy)-2-methyl-1-naphthyl]ethyl}tetrahydro-4-t-butyldimethylsilyloxy-2H-pyran-2-one [prepared as described in Example 2, above], to provide 649 mg of the title compound, melting at 158° C.

Elemental Analysis: Calculated for $C_{24}H_{36}O_6$: C: 68.55%; H: 8.63%; Found: C: 68.33%; H: 8.71%.

Nuclear Magnetic Resonance Spectrum (270 MHz, CDCl$_3$) δ ppm: 4.32–4.46 (2H, multiplet); 4.54–4.66 (1H, multiplet); 5.45 (1H, broad singlet); 5.58 (1H, broad singlet); 5.90 (1H, doublet of doublets, J=9.8 & 5.9 Hz); 6.02 (1H, doublet, J=9.8 Hz).

Infrared Absorption Spectrum (CHCl$_3$) $\nu_{max}$ cm$^{-1}$: 3450, 2950, 1720.

Mass Spectrum (m/e): 420 (M$^+$), 403, 321, 304, 286.

$[\alpha]_D^{25}$ +184.20 (c=0.33, acetone).

EXAMPLE 26

(4R,6R)-6-{2-[(1S,2S,6S,8S,8aR)-1,2,6,7,8,8a-Hexahydro-6-hydroxy-8-[(S)-2-methylvaleryloxy]-2-methyl-1-naphthyl]ethyl}tetrahydro-4-hydroxy-2H-pyran-2-one

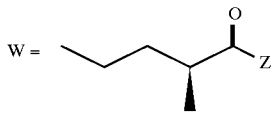

A procedure similar to that described in Example 24, above, was followed, but using 1.38 g (2.1 mmol) of (4R,6R)-6-{2-[(1S,2S,6S,8S,8aR)-1,2,6,7,8,8a-hexahydro-6-t-butyldimethylsilyloxy-8-[(S)-2-methylvaleryloxy]-2-methyl-1-naphthyl]ethyl}tetrahydro-4-t-butyldimethylsilyloxy-2H-pyran-2-one [prepared as described in Example 3, above], to provide 674 mg of the title compound, melting at 134° C.

Elemental Analysis: Calculated for $C_{24}H_{36}O_6$: C: 68.55%; H: 8.63%; Found: C: 68.36%; H: 8.77%.

Nuclear Magnetic Resonance Spectrum (270 MHz, CDCl$_3$) δ ppm: 0.89 (3H, triplet, J=7.3 Hz); 0.91 (3H, doublet, J=7.3 Hz); 1.11 (3H, doublet, J=7.3 Hz); 2.32 (1H, broad singlet, interchangeable with D$_2$O); 2.73 (1H, doublet of doublets, J=17.6 & 5.1 Hz); 4.33–4.43 (2H, multiplet); 4.57–4.64 (1H, multiplet); 5.41 (1H, singlet); 5.57 (1H, singlet); 5.90 (1H, doublet of doublets, J=9.5 & 5.9 Hz); 6.00 (1H, doublet, J=9.5 Hz).

Infrared Absorption Spectrum (CHCl$_3$) $\nu_{max}$ cm$^{-1}$: 3501, 3453, 2964, 1724, 1699, 1182, 1044, 861.

Mass Spectrum (m/e): 420 (M$^+$), 403, 304.

$[\alpha]_D^{25}$ +189.5° (c=0.65, acetone).

EXAMPLE 27

(4R,6R)-6-{2-[(1S,2S,6S,8S,8aR)-1,2,6,7,8,8a-Hexahydro-6-hydroxy-8-(2-propylvaleryloxy)-2-methyl-1-naphthyl]ethyl}tetrahydro-4-hydroxy-2H-pyran-2-one

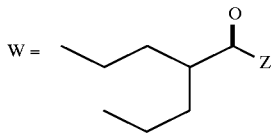

A procedure similar to that described in Example 24, above, was followed, but using 1.13 g (1.7 mmol) of (4R,6R)-6-{2-[(1S,2S,6S,8S,8aR)-1,2,6,7,8,8a-hexahydro-6-t-butyldimethylsilyloxy-8-(2-propylvaleryloxy)-2-methyl-1-naphthyl]ethyl}tetrahydro-4-t-butyldimethylsilyloxy-2H-pyran-2-one [prepared as described in Example 4, above], to provide 668 mg of the title compound, melting at between 165° and 166° C.

Elemental Analysis: Calculated for $C_{26}H_{40}O_6$: C: 69.61%; H: 8.99%; Found: C: 69.67%; H: 8.95%.

Nuclear Magnetic Resonance Spectrum (270 MHz, CDCl$_3$) δ ppm: 4.33–4.45 (2H, multiplet); 4.54–4.65 (1H, multiplet); 5.43 (1H, broad singlet); 5.56 (1H, broad singlet); 5.90 (1H, doublet of doublets, J=9.8 & 5.9 Hz); 6.01 (1H, doublet, J=9.8 Hz).

Infrared Absorption Spectrum (CHCl$_2$) $v_{max}$ cm$^{-1}$: 3450, 2950, 1720.

Mass Spectrum (m/e): 448 (M$^+$), 430, 304, 286.

$[\alpha]_D^{25}$ +176.1° (c=0.36, acetone).

EXAMPLE 28

(4R,6R)-6-{2-[(1S,2S,6S,8S,8aR)-1,2,6,7,8,8a-Hexahydro-6-hydroxy-8-(3,3-dimethylbutyryloxy)-2-methyl-1-naphthyl]ethyl}tetrahydro-4-hydroxy-2H-pyran-2-one

A procedure similar to that described in Example 24, above, was followed, but using 1.45 g (1.8 mmol) of (4R,6R)-6-{2-[(1S,2S,6S,8S,8aR)-1,2,6,7,8,8a-hexahydro-6-t-butyldimethylsilyloxy-8-(3,3-dimethylbutyryloxy)-2-methyl-1-naphthyl]ethyl}tetrahydro-4-t-butyldimethylsilyloxy-2H-pyran-2-one [prepared as described in Example 1, above], to provide 640 mg of the title compound melting at 155° C.

Elemental Analysis: Calculated for C$_{24}$H$_{36}$O$_6$: C: 68.55%; H: 8.63%; Found: C: 68.32%; H: 8.81%

Nuclear Magnetic Resonance Spectrum (270 MHz, CDCl$_3$) δ ppm: 0.80 (3H, doublet, J=6.8 Hz); 1.02 (9H, singlet); 2.05 (1H, multiplet, interchangeable with D$_2$O); 2.20 (2H, singlet); 4.32–4.48 (2H, multiplet); 4.56–4.67 (1H, multiplet); 5.40 (1H, broad singlet); 5.55 (1H, broad singlet); 5.88 (1H, doublet of doublets, J=9.8 & 5.9 Hz); 6.00 (1H, doublet, J=9.8 Hz).

Infrared Absorption Spectrum (CHCl$_3$) $v_{max}$ cm$^{-1}$: 3400, 2950, 1720.

Mass Spectrum (m/e): 420 (M$^+$), 402, 384, 346, 321.

$[\alpha]_D^{25}$ +189.1° (c=0.33, acetone).

EXAMPLE 29

(4R,6R)-6-{2-[(1S,2S,6S,8S,8aR)-1,2,6,7,8,8a-Hexahydro-6-hydroxy-8-(2,2-diethylbutyryloxy)-2-methyl-1-naphthyl]ethyl}tetrahydro-4-hydroxy-2H-pyran-2-one

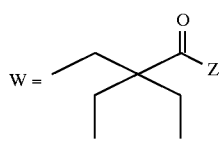

A procedure similar to that described in Example 24, above, was followed, but using 2.52 g (3.8 mmol) of (4R,6R)-6-{2-[(1S,2S,6S,8S,8aR)-1,2,6,7,8,8a-hexahydro-6-t-butyldimethylsilyloxy-8-(2,2-diethylbutyryloxy)-2-methyl-1-naphthyl]ethyl}tetrahydro-4-t-butyldimethylsilyloxy-2H-pyran-2-one [prepared as described in Example 6, above], to provide 1.05 g of the title compound, melting at between 146° and 148° C., with decomposition.

Elemental Analysis: Calculated for C$_{26}$H$_{40}$O$_6$: C: 69.61%; H: 8.99%; Found: C: 69.53%; H: 9.10%.

Nuclear Magnetic Resonance Spectrum (360 MHz, CDCl$_3$) δ ppm: 0.76 (9H, triplet, J=7.5 Hz); 0.91 (3H, doublet, J=7.0 Hz); 4.35–4.41 (2H, multiplet); 4.56–4.64 (1H, multiplet); 5.45 (1H, broad singlet); 5.57 (1H, broad singlet); 5.90 (1H, doublet of doublets, J=9.7 & 5.9 Hz); 6.01 (1H, doublet, J=9.7 Hz).

Infrared Absorption Spectrum (KBr) $v_{max}$ cm$^{-1}$: 3428, 2967, 1717, 1255, 1142, 1041.

Mass Spectrum (m/e): 448 (M$^+$), 430, 304, 286.

$[\alpha]_D^{25}$ +167.8° (c=0.32, acetone).

EXAMPLE 30

(4R,6R)-6-{2-[(1S,2S,6S,8S,8aR)-1,2,6,7,8,8a-Hexahydro-6-hydroxy-8-(2,2-dimethyl-4-pentenoyloxy)-2-methyl-1-naphthyl]ethyl}tetrahydro-4-hydroxy-2H-pyran-2-one

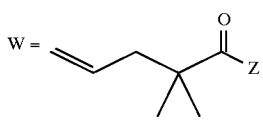

A procedure similar to that described in Example 24, above, was followed, but using 227 mg (0.3 mmol) of (4R,6R)-6-{2-[(1S,2S,6S,8S,8aR)-1,2,6,7,8,8a-hexahydro-6-t-butyldimethylsilyloxy-8-(2,2-dimethyl-4-pentenoyloxy)-2-methyl-1-naphthyl]ethyl}tetrahydro-4-t-butyldimethylsilyloxy-2H-pyran-2-one [prepared as described in Example 7, above], to provide 127 mg of the title compound, melting at between 141° and 142° C.

Elemental Analysis: Calculated for C$_{25}$H$_{36}$O$_6$: C: 69.42%; H: 8.39%; Found: C: 69.15%; H: 8.34%.

Nuclear Magnetic Resonance Spectrum (270 MHz, CDCl$_3$) δ ppm: 0.90 (3H, doublet, J=7.3 Hz); 1.14 (6H, singlet); 2.25 (2H, doublet, J=7.3 Hz); 4.33–4.45 (2H, multiplet); 4.55–4.66 (1H, multiplet); 5.01–5.10 (2H, multiplet); 5.37 (1H, broad singlet); 5.57 (1H, broad singlet); 5.61–5.76 (1H, multiplet); 5.79 (1H, doublet of doublets, J=9.8 & 5.9 Hz); 6.00 (1H, doublet, J=9.8 Hz).

Infrared Absorption Spectrum (CHCl$_3$) $v_{max}$ cm$^{-1}$: 3450, 2950, 1720, 1250.

Mass Spectrum (m/e): 432 (M$^+$), 415, 345, 304, 286.

$[\alpha]_D^{25}$ +188.0° (c=0.44, acetone).

EXAMPLE 31

(4R,6R)-6-{2-[(1S,2S,6S,8S,8aR)-1,2,6,7,8,8a-Hexahydro-6-hydroxy-8-(2-allyl-4-pentenoyloxy)-2-methyl-1-naphthyl]ethyl}tetrahydro-4-hydroxy-2H-pyran-2-one

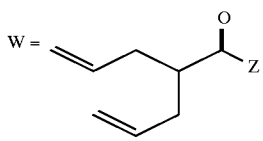

A procedure similar to that described in Example 24, above, was followed, but using 966 mg (1.4 mmol) of (4R,6R)-6-{2-[(1S,2S,6S,8S,8aR)-1,2,6,7,8,8a-hexahydro-6-t-butyldimethylsilyloxy-8-(2-allyl-4-pentenoyloxy)-2-methyl-1-naphthyl]ethyl}tetrahydro-4-t-butyldimethylsilyloxy-2H-pyran-2-one [prepared as described in Example 8, above], to provide 555 mg of the title compound, melting at between 159° and 160° C.

Elemental Analysis: Calculated for $C_{26}H_{36}O_6 \cdot \frac{1}{2}H_2O$: C: 68.85%; H: 8.22%; Found: C: 68.85%; H: 8.10%.

Nuclear Magnetic Resonance Spectrum (270 MHz, hexadeuterated dimethyl sulfoxide) δ ppm: 0.84 (3H, doublet, J=6.8 Hz); 4.08–4.25 (2H, multiplet); 4.41–4.52 (1H, multiplet); 4.76 (1H, doublet, J=5.9 Hz, interchangeable with $D_2O$); 4.99–5.07 (4H, multiplet); 5.17 (1H, doublet, J=2.9 Hz, interchangeable with $D_2O$); 5.26 (1H, broad singlet); 5.49 (1H, broad singlet); 5.61–5.78 (2H, multiplet); 5.84 (1H, doublet of doublets, J=9.8 & 5.9 Hz); 5.96 (1H, doublet, J=9.8 Hz).

Infrared Absorption Spectrum ($CHCl_3$) $v_{max}$ cm$^{-1}$: 3400, 2950, 1720, 1240.

Mass Spectrum (m/e): 444 (M$^+$), 427, 304, 161.

$[\alpha]_D^{25}$ +179.0° (c=0.54, acetone).

EXAMPLE 32

(4R,6R)-6-{2-[(1S,2S,6S,8S,8aR)-1,2,6,7,8,8a-Hexahydro-6-hydroxy-8-(2-butylhexanoyloxy)-2-methyl-1-naphthyl]ethyl}tetrahydro-4-hydroxy-2H-pyran-2-one A procedure similar to that described in Example 24, above, was followed, but using 785 mg (1.1 mmol) of (4R,6R)-6-{2-[(1S,2S,6S,8S,8aR)-1,2,6,7,8,8a-hexahydro-6-t-butyldimethylsilyloxy-8-(2-butylhexanoyloxy)-2-methyl-1-naphthyl]ethyl}tetrahydro-4-t-butyldimethylsilyloxy-2H-pyran-2-one [prepared as described in Example 9, above], to provide 520 mg of the title compound, melting at between 143° and 145° C.

Elemental Analysis: Calculated for $C_{28}H_{44}O_6$: C: 70.56%; H: 9.30%; Found: C: 70.27%; H: 9.36%.

Nuclear Magnetic Resonance Spectrum (270 MHz, $CDCl_3$) δ ppm: 4.34–4.45 (2H, multiplet); 4.55–4.65 (1H, multiplet); 5.47 (1H, broad singlet); 5.59 (1H, broad singlet); 5.89 (1H, doublet of doublets, J=9.8 & 5.9 Hz); 6.01 (1H, doublet, J=9.8 Hz).

Infrared Absorption Spectrum ($CHCl_3$) $v_{max}$ cm$^{-1}$: 3450, 2950, 1720.

Mass Spectrum (m/e): 476 (M$^+$), 459, 356, 321.

$[\alpha]_D^{25}$ +157.8° (c=0.32, acetone).

EXAMPLE 33

(4R,6R)-6-{2-[(1S,2S,6S,8S,8aR)-1,2,6,7,8,8a-Hexahydro-6-hydroxy-8-hexanoyloxy-2-methyl-1-naphthyl)ethyl}tetrahydro-4-hydroxy-2H-pyran-2-one A procedure similar to that described in Example 24, above, was followed, but using 338 mg (0.5 mmol) of (4R,6R)-6-{2-[(1S,2S,6S,8S,8aR)-1,2,6,7,8,8a-hexahydro-6-t-butyldimethylsilyloxy-8-hexanoyloxy-2-methyl-1-naphthyl]ethyl}tetrahydro-4-t-butyldimethylsilyloxy-2H-pyran-2-one [prepared as described in Example 10, above], to provide 195 mg of the title compound, melting at between 138° and 139° C.

Elemental Analysis: Calculated for $C_{24}H_{36}O_6$: C: 68.55%; H: 8.63%; Found: C: 68.34%, H: 8.67%.

Nuclear Magnetic Resonance Spectrum (270 MHz, $CDCl_3$) δ ppm: 4.35–4.46 (2H, multiplet); 4.58–4.68 (1H, multiplet); 5.42 (1H, broad singlet); 5.57 (1H, broad singlet); 5.90 (1H, doublet of doublets, J=9.8 & 5.9 Hz); 6.00 (1H, doublet, J=9.8 Hz).

Infrared Absorption Spectrum ($CHCl_3$) $v_{max}$ cm$^-$: 3450, 2950, 1720, 1250.

Mass Spectrum (m/e): 420 (M$^+$), 403, 321, 304.

$[\alpha]_D^{25}$ +189.6° (c=0.25, acetone).

EXAMPLE 34

(4R,6R)-6-{2-[(1S,2S,6S,8S,8aR)-1,2,6,7,8,8a-Hexahydro-6-hydroxy-8-isovaleryloxy-2-methyl-1-naphthyl]ethyl}tetrahydro-4-hydroxy-2H-pyran-2-one A procedure similar to that described in Example 24, above, was followed, but using 1.1 g (1.7 mmol) of (4R,6R)-6-{2-[(1S,2S,6S,8S,8aR)-1,2,6,7,8,8a-hexahydro-6-t-butyldimethylsilyloxy-8-isovaleryloxy-2-methyl-1-naphthyl]ethyl}tetrahydro-4-t-butyldimethylsilyloxy-2H-pyran-2-one [prepared as described in Example 11, above], to provide 488 mg of the title compound, melting at between 153° and 155° C.

Elemental Analysis: Calculated for $C_{23}H_{34}O_6 \cdot \frac{1}{2}H_2O$: C: 67.96%; H: 8.43%; Found: C: 67.91%; H: 8.30%.

Nuclear Magnetic Resonance Spectrum (270 MHz, hexadeuterated dimethyl sulfoxide) δ ppm: 0.84 (3H, doublet, J=6.8 Hz); 0.88 (6H, doublet, J=6.8 Hz); 4.04–4.10 (1H, multiplet); 4.10–4.16 (1H, multiplet); 4.43–4.50 (1H, multiplet); 4.77 (1H, doublet, J=6.3 Hz, interchangeable with $D_2O$); 5.16 (1H, doublet, J=2.9 Hz, interchangeable with $D_2O$); 5.23 (1H, broad singlet); 5.49 (1H, broad singlet); 5.84 (1H, doublet of doublets, J=9.8 & 5.9 Hz); 5.96 (1H, doublet, J=9.8 Hz).

Infrared Absorption Spectrum ($CHCl_3$) $v_{max}$ cm$^{-1}$: 3350, 2880, 1725, 1250.

Mass Spectrum (m/e): 406 (M$^+$), 322, 304.

$[\alpha]_D^{25}$ +184.0° (c=0.45, acetone).

EXAMPLE 35

(4R,6R)-6-{2-[(1S,2S,6S,8S,8aR)-1,2,6,7,8,8a-Hexahydro-6-hydroxy-8-pivaloyloxy-2-methyl-1-naphthyl]ethyl}tetrahydro-4-hydroxy-2H-pyran-2-one

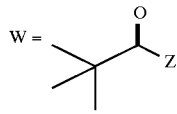

A procedure similar to that described in Example 24, above, was followed, but using 571 mg (0.9 mmol) of (4R,6R)-6-{2-[(1S,2S,6S,8S,8aR)-1,2,6,7,8,8a-hexahydro-6-t-butyldimethylsilyloxy-8-pivaloyloxy-2-methyl-1-naphthyl]ethyl}tetrahydro-4-t-butyldimethylsilyloxy-2H-pyran-2-one [prepared as described in Example 12, above], to provide 354 mg of the title compound, melting at between 132° and 133° C.

Elemental Analysis: Calculated for $C_{23}H_{34}O_6$: C: 67.96%; H: 8.43%; Found: C: 67.87%; H: 8.53%.

Nuclear Magnetic Resonance Spectrum (270 MHz, hexadeuterated dimethyl sulfoxide) δ ppm: 0.85 (3H, doublet, J=7.0 Hz); 1.10 (9H, singlet); 4.08–4.15 (2H, multiplet); 4.46–4.50 (1H, multiplet); 4.78 (1H, doublet, J=6.3 Hz, interchangeable with $D_2O$); 5.17 (1H, broad singlet); 5.17 (1H, doublet, J=3.3 Hz, interchangeable with $D_2O$); 5.51 (1H, broad singlet); 5.84 (1H, doublet of doublets, J=9.7 & 5.8 Hz); 5.97 (1H, doublet, J=9.7 Hz).

Infrared Absorption Spectrum ($CHCl_3$) $v_{max}$ cm$^{-1}$: 3450, 2950, 1720, 1160.

Mass Spectrum (m/e): 406 (M$^+$), 321, 304, 286.
$[\alpha]_D^{25}$ +179.0° (c=0.48, acetone).

EXAMPLE 36

(4R,6R)-6-{2-[(1S,2S,6S,8S,8aR)-1,2,6,7,8,8a-Hexahydro-6-hydroxy-8-(2,2-dimethylvaleryloxy)-2-methyl-1-naphthyl]ethyl}tetrahydro-4-hydroxy-2H-pyran-2-one

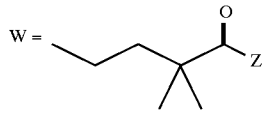

A procedure similar to that described in Example 24, above, was followed, but using 1.29 g (1.9 mmol) of (4R,6R)-6-{2-[(1S,2S,6S,8S,8aR)-1,2,6,7,8,8a-hexahydro-6-t-butyldimethylsilyloxy-8-(2,2-dimethylvaleryloxy)-2-methyl-1-naphthyl]ethyl}tetrahydro-4-t-butyldimethylsilyloxy-2H-pyran-2-one [prepared as described in Example 13, above], to provide 817 mg of the title compound, melting at between 143° and 144° C.

Elemental Analysis: Calculated for $C_{25}H_{38}O_6$: C: 69.10%; H: 8.81%; Found: C: 68.86%; H: 8.91%.

Nuclear Magnetic Resonance Spectrum (270 MHz, $CDCl_3$) δ ppm: 1.13 (6H, singlet); 4.32–4.43 (2H, multiplet); 4.54–4.66 (1H, multiplet); 5.35 (1H, broad singlet); 5.56 (1H, broad singlet); 5.90 (1H, doublet of doublets, J=9.8 & 5.9 Hz); 6.01 (1H, doublet, J=9.8 Hz).

Infrared Absorption Spectrum ($CHCl_3$) $v_{max}$ cm$^{-1}$: 3450, 2950, 1720, 1160.

Mass Spectrum (m/e): 434 (M$^+$), 321, 304, 286.
$[\alpha]_D^{25}$ +170.5° (c=0.55, acetone).

EXAMPLE 37

(4R,6R)-6-{2-[(1S,2S,6S,8S,8aR)-1,2,6,7,8,8a-Hexahydro-6-hydroxy-8-(2-allyl-2-methyl-4-pentenoyloxy)-2-methyl-1-naphthyl]ethyl}tetrahydro-4-hydroxy-2H-pyran-2-one

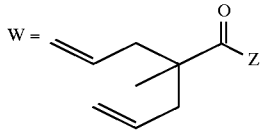

A procedure similar to that described in Example 24, above, was followed, but using 2.07 g (3.0 mmol) of (4R,6R)-6-{2-[(1S,2S,6S,8S,8aR)-1,2,6,7,8,8a-hexahydro-6-t-butyldimethylsilyloxy-8-(2-allyl-2-methyl-4-pentenoyloxy)-2-methyl-1-naphthyl]ethyl}tetrahydro-4-t-butyldimethylsilyloxy-2H-pyran-2-one [prepared as described in Example 14, above], to provide 1.29 g of the title compound, melting at between 115° and 116° C.

Elemental Analysis: Calculated for $C_{27}H_{38}O_6$: C: 70.72%; H: 8.35%; Found: C: 70.48%; H: 8.46%.

Nuclear Magnetic Resonance Spectrum (270 MHz, hexadeuterated dimethyl sulfoxide) δ ppm: 0.84 (3H, doublet, J=6.9 Hz); 1.01 (3H, singlet); 4.09–4.11 (1H, multiplet); 4.15–4.18 (1H, multiplet); 4.45–4.50 (1H, multiplet); 4.79 (1H, doublet, J=6.0 Hz, interchangeable with $D_2O$); 5.04–5.08 (4H, multiplet); 5.19 (1H, doublet, J=3.2 Hz, interchangeable with $D_2O$); 5.25 (1H, broad singlet); 5.50 (1H, broad singlet); 5.59–5.70 (2H, multiplet); 5.84 (1H, doublet of doublets, J=9.5 & 5.9 Hz); 5.97 (1H, doublet, J=9.7 Hz).

Infrared Absorption Spectrum ($CHCl_3$) $v_{max}$ cm$^{-1}$: 3450, 2950, 1720, 1250.

Mass Spectrum (m/e): 458 (M$^+$), 422, 304, 286.
$[\alpha]_D^{25}$ +182.0° (c=0.66, acetone).

EXAMPLE 38

(4R,6R)-6-{2-[(1S,2S,6S,8S,8aR)-1,2,6,7,8,8a-Hexahydro-6-hydroxy-8-(2-methyl-2-propylvaleryloxy)-2-methyl-1-naphthyl]ethyl}tetrahydro-4-hydroxy-2H-pyran-2-one

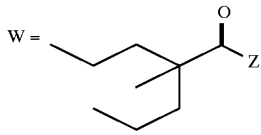

A procedure similar to that described in Example 24, above, was followed, but using 956 mg (1.4 mmol) of (4R,6R)-6-{2-[(1S,2S,6S,8S,8aR)-1,2,6,7,8,8a-hexahydro-6-t-butyldimethylsilyloxy-8-(2-methyl-2-propylvaleryloxy)-2-methyl-1-naphthyl]ethyl}tetrahydro-4-t-butyldimethylsilyloxy-2H-pyran-2-one [prepared as described in Example 15, above] to provide 550 mg of the title compound, melting at between 109° and 111° C.

Elemental Analysis: Calculated for $C_{27}H_{42}O_6 \cdot H_2O$: C: 67.61%; H: 8.83%; Found: C: 67.65%; H: 8.79%.

Nuclear Magnetic Resonance Spectrum (270 MHz, $CDCl_3$) δ ppm: 4.35–4.40 (2H, multiplet); 4.57–4.63 (1H, multiplet); 5.40 (1H, broad singlet); 5.58 (1H, broad singlet); 5.90 (1H, doublet of doublets, J=9.7 & 5.9 Hz); 6.02 (1H, doublet, J=9.7 Hz).

Infrared Absorption Spectrum (CHCl$_3$) $v_{max}$ cm$^{-1}$: 3450, 2950, 1720, 1150.

Mass Spectrum (m/e): 462 (M$^+$), 444, 321, 304.

$[\alpha]_D^{25}$ +142.2° (c=0.59, acetone).

EXAMPLE 39

(4R,6R)-6-{2-[(1S,2S,6S,8S,8aR)-1,2,6,7,8,8a-Hexahydro-6-hydroxy-8-(2,2-diethylvaleryloxy)-2-methyl-1-naphthyl]ethyl}tetrahydro-4-hydroxy-2H-pyran-2-one

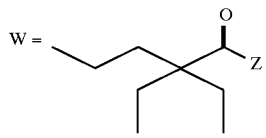

A procedure similar to that described in Example 24, above, was followed, but using 184 mg (0.3 mmol) of (4R,6R)-6-{2-[(1S,2S,6S,8S,8aR)-1,2,6,7,8,8a-hexahydro-6-t-butyldimethylsilyloxy-8-(2,2-diethylvaleryloxy)-2-methyl-1-naphthyl]ethyl}tetrahydro-4-t-butyldimethylsilyloxy-2H-pyran-2-one [prepared as described in Example 16, above], to provide 97 mg of the title compound, melting at between 130° and 131° C.

Elemental Analysis: Calculated for C$_{27}$H$_{42}$O$_6$.CH$_3$COOC$_2$H$_5$: C: 67.60; H: 9.15; Found: C: 67.32; H: 9.10.

Nuclear Magnetic Resonance Spectrum (270 MHz, CDCl$_3$) δ ppm: 0.76 (3H, triplet, J=7.6 Hz); 2.74 (1H, doublet of doublets, J=17.6 & 5.1 Hz); 4.35–4.42 (2H, multiplet); 4.56–4.63 (1H, multiplet); 5.44 (1H, broad singlet); 5.57 (1H, broad singlet); 5.89 (1H, doublet of doublets, J=9.7 & 5.9 Hz); 6.01 (1H, doublet, J=9.7 Hz).

Infrared Absorption Spectrum (KBr) $v_{max}$ cm$^{-1}$: 3350, 2950, 1720, 1700.

Mass Spectrum (m/e): 462 (M$^+$), 444, 321, 304.

$[\alpha]_D^{25}$ +140.4° (c=0.52, acetone).

EXAMPLE 40

(4R,6R)-6-{2-[(1S,2S,6S,8S,8aR)-1,2,6,7,8,8a-Hexahydro-6-hydroxy-8-(2-isopropyl-3-methylbutyryloxy)-2-methyl-1-naphthyl]ethyl}tetrahydro-4-hydroxy-2H-pyran-2-one

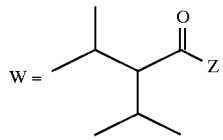

A procedure similar to that described in Example 24, above, was followed, but using 190 mg (0.3 mmol) of (4R,6R)-6-{2-[(1S,2S,6S,8S,8aR)-1,2,6,7,8,8a-hexahydro-6-t-butyldimethylsilyloxy-8-(2-isopropyl-3-methylbutyryloxy)-2-methyl-1-naphthyl]ethyl}tetrahydro-4-t-butyldimethylsilyloxy-2H-pyran-2-one [prepared as described in Example 17, above], to provide 100 mg of the title compound, melting at between 210° and 211° C.

Elemental Analysis: Calculated for C$_{26}$H$_{40}$O$_6$: C: 69.61%; H: 8.99%; Found: C: 69.35%; H: 9.04%.

Nuclear Magnetic Resonance Spectrum (270 MHz, CDCl$_3$) δ ppm: 2.32–2.44 (2H, multiplet); 2.56–2.66 (2H, multiplet); 2.75 (1H, doublet of doublets, J=17.6 & 5.1 Hz); 4.34–4.40 (1H, multiplet); 4.43–4.50 (1H, multiplet); 4.56–4.64 (1H, multiplet); 5.50 (1H, broad singlet); 5.57 (1H, broad singlet); 5.90 (1H, doublet of doublets, J=9.8 & 6.0 Hz); 6.01 (1H, doublet, J=9.8 Hz).

Infrared Absorption Spectrum (CHCl$_3$) $v_{max}$ cm$^{-1}$: 3450, 2950, 1720.

Mass Spectrum (m/e): 448 (M$^+$), 418, 321, 304.

$[\alpha]_D^{25}$ +172.6° (c=0.35, acetone).

EXAMPLE 41

(4R,6R)-6-{2-[(1S,2S,6S,8S,8aR)-1,2,6,7,8,8a-Hexahydro-6-hydroxy-8-(2,2-diethyl-4-pentenoyloxy)-2-methyl-1-naphthyl]ethyl}tetrahydro-4-hydroxy-2H-pyran-2-one

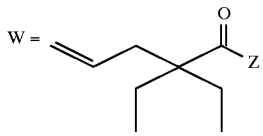

A procedure similar to that described in Example 24, above, was followed, but using 1.95 g (2.8 mmol) of (4R,6R)-6-{2-[(1S,2S,6S,8S,8aR)-1,2,6,7,8,8a-hexahydro-6-t-butyldimethylsilyloxy-8-(2,2-diethyl-4-pentenoyloxy)-2-methyl-1-naphthyl]ethyl}tetrahydro-4-t-butyldimethylsilyloxy-2H-pyran-2-one [prepared as described in Example 18, above], to provide 1.04 g of the title compound, melting at between 107° and 108° C.

Elemental Analysis: Calculated for C$_{27}$H$_{40}$O$_6$.CH$_2$Cl$_2$: C: 61.64%; H: 7.76%; Found: C: 61.63%; H: 7.95%.

Nuclear Magnetic Resonance Spectrum (270 MHz, CDCl$_3$) δ ppm: 0.90 (3H, doublet, J=7.1 Hz); 2.30 (2H, doublet, J=7.3 Hz); 2.75 (1H, doublet of doublets, J=17.6 & 5.1 Hz); 4.35–4.45 (2H, multiplet); 4.55–4.64 (1H, multiplet); 5.03–5.12 (2H, multiplet); 5.45 (1H, broad singlet); 5.57 (1H, broad singlet); 5.57–5.69 (1H, multiplet); 5.90 (1H, doublet of doublets, J=9.7 & 5.9 Hz); 6.01 (1H, doublet, J=9.7 Hz).

Infrared Absorption Spectrum (KBr) $v_{max}$ cm$^{-1}$: 3340, 2970, 1720, 1690.

Mass Spectrum (m/e): 460 (M$^+$), 442, 321, 304.

$[\alpha]_D^{25}$ +136.7° (c=0.21, acetone).

EXAMPLE 42

(4R,6R)-6-{2-[(1S,2S,6S,8S,8aR)-1,2,6,7,8,8a-Hexahydro-6-hydroxy-8-(2-allyl-2-ethyl-4-pentenoyloxy)-2-methyl-1-naphthyl]ethyl}tetrahydro-4-hydroxy-2H-pyran-2-one

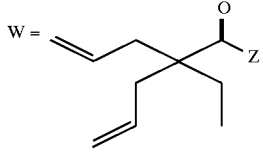

A procedure similar to that described in Example 24, above, was followed, but using 1.63 g (2.3 mmol) of (4R,6R)-6-{2-[(1S,2S,6S,8S,8aR)-1,2,6,7,8,8a-hexahydro-6-t-butyldimethylsilyloxy-8-(2-allyl-2-ethyl-4-pentenoyloxy)-2-methyl-1-naphthyl]ethyl}tetrahydro-4-t-butyldimethylsilyloxy-2H-pyran-2-one [prepared as described in Example 19, above], to provide 1.10 g of the title compound, melting at between 99° and 100° C.

Elemental Analysis: Calculated for $C_{28}H_{40}O_6 \cdot ½H_2O$: C: 69.82%; H: 8.58%; Found: C: 69.33%; H: 8.62%.

Nuclear Magnetic Resonance Spectrum (270 MHz, hexadeuterated dimethyl sulfoxide) δ ppm: 0.75 (3H, triplet, J=7.4 Hz); 0.84 (3H, doublet, J=6.8 Hz); 4.09–4.10 (1H, multiplet); 4.14–4.17 (1H, multiplet); 4.44–4.48 (1H, multiplet); 4.81 (1H, doublet, J=6.2 Hz, interchangeable with $D_2O$); 5.06–5.10 (4H, multiplet); 5.19 (1H, doublet, J=3.1 Hz, interchangeable with $D_2O$); 5.29 (1H, broad singlet); 5.50 (1H, broad singlet); 5.56–5.66 (2H, multiplet); 5.84 (1H, doublet of doublets, J=9.7 & 5.8 Hz); 5.98 (1H, doublet, J=9.7 Hz).

Infrared Absorption Spectrum (KBr) $v_{max}$ cm$^{-1}$: 3350, 2950, 1710, 1255, 1040.

Mass Spectrum (m/e): 472 (M$^+$), 321, 304, 286.

$[α]_D^{25}$ +176.0° (c=0.45, acetone).

EXAMPLE 43

(4R,6R)-6-{2-[(1S,2S,6S,8S,8aR)-1,2,6,7,8,8a-Hexahydro-6-hydroxy-8-(2,2-diallyl-4-pentenoyloxy)-2-methyl-1-naphthyl]ethyl}tetrahydro-4-hydroxy-2H-pyran-2-one

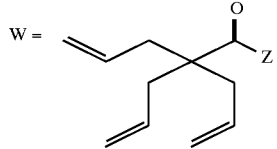

A procedure similar to that described in Example 24, above, was followed, but using 267 mg (0.4 mmol) of (4R,6R)-6-{2[(1S,2S,6S,8S,8aR)-1,2,6,7,8,8a-hexahydro-6-t-butyldimethylsilyloxy-8-(2,2-diallyl-4-pentenoyloxy)-2-methyl-1-naphthyl]ethyl}tetrahydro-4-t-butyldimethylsilyloxy-2H-pyran-2-one [prepared as described in Example 20, above], to provide 180 mg of the title compound, melting at between 118° and 119° C.

Elemental Analysis: Calculated for $C_{29}H_{40}O_6$: C: 71.87%; H: 8.32%; Found: C: 71.84%; H: 8.29%.

Nuclear Magnetic Resonance Spectrum (270 MHz, hexadeuterated dimethyl sulfoxide) δ ppm: 0.84 (3H, doublet, J=7.0 Hz); 2.21 (6H, doublet, J=7.3 Hz); 4.08–4.12 (1H, multiplet); 4.16–4.19 (1H, multiplet); 4.45–4.49 (1H, multiplet); 4.80 (1H, doublet, J=6.3 Hz, interchangeable with $D_2O$); 5.06–5.10 (6H, multiplet); 5.20 (1H, doublet, J=3.3 Hz, interchangeable with $D_2O$); 5.30 (1H, broad singlet); 5.51 (1H, broad singlet); 5.59–5.71 (3H, multiplet); 5.84 (1H, doublet of doublets, J=9.7 & 5.8 Hz); 5.98 (1H, doublet, J=9.7 Hz).

Infrared Absorption Spectrum (CHCl$_3$) $v_{max}$ cm$^{-1}$: 3450, 2950, 1720, 1220.

Mass Spectrum (m/e): 484 (M$^+$), 438, 304, 286.

$[α]_D^{25}$ +204.0° (c=0.54, acetone).

EXAMPLE 44

(4R,6R)-6-{2-[(1S,2S,6S,8S,8aR)-1,2,6,7,8,8a-Hexahydro-6-hydroxy-8-(2-ethyl-2-methylvaleryloxy)-2-methyl-1-naphthyl]ethyl}tetrahydro-4-hydroxy-2H-pyran-2-one

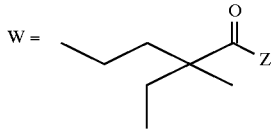

A procedure similar to that described in Example 24, above, was followed, but using 899 mg (2.0 mmol) of (4R,6R)-6-{2-[(1S,2S,6S,8S,8aR)-1,2,6,7,8,8a-hexahydro-6-t-butyldimethylsilyloxy-8-(2-ethyl-2-methylvaleryloxy)-2-methyl-14-naphthyl]ethyl}tetrahydro-4-t-butyldimethylsilyloxy-2H-pyran-2-one [prepared as described in Example 21, above], to provide 279 mg of the title compound, melting at between 126° and 128° C.

Elemental Analysis: Calculated for $C_{26}H_{40}O_6$: C: 69.61%; H: 8.99%; Found: C: 69.33%; H: 9.22%.

Nuclear Magnetic Resonance Spectrum (270 MHz, CDCl$_3$) δ ppm: 1.07 (3H, singlet); 4.37–4.39 (2H, multiplet); 4.57–4.63 (1H, multiplet); 5.41 (1H, broad singlet); 5.57 (1H, broad singlet); 5.89 (1H, doublet of doublets, J=9.7 & 5.9 Hz); 6.00 (1H, doublet, J=9.7 Hz).

Infrared Absorption Spectrum (CHCl$_3$) $v_{max}$ cm$^{-1}$: 3400, 2950, 1720, 1150.

Mass Spectrum (m/e): 448 (M$^+$), 304, 286, 268.

$[α]_D^{25}$ +171.2° (c=0.43, acetone).

The procedure of Example 44, above, may be followed using one of the stereoisomers produced in Example 21, above, as starting material in order to prepare the corresponding stereoisomer of the compound of Example 44, for example as shown in Example 45.

EXAMPLE 45

(4R,6R)-6-{2-[(1S,2S,6S,8S,8aR)-1,2,6,7,8,8a-Hexahydro-6-hydroxy-8-[(2S)-2-ethyl-2-methylvaleryloxy]-2-methyl-1-naphthyl]ethyl}tetrahydro-4-hydroxy-2H-pyran-2-one

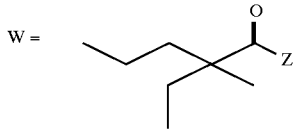

A procedure similar to that described in Example 28, above, was followed, but using 80 mg (0.12 mmol) of (4R,6R)-6-{2-[(1S,2S,6S,8S,8aR)-1,2,6,7,8,8a-hexahydro-6-t-butyldimethylsilyloxy-8-[(2S)-2-ethyl-2-methylvaleryloxy]-2-methyl-1-naphthyl]ethyl}tetrahydro-4-t-butyldimethylsilyloxy-2H-pyran-2-one [prepared as described in Example 22, above], to provide 50 mg of the title compound, melting at 127° C.

Nuclear Magnetic Resonance Spectrum (270 MHz, CDCl$_3$) δ ppm: 1.07 (3H, singlet); 4.37–4.39 (2H, multiplet); 4.57–4.63 (1H, multiplet); 5.41 (1H, broad singlet); 5.57 (1H, broad singlet); 5.89 (1H, doublet of doublets, J=9.7 & 5.9 Hz); 6.00 (1H, doublet, J=9.7 Hz).

Infrared Absorption Spectrum (CHCl$_3$) $v_{max}$ cm$^{-1}$: 3400, 2950, 1720, 1150.

Mass Spectrum (m/e): 448 (M$^+$).

$[\alpha]_D^{25}$ +167.0° (c=0.31, acetone).

EXAMPLE 46

(4R,6R)-6-{2-[(1S,2S,6S,8S,8aR)-1,2,6,7,8,8a-Hexahydro-6-hydroxy-8-(2,2-dimethylhexanoyloxy)-2-methyl-1-naphthyl]ethyl}tetrahydro-4-hydroxy-2H-pyran-2-one

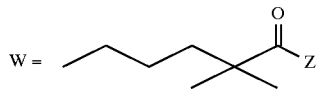

A procedure similar to that described in Example 24, above, was followed, but using 1.16 g (1.72 mmol) of (4R,6R)-6-{2-[(1S,2S,6S,8S,8aR)-1,2,6,7,8,8a-hexahydro-6-t-butyldimethylsilyloxy-8-(2,2-dimethylhexanoyloxy)-2-methyl-1-naphthyl]ethyl}tetrahydro-4-t-butyldimethylsilyloxy-2H-pyran-2-one [prepared as described in Example 23, above], to provide 660 mg of the title compound.

Elemental Analysis: Calculated for C$_{26}$H$_{40}$O$_6$·¼H$_2$O: C: 68.91%; H: 9.01%; Found: C: 69.05%; H: 8.96%.

Nuclear Magnetic Resonance Spectrum (400 MHz, hexadeuterated dimethyl sulfoxide) δ ppm: 0.84 (3H, doublet, J=7.0 Hz); 0.85 (3H, triplet, J=7.0 Hz); 1.06 (6H, singlet); 4.08–4.15 (2H, multiplet); 4.45–4.49 (1H, multiplet); 4.79 (1H, doublet, J=6.0 Hz); 5.18 (1H, doublet, J=3.6 Hz); 5.20 (1H, broad singlet); 5.50 (1H, broad singlet); 5.84 (1H, doublet of doublets, J=9.7 & 6.0 Hz); 5.97 (1H, doublet, J=9.7 Hz).

Infrared Absorption Spectrum (CHCl$_3$) $v_{max}$ cm$^{-1}$: 3450, 2950, 1720, 1160.

Mass Spectrum (m/e): 448 (M$^+$), 304, 286, 268.

$[\alpha]_D^{25}$ +171.0° (c=0.41, acetone).

Each of the following Examples 47 to 69, describes the preparation of compounds of the following formula:

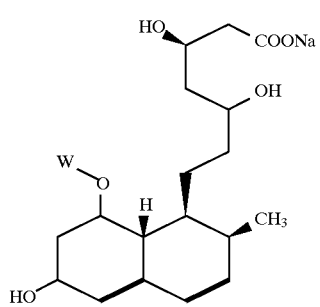

i.e. compounds of formula (I) in which R$^1$ represents a group of formula (II), R$^5$ represents a sodium atom and R$^6$ represents a hydrogen atom. Each group W, as defined in the following Examples, is attached to the formula shown above via the bond marked Z.

EXAMPLE 47

Sodium(3R,5R)-3,5-dihydroxy-7-[(1S,2S,6S,8S,8aR)-6-hydroxy-2-methyl-8-(3,3-dimethylbutyryloxy)-1,2,6,7,8,8a-hexahydro-1-naphthyl]heptanoate

0.5 ml of water was added to a solution of 32 mg (0.076 mmol) of (4R,6R)-6-{2-[(1S,2S,6S,8S,8aR)-1,2,6,7,8,8a-hexahydro-6-hydroxy-8-(3,3-dimethylbutyryloxy)-2-methyl-1-naphthyl]ethyl}tetrahydro-4-hydroxy-2H-pyran-2-one [prepared as described in Example 28, above], in 1 ml of dioxane, after which 0.8 ml (0.08 mmol) of a 0.1N aqueous solution of sodium hydroxide was added to the mixture. The resulting mixture was stirred at room temperature for 30 minutes. At the end of this time, the reaction mixture was lyophilized to give 35 mg of the title compound as a colorless powder.

EXAMPLE 48

Sodium(3R,5R)-3,5-dihydroxy-7-[(1S,2S,6S,8S,8aR)-6-hydroxy-2-methyl-8-(2-ethylbutyryloxy)-1,2,6,7,8,8a-hexahydro-1-naphthyl]heptanoate

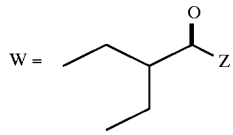

A procedure similar to that described in Example 47, above, was followed, but using 31 mg (0.074 mmol) of (4R,6R)-6-{2-[(1S,2S,6S,8S,8aR)-1,2,6,7,8,8a-hexahydro-6-hydroxy-8-(2-ethylbutyryloxy)-2-methyl-1-naphthyl]ethyl}tetrahydro-4-hydroxy-2H-pyran-2-one [prepared as described in Example 25, above], to provide 36 mg of the title compound as a colorless powder.

EXAMPLE 49

Sodium(3R,5R)-3,5-dihydroxy-7-[(1S,2S,6S,8S,8aR)-6-hydroxy-2-methyl-8-[(S)-2-methylvaleryloxy]-1,2,6,7,8,8a-hexahydro-1-naphthyl]heptanoate

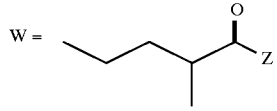

A procedure similar to that described in Example 47, above, was followed, but using 537 mg (1.28 mmol) of (4R,6R)-6-{2-[(1S,2S,6S,8S,8aR)-1,2,6,7,8,8a-hexahydro-6-hydroxy-8-(S)-2-methylvaleryloxy]-2-methyl-1-naphthyl]ethyl}tetrahydro-4-hydroxy-2H-pyran-2-one [prepared as described in Example 26, above], to provide 587 mg of the title compound as a colorless powder.

EXAMPLE 50

Sodium(3R,5R)-3,5-dihydroxy-7-[(1S,2S,6S,8S,8aR)-6-hydroxy-2-methyl-8-(2-propylvaleryloxy)-1,2,6,7,8,8a-hexahydro-1-naphthyl]heptanoate

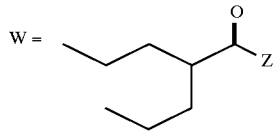

A procedure similar to that described in Example 47, above, was followed, but using 23 mg (0.051 mmol) of (4R,6R)-6-{2-[(1S,2S,6S,8S,8aR)-1,2,6,7,8,8a-hexahydro-6-hydroxy-8-(2-propylvaleryloxy)-2-methyl-1-naphthyl]ethyl}tetrahydro-4-hydroxy-2H-pyran-2-one [prepared as described in Example 27, above], to provide 25 mg of the title compound as a colorless powder.

EXAMPLE 51

Sodium(3R,5R)-3,5-dihydroxy-7-[(1S,2S,6S,8S,8aR)-6-hydroxy-2-methyl-8-(2-ethyl-2-methylbutyryloxy)-1,2,6,7,8,8a-hexahydro-1-naphthyl]heptanoate

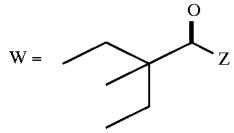

A procedure similar to that described in Example 47, above, was followed, but using 22 mg (0.051 mmol) of (4R,6R)-6-{2-[(1S,2S,6S,8S,8aR)-1,2,6,7,8,8a-hexahydro-6-hydroxy-8-(2-ethyl-2-methylbutyryloxy)-2-methyl-1-naphthyl]ethyl}tetrahydro-4-hydroxy-2H-pyran-2-one [prepared as described in Example 24, above], to provide 25 mg of the title compound as a colorless powder.

EXAMPLE 52

Sodium(3R,5R)-3,5-dihydroxy-7-[(1S,2S,6S,8S,8aR)-6-hydroxy-2-methyl-8-(2,2-diethylbutyryloxy)-1,2,6,7,8,8a-hexahydro-1-naphthyl]heptanoate

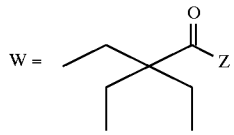

A procedure similar to that described in Example 47, above, was followed, but using 215 mg (0.48 mmol) of (4R,6R)-6-{2-[(1S,2S,6S,8S,8aR)-1,2,6,7,8,8a-hexahydro-6-hydroxy-8-(2,2-diethylbutyryloxy)-2-methyl-1-naphthyl]ethyl}tetrahydro-4-hydroxy-2H-pyran-2-one [prepared as described in Example 29, above], to provide 234 mg of the title compound as a colorless powder.

EXAMPLE 53

Sodium(3R,5R)-3,5-dihydroxy-7-[(1S,2S,6S,8S,8aR)-6-hydroxy-2-methyl-8-(2,2-dimethyl-4-pentenoyloxy)-1,2,6,7,8,8a-hexahydro-1-naphthyl]heptanoate

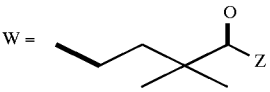

A procedure similar to that described in Example 47, above, was followed, but using 23 mg (0.053 mmol) of (4R,6R)-6-{2-[(1S,2S,6S,8S,8aR)-1,2,6,7,8,8a-hexahydro-6-hydroxy-8-(2,2-dimethyl-4-pentenoyloxy)-2-methyl-1-naphthyl]ethyl}tetrahydro-4-hydroxy-2H-pyran-2-one [prepared as described in Example 30, above], to provide 26 mg of the title compound as a colorless powder.

EXAMPLE 54

Sodium(3R,5R)-3,5-dihydroxy-7-[(1S,2S,6S,8S,8aR)-6-hydroxy-2-methyl-8-[2-allyl-4-pentenoyloxy]-1,2,6,7,8,8a-hexahydro-1-naphthyl]heptanoate

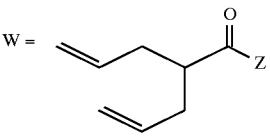

A procedure similar to that described in Example 47, above, was followed, but using 27 mg (0.061 mmol) of (4R,6R)-6-{2-[(1S,2S,6S,8S,8aR)-1,2,6,7,8,8a-hexahydro-6-hydroxy-8-(2-allyl-4-pentenoyloxy)-2-methyl-1-naphthyl]ethyl}tetrahydro-4-hydroxy-2H-pyran-2-one [prepared as described in Example 31, above], to provide 29 mg of the title compound as a colorless powder.

EXAMPLE 55

Sodium(3R,5R)-3,5-dihydroxy-7-[(1S,2S,6S,8S,8aR)-6-hydroxy-2-methyl-8-(2-butylhexanoyloxy)-1,2,6,7,8,8a-hexahydro-1-naphthyl]heptanoate

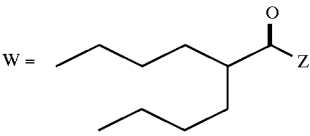

A procedure similar to that described in Example 47, above, was followed, but using 22 mg (0.046 mmol) of (4R,6R)-6-{2-[(1S,2S,6S,8S,8aR)-1,2,6,7,8,8a-hexahydro-6-hydroxy-8-(2-butylhexanoyloxy)-2-methyl-1-naphthyl]ethyl}tetrahydro-4-hydroxy-2H-pyran-2-one [prepared as described in Example 32, above], to provide 24 mg of the title compound as a colorless powder.

EXAMPLE 56

Sodium(3R,5R)-3,5-dihydroxy-7-[(1S,2S,6S,8S,8aR)-6-hydroxy-2-methyl-8-hexanoyloxy-1,2,6,7,8,8a-hexahydro-1-naphthyl]heptanoate

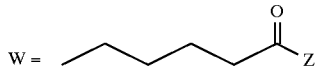

A procedure similar to that described in Example 47, above, was followed, but using 21 mg (0.050 mmol) of (4R,6R)-6-{2-[(1S,2S,6S,8S,8aR)-1,2,6,7,8,8a-hexahydro-6-hydroxy-8-hexanoyloxy-2-methyl-1-naphthyl)ethyl}tetra-hydro-4-hydroxy-2H-pyran-2-one [prepared as described in Example 33, above], to provide 23 mg of the title compound as a colorless powder.

EXAMPLE 57

Sodium(3R,5R)-3,5-dihydroxy-7-[(1S,2S,6S,8S,8aR)-6-hydroxy-2-methyl-8-isovaleryloxy-1,2,6,7,8,8a-hexahydro-1-naphthyl]heptanoate

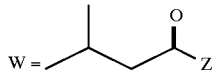

A procedure similar to that described in Example 47, above, was followed, but using 26 mg (0.064 mmol) of (4R,6R)-6-{2-[(1S,2S,6S,8S,8aR)-1,2,6,7,8,8a-hexahydro-6-hydroxy-8-isovaleryloxy-2-methyl-1-naphthyl]ethyl}tetrahydro-4-hydroxy-2H-pyran-2-one [prepared as described in Example 34, above], to provide 29 mg of the title compound as a colorless powder.

EXAMPLE 58

Sodium(3R,5R)-3,5-dihydroxy-7-[(1S,2S,6S,8S,8aR)-6-hydroxy-2-methyl-8-pivaloyloxy-1,2,6,7,8,8a-hexahydro-1-naphthyl]heptanoate

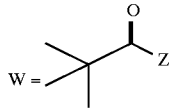

A procedure similar to that described in Example 47, above, was followed, but using 24 mg (0.060 mmol) of (4R,6R)-6-{2-[(1S,2S,6S,8S,8aR)-1,2,6,7,8,8a-hexahydro-6-hydroxy-8-pivaloyloxy-2-methyl-1-naphthyl]ethyl}tetrahydro-4-hydroxy-2H-pyran-2-one [prepared as described in Example 35, above], to provide 29 mg of the title compound as a colorless powder.

EXAMPLE 59

Sodium(3R,5R)-3,5-dihydroxy-7-(1S,2S,6S,8S,8aR)-6-hydroxy-2-methyl-8-(2,2-dimethylvaleryloxy)-1,2,6,7,8,8a-hexahydro-1-naphthyl]heptanoate

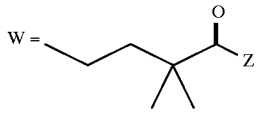

A procedure similar to that described in Example 47, above, was followed, but using 27 mg (0.062 mmol) of (4R,6R)-6-{2-[(1S,2S,6S,8S,8aR)-1,2,6,7,8,8a-hexahydro-6-hydroxy-8-(2,2-dimethylvaleryloxy)-2-methyl-1-naphthyl]ethyl}tetrahydro-4-hydroxy-2H-pyran-2-one [prepared as described in Example 36, above], to provide 29 mg of the title compound as a colorless powder.

EXAMPLE 60

Sodium(3R,5R)-3,5-dihydroxy-7-[(1S,2S,6S,8S,8aR)-6-hydroxy-2-methyl-8-(2-allyl-2-methyl-4-pentenoyloxy)-1,2,6,7,8,8a-hexahydro-1-naphthyl]heptanoate

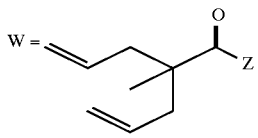

A procedure similar to that described in Example 47, above, was followed, but using 27 mg (0.059 mmol) of (4R,6R)-6-{2-[(1S,2S,6S,8S,8aR)-1,2,6,7,8,8a-hexahydro-6-hydroxy-8-(2-allyl-2-methyl-4-pentenoyloxy)-2-methyl-1-naphthyl]ethyl}tetrahydro-4-hydroxy-2H-pyran-2-one [prepared as described in Example 37, above], to provide 30 mg of the title compound as a colorless powder.

EXAMPLE 61

Sodium(3R,5R)-3,5-dihydroxy-7-[(1S,2S,6S,8S,8aR)-6-hydroxy-2-methyl-8-(2-methyl-2-propylvaleryloxy)-1,2,6,7,8,8a-hexahydro-1-naphthyl]heptanoate

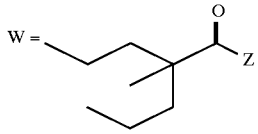

A procedure similar to that described in Example 47, above, was followed, but using 22 mg (0.048 mmol) of (4R,6R)-6-{2-[(1S,2S,6S,8S,8aR)-1,2,6,7,8,8a-hexahydro-6-hydroxy-8-(2-methyl-2-propylvaleryloxy)-2-methyl-1-naphthyl]ethyl}tetrahydro-4-hydroxy-2H-pyran-2-one [prepared as described in Example 38, above], to provide 24 mg of the title compound as a colorless powder.

EXAMPLE 62

Sodium(3R,5R)-3,5-dihydroxy-7-[(1S,2S,6S,8S,8aR)-6-hydroxy-2-methyl-8-(2,2-diethylvaleryloxy)-1,2,6,7,8,8a-hexahydro-1-naphthyl]heptanoate

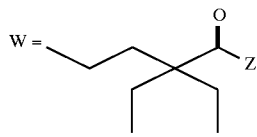

A procedure similar to that described in Example 47, above, was followed, but using 19 mg (0.041 mmol) of (4R,6R)-6-{2-[(1S,2S,6S,8S,8aR)-1,2,6,7,8,8a-hexahydro-6-hydroxy-8-(2,2-diethylvaleryloxy)-2-methyl-1-naphthyl]ethyl}tetrahydro-4-hydroxy-2H-pyran-2-one [prepared as described in Example 39, above], to provide 21 mg of the title compound as a colorless powder.

EXAMPLE 63

Sodium(3R,5R)-3,5-dihydroxy-7-[(1S,2S,6S,8S,8aR)-6-hydroxy-2-methyl-8-(2-isopropyl-3-methylbutyryloxy)-1,2,6,7,8,8a-hexahydro-1-naphthyl]heptanoate

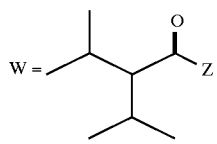

A procedure similar to that described in Example 47, above, was followed, but using 17 mg (0.038 mmol) of (4R,6R)-6-{2-[(1S,2S,6S,8S,8aR)-1,2,6,7,8,8a-hexahydro-6-hydroxy-8-(2-isopropyl-3-methylbutyryloxy)-2-methyl-1-naphthyl]ethyl}tetrahydro-4-hydroxy-2H-pyran-2-one [prepared as described in Example 40, above], to provide 19 mg of the title compound as a colorless powder.

EXAMPLE 64

Sodium(3R,5R)-3,5-dihydroxy-7-[(1S,2S,6S,8S,8aR)-6-hydroxy-2-methyl-8-(2,2-diethyl-4-pentenoyloxy)-1,2,6,7,8,8a-hexahydro-1-naphthyl]heptanoate

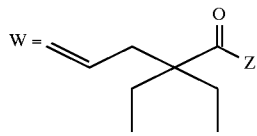

A procedure similar to that described in Example 47, above, was followed, but using 12 mg (0.026 mmol) of (4R,6R)-6-{2-[(1S,2S,6S,8S,8aR)-1,2,6,7,8,8a-hexahydro-6-hydroxy-8-(2,2-diethyl-4-pentenoyloxy)-2-methyl-1-naphthyl]ethyl}tetrahydro-4-hydroxy-2H-pyran-2-one [prepared as described in Example 41, above], to provide 13 mg of the title compound as a colorless powder.

EXAMPLE 65

Sodium(3R,5R)-3,5-dihydroxy-7-[(1S,2S,6S8S,8aR)-6-hydroxy-2-methyl-8-(2-allyl-2-ethyl-4-pentenoyloxy)-1,2,6,7,8,8a-hexahydro-1-naphthyl]heptanoate

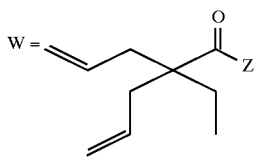

A procedure similar to that described in Example 47, above, was followed, but using 24 mg (0.051 mmol) of (4R,6R)-6-{2-[(1S,2S,6S,8S,8aR)-1,2,6,7,8,8a-hexahydro-6-hydroxy-8-(2-allyl-2-ethyl-4-pentenoyloxy)-2-methyl-1-naphthyl]ethyl}tetrahydro-4-hydroxy-2H-pyran-2-one [prepared as described in Example 42, above], to provide 25 mg of the title compound as a colorless powder.

EXAMPLE 66

Sodium(3R,5R)-3,5-dihydroxy-7-[(1S,2S,6S,8S,8aR)-6-hydroxy-2-methyl-8-(2,2-diallyl-4-pentenoyloxy)-1,2,6,7,8,8a-hexahydro-1-naphthyl]heptanoate

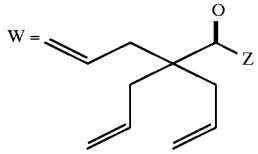

A procedure similar to that described in Example 47, above, was followed, but using 22 mg (0.045 mmol) of (4R,6R)-6-{2-[(1S,2S,6S,8S,8aR)-1,2,6,7,8,8a-hexahydro-6-hydroxy-8-(2,2-diallyl-4-pentenoyloxy)-2-methyl-1-naphthyl]ethyl}tetrahydro-4-hydroxy-2H-pyran-2-one [prepared as described in Example 43, above], to provide 25 mg of the title compound as a colorless powder.

EXAMPLE 67

Sodium(3R,5R)-3,5-dihydroxy-7-[(1S,2S,6S,8S,8aR)-6-hydroxy-2-methyl-8-(2-ethyl-2-methylvaleryloxy)-1,2,6,7,8,8a-hexahydro-1-naphthyl]heptanoate

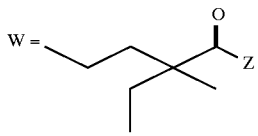

A procedure similar to that described in Example 47, above, was followed, but using 18 mg (0.040 mmol) of (4R,6R)-6-{2-[(1S,2S,6S,8S,8aR)-1,2,6,7,8,8a-hexahydro-6-hydroxy-8-(2-ethyl-2-methylvaleryloxy)-2-methyl-1-naphthyl]ethyl}tetrahydro-4-hydroxy-2H-pyran-2-one [prepared as described in Example 44, above], to provide 20 mg of the title compound as a colorless powder.

The procedure of Example 67, above, may be followed using one of the stereoisomers produced in Example 44,

107 above, as starting material in order to prepare the corresponding stereoisomer of the compound of Example 67, for example as shown in Example 68.

EXAMPLE 68

Sodium(3R,5R)-3,5-dihydroxy-7-[(1S,2S,6S,8S,8aR)-6-hydroxy-2-methyl-8-[(2S)-2-ethyl-2-methylvaleryloxy]-1,2,6,7,8,8a-hexahydro-1-naphthyl]heptanoate

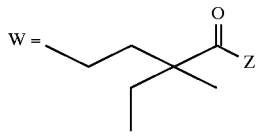

A procedure similar to that described in Example 47, above, was followed, but using 5.8 mg (0.012 mmol) of (4R,6R)-6-{2-[(1S,2S,6S,8S,8aR)-1,2,6,7,8,8a-hexahydro-6-hydroxy-8-[(2S)-2-ethyl-2-methylvaleryloxy]-2-methyl-1-naphthyl]ethyl}tetrahydro-4-hydroxy-2H pyran-2-one [prepared as described in Example 45, above], to provide 6.2 mg of the title compound as a colorless powder.

EXAMPLE 69

Sodium(3R,5R)-3,5-dihydroxy-7-[(1S,2S,6S,8S,8aR)-6-hydroxy-2-methyl-8-[2,2-dimethylhexanoyloxy)-1,2,6,7,8,8a-hexahydro-1-naphthyl]heptanoate

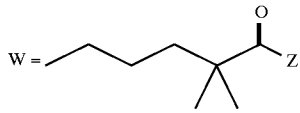

A procedure similar to that described in Example 47, above, was followed, but using 28 mg (0.062 mmol) of (4R,6R)-6-{2-[(1S,2S,6S,8S,8aR)-1,2,6,7,8,8a-hexahydro-6-hydroxy-8-(2,2-dimethylhexanoyloxy)-2-methyl-1-naphthyl]ethyl}tetrahydro-4-hydroxy-2H-pyran-2-one [prepared as described in Example 46, above], to provide 32 mg of the title compound as a colorless powder.

Each of the following Examples 70 to 74 describes the preparation of a compound of the following formula:

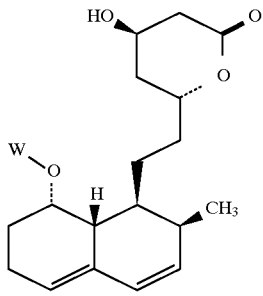

i.e. a compound of formula (IV) in which $R^1$ represents a group of formula (III) and $R^6$ represents a hydrogen atom. Each group W, as defined in the following Examples, is attached to the formula shown above via the bond marked Z.

108

EXAMPLE 70

(4R,6R)-6-{2-[(1S,2S,8S,8aR)-1,2,6,7,8,8a-Hexahydro-8-[(S)-2-methylvaleryloxy]-2-methyl-1-naphthyl]ethyl}tetrahydro-4-hydroxy-2H-pyran-2-one

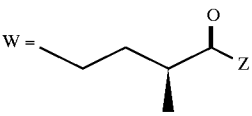

70-(1) (4R,6R)-6-{2-[(1S,2S,8S,8aR)-1,2,6,7,8,8a-Hexahydro-8-[(S)-2-methylvaleryloxy]-2-methyl-1-naphthyl]ethyl}tetrahydro-4-t-butyldimethylsilyloxy-2H-pyran-2-one A procedure similar to that described in Example 4, above, was followed, but using 12.6 g (30.0 mmol) of (4R,6R)-6-{2-[(1S,2S,8S,8aR)-1,2,6,7,8,8a-hexahydro-8-hydroxy-2-methyl-1-naphthyl]ethyl}tetrahydro-4-t-butyldimethylsilyloxy-2H-pyran-2-one (prepared as described in Japanese Patent Kokai Application No. Sho 59-175450] and 4.0 g (29.7 mmol) of (S)-2-methylvaleryl chloride, to provide 12.2 g of the title compound.

Nuclear Magnetic Resonance Spectrum (270 MHz, CDCl$_3$) δ ppm: 1.12 (3H, doublet, J=7.3 Hz); 4.27–4.30 (1H, multiplet); 4.54–4.64 (1H, multiplet); 5.32 (1H, broad singlet); 5.56 (1H, broad singlet); 5.75 (1H, doublet of doublets, J=9.2 & 5.9 Hz); 5.98 (1H, doublet, J=9.2 Hz).

Infrared Absorption Spectrum (CHCl$_3$) $\nu_{max}$ cm$^{-1}$: 2950, 1720, 1250, 1080.

Mass Spectrum (m/e): 519 (M$^+$+1), 477, 435, 387.

$[\alpha]_D^{25}$ +110.6° (c=0.34, acetone).

70-(2) (4R,6R)-6-{2-[(1S,2S,8S,8aR)-1,2,6,7,8,8a-Hexahydro-8-[(S)-2-methylvaleryloxy]-2-methyl-1-naphthyl]ethyl}tetrahydro-4-hydroxy-2H-pyran-2-one A procedure similar to that described in Example 28, above, was followed, but using 12.2 g (23.5 mmol) of (4R,6R)-6-{2-[(1S,2S,8S,8aR)-1,2,6,7,8,8a-hexahydro-8-[(S)-2-methylvaleryloxy]-2-methyl-1-naphthyl]ethyl}tetrahydro-4-t-butyldimethylsilyloxy-2H-pyran-2-one [prepared as described in step (1), above], to provide 5.5 g of the title compound, melting at between 110° and 111.5° C.

Elemental Analysis: Calculated for C$_{24}$H$_{36}$O$_5$: C: 71.26%; H: 8.97%; Found: C: 71.00%; H: 8.82%.

Nuclear Magnetic Resonance Spectrum (270 MHz, CDCl$_3$) δ ppm: 1.12 (3H, doublet, J=6.8 Hz); 4.35–4.40 (1H, multiplet); 4.56–4.66 (1H, multiplet); 5.33 (1H, broad singlet); 5.55 (1H, broad singlet); 5.74 (1H, doublet of doublets, J=9.3 & 5.9 Hz); 5.98 (1H, doublet, J=9.3 Hz).

Infrared Absorption Spectrum (CHCl$_3$) $\nu_{max}$ cm$^{-1}$: 3450, 2950, 1720, 1250, 1080.

Mass Spectrum (m/e): 404 (M$^+$), 270, 255, 229.

$[\alpha]_D^{25}$ +267.8° (c=0.64, acetone).

EXAMPLE 71

(4R,6R)-6-{2-[(1S,2S,8S,8aR)-1,2,6,7,8,8a-Hexahydro-8-(2-ethyl-2-methylbutyryloxy)-2-methyl-1-naphthyl]ethyl}tetrahydro-4-hydroxy-2H-pyran-2-one

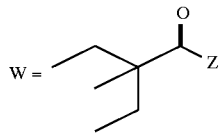

71-(1) (4R,6R)-6-{2-[(1S,2S,8S,8aR)-1,2,6,7,8,8a-Hexahydro-8-(2-ethyl-2-methylbutyryloxy)-2-methyl-1-naphthyl]ethyl}tetrahydro-4-t-butyldimethylsilyloxy-2H-pyran-2-one A procedure similar to that described in Example 4, above, was followed, but using 1.0 g (2.4 mmol) of (4R,6R)-6-{2-[(1S,2S,8S,8aR)-1,2,6,7,8,8a-hexahydro-8-hydroxy-2-methyl-1-naphthyl]ethyl}tetrahydro-4-t-butyldimethylsilyloxy-2H-pyran-2-one [prepared as described in Japanese Patent Kokai Application No. Sho 59-175450] and 1.4 g (9.4 mmol) of 2-ethyl-2-methylbutyryl chloride, to provide 951 mg of the title compound.

Nuclear Magnetic Resonance Spectrum (270 MHz, CDCl$_3$) δ ppm: 4.26–4.29 (1H, multiplet); 4.54–4.61 (1H, multiplet); 5.31 (1H, broad singlet); 5.54 (1H, broad singlet); 5.73 (1H, doublet of doublets, J=9.7 & 6.0 Hz); 5.98 (1H, doublet, J=9.7 Hz).

Infrared Absorption Spectrum (CHCl$_3$) $v_{max}$ cm$^{-1}$: 2950, 1720, 1250, 1150, 1080, 840.

Mass Spectrum (m/e): 532 (M$^+$), 402, 345, 327.

$[\alpha]_D^{25}$ +163.1° (c=0.48, acetone).

71-(2) (4R,6R)-6-{2-[(1S,2S,8S,8aR)-1,2,6,7,8,8a-Hexahydro-8-(2-ethyl-2-methylbutyryloxy)-2-methyl-1-naphthyl]ethyl}tetrahydro-4-hydroxy-2H-pyran-2-one A procedure similar to that described in Example 28, above, was followed, but using 951 mg (1.9 mmol) of (4R,6R)-6-{2-[(1S,2S,8S,8aR)-1,2,6,7,8,8a-hexahydro-8-(2-ethyl-2-methylbutyryloxy)-2-methyl-1-naphthyl]ethyl}tetrahydro-4-t-butyldimethylsilyloxy-2H-pyran-2-one [prepared as described in step (1), above], to provide 581 mg of the title compound, melting at between 61° and 64° C.

Nuclear Magnetic Resonance Spectrum (270 MHz, CDCl$_3$) δ ppm: 0.81 (3H, triplet, J=7.4 Hz); 0.83 (3H, triplet, J=7.4 Hz); 0.90 (3H, doublet, J=7.1 Hz); 1.06 (3H, singlet); 4.37 (1H, broad singlet); 4.57–4.64 (1H, multiplet); 5.34 (1H, broad singlet); 5.55 (1H, broad singlet); 5.74 (1H, doublet of doublets, J=9.7 & 6.0 Hz); 5.99 (1H, doublet, J=9.7 Hz).

Infrared Absorption Spectrum (CHCl$_3$) $v_{max}$ cm$^{-1}$: 3450, 2950, 1720, 1250, 1150, 1080, 840.

Mass Spectrum (m/e): 418 (M$^+$), 400, 369, 288.

Elemental Analysis: Calculated for C$_{25}$H$_{38}$O$_5$: C: 71.74%; H: 9.15%; Found: C: 71.19%; H: 9.29%.

$[\alpha]_D^{25}$ +238.7° (c=0.48, acetone).

EXAMPLE 72

(4R,6R)-6-{2-[(1S,2S,8S,8aR)-1,2,6,7,8,8a-Hexahydro-8-(2-propylvaleryloxy)-2-methyl-1-naphthyl]ethyl}tetrahydro-4-hydroxy-2H-pyran-2-one

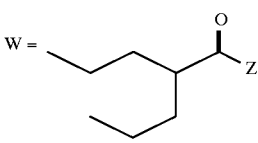

72-(1) (4R,6R)-6-{2-[(1S,2S,8S,8aR)-1,2,6,7,8,8a-Hexahydro-8-(2-propylvaleryloxy)-2-methyl-1-naphthyl]ethyl}tetrahydro-4-t-butyldimethylsilyloxy-2H-pyran-2-one A procedure similar to that described in Example 3, above, was followed, but using 1.0 g (2.4 mmol) of (4R,6R)-6-{2-[(1S,2S,8S,8aR)-1,2,6,7,8,8a-hexahydro-8-hydroxy-2-methyl-1-naphthyl]ethyl}tetrahydro-4-t-butyldimethylsilyloxy-2H-pyran-2-one [prepared as described in Japanese Patent Kokai Application No. Sho 59-175450] and 686 mg (4.8 mmol) of 2-propylvaleric acid, to provide 1.3 g of the title compound.

Nuclear Magnetic Resonance Spectrum (270 MHz, CDCl$_3$) δ ppm: 4.25–4.31 (1H, multiplet); 4.53–4.61 (1H, multiplet); 5.35 (1H, broad singlet); 5.55 (1H, broad singlet); 5.74 (1H, doublet of doublets, J=9.8 & 5.9 Hz); 5.96 (1H, doublet, J=9.8 Hz).

Infrared Absorption Spectrum (CHCl$_3$) $v_{max}$ cm$^{-1}$: 2950, 1720, 1250, 1080, 838.

Mass Spectrum (m/e): 546 (M$^+$), 402, 345, 327.

$[\alpha]_D^{25}$ +116.3° (c=0.51, acetone).

72-(2) (4R,6R)-6-{2-[(1S,2S,8S,8aR)-1,2,6,7,8,8a-Hexahydro-8-(2-propylvaleryloxy)-2-methyl-1-naphthyl]ethyl}tetrahydro-4-hydroxy-2H-pyran-2-one A procedure similar to that described in Example 28, above, was followed, but using 1.20 g (2.2 mmol) of (4R,6R)-6-{2-[(1S,2S,8S,8aR)-1,2,6,7,8,8a-hexahydro-8-(2-propylvaleryloxy)-2-methyl-1-naphthyl]ethyl}tetrahydro-4-t-butyldimethylsilyloxy-2H-pyran-2-one [prepared as described in step (1), above], to provide 650 mg of the title compound, melting at between 92° and 94° C.

Nuclear Magnetic Resonance Spectrum (270 MHz, CDCl$_3$) δ ppm: 4.37 (1H, broad singlet); 4.57–4.64 (1H, multiplet); 5.38 (1H, broad singlet); 5.56 (1H, broad singlet); 5.75 (1H, doublet of doublets, J=9.6 & 6.0 Hz); 5.97 (1H, doublet, J=9.6 Hz).

Infrared Absorption Spectrum (KBr) $v_{max}$ cm$^{-1}$: 3450, 2950, 1720.

Mass Spectrum (m/e): 432 (M$^+$), 414, 368, 357.

Elemental Analysis: Calculated for C$_{26}$H$_{40}$O$_5$.½H$_2$O: C: 70.72%; H: 9.36%; Found: C: 70.80%; H: 9.31%.

$[\alpha]_D^{25}$ +223.3° (c=0.51, acetone).

EXAMPLE 73

(4R,6R)-6-{2-[(1S,2S,8S,8aR)-1,2,6,7,8,8a-Hexahydro-8-(2,2-diethylbutyryloxy)-2-methyl-1-naphthyl]ethyl}tetrahydro-4-hydroxy-2H-pyran-2-one

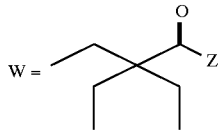

73-(1) (4R,6R)-6-{2-[(1S,2S,8S,8aR)-1,2,6,7,8,8a-Hexahydro-8-(2,2-diethylbutyryloxy)-2-methyl-1-naphthyl]ethyl}tetrahydro-4-t-butyldimethylsilyloxy-2H-pyran-2-one A procedure similar to that described in Example 6, above, was followed, but using 1.26 g (3.0 mmol) of (4R,6R)-6-{2-[(1S,2S,8S,8aR)-1,2,6,7,8,8a-hexahydro-8-hydroxy-2-methyl-1-naphthyl]ethyl}tetrahydro-4-t-butyldimethylsilyloxy-2H-pyran-2-one (prepared as described in Japanese Patent Kokai Application No. Sho 59-175450] and 2.22 g (13.6 mmol) of 2,2-diethylbutyryl chloride, to provide 800 mg of the title compound.

Nuclear Magnetic Resonance Spectrum (400 MHz, CDCl$_3$) δ ppm: 0.75 (9H, triplet, J=7.5 Hz); 1.56 (6H, quartet, J=7.5 Hz); 4.26–4.30 (1H, multiplet); 4.54–4.61 (1H, multiplet); 5.34 (1H, broad singlet); 5.55 (1H, broad singlet); 5.74 (1H, doublet of doublets, J=9.6 & 6.0 Hz); 5.98 (1H, doublet, J=9.6 Hz).

Infrared Absorption Spectrum (CHCl$_3$) $v_{max}$ cm$^{-1}$: 2875, 1715, 1255, 1080, 840.

Mass Spectrum (m/e): 546 (M$^+$), 489, 387, 345, 327.

$[\alpha]_D^{25}$ +185.0° (c=0.97, acetone).

73-(2) (4R,6R)-6-{2-[(1S,2S,8S,8aR)-1,2,6,7,8,8a-Hexahydro-8-(2,2-diethylbutyryloxy)-2-methyl-1-naphthyl]ethyl}tetrahydro-4-hydroxy-2H-pyran-2-one A procedure similar to that described in Example 28, above, was followed, but using 830 mg (1.5 mmol) of (4R,6R)-6-{2-[(1S,2S,8S,8aR)-1,2,6,7,8,8a-hexahydro-8-(2,2-diethylbutyryloxy)-2-methyl-1-naphthyl]ethyl}tetrahydro-4-t-butyldimethylsilyloxy-2H-pyran-2-one [prepared as described in step (1), above], to provide 575 mg of the title compound, melting at between 65° and 68° C.

Elemental Analysis: Calculated for C$_{26}$H$_{40}$O$_5$: C: 72.19%; H: 9.32%; Found: C: 72.00%; H: 9.56%.

Nuclear Magnetic Resonance Spectrum (400 MHz, hexadeuterated dimethyl sulfoxide) δ ppm: 0.71 (9H, triplet, J=7.4 Hz); 0.84 (3H, doublet, J=6.9 Hz); 1.48 (6H, quartet, J=7.4 Hz); 4.08–4.10 (1H, multiplet); 4.42–4.48 (1H, multiplet); 5.17 (1H, doublet, J=3.2 Hz, interchangeable with D$_2$O); 5.23 (1H, broad singlet); 5.53 (1H, broad singlet); 5.74 (1H, doublet of doublets, J=9.6 & 6.0 Hz); 5.95 (1H, doublet, J=9.6 Hz).

Infrared Absorption Spectrum (CHCl$_3$) $v_{max}$ cm$^{-1}$: 3350, 2880, 1710, 1220.

Mass Spectrum (m/e): 432 (M$^+$), 353, 288, 270, 210.

$[\alpha]_D^{25}$ +252.5° (c=0.63, acetone).

EXAMPLE 74

(4R,6R)-6-{2-[(1S,2S,8S,8aR)-1,2,6,7,8,8a-Hexahydro-8-(2,2-diethyl-4-pentenoyloxy)-2-methyl-1-naphthyl]ethyl}tetrahydro-4-hydroxy-2H-pyran-2-one

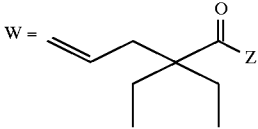

74-(1) (4R,6R)-6-{2-[(1S,2S,8S,8aR)-1,2,6,7,8,8a-Hexahydro-8-(2,2-diethyl-4-pentenoyloxy)-2-methyl-1-naphthyl]ethyl}tetrahydro-4-t-butyldimethylsilyloxy-2H-pyran-2-one A procedure similar to that described in Example 6, above, was followed, but using 1.26 g (3.0 mmol) of (4R,6R)-6-{2-[(1S,2S,8S,8aR)-1,2,6,7,8,8a-hexahydro-8-hydroxy-2-methyl-1-naphthyl]ethyl}tetrahydro-4-t-butyldimethylsilyloxy-2H-pyran-2-one [prepared as described in Japanese Patent Kokai Application No. Sho 59-175450] and 2.09 g (12.2 mmol) of 2,2-diethyl-4-pentenoyl chloride, to provide 1.30 g of the title compound.

Nuclear Magnetic Resonance Spectrum (400 MHz, CDCl$_3$) δ ppm: 0.778 (3H, triplet, J=7.4 Hz); 0.784 (3H, triplet, J=7.4 Hz); 2.31 (2H, doublet, J=7.2 Hz); 4.27–4.30 (1H, multiplet); 4.55–4.61 (1H, multiplet); 5.01–5.09 (2H, multiplet); 5.36 (1H, broad singlet); 5.54 (1H, broad singlet); 5.59–5.69 (1H, multiplet); 5.74 (1H, doublet of doublets, J=9.7 & 6.0 Hz); 5.98 (1H, doublet, J=9.7 Hz).

Infrared Absorption Spectrum (CHCl$_3$) $v_{max}$ cm$^{-1}$: 2875, 1715, 1255, 1080, 840.

Mass Spectrum (m/e): 558 (M$^+$), 501, 387, 345, 327.

$[\alpha]_D^{25}$ +209.0° (c=0.41, acetone).

74-(2) (4R,6R)-6-{2-[(1S,2S,8S,8aR)-1,2,6,7,8,8a-Hexahydro-8-(2,2-diethyl-4-pentenoyloxy)-2-methyl-1-naphthyl]ethyl}tetrahydro-4-hydroxy-2H-pyran-2-one A procedure similar to that described in Example 28, above, was followed, but using 1.15 g (2.1 mmol) of (4R,6R)-6-{2-[(1S,2S,8S,8aR)-1,2,6,7,8,8a-hexahydro-8-(2,2-diethyl-4-pentenoyloxy)-2-methyl-1-naphthyl]ethyl}tetrahydro-4-t-butyldimethylsilyloxy-2H-pyran-2-one [prepared as described in step (1), above], to provide 770 mg of the title compound.

Elemental Analysis: Calculated for C$_{27}$H$_{40}$O$_5$: C: 72.94%; H: 9.07%; Found: C: 72.54%; H: 9.33%.

Nuclear Magnetic Resonance Spectrum (400 MHz, hexadeuterated dimethyl sulfoxide) δ ppm: 0.74 (6H, triplet, J=7.3 Hz); 0.84 (3H, doublet, J=7.0 Hz); 2.23 (2H, doublet, J=7.3 Hz); 4.08–4.12 (1H, multiplet); 4.43–4.49 (1H, multiplet); 5.04–5.11 (2H, multiplet); 5.18 (1H, d, J=3.4 Hz, interchangeable with D$_2$O); 5.24 (1H, broad singlet); 5.54 (1H, broad singlet); 5.55–5.65 (1H, multiplet); 5.73 (1H, doublet of doublets, J=9.6 & 6.0 Hz); 5.95 (1H, doublet, J=9.6 Hz).

Infrared Absorption Spectrum (CHCl$_3$) $v_{max}$ cm$^{-1}$: 3350, 2880, 1710, 1220.

Mass Spectrum (m/e): 445 (M$^+$), 427, 288, 270, 210.

$[\alpha]_D^{25}$ +259.00° (c=0.46, acetone).

Each of the following Examples 75 to 79 describes the preparation of compounds of the following formula:

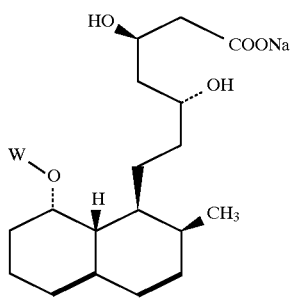

i.e. compounds of formula (IV) in which $R^1$ represents a group of formula (II), $R^5$ represents a sodium atom and $R^6$ represents a hydrogen atom. Each group W, as defined in the following Examples, is attached to the formula shown above via the bond marked Z.

EXAMPLE 75

Sodium(3R,5R)-3,5-dihydroxy-7-{(1S,2S,8S,8aR)-2-methyl-8-[(S)-2-methylvaleryloxy]-1,2,6,7,8,8a-hexahydro-1-naphthyl}heptanoate

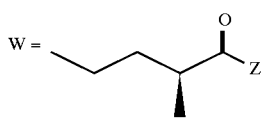

A procedure similar to that described in Example 47, above, was followed but using 1.01 g (2.5 mmol) of (4R,6R)-6-{2-[(1S,2S,8S,8aR)-1,2,6,7,8,8a-hexahydro-8-[(S)-2-methylvaleryloxy]-2-methyl-1-naphthyl]ethyl}tetrahydro-4-hydroxy-2H-pyran-2-one [prepared as described in Example 70, above], to provide 1.12 g of the title compound as a colorless powder.

EXAMPLE 76

Sodium(3R,5R)-3,5-dihydroxy-7-[(1S,2S,8S,8aR)-2-methyl-8-(2-ethyl-2-methylbutyryloxy)-1,2,6,7,8,8a-hexahydro-1-naphthyl]heptanoate

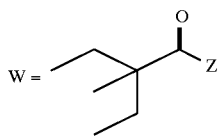

A procedure similar to that described in Example 47, above, was followed, but using 210 mg (0.50 mmol) of (4R,6R)-6-{2-[(1S,2S,8S,8aR)-1,2,6,7,8,8a-hexahydro-8-(2-ethyl-2-methylbutyryloxy)-2-methyl-1-naphthyl]ethyl}tetrahydro-4-hydroxy-2H-pyran-2-one [prepared as described in Example 71, above], to provide 227 mg of the title compound as a colorless powder.

EXAMPLE 77

Sodium(3R,5R)-3,5-dihydroxy-7-[(1S,2S,8S,8aR)-2-methyl-8-(2-propylvaleryloxy)-1,2,6,7,8,8a-hexahydro-1-naphthyl]heptanoate

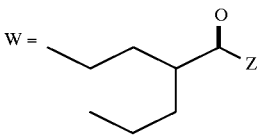

A procedure similar to that described in Example 47, above, was followed, but using 200 mg (0.45 mmol) of (4R,6R)-6-{2-[(1S,2S,8S,8aR)-1,2,6,7,8,8a-hexahydro-8-(2-propylvaleryloxy)-2-methyl-1-naphthyl]ethyl}tetrahydro-4-hydroxy-2H-pyran-2-one [prepared as described in Example 72, above], to provide 223 mg of the title compound as a colorless powder.

EXAMPLE 78

Sodium(3R,5R)-3,5-dihydroxy-7-[(1S,2S,8S,8aR)-2-methyl-8-(2,2diethylbutyryloxy)-1,2,6,7,8,8a-hexahydro-1-naphthyl]heptanoate

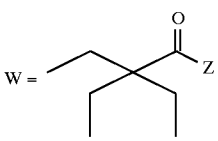

A procedure similar to that described in Example 47, above was followed, but using 20 mg (0.047 mmol) of (4R,6R)-6-{2-[(1S,2S,8S,8aR)-1,2,6,7,8,8a-hexahydro-8-(2,2-diethylbutyryloxy)-2-methyl-1-naphthyl]ethyl}tetrahydro-4-hydroxy-2H-pyran-2-one (prepared as described in Example 73, above], to provide 22 mg of the title compound as a colorless powder.

EXAMPLE 79

Sodium(3R,5R)-3,5-dihydroxy-7-[(1S,2S,8S,8aR)-2-methyl-8-(2,2-diethyl-4-pentenoyloxy)-1,2,6,7,8,8a-hexahydro-1-naphthyl]heptanoate

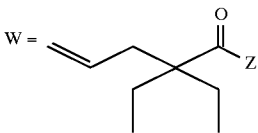

A procedure similar to that described in Example 47, above, was followed, but using 22 mg (0.048 mmol) of (4R,6R)-6-{2-[(1S,2S,8S,8aR)-1,2,6,7,8,8a-hexahydro-8-(2,2-diethyl-4-pentenoyloxy)-2-methyl-1-naphthyl]ethyl}tetrahydro-4-hydroxy-2H-pyran-2-one [prepared as described in Example 74, above], to provide 23 mg of the title compound as a colorless powder.

Each of the following Examples 80 to 84 describes the preparation of compounds of the following formula:

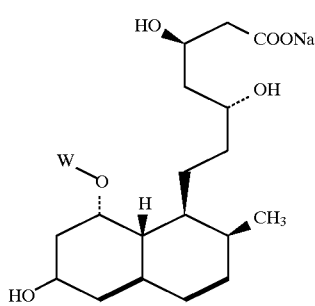

i.e. compounds of formula (I) in which R¹ represents a group of formula (II), R⁵ represents a sodium atom and R⁶ represents a hydrogen atom. Each group W, as defined in the following Examples, is attached to the formula shown above via the bond marked Z.

EXAMPLE 80

Sodium(3R,5R)-3,5-dihydroxy-7-{(1S,2S,6S,8S,8aR)-6-hydroxy-2-methyl-8-[(S)-2-methylvaleryloxy]-1,2,6,7,8,8a-hexahydro-1-naphthyl}heptanoate

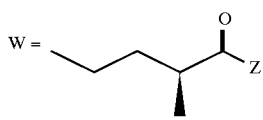

Method (1)

Each of twenty 500 ml Erlenmeyer flasks, containing 100 ml per flask of TS-C medium having the composition shown below, was inoculated with one platinum loop of an inoculum of *Mucor hiemalis* Wehmer SANK 36372 (FERM BP-4108). The inoculated flasks were incubated for 3 days at 26° C., on a rotary shaker maintained at a speed of 200 revolutions per minute.

| TS-C Culture Medium | |
|---|---|
| Glucose | 1% (w/v) |
| Polypeptone | 0.2% (w/v) |
| (Daigo Nutrition Chemicals Co.) | |
| Meat extract | 0.1% (w/v) |
| Yeast extract (Difco) | 0.1% (w/v) |
| Tap water | to 100% |
| pH: not adjusted | |

At the end of this time, 0.1 ml of a solution of (4R,6R)-6-{2-[(1S,2S,8S,8aR)-1,2,6,7,8,8a-hexahydro-8-[(S)-2-methylvaleryloxy]-2-methyl-1-naphthyl]ethyl}tetrahydro-4-hydroxy-2H-pyran-2-one [prepared as described in Example 70, above], in dimethyl sulfoxide, was added to each of the flasks, with the result that the final concentration of the compound in the culture medium was 0.01% w/v. The cultivation was then continued for a further 3 days, under the conditions outlined above.

At the end of this further period of cultivation, the fermentation broth was filtered and the filtrate was adsorbed onto a column containing 200 ml of Diaion HP-20™ resin (Mitsubishi Kasei Corporation). The resin was then washed with 500 ml of distilled water, after which fractions containing the title compound were eluted from the column with 600 ml of a 50% v/v aqueous solution of acetone. The eluates were combined, and the resulting solution was concentrated to dryness by evaporation under reduced pressure. The resulting residue was purified by chromatography through a preparative ODS column (ODS-H-5251 is a trademark for a product of Senshu Scientific Co., Ltd.) using a 450:550:1 by volume mixture of acetonitrile, water and acetic acid as the eluent. The chromatography was monitored by ultraviolet absorption at 237 nm. The pH of the resulting eluate was adjusted to pH 8.0 by the addition of an appropriate amount of an aqueous solution of sodium hydroxide, and the resulting mixture was concentrated to dryness by evaporation under reduced pressure. The residue was then dissolved in 20 ml of water and the solution was adsorbed onto a column containing 20 ml of Diaion HP-20™. The resin was washed with 50 ml of water, after which the resin was eluted with 60 ml of a 50% v/v aqueous solution of acetone to give 8 mg of a substantially pure form of the title compound.

Method (2)

One platinum loop of an inoculum of *Streptomyces carbophilus* SANK 62585 (FERM BP-4128) was inoculated into a 500 ml Erlenmeyer flask containing 100 ml of SC medium, having the composition shown below. The inoculated flask was then incubated at 28° C. on a rotary shaker maintained at a speed of 200 revolutions per minute.

| SC Medium | |
|---|---|
| Yeast extract (Difco) | 0.1% (w/v) |
| Polypeptone | 1.0% (w/v) |
| (Daigo Nutrition Chemicals Co.) | |
| Glucose | 2.0% (w/v) |
| Tap water | to 100% |
| pH 7.0 (before sterilization). | |

After incubation of the inoculated medium for 3 days, a portion of that medium was transferred to each of twenty 500 ml Erlenmeyer flasks, containing 100 ml of SC medium per flask, such that the concentration of the inoculated seed medium in the fresh medium was 5.0% w/v. This freshly inoculated medium was then incubated for a further three days under the conditions outlined above.

At the end of the incubation period, an amount of an aqueous solution of sodium (3R,5R)-3,5-dihydroxy-7-{(1S,2S,8S,8aR)-2-methyl-8-[(S)-2-methylvaleryloxy]-1,2,6,7,8,8a-hexahydro-1-naphthyl}heptanoate [prepared as described in Example 75, above] was added to the medium, such that the final concentration of that compound in the resulting solution was 0.01% w/v. Cultivation was then continued for a further period of 3 days under the conditions outlined above.

At the end of the cultivation period, the fermentation broth was filtered and the filtrate was adsorbed onto a column containing 200 ml of nonionic Diaion HP-20™. The resin was washed with 300 ml of distilled water, after which fractions containing the title compound were eluted with 400 ml of a 50% v/v aqueous acetone solution. The fractions obtained were combined and the resulting eluate was concentrated to dryness by evaporation under reduced pressure. The residue was then purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm.

The pH of the combined fractions containing the purified compound was then adjusted to pH 8.0 by the addition of an appropriate amount of an aqueous solution of sodium hydroxide, and the resulting mixture was concentrated to dryness by evaporation under reduced pressure. The resulting residue was dissolved in 20 ml of water, after which the solution was adsorbed onto a column 20 ml of Diaion HP-20™. The resin was washed with 30 ml of water and then eluted with 100 ml of a 50% v/v aqueous acetone solution to give 10 mg of a substantially pure form of the title compound.

The physico-chemical properties of the compound thus obtained were shown to be identical to those of the compound of Example 49, above.

EXAMPLE 81

Sodium(3R,5R)-3,5-dihydroxy-7-[(1S,2S,6S,8S, 8aR)-6-hydroxy-2-methyl-8-(2-ethyl-2-methylbutyryloxy)-1,2,6,7,8,8a-hexahydro-1-naphthyl]heptanoate

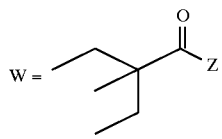

Method 1

One platinum loop of an inoculum of *Amycolata autotrophica* SANK 62981 (FERM BP-4105) was inoculated into a 500 ml Erlenmeyer flask containing 100 ml of Yeast MY medium, having the composition shown below. The inoculated flask was incubated at 28° C. on a rotary shaker maintained at a speed of 200 revolutions per minute.

| Yeast MY medium | |
|---|---|
| Yeast extract (Difco) | 0.3% (w/v) |
| Malt extract (Difco) | 0.3% (w/v) |
| Polypeptone (Daigo Nutrition Chemicals Co.) | 0.5% (w/v) |
| Glucose | 1.0% (w/v) |
| Tap water | to 100% |

The pH of medium was not adjusted.

After incubation of the inoculated seed medium for 3 days, the seed medium was divided and transferred to twenty 500 ml Erlenmeyer flasks, containing 100 ml of Yeast MY medium per flask, such that the concentration of the seed medium in the fresh Yeast MY medium was 0.5% w/v. The flasks were then incubated for a further 2 days under the conditions outlined above.

At the end of the incubation period, an amount of an aqueous solution of sodium (3R,5R)-3,5-dihydroxy-7-[(1S, 2S,8S,8aR)-2-methyl-8-(2-ethyl-2-methylbutyryloxy)-1,2, 6,7,8,8a-hexahydro-1-naphthyl]heptanoate [prepared as described in Example 76, above], was added to the culture broth such that the final concentration of that compound in the resulting solution was 0.01% w/v. Cultivation was then continued for a further period of 5 days, under the conditions outlined above.

At the end of the cultivation period, the fermentation broth was filtered and the filtrate was adsorbed onto a column containing 200 ml of Diaion HP-20™. The resin was washed with 300 ml of distilled water, after which fractions containing the title compound were eluted with 400 ml of a 50% v/v aqueous acetone solution.

The resulting eluate was concentrated to dryness by evaporation under reduced pressure and the residue was then purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The pH of the eluate obtained from the chromatography was then adjusted to pH 8.0 by the addition of an appropriate amount of an aqueous solution of sodium hydroxide, after which the solution was concentrated to dryness by evaporation under reduced pressure. The concentrate was dissolved in 20 ml of water and the solution was then adsorbed onto a column containing 20 ml of Diaion HP-20™. The resin was washed with 30 ml of water and then eluted with 100 ml of a 50% v/v aqueous acetone solution to give 5.1 mg of a substantially pure form of the title compound.

Method 2

One platinum loop of an inoculum of *Mucor hiemalis* Wehmer SANK 36372 (FERM BP-4108) was inoculated into each of twenty 500 ml Erlenmeyer flasks, containing 100 ml of TS-C medium per flask, and the inoculated flasks were incubated at 26° C. on a rotary shaker maintained at a speed of 200 revolutions per minute.

After 3 days of incubation under these conditions, 0.1 ml of a solution of (4R,6R)-6-{2-[(1S,2S,8S,8aR)-1,2,6,7,8,8a-hexahydro-8-[(S)-2-methylvaleryloxy]-2-methyl-1-naphthyl]ethyl}tetrahydro-4-hydroxy-2H-pyran-2-one [prepared as described in Example 70, above], in dimethyl sulfoxide was added to the medium, such that the final concentration of that compound in the medium was 0.01% w/v. The incubation was then continued for a further 3 days under the conditions outlined above.

At the end of the incubation period, the fermentation broth was filtered and the filtrate was adsorbed onto a column containing 200 ml of Diaion HP-20™. The resin was washed with 300 ml of distilled water, after which the fractions containing the title compound were eluted with 400 ml of a 50% v/v aqueous acetone solution. The resulting eluate was then concentrated to dryness by evaporation under reduced pressure, and the concentrate was purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The pH of the resulting eluate was then adjusted to pH 8.0, by the addition of an appropriate amount of an aqueous solution of sodium hydroxide, after which the solution was concentrated to dryness by evaporation under reduced pressure. The concentrate was then dissolved in 20 ml of water and the solution was adsorbed onto a column containing 20 ml of Diaion HP-20™. The resin was washed with 30 ml of water, and then eluted with 100 ml of a 50% v/v aqueous acetone solution, to give 48 mg of a substantially pure form of the title compound.

The physico-chemical properties of the title compound obtained in this manner were identical with those of the compound of Example 51, above.

Method 3

One platinum loop of an inoculum of *Syncephalastrum nigricans* SANK 42372 (FERM BP-4106) was used to inoculate 100 ml of TS-C medium in a 500 ml Erlenmeyer flask. The inoculated medium was then incubated at 26° C. on a rotary shaker maintained at a speed of 200 revolutions per minute.

After incubation under these conditions for a period of 3 days, 0.1 ml of a solution of (4R,6R)-6-{2-[(1S,2S,8S,8aR)-1,2,6,7,8,8a-hexahydro-8-(2-ethyl-2-methylbutyryloxy)-2-methyl-1-naphthyl]ethyl}tetrahydro-4-hydroxy-2H-pyran-2-one [prepared as described in Example 71, above], in dimethyl sulfoxide was added to the medium, such that the final concentration of that compound in the medium was 0.01% w/v. Cultivation was then continued for a further 9 days under the conditions outlined above.

At the end of this period of cultivation, the fermentation broth was filtered and the filtrate was adsorbed onto a column containing 200 ml of Diaion HP-20™. The resin was then washed with 300 ml of distilled water, after which fractions containing the title compound were eluted with 600 ml of a 50% v/v aqueous acetone solution. The resulting eluates were combined and then concentrated to dryness by evaporation under reduced pressure. The residue obtained was purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The eluate obtained from the chromatography was then neutralized by mixing the eluate, without further purification, with a 0.1M aqueous solution (pH 8.0) of sodium dihydrogenphosphate and sodium hydroxide. The pH of the fractions containing the title compound was then adjusted to pH 8.0 and the mixture was concentrated to dryness by evaporation under reduced pressure. The resulting residue was dissolved in 20 ml of water, after which the solution was adsorbed onto a column containing 20 ml of Diaion HP-20™. The resin was then washed with 30 ml of distilled water and eluted with 100 ml of a 50% v/v aqueous acetone solution to give 24.1 mg of a substantially pure form of the title compound.

Nuclear Magnetic Resonance Spectrum (360 MHz, CD$_3$OD) δ ppm: 0.85–0.92 (6H, multiplet); 0.92 (3H, doublet, J=7.1 Hz); 1.15–1.74 (14H, multiplet); 1.76 (1H, multiplet); 1.92 (1H, doubled doublet of doublets, J=15.4 & 5.9 & 2.1 Hz); 2.15–2.50 (6H, multiplet); 3.69 (1H, multiplet); 4.10 (1H, multiplet); 4.25 (1H, multiplet); 5.33 (1H, multiplet); 5.65 (1H, multiplet); 5.95 (1H, doublet of doublets, J=9.7 & 6.1 Hz); 6.02 (1H, doublet, J=9.7 Hz).

Molecular weight: 488 (determined by High Resolution Fast Atom Bombardment Mass Spectrometry as C$_{26}$H$_{41}$O$_7$Na).

$[\alpha]_D^{25}$ +201.1° (c=0.36, methanol)

EXAMPLE 82

Sodium(3R,5R)-3,5-dihydroxy-7-[(1S,2S,6S,8S,8aR)-6-hydroxy-2-methyl-8-(2-propylvaleryloxy)-1,2,6,7,8,8a-hexahydro-1-naphthyl]heptanoate

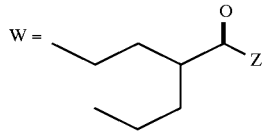

Method 1

One platinum loop of an inoculum of *Mucor hiemalis* Wehmer SANK 36372 (FERM BP-4108) was used to inoculate 100 ml of TS-C medium, having the composition shown in Example 80, in each of twenty 500 ml Erlenmeyer flasks. The inoculated flasks were then incubated at 26° C. on a rotary shaker maintained at a speed of 200 revolutions per minute.

At the end of a three day period of incubation, 0.1 ml of a solution of (4R,6R)-6-{2-[(1S,2S,8S,8aR)-1,2,6,7,8,8a-hexahydro-8-(2-propylvaleryloxy)-2-methyl-1-naphthyl]ethyl}tetrahydro-4-hydroxy-2H-pyran-2-one [prepared as described in Example 72, above], in dimethyl sulfoxide was added to the medium, such that the final concentration of that compound in the medium was 0.01% w/v. Cultivation was then continued for a further 3 days under the conditions outlined above.

At the end of this additional cultivation period, the fermentation broth was filtered and the filtrate was adsorbed onto a column containing 200 ml of Diaion HP-20™. The resin was washed with 500 ml of distilled water, after which fractions containing the title compound were eluted with 600 ml of a 50% v/v aqueous acetone solution. The desired fractions were then combined, after which the combined eluate was concentrated to dryness by evaporation under reduced pressure. The resulting residue was then purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The pH of the eluate was then adjusted to pH 8.0 by the addition of an appropriate amount of an aqueous solution of sodium hydroxide, after which the mixture was concentrated to dryness by evaporation under reduced pressure. The resulting residue was dissolved in 20 ml of water and the solution obtained was adsorbed onto a column containing 20 ml of Diaion HP-20™. The resin was washed with 50 ml of water, after which the resin was eluted with 60 ml of a 50% v/v aqueous acetone solution to give 48 mg of a substantially pure form of the title compound.

The physico-chemical properties of the compound obtained in this manner were identical with those of the compound of Example 50.

Method 2

One platinum loop of an inoculum of *Syncephalastrum racemosum* (Cohn) Schroeter SANK 41872 (FERM BP-4107) was used to inoculate 100 ml of TS-C medium, having the composition shown in Example 80, above, in each of twenty 500 ml Erlenmeyer flasks. The inoculated flasks were then incubated at 26° C. on a rotary shaker maintained at a speed of 200 revolutions per minute.

At the end of a 3 day period of incubation, 0.1 ml of a solution of (4R,6R)-6-{2-[(1S,2S,8S,8aR)-1,2,6,7,8,8a-hexahydro-8-(2-propylvaleryloxy)-2-methyl-1-naphthyl]ethyl}tetrahydro-4-hydroxy-2H-pyran-2-one [prepared as described in Example 72, above], in dimethyl sulfoxide was added to the medium, such that the final concentration of that compound in the medium was 0.01% w/v. Cultivation was then continued for a further 7 days at 26° C. on a rotary shaker at a speed of 200 revolutions per minute.

At the end of this additional cultivation period, the fermentation broth was filtered and the filtrate was adsorbed onto a column containing 200 ml of Diaion HP-20™. The resin was washed with 300 ml of distilled water, after which fractions containing the title compound were eluted with 600 ml of a 50% v/v aqueous acetone solution. The eluates obtained were combined and then concentrated to dryness by evaporation under reduced pressure. The resulting residue was purified by chromatography through a preparative ODS column (ODS-H-5251™, Senshu Scientific Co., Ltd.) using a 450:550:1 by volume mixture of acetonitrile, water and acetic acid as the eluent. The desired fractions eluted with an ultraviolet absorption at 237 nm. The eluate obtained was neutralized by mixing, without further purification, with a 0.1M aqueous solution of sodium dihydrogenphosphate (pH 8) and sodium hydroxide. The pH of the fractions containing the title compound was adjusted to pH 8.0, after which the mixture was concentrated to dryness by evaporation under reduced pressure. The resulting residue was dissolved in 20 ml of water and the solution was then adsorbed onto a column containing 20 ml of Diaion HP-20™. The resin was washed with 50 ml of water and then eluted with 100 ml of a 50% v/v aqueous acetone solution, to give 33 mg of a substantially pure form of the title compound.

Nuclear Magnetic Resonance Spectrum (360 MHz, CD$_3$OD) δ ppm: 0.83 (6H, triplet, J=7.4 Hz); 0.91 (3H, doublet, J=7.2 Hz); 1.07 (3H, singlet); 1.2–1.9 (11H, multiplet); 1.92 (1H, doubled doublet of doublets, J=15.4 & 6.1 & 2.1 Hz); 2.2–2.5 (5H, multiplet); 3.68 (1H, multiplet); 4.10 (1H, mulitplet) 4.28 (1H, multiplet); 5.27 (1H, multiplet); 5.64 (1H, multiplet); 5.94 (1H, doublet of doublets, J=9.7 & 6.1 Hz); 6.02 (1H, doublet, J=9.7 Hz).

Molecular weight: 474 (determined by High Resolution Fast Atom Bombardment Mass Spectrometry as C$_{25}$H$_{39}$O$_7$Na).

$[\alpha]_D^{25}$ +203.0° (c=0.37, methanol).

EXAMPLE 83

Sodium(3R,5R)-3,5-dihydroxy-7-[(1S,2S,6S,8S, 8aR)-6-hydroxy-2-methyl-8-(2,2-diethylbutyryloxy)- 1,2,6,7,8,8a-hexahydro-1-naphthyl]heptanoate

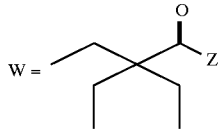

Method 1

One platinum loop of an inoculum of *Mucor hiemalis* Wehmer SANK 36372 (FERM BP-4108) was used to inoculate 100 ml of TS-C medium, having the composition shown in Example 80, above, in each of twenty 500 ml Erlenmeyer flasks. The inoculated flasks were incubated at 26° C. on a rotary shaker maintained at a speed of 200 revolutions per minute.

At the end of a 3 day incubation period, 0.1 ml of a solution of (4R,6R)-6-{2-[(1S,2S,8S,8aR)-1,2,6,7,8,8a-hexahydro-8-(2,2-diethylbutyryloxy)-2-methyl-1-naphthyl] ethyl}tetrahydro-4-hydroxy-2H-pyran-2-one [prepared as described in Example 73, above] in dimethyl sulfoxide was added to the medium, such that the final concentration of that compound in the medium was 0.01% w/v. Cultivation was then continued for a further 3 days at 26° C. on a rotary shaker maintained at a speed of 200 revolutions per minute.

At the end of this time, the fermentation broth was filtered and the filtrate was adsorbed onto a column containing 200 ml of Diaion HP-20™. The resin was washed with 500 ml of distilled water and fractions containing the title compound were eluted with 800 ml of a 50% v/v aqueous acetone solution. The desired fractions were combined and the resulting solution was concentrated to dryness by evaporation under reduced pressure. The resulting residue was purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The pH of the eluate was then adjusted to pH 8.0 by the addition of an appropriate amount of an aqueous solution of sodium hydroxide, and the mixture was then concentrated to dryness by evaporation under reduced pressure. The residue was dissolved in 20 ml of water and the solution was adsorbed onto a column containing 20 ml of Diaion HP-20™, after which the resin was washed with 80 ml of water and then eluted with 100 ml of a 50% v/v aqueous acetone solution to give 78 mg of a substantially pure form of the title compound.

The physico-chemical properties of the product were shown to be identical with those of the compound prepared in Example 52, above.

Method 2

One platinum loop of an inoculum of *Syncephalastrum nigricans* Vuillemin SANK 42372 (FERM BP-4106) was used to inoculate 100 ml of TS-C medium, having the composition shown in Example 80, above, in each of twenty 500 ml Erlenmeyer flasks. The inoculated flasks were then incubated at 26° C. on a rotary shaker maintained at a speed of 200 revolutions per minute.

After 3 days of incubation under these conditions, 0.1 ml of a solution of (4R,6R)-6-{2-[(1S,2S,8S,8aR)-1,2,6,7,8,8a-hexahydro-8-(2,2-diethylbutyryloxy)-2-methyl-1-naphthyl] ethyl}tetrahydro-4-hydroxy-2H-pyran-2-one [prepared as described in Example 73, above] in dimethyl sulfoxide was added to the medium, such that the final concentration of that compound in the medium was 0.01% w/v. Cultivation was continued for a further 5 days under the same conditions.

At the end of this additional period of cultivation, the fermentation broth was analyzed using high speed liquid chromatography through a Nova-Pak™ cartridge C$_{18}$ (8×100 mm, Waters Inc.). The column was eluted using a 43:57 by volume mixture of acetonitrile and 0.1% w/v triethylamine (adjusted to pH 3.2% with an aqueous solution of phosphoric acid) at a flow speed of 1.5 ml/min. The title compound was eluted as a fraction having a retention time of 6.38 minutes. (The same compound produced by the method of Method 1, above, eluted from the column as a fraction having a retention-time of 5.13 minutes.)

The fermentation broth was filtered and the filtrate was adsorbed onto a column containing 200 ml of Diaion HP-20™. The resin was washed with 300 ml of distilled water and the fractions containing the title compound were eluted with 800 ml of a 50% v/v aqueous acetone solution. The eluate was concentrated to dryness by evaporation under reduced pressure and the concentrate was purified by chromatography through an ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The resulting eluate was neutralized by mixing directly with a 0.1M aqueous solution of sodium dihydrogenphosphate and sodium hydroxide (pH 8.0). The pH of the fractions containing the title compound was then adjusted to pH 8.0, after which the fractions were concentrated to dryness by evaporation under reduced pressure. The resulting concentrate was then dissolved in 20 ml of water, and the solution was adsorbed onto a column containing 20 ml of Diaion HP-20™. The resin was washed with 30 ml of water and then eluted with 100 ml of a 50% v/v aqueous acetone solution to give 68 mg of a substantially pure form of the title compound purified.

Nuclear Magnetic Resonance Spectrum (270 MHz, CD$_3$OD) δ ppm: 0.78 (9H, triplet, J=7.4 Hz); 0.91 (3H, doublet, J=7.0 Hz); 1.2–1.9 (13H, multiplet); 1.94 (1H, doubled doublet of doublets, J=15.5 & 6.2 & 2.0 Hz); 2.2–2.5 (5H, multiplet); 3.68 (1H, multiplet); 4.07 (1H, multiplet); 4.28 (1H, multiplet); 5.30 (1H, multiplet); 5.63 (1H, multiplex); 5.94 (1H, doublet of doublets, J=9.7 & 6.1 Hz); 6.02 (1H, doublet, J=9.7 Hz).

Molecular weight: 488 (determined by High Resolution Fast Atom Bombardment Mass Spectrometry as C$_{27}$H$_{41}$O$_7$Na).

$[\alpha]_D^{25}$ +200.7° (c=0.14, acetone).

EXAMPLE 84

Sodium(3R,5R)-3,5-dihydroxy-7-[(1S,2S,6S,8S,8aR)-6-hydroxy-2-methyl-8-(2,2-diethyl-4-pentenoyloxy)-1,2,6,7,8,8a-hexahydro-1-naphthyl]heptanoate

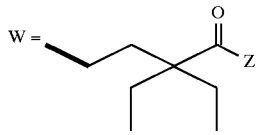

One platinum loop of an inoculum of *Amycolata autotrophica* SANK 62981 (FERM BP-4105) was used to inoculate 100 ml of Yeast MY medium, having the composition shown in Example 81, above, in a 500 ml Erlenmeyer flask. The inoculated flask was then incubated at 28° C. on a rotary shaker maintained at a speed of 200 revolutions per minute.

After 3 days of incubation under these conditions, a portion of the inoculated, seed, medium was transferred to each of twenty 500 ml Erlenmeyer flasks containing fresh Yeast MY medium, such that the final concentration of the seed medium in the fresh medium was 0.5% w/v. The flasks were then further incubated at 28° C. on a rotary shaker maintained at a speed of 200 revolutions per minute.

After 2 days of incubation under these conditions, an aqueous solution of sodium (3R,5R)-3,5-dihydroxy-7-[(1S,2S,8S,8aR)-2-methyl-8-(2,2-diethyl-4-pentenoyloxy)-1,2,6,7,8,8a-hexahydro-1-naphthyl]heptanoate [prepared as described in Example 79] was added to the medium, such that the final concentration of that compound in the medium was 0.01% w/v. Cultivation was then continued for a further 5 days under the conditions outlined above.

At the end of this cultivation period, the fermentation broth was filtered and the filtrate was adsorbed onto a column containing 200 ml of Diaion HP-20™. The resin was washed with 300 ml of distilled water, after which fractions containing the title compound were eluted with 800 ml of a 50% v/v aqueous acetone solution.

The desired fractions were combined and the combined eluate was concentrated to dryness by evaporation under reduced pressure. The resulting residue was purified by chromatography through a preparative ODS column (ODS-H-5251™, Senshu Scientific Co., Ltd.) using a 450:550:1 by volume mixture of acetonitrile, water and acetic acid as the eluent. The chromatography was monitored by ultraviolet absorption at 237 nm. The pH of the eluate was adjusted to pH 8.0 by the addition of an appropriate amount of an aqueous solution of sodium hydroxide and the resulting mixture was concentrated to dryness by evaporation under reduced pressure. The resulting residue was dissolved in 50 ml of water and the solution was then adsorbed onto a column containing 20 ml of Diaion HP-20™. The resin was washed with 100 ml of distilled water and then eluted with 300 ml of a 50% v/v aqueous acetone solution to give 28 mg of a substantially pure form of the title compound.

The physico-chemical properties of the compound obtained in this manner were shown to be identical with those of the compound of Example 64.

EXAMPLE 85

(4R,6R)-6-{2-[(1S,2S,8S,8aR)-1,2,6,7,8,8a-Hexahydro-8-[(S)-2-methylvaleryloxy]-2-methyl-1-naphthyl]ethyl}tetrahydro-4-hydroxy-2H-pyran-2-one

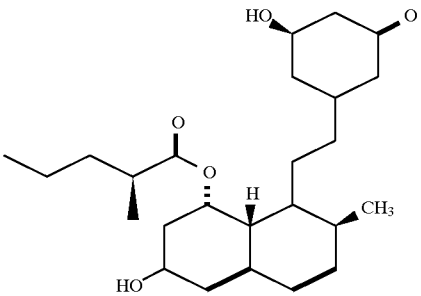

Acetonitrile was removed from fractions having a retention time of 40 to 50 minutes [obtained from the high performance liquid chromatography described in step 2 of Preparation 1, below], by evaporation under reduced pressure, using a rotary evaporator. The resulting concentrate was then extracted twice, each time with an amount of ethyl acetate equal to one half of the volume of the concentrate. The extracts were combined and then concentrated by evaporation under reduced pressure to give 5.2 g of an oily material. This material was then treated in one of two ways:

(i) The oily material obtained in this manner was dissolved in 20 ml of acetonitrile. 2 ml of the resulting solution were then injected into a YMC-Pak S-346-15 S-15™ ODS column [30 mm internal diameter×300 mm, YMS Inc.]. The column was then developed and eluted as a mobile phase using a 70% w/v aqueous acetonitrile solution at a flow rate of 10 ml/min, using a refractometer as a guide. Eluates having a retention time of between 51 and 54 minutes were collected.

A portion of the eluate obtained above was purified by high performance liquid chromatography through a Radial-Pak cartridge™ column [8 NVC 184, 8 mm internal diameter×10 cm, Waters Co.] as a mobile phase, using a 70% v/v aqueous methanol solution at a flow rate of 2.0 ml/min. The desired fractions show an ultraviolet absorption at 236 nm. The desired fraction had a retention time of 4.7 minutes.

Under the conditions outlined above, the retention time of the compound of Preparation 1 was 3.6 minutes.

The above chromatographic purification was then repeated a further ten times until fractions having a retention time of 3.6 minutes were obtained. The eluates obtained as a result of this further purification were combined and the mixture was then concentrated to dryness by evaporation under reduced pressure, using a rotary evaporator, to give 30 mg of the title compound as a crude product.

(ii) In an alternative method, the oily material obtained above was dissolved in 1.5 ml of acetonitrile and the resulting solution was then injected into a preparative column [ODS-5251-S™, 20 mm internal diameter×250 mm, Senshu Scientific Co., Ltd.]. The column was eluted as a mobile phase using a 70% w/v aqueous solution of acetonitrile at a flow rate of 5 ml/min. Eluates having a retention time of between 33 and 37 minutes were collected, using a refractometer as a guide.

The resulting eluates were combined and decolorized by mixing with 15 mg of active charcoal powder, after which the mixture was stirred at room temperature for 10 minutes.

The mixture was then filtered through a filter paper, and the decolorized filtrate was concentrated to dryness by evaporation under reduced pressure using a rotary evaporator, to give 13 mg of a substantially pure form of the title compound.

Mass spectrum (m/e): 404 (M$^+$)

Molecular formula: $C_{24}H_{36}O_5$

UV spectrum (ethanol) $\lambda_{max}$ nm ($E_{1\ cm}^{1}$%): 236.5 (576).

$^{13}$C-Nuclear Magnetic Resonance Spectrum (90 MHz, CDCl$_3$) δ ppm (tetramethylsilane was used as an internal standard; a signal of deuterated chloroform appeared at 70.0 δ ppm): 170.3, 176.9, 132.6, 133.6, 128.1, 123.6, 76.2, 67.6, 62.61, 20.90, 38.61, 36.20, 39.94, 37.51, 36.89, 26.19, 33.03, 35.92, 30.9, 24.0, 20.6, 17.4, 13.9, 13.9.

There were signals observed due to 24 carbon atoms in the $^{13}$C-NMR spectrum in agreement with the mass spectrographic result.

$^1$H-Nuclear Magnetic Resonance Spectrum (360 MHz, CDCl$_3$) δ ppm: 5.88, 5.98, 5.51, 3.68, 5.36, 4.10, 4.29, 2.34, 2.24, 1.53, 1.57, 2.45, 2.37, 1.67, 1.58, 2.48, 1.35, 1.54, 1.22, 1.55, 2.42, 1.32, 1.32, (each, 1H); 1.12, 0.92, 0.91 (each, 3H).

Infrared Spectrum (KBr) $v_{max}$ cm$^{-1}$: 3513, 1741, 1700, 1234, 1180.

$[\alpha]_D^{25}$ +266° (c=0.96, acetone).

These spectral data indicate that the compound is identical with the compound prepared in Example 70, above.

EXAMPLE 86

Sodium(3R,5R)-3,5-dihydroxy-7-{(1S,2S,8S,8aR)-2-methyl-8-[(S)-2-methylvaleryloxy]-1,2,6,7,8,8a-hexahydro-1-naphthyl}heptanoate

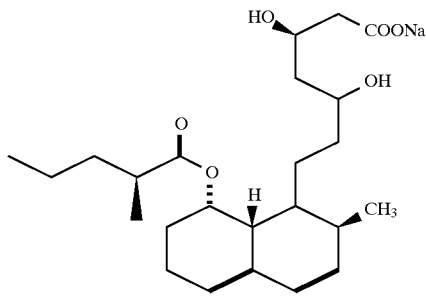

0.1 ml of a 0.1N aqueous solution of sodium hydroxide was added to a solution of 10 mg of (4R,6R)-6-{2-[(1S,2S,8S,8aR)-1,2,6,7,8,8a-hexahydro-8-[(S)-2-methylvaleryloxy]-2-methyl-1-naphthyl]ethyl}tetrahydro-4-hydroxy-2H-pyran-2-one [prepared as described in Example 85, above] in 0.2 ml of 1,4-dioxane, and the mixture was heated at 60° C. for 30 minutes. At the end of this time, 10 ml of water were added to the mixture and the pH of the mixture was adjusted to pH 8.5 with the addition of an appropriate amount of a 0.1N solution of aqueous hydrogen chloride. The resulting mixture was then adsorbed onto a column containing 5 ml of Diaion HP-20™. The resin was washed with 20 ml of water and then eluted with a 60% w/v aqueous acetone solution. The resulting eluate was concentrated by evaporation under reduced pressure, using a rotary evaporator, and the concentrate was lyophilized to give 9.8 mg of the title compound.

Molecular weight: 444 (as determined by Fast Atom Bombardment Mass Spectrometry).

Molecular formula: $C_{24}H_{37}O_6$.Na (determined by High Resolution Fast Atom Bombardment Mass Spectrometry).

Ultraviolet Spectrum (H$_2$O) $\lambda_{max}$ nm: 237.4.

$^{13}$C-Nuclear Magnetic Resonance Spectrum (90 MHz, CD$_3$OD) δ ppm (tetramethylsilane was used as an internal standard; a signal of deuterated methanol appeared at 49.0 ppm. Signals were observed due to 24 carbon atoms, in agreement with the molecular formula.): 180.5, 178.5, 135.4, 133.9, 129.3, 124.1, 71.8, 69.4, 69.4, 45.4, 45.2, 41.2, 38.8, 38.5, 37.2, 35.8, 32.1, 27.1, 25.6, 21.9, 21.6, 17.9, 14.4, 14.1.

$^1$H-Nuclear Magnetic Resonance Spectrum (360 MHz, CD$_3$OD) δ ppm: 5.9, 5.7, 5.5, 5.3, 4.1, 3.7, 3.3 (each, 1H); 1.1 (3H); 0.9 (6H).

Infrared Spectrum (KBr) $v_{max}$ cm$^{-1}$: 3385, 2936, 1728, 1578, 1409, 1085, 836.

$[\alpha]_D^{25}$ +180° (c=1.03, ethanol).

The physico-chemical data for the compound obtained in this manner were shown to be identical to those of the compound of Example 75, above.

EXAMPLE 87

Sodium(3R,5R)-3,5-dihydroxy-7-{(1S,2S,6S,8S,8aR)-6-hydroxy-2-methyl-8-[(S)-2methylvaleryloxy]-1,2,6,7,8,8a-hexahydro-1-naphthyl}heptanoate

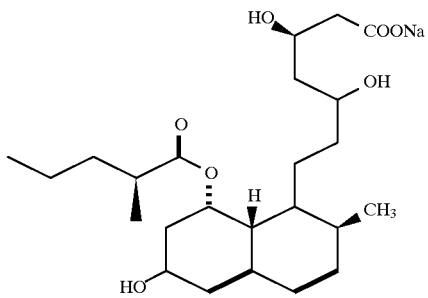

One platinum loop of an inoculum of *Streptomyces carbophilus* SANK 62585 (FERM BP-4128) was used to inoculate 100 ml of SC medium, having a composition as shown in Example 80, above, in a 500 ml Erlenmeyer flask, and the inoculated flask was incubated at 28° C. on a rotary shaker maintained at a speed of 200 revolutions per minute.

After a 3 day incubation period, a portion of the inoculated seed medium was transferred to each of five 500 ml Erlenmeyer flasks, containing 100 ml of fresh SC medium per flask, such that the concentration of the seed medium in the fresh medium was 5.0% w/v. The flasks were then incubated at 28° C. on a rotary shaker maintained at a speed of 200 revolutions per minute.

After a further 3 days of incubation, an aqueous solution of 100 mg of sodium (3R,5R)-3,5-dihydroxy-7-{(1S,2S,8S,8aR)-2-methyl-8-[(S)-2-methylvaleryloxy]-1,2,6,7,8,8a-hexahydro-1-naphthyl}heptanoate [prepared as described in Example 10, above] was added the culture medium, such that the final concentration of that compound in the medium was 0.02% w/v. Cultivation was then continued for a further 3 days under the conditions outlined above.

At the end of this additional period of cultivation, the fermentation broth was centrifuged for 10 minutes at a speed of 3000 revolutions per minute in order to separate the mixture into mycelia and supernatant fluid.

400 ml of the supernatant fluid were removed, and the pH of this fluid was adjusted to pH 8 with the addition of an appropriate amount of a 2N aqueous solution of sodium hydroxide. The mixture was adsorbed onto a column containing 20 ml of Diaion HP-20™ (Mitsubishi Kasei Corporation). The resin was washed with 200 ml of distilled water and then eluted with 20 ml of a 20% v/v aqueous methanol solution, 20 ml of a 40% v/v aqueous solution of methanol and 40 ml of a 60% v/v aqueous methanol solution, in that order.

The fractions which eluted with a 40% v/v aqueous methanol solution and a 60% v/v aqueous methanol solution were combined and then concentrated to dryness by evaporation under reduced pressure, using a rotary evaporator, to give 50 mg of the title compound as a crude product.

The crude product obtained in this manner was purified by chromatography through a μBonda-PAK™ column (ODS, 8 mm×30 cm, Waters Inc.) as a mobile phase, using a 550:450:1 by volume mixture of methanol, water and acetic acid as the eluent, at a flow rate of 3 ml/min. The elution was monitored using a differential refractometer. Fractions having a retention time of 13 minutes were collected.

The pH of the fractions collected was adjusted to pH 9 with the addition of an appropriate amount of a 2N aqueous solution of sodium hydroxide, and methanol was then removed from the mixture by distillation under reduced pressure, using a rotary evaporator. The pH of the resulting residue was adjusted to pH 8 and the mixture was adsorbed onto a column containing 3 ml of Diaion HP-20™. The resin was washed with 10 ml of distilled water and then eluted with 20 ml of a 60%/v aqueous methanol solution.

The resulting eluate was concentrated by evaporation under reduced pressure and then lyophilized to give 3.4 mg of a substantially pure form of the title compound.

Molecular weight (determined by Fast Atom Bombardment Mass Spectrometry) (M+H)$^+$: Found: 461.2524; Calculated: 461.2515.

Molecular formula: $C_{24}H_{37}O_7$.Na (determined by Fast Atom Bombardment Mass Spectrometry).

Ultraviolet Spectrum (H$_2$O) $\lambda_{max}$ nm (E$_{1\ cm}^{1}$%): 238.7 (629).

$^{13}$C-Nuclear Magnetic Resonance Spectrum (90 MHz, CD$_3$OD) δ ppm: (tetramethylsilane was used as an internal standard, a signal of deuterated methanol appeared at 49.0 ppm): 179.8, 178.1, 136.8, 136.5, 128.6, 127.4, 71.5, 71.0, 69.2, 65.4, 45.1, 45.1, 41.2, 38.9, 38.3, 37.1, 37.1, 35.7, 32.3, 21.6, 17.8, 14.4, 13.9

$^1$H-Nuclear Magnetic Resonance Spectrum (360 MHz, CD$_3$OD) δ ppm: 5.88, 5.98, 5.51, 3.68, 5.36, 4.10, 4.29, 2.34, 2.24, 1.53, 1.57, 2.45, 2.37, 1.67, 1.58, 2.48, 1.35, 1.54, 1.22, 1.55, 2.42 (each, 1H); 1.32 (2H); 1.12, 0.92, 0.91 (each, 3H).

Infrared Spectrum (KBr) $v_{max}$ cm$^{-1}$: 3391, 2960, 2935, 1728, 1400, 1181, 1043, 855.

$[\alpha]_D^{25}$ +130° (c=0.93, ethanol).

The physico-chemical data of the compound obtained in this manner were shown to be identical to those of the compound of Example 49.

PREPARATION 1

Preparation of ML-236B

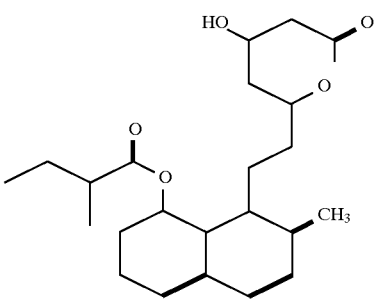

(1) Culture
Seed culture medium

| | |
|---|---|
| Glycerin | 30 g |
| Glucose | 20 g |
| Soybean meal | 20 g |
| Mikuni-peptone (Mikuni Chemical Industries Co., Ltd.) | 8 g |
| Sodium nitrate | 2 g |
| Magnesium sulfate | 1 g |
| Tap water | to 1000 ml |
| (pH: 6.0–6.5). | |

50 ml of the seed culture medium having the composition described above was charged into a 500 ml Erlenmeyer flask and autoclaved at 120° C. for 30 minutes before the inoculation of the microorganism. One platinum loop from a slant of *Penicillium citrinum* Thom SANK 13380 (FERM BP-4129) was aseptically transferred into the flask containing this medium. The inoculated flask was incubated at 24° C. for 3 days on a rotary shaker at a speed of 210 rpm.

A 2000 ml Erlenmeyer flask containing 700 ml of the seed culture medium was then autoclaved at 120° C. for 30 minutes, after which it was inoculated with the whole (about 50 ml) of the fermentation broth obtained as described above. This flask was incubated for 2 days at 24° C. on a rotary shaker at a speed of 210 rpm, to prepare a second generation culture.

The following media were used in the subsequent production of the title compound. Production culture medium (1):

Sufficient tap water was added to 150 g of glycerin and 600 g of liquid Sanmalt (Sanwa Cornstarch Industry, Ltd.) to adjust the total volume of the solution to 5 liters. The production culture medium (1) was then sterilized by autoclaving for 30 minutes at 120° C.

Production culture medium (2)
The following components were mixed:

| | |
|---|---|
| Soybean meal | 300 g |
| Mikuni-peptone (Mikuni Chemical Industries Co., Ltd.) | 150 g |
| Honen CSL (Honen Corporation) | 300 g |
| Gluten meal (Nihon Shokuhin Kako Co., Ltd.) | 150 g |
| Magnesium sulfate | 15 g |

The pH was adjusted to a value of 6.0–6.5 by the addition of a 10% w/v aqueous solution of sodium hydroxide, and then the total volume was adjusted to 10 liters by the addition of tap water. The production culture medium (2) was then sterilized by autoclaving for 30 minutes at 120° C.

Feed liquor A

Tap water was added to a mixture of 1600 g of glycerin and 6400 g of Sanmalt S (Sanwa Cornstarch Industry, Ltd.), and then the mixture was heated to above 90° C. After the Sanmalt S had completely dissolved, tap water was added to the solution to make a total volume of 10 liters. The solution was then autoclaved at 120° C. for 30 minutes.

Feed liquor B 600 ml of Sannicks PP 2000 (Sanyo Chemical Industries Ltd.) medium were autoclaved at 120° C. for 30 minutes.

5 liters of production culture medium (1) and 10 liters of production culture medium (2) were autoclaved and then charged into a stainless-steel 30 liter jar fermentor to produce a second generation culture.

The whole contents of an Erlenmeyer flask (about 700 ml) containing the second generation culture prepared as described above was then used to inoculate the autoclaved production culture medium in the jar fermentor. The fermentor was incubated at 24° C. with stirring at an automatically controlled range of 260 to 500 rpm, whilst aerating at an air flow of 7.5 liters per minute and at a pressure of 0.5 kg/cm$^2$ such as to maintain a dissolved oxygen concentration of from 3 to 5 ppm.

During the period from the third to the sixth day after commencement of the incubation, 150 ml of Feed liquor B were added to the culture medium once per day (a total of 4 times). After the concentration of reducing sugar was estimated to be no more than 1%, Feed liquor A was continuously added in order to ensure that the pH of the broth was kept at a value of about pH 4.

After 14 days, the resulting broth was harvested.

(2) Isolation

The pH of the culture broth (40 liters) was adjusted to a value of 12 by the addition of 800 ml of a 6N aqueous solution of sodium hydroxide, and the resulting mixture was stirred for 60 minutes at room temperature. At the end of this time, the broth was mixed with 1.5 kg of a Celite filter aid (Celite #545, a trade mark for a product of Johns-Manville Products Corp.), and the mixture was stirred. The resulting mixture was filtered through a filter press to produce a filtrate.

850 ml of 6N aqueous hydrochloric acid were carefully added to the filtrate, and the pH of the mixture was adjusted to a value of 5.0. 80 liters of ethyl acetate were added to the resulting solution, and the mixture was stirred to extract the desired product. The organic layer was separated and the aqueous layer was treated with 40 liters of ethyl acetate and stirred to extract the desired product. The combined ethyl acetate extracts were then extracted with 10 liters of a 3% w/v aqueous solution of sodium hydrogencarbonate. The aqueous layer was separated and the organic layer was again extracted with a 3% w/v aqueous solution of sodium hydrogencarbonate.

1600 ml of 6N aqueous hydrochloric acid were carefully added to the combined aqueous extracts, and the pH of the mixture was adjusted to a value of 5.0. 20 liters of ethyl acetate were added to the resulting mixture, and the mixture was stirred to extract the desired product. The organic layer was separated and the aqueous layer was treated with 10 liters of ethyl acetate and stirred to extract the desired product. The combined ethyl acetate extracts were washed with 15 liters of a 10% w/v aqueous solution of sodium chloride. The extract was then dried over 3000 g of anhydrous sodium sulfate, and the solvent was removed by evaporation to dryness under reduced pressure, using a rotary evaporator to afford an oily residue.

This oily residue was dissolved in 1000 ml of ethyl acetate. 0.5 ml of trifluoroacetic acid was added to the solution, and the mixture was heated under reflux for 30 minutes in a vessel fitted with a reflux condenser. The contents were cooled to 10° C., and then washed twice, each time with 500 ml of a 3% w/v aqueous solution of sodium hydrogencarbonate, and once with 500 ml of a 10% w/v aqueous solution of sodium chloride, in that order. The organic layer was dried over 100 g of anhydrous sodium sulfate and filtered. The filtrate was freed from the solvent by evaporation to dryness under reduced pressure, using a rotary evaporator, to afford 50 g of an oily residue.

The whole of this oily residue was dissolved in 500 ml of acetonitrile, and the resulting solution was divided into five parts. Each part was purified by chromatography through an ODS reverse phase column [ODS-1050-20SR, 10 cm (internal diameter)×50 cm, 15–30 μm (particle size); Kurita Kogyo Co., Ltd.]. The column was eluted with 70% v/v aqueous acetonitrile, used as the mobile phase, at a flow rate of 200 ml/minute. The fractions recovered from the column were monitored by ultraviolet absorption and, on the basis of the peaks thus detected, those fractions having retention times between 30 and 36 minutes were collected.

The purity of these fractions was assessed by high performance liquid chromatography through a column (ODS-262, Senshu Scientific Co., Ltd.) using 70% v/v aqueous methanol as the mobile phase at flow rate of 1.0 ml/minute, whilst monitoring the fractions by ultraviolet absorption at 236 nm. A fraction having a retention time of 11 minutes showed a single peak of characteristic ultraviolet absorption.

Eluates having a retention time of from 40 to 50 minutes were stored and then used for the recovery of the compound of Example 85.

Those fractions having a retention time between 30 and 36 minutes from the reverse phase column chromatography were concentrated by distillation under reduced pressure, using a rotary evaporator to distill off the acetonitrile. The concentrate was twice extracted with one half its volume of ethyl acetate. The ethyl acetate extracts were combined and concentrated by evaporation to dryness under reduced pressure, to afford 30 g of oily residue.

The oil was triturated with a mixture of ethanol and water to induce crystallization. 17 g of the title compound were obtained as colorless crystals.

The physico-chemical properties of this compound are known and are identical with those described in Japanese Patent Publication No. Sho 56-12114 (=GB Patent No. 1453425) and other literature.

PREPARATION 2

Preparation of the sodium salt of Pravastatin

A 500 ml Erlenmeyer flask containing 100 ml of yeast MY culture medium having the composition shown in Example 81, above, was inoculated with a platinum loop from a slant of *Amycolata autotrophica* SANK 62981 (FERM BP-4105). The flask was incubated at 28° C. on a rotary shaker at a speed of 200 rpm.

After 3 days, twenty 500 ml Erlenmeyer flasks each containing 100 ml of the yeast MY culture medium, having the composition shown in Example 81, above, were each inoculated with 0.5% of the flask contents of the seed culture. The cultures were then incubated at 28° C. on a rotary shaker at a speed of 200 rpm. After 2 days, an aqueous solution of the sodium salt of ML-236B was added to a final concentration of 0.1% of the sodium salt, and the mixture was incubated at 28° C. on a rotary shaker at a speed of 200 rpm for 5 days.

At the end of this time, the fermentation broth was filtered, and the filtrate was absorbed on 200 ml of a non-ionic resin, Diaion HP-20 (trade mark). The resin was washed with 300 ml of distilled water and the fractions containing the title compound were eluted with 800 ml of 50% v/v aqueous acetone.

The eluate was concentrated by evaporation to dryness under reduced pressure, and the concentrate was purified by chromatography through a preparative ODS column (ODS-H-5251) using a 480:520:1 by volume mixture of acetonitrile, water and acetic acid as the eluent, whilst monitoring the fractions by ultraviolet absorption at 237 nm. The desired fractions were collected, and their pH was adjusted to a value of 8.0 by the addition of an aqueous solution of sodium hydroxide. The mixture was then concentrated by evaporation under reduced pressure. The concentrate was dissolved in 50 ml of water, and the resulting aqueous solution was treated with 50 ml of Diaion HP-20. The resin was washed with 100 ml of distilled water and then eluted with 200 ml of 50% v/v aqueous acetone, to afford 618 mg of the title compound.

The physico-chemical properties are known and are identical with those described in Japanese Patent Publication No. Sho 61-13699 (=GB Patent No. 2077264) and other literature.

PREPARATION 3

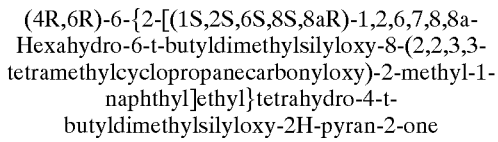

(4R,6R)-6-{2-[(1S,2S,6S,8S,8aR)-1,2,6,7,8,8a-Hexahydro-6-t-butyldimethylsilyloxy-8-(2,2,3,3-tetramethylcyclopropanecarbonyloxy)-2-methyl-1-naphthyl]ethyl}tetrahydro-4-t-butyldimethylsilyloxy-2H-pyran-2-one A procedure similar to that described in Example 4, above, was followed, but using 1.0 g (1.8 mmol) of (4R,6R)-6-{2-[(1S,2S,6S,8S,8aR)-1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], and 1.17 g of 2,2,3,3-tetramethylcyclopropanecarbonyl chloride, to provide 833 mg of the title compound.

Nuclear Magnetic Resonance Spectrum (270 MHz, CDCl$_3$) δ ppm: 4.24–4.29 (1H, multiplet); 4.30–4.49 (1H, multiplet); 4.56–4.63 (1H, multiplet); 5.41 (1H, broad singlet); 5.84 (1H, doublet of doublets, J=9.8 & 5.9 Hz); 5.99 (1H, doublet, J=9.8 Hz).

Infrared Spectrum (CHCl$_3$) ν$_{max}$ cm$^{-1}$: 2950, 1720, 1250, 1080, 840.

Mass Spectrum (m/e): 674 (M$^+$), 659, 617, 532.

$[α]_D^{25}$ +104.8° (c=0.66, acetone).

PREPARATION 4

(4R,6R)-6-{2-[(1S,2S,6S,8S,8aR)-1,2,6,7,8,8a-Hexahydro-6-hydroxy-8-(2,2,3,3-tetramethylcyclopropanecarbonyloxy)-2-methyl-1-naphthyl]ethyl}tetrahydro-2H-pyran-2-one A procedure similar to that described in Example 24, above, was followed, but using 812 mg of (4R,6R)-6-{2-[(1S,2S,6S,8S,8aR)-1,2,6,7,8,8a-hexahydro-6-t-butyldimethylsilyloxy-8-(2,2,3,3-tetramethylcyclopropanecarbonyloxy)-2-methyl-1-naphthyl]ethyl}tetrahydro-4-t-butyldimethylsilyloxy-2H-pyran-2-one [prepared as described in Preparation 3, above], to provide 480 mg of the title compound, melting at between 124° and 126° C.

Elemental Analysis: Calculated for C$_{26}$H$_{38}$O$_6$.½H$_2$O: C: 68.54%; H: 8.41%; Found: C: 68.65%; H: 8.60%.

Nuclear Magnetic Resonance Spectrum (270 MHz, CDCl$_3$) δ ppm: 0.91 (3H, doublet, J=7.3 Hz); 1.15 (3H, singlet); 1.17 (3H, singlet); 1.22 (3H, singlet); 1.24 (3H, singlet); 2.93–3.03 (1H, multiplet); 4.35–4.50 (2H, multiplet); 4.56–4.68 (1H, multiplet); 5.39 (1H, broad singlet); 5.59 (1H, broad singlet); 5.90 (1H, doublet of doublets, J=9.8 & 5.9 Hz); 6.01 (1H, doublet, J=9.8 Hz).

Infrared Spectrum (CHCl$_3$) ν$_{max}$ cm$^{-1}$: 3450, 2950, 1720, 1180.

Mass Spectrum (m/e): 446 (M$^+$), 428, 321, 304.

$[α]_D^{25}$ +188.4° (c=0.51, acetone).

PREPARATION 5

Preparation of a compound of formula (XIV)

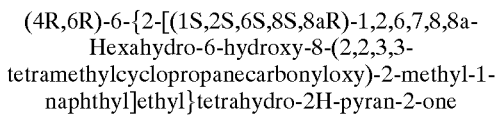

The pH of 4 liters of a seed culture medium prepared in a manner similar to that described in Step (1) of Preparation 1, above, was adjusted to pH 12, by the addition of 80 ml of a 6N aqueous solution of sodium hydroxide. The mixture was then stirred at room temperature for 60 minutes.

At the end of this time, 0.1 kg of Celite (Celite #545, a trade mark for a product of Johns-Manville Products Corp.) was mixed with the broth as an aid for filtration, and the broth was then filtered. The pH of the filtrate was adjusted to pH 5.0 by the careful addition of 85 ml of a 6N aqueous solution of hydrogen chloride, after which the mixture was extracted with 8 liters of ethyl acetate.

The organic layer was then separated and the aqueous layer was again extracted with 4 liters of ethyl acetate. The extracts were combined and then extracted twice, each time with 1 liter of a 3% w/v aqueous solution of sodium hydrogencarbonate. The resulting aqueous extracts were combined and the pH was adjusted to pH 5.0 by the careful addition of 160 ml of a 6N aqueous solution of hydrogen chloride. The mixture was then extracted with 2 liters of ethyl acetate, after which the aqueous layer was separated and was extracted once more with 1 liter of ethyl acetate. The extracts were combined, washed with 1.5 liters of a saturated aqueous solution of sodium chloride and then dried over 300 g of anhydrous sodium sulfate. The solvent was removed by distillation under reduced pressure, using a rotary evaporator, to give an oily residue. 0.1 ml of trifluoroacetic acid was added to a solution of the residue in 100 ml of ethyl acetate, and the mixture was heated under reflux for 30 minutes in a flask provided with a reflux condenser.

At the end of this time, the mixture was cooled to 10° C. and the resulting mixture was washed twice with 50 ml each time of a 3% w/v aqueous solution of sodium hydrogencarbonate and then twice with 50 ml each time of a 10% w/v aqueous solution of sodium chloride. The organic layer was then dried over 10 g of anhydrous sodium sulfate, after which this layer was filtered and concentrated by evaporation under reduced pressure, using a rotary evaporator, to give 5 g of an oily material.

The whole of the oily material produced was dissolved in 100 ml of acetonitrile and the solution was purified by chromatography through an ODS reverse phase column [ODS-1050-20-SR™, 10 cm internal diameter×50 cm, 15–30 μm, (Kurita Water Industries Ltd.)] using a 40% v/v aqueous solution of acetonitrile as a mobile phase, at a flow rate of 200 ml/min. The chromatography was monitored by ultraviolet absorption at 236 nm. Fractions having a retention time of from 33 to 39 minutes were collected. Acetonitrile was then removed from the fractions by distillation under reduced pressure, using a rotary evaporator, to provide an oily material.

All of the oily material produced was dissolved in 5 ml of acetonitrile and then purified again by chromatography through a preparative ODS column (ODS-H-5251™, Senshu Scientific Co., Ltd.) using a 35:65 by volume mixture of acetonitrile and water as the mobile phase. The refraction index of a differential refractometer was used to monitor the chromatography. Fractions having a retention time of from 30 to 35 minutes were collected and acetonitrile was removed from these fractions by distillation under reduced pressure, using a rotary evaporator. The residue was then extracted twice, each time with an amount of ethyl acetate equivalent to half the volume of the residue. The extracts were combined and then concentrated to dryness by evaporation under reduced pressure to give 100 mg of the title compound.

The physico-chemical properties of the compound are known and were shown to be identical with those described for the compound in, for example, Japanese Patent Kokai Application No. Sho 51-136885.

Mass Spectrum (m/z): 306 (M$^+$), 270, 210, 145.

$^1$H-Nuclear Magnetic Resonance Spectrum (270 MHz, CDCl$_3$) δ ppm: 5.9 (1H, doublet); 5.75 (1H, doublet of doublets); 5.55 (1H, broad singlet); 4.7 (1H, multiplet); 4.35 (1H, multiplet); 4.25 (1H, multiplet); 0.9 (2H, doublet).

$^{13}$C-Nuclear Magnetic Resonance Spectrum (90 MHz, CDCl$_3$) δ ppm: 171.3, 133.4, 128.4, 123.7, 76.4, 64.4, 62.5, 38.8, 38.5, 36.4, 36.1, 32.7, 30.8, 29.2, 23.8, 20.4, 13.9.

The following Preparations 6 to 18 describe the preparation of various stereoisomeric compounds suitable for use as starting materials in the preceding Examples, according to the following Reaction Scheme.

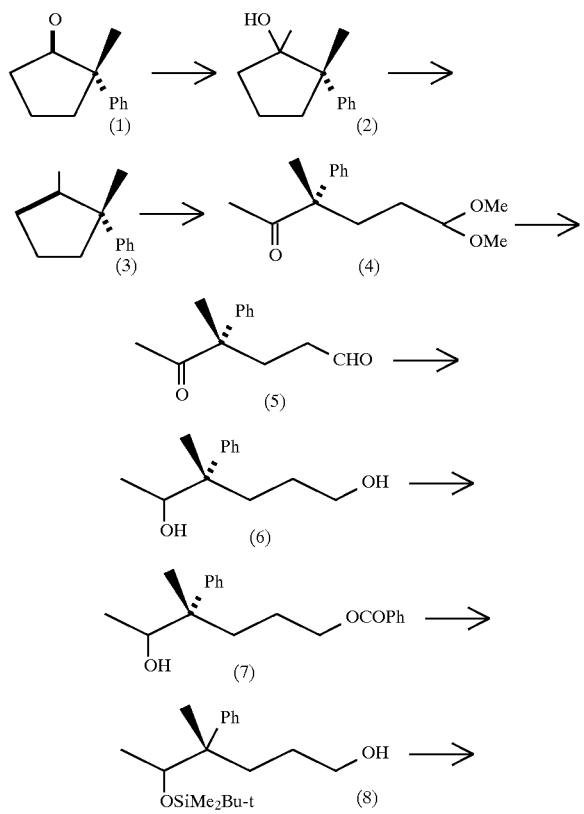

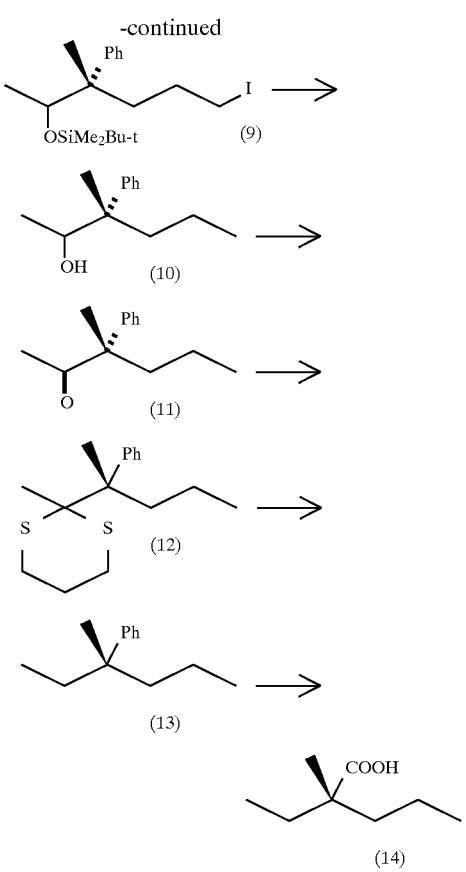

PREPARATION 6

(+)-(2S)-1,2-Dimethyl-2-phenyl-1-cyclopentanol

[Compound 2]

A catalytic amount of iodine was added to a suspension of 5.24 g (216 mmol) of magnesium in 30 ml of dry diethyl ether, whilst stirring in a stream of nitrogen. A solution of 13.4 ml (216 mmol) of methyl iodide in 180 ml of diethyl ether was then added dropwise to the mixture over a period of one hour. The mixture was then stirred for 20 minutes. At the end of this time, a solution of 3.76 g (21.6 mmol) of (+)-(2S)-2-methyl-2-phenylcyclopentane [Compound 1] (optical purity of 95% enantiomeric excess), which was synthesized according to the procedure reported by Koga et al. in Chemical and Pharmaceutical Bulletin (Japan) 27, 2760 (1979), in 30 ml of diethyl ether was added dropwise to the mixture over a period of 10 minutes. The resulting mixture was then heated to reflux for 2 hours. At the end of this time, the reaction mixture was ice-cooled, after which 250 ml of a saturated aqueous solution of ammonium chloride were added dropwise to the mixture over a period of 20 minutes. The resulting mixture was then diluted with 100 ml of water and the aqueous mixture formed was extracted twice, each time with 100 ml of ethyl acetate. The extracts were combined, washed with a saturated aqueous solution of sodium chloride and then dried over anhydrous sodium sulfate. The solvent was then removed by distillation under reduced pressure to provide the title compound as a pale-yellow oil in the form of two diastereomers. The product consisting of the two diastereomers may be used directly in the following reaction, i.e. without separation of the diastereomers. The pale-yellow oily product was purified by flash column chromatography through silica gel, using a 5:1 by volume mixture of hexane and ethyl acetate as the eluent, to give 863 mg (21% yield) as a pale-yellow oil from the less polar fractions.

Nuclear Magnetic Resonance Spectrum (270 MHz, CDCl$_3$) δ ppm: 1.26 (3H, singlet); 1.32 (3H, singlet); 1.60–2.10 (6H, multiplet; 1H exchangeable for D$_2$O); 2.69–2.80 (1H, multiplet); 7.22–7.53 (5H, multiplet).

Infrared Spectrum (CHCl$_3$) ν$_{max}$ cm$^{-1}$: 3350, 2950, 1730, 1500, 1440, 1380, 1140, 700.

Mass Spectrum m/e: 190 (M$^+$).

$[\alpha]_D^{25}$ +39.5° (c=0.40, ethanol).

The above procedure also resulted in the isolation of 2.43 g (59% yield) of the title compound as a pale-yellow oil from the more polar fractions.

Nuclear Magnetic Resonance Spectrum (270 MHz, CDCl$_3$) δ ppm: 0.93 (3H, singlet); 1.38 (3H, singlet); 1.70–1.97 (6H, multiplet; 1H exchangeable for D$_2$O); 2.25–2.36 (1H, multiplet); 7.17–7.46 (5H, multiplet).

Infrared Spectrum (CHCl$_3$) ν$_{max}$ cm$^{-1}$: 3350, 2950, 1730, 1600, 1500, 1370, 1100, 1050, 700.

Mass Spectrum m/e: 190 (M$^+$).

$[\alpha]_D^{25}$ +22.8° (c=0.46, ethanol).

PREPARATION 7

(+)-(1S)-1,2-Dimethyl-1-phenyl-2-cyclopentene

[Compound 3]

38.6 ml of phosphorous oxychloride were added dropwise over a period of 30 minutes to a solution of 7.47 g (39.2 mmol) of (+)-(2S)-1,2-dimethyl-2-phenyl-1-cyclopentanol [prepared as described in Preparation 6, above] in 77 ml of dry pyridine, whilst ice-cooling in a stream of nitrogen. The resulting mixture was then stirred, first at room temperature for 16 hours and then at 70° C. for 2 hours. At the end of this time, the reaction mixture was ice-cooled and poured little by little into 700 ml of ice-water. The resulting aqueous mixture was extracted twice, each time with 400 ml of ethyl acetate. The extracts were combined, washed first with a saturated aqueous solution of sodium hydrogencarbonate and afterwards with a saturated aqueous solution of sodium chloride, and then dried over anhydrous sodium sulfate. The solvent was removed by distillation under reduced pressure, to provide 6.70 g of a pale-yellow oily residue.

6.70 g of the pale-yellow oily residue were dissolved in 500 ml of dioxane, and then 6.70 g (38.9 mmol) of p-toluenesulfonic acid were added to the solution. The resulting mixture was heated to reflux for 18 hours. At the end of this time, the reaction mixture was concentrated by evaporation under reduced pressure, and the concentrate was diluted with 300 ml of water and then extracted twice, each time with 400 ml of ethyl acetate. The extracts were combined, washed first with a saturated aqueous solution of sodium hydrogencarbonate and afterwards with a saturated aqueous solution of sodium chloride, and then dried over anhydrous sodium sulfate. The solvent was removed by distillation under reduced pressure, to provide a pale-yellow residue. This residue was purified by flash column chromatography through silica gel, using hexane as the eluent, to give 4.84 g (72% yield) of the title compound as a pale-yellow oil.

Nuclear Magnetic Resonance Spectrum (270 MHz, CDCl$_3$) δ ppm: 1.47 (3H, singlet); 1.50 (3H, singlet); 1.95–2.16 (2H, multiplet); 2.30–2.39 (2H, multiplet); 5.53 (1H, singlet); 7.16–7.34 (5H, multiplet).

Infrared Spectrum (CHCl$_3$) ν$_{max}$ cm$^{-1}$: 2950, 1600, 1490, 1440, 1370, 1020, 700.

Mass Spectrum m/e: 172 (M$^+$).

$[\alpha]_D^{25}$ +95.8° (c=0.40, ethanol).

PREPARATION 8

(+)-(2S)-6,6-Dimethoxy-3-phenyl-3-methyl-2-hexanone

[Compound 4]

A stream of air including 10 g/m$^3$ of ozone was bubbled through a solution of 764 mg (4.43 mmol) of (+)-(1S)-1,2-dimethyl-1-phenyl-2-cyclopentene [prepared as described in Preparation 7, above] in 15 ml of methanol, whilst ice-cooling, for 2.5 hours. At the end of this time, the reaction mixture was cooled to −78° C., after which 0.65 ml of dimethyl sulfide was added to the reaction mixture. The temperature of the reaction mixture was allowed to rise to room temperature, and the reaction mixture was then stirred for 15 hours. The mixture was then concentrated by evaporation under reduced pressure. The resulting concentrate was diluted with 50 ml of water, and the diluted solution was extracted twice, each time with 50 ml of ethyl acetate. The extracts were combined, washed with a saturated aqueous solution of sodium chloride and then dried over anhydrous sodium sulfate. The solvents were then removed by distillation under reduced pressure, to provide a colorless oily residue. This residue was purified by flash column chromatography through silica gel, using a 5:1 by volume mixture of hexane and ethyl acetate as the eluent, to give 971 mg (88% yield) of the title compound as a colorless oil.

Nuclear Magnetic Resonance Spectrum (270 MHz, CDCl$_3$) δ ppm: 1.26–1.47 (2H, multiplet); 1.50 (3H, singlet) 1.92 (3H, singlet); 1.92–2.00 (2H, multiplet); 3.24 (3H, singlet); 3.30 (3H, singlet); 4.32 (1H, triplet, J=5.9 Hz); 7.20–7.39 (5H, multiplet).

Infrared Spectrum (CHCl$_3$) ν$_{max}$ cm$^{-1}$: 2950, 1700, 1440, 1350, 1120.

Mass Spectrum m/e: 249 (M$^+$−1).

$[\alpha]_D^{25}$ +61.1° (c=0.37, ethanol).

PREPARATION 9

(+)-(4S)-5-Oxo-4-phenyl-4-methylhexanal

[Compound 5]

6.0 ml of water and then 6.0 ml of trifluoroacetic acid were added to a solution of 953 mg (3.81 mmol) of (+)-(2S)-6,6-dimethoxy-3-phenyl-3-methyl-2-hexanone [prepared as described in Preparation 8, above] in 12 ml of chloroform, whilst ice-cooling and stirring, and the resulting mixture was stirred vigorously at room temperature for 3 hours. At the end of this time, the reaction mixture was diluted with 50 ml of water and the diluted solution was extracted twice, each time with 100 ml of methylene chloride. The extracts were combined, then washed, first with a saturated aqueous solution of sodium hydrogencarbonate and afterwards with a saturated aqueous solution of sodium chloride, and then dried over anhydrous sodium sulfate. The solvent was removed by distillation under reduced pressure, to provide a colorless oily residue. This residue was purified by flash column chromatography through silica gel, using a 3:1 by volume mixture of hexane and ethyl acetate as the eluent, to give 699 mg (90% yield) of the title compound as a colorless oil.

Nuclear Magnetic Resonance Spectrum (270 MHz, CDCl$_3$) δ ppm: 1.51 (3H, singlet); 1.93 (3H, singlet); 2.15–2.33 (4H, multiplet); 7.20–7.41 (5H, multiplet); 9.66 (1H, singlet).

Infrared Spectrum (CHCl$_3$) $v_{max}$ cm$^{-1}$: 1720, 1600, 1350.

Mass Spectrum m/e: 203 (M$^+$–1).

$[\alpha]_D^{25}$ +61.1° (c=0.97, ethanol).

PREPARATION 10

(–)-(3S)-6-Hydroxy-3-phenyl-3-methyl-2-hexanol

[Compound 6]

259 mg (6.84 mmol) of sodium borohydride were added, little-by-little, to a solution of 699 mg (3.42 mmol) of (+)-(4S)-5-oxo-4-phenyl-4-methylhexanal [prepared as described in Preparation 9, above] in 14 ml of ethanol, and the resulting mixture was stirred at room temperature for one hour. At the end of this time, 4.0 ml of acetone were added to the mixture and the mixture was stirred for 20 minutes. The reaction mixture was then concentrated by evaporation under reduced pressure, and the concentrate was mixed with 30 ml of water. The resulting mixture was extracted twice, each time with 30 ml of ethyl acetate, the extracts were combined, washed with a saturated aqueous solution of sodium chloride and then dried over anhydrous sodium sulfate. The solvent was then removed by distillation under reduced pressure, to provide the title compound, consisting of two diastereomers, as a colorless oil. This mixture consisting of the two diastereomers can be used directly in the following reaction, i.e. without further separation.

The oily product obtained was purified by flash column chromatography through silica gel, using a 1:1 by volume mixture of hexane and ethyl acetate as the eluent, to give 208 mg (29% yield) of a first isomer of the title compound as colorless powdery crystals from the less polar fractions and 386 mg (54% yield) of a second isomer of the title compound as colorless powdery crystals from the more polar fractions.

The compound which eluted first has the following characteristics:

Melting point: 100° C. (after recrystallization from a mixture of methylene chloride and hexane).

Nuclear Magnetic Resonance Spectrum (270 MHz, CDCl$_3$) δ ppm: 1.08–1.19 (1H, multiplet); 1.12 (3H, doublet, J=6.5 Hz); 1.31 (3H, singlet); 1.34–1.49 (1H, multiplet); 1.54–1.62 (3H, multiplet; 2H exchangeable for D$_2$O); 1.90–1.99 (1H, multiplet); 3,56 (2H, triplet, J=6.5 Hz); 3.87 (1H, quartet, J=6.5 Hz); 7.21–7.39 (5H, multiplet).

Infrared Spectrum (CHCl$_3$) $v_{max}$ cm$^{-1}$: 3600, 2950, 1380, 1260, 1150, 1130, 1100, 700

Mass Spectrum m/e: 209 (M$^+$+1)

Elemental Analysis: Calculated for C$_{13}$H$_{20}$O$_2$: C: 74.96%; H: 9.68%; Found: C: 74.75%; H: 9.65%.

$[\alpha]_D^{25}$ –4.1° (c=0.91, ethanol).

The compound which eluted later has the following characteristics:

The compound melts between: 105° and 106° C. (after recrystallization from a mixture of methylene chloride and hexane).

Nuclear Magnetic Resonance Spectrum (270 MHz, CDCl$_3$) δ ppm: 0.96 (3H, doublet, J=6.4 Hz); 1.16–1.27 (1H, multiplet) 1.32 (3H, singlet); 1.38–1.55 (3H, multiplet; 2H exchangeable for D$_2$O); 1.71–1.79 (1H, multiplet); 1.82–2.02 (1H, multiplet); 3,58 (2H, triplet, J=6.5 Hz); 3.87 (1H, quartet, J=6.4 Hz); 7.19–7.38 (5H, multiplet).

Infrared Spectrum (CHCl$_3$) $v_{max}$ cm$^{-1}$: 3650, 3450, 2950, 1380, 1150, 700.

Mass Spectrum m/e: 209 (M$^+$+1).

Elemental Analysis: Calculated for C$_{13}$H$_{20}$O$_2$: C: 74.96%; H: 9.68%. Found: C, 74.70%; H: 9.63%.

$[\alpha]_D^{25}$ –10.9° (c=0.23, ethanol).

PREPARATION 11

(–)-(3S)-6-Benzoyloxy-3-phenyl-3-methyl-2-hexanol

[Compound 7]

A catalytic amount (20 mg) of 4-dimethylaminopyridine in a stream of nitrogen was added to a solution of 4.04 g (19.4 mmol) of a mixture of the two diastereomers of (–)-(3S)-6-hydroxy-3-phenyl-3-methyl-2-hexanol [prepared as described in Preparation 10, above] in 100 ml of dry pyridine, after which 2.36 ml (20.4 mmol) of benzoyl chloride were added dropwise to the mixture over a period of 15 minutes, whilst stirring and ice-cooling. The temperature of the mixture was then allowed to rise from ice temperature to room temperature, and the reaction mixture was then stirred for 16 hours. At the end of this time, the mixture was concentrated by evaporation under reduced pressure. The concentrate was diluted with 300 ml of water and the diluted solution was extracted twice, each time with 200 ml of ethyl acetate. The extracts were combined, then washed with a 5% w/v aqueous solution of hydrogen chloride, a saturated aqueous solution of sodium hydrogencarbonate and a saturated aqueous solution of sodium chloride, in that order, and then dried over anhydrous sodium sulfate. The solvent was then removed by distillation under reduced pressure, to provide a colorless oil. This oil is a mixture of two diastereomers derived from the diastereomeric starting material. The product was purified by flash column chromatography through silica gel, using a 2:1 by volume mixture of hexane and ethyl acetate as the eluent, to give 5.54 g (91% yield) of the title compound, consisting of two diastereomers, as a colorless oil.

Nuclear Magnetic Resonance Spectrum (270 MHz, CDCl$_3$) δ ppm: 0.97 (1.2H, doublet, J=6.6 Hz); 1.12 (1.8H, doublet, J=6.6 Hz); 1.30–1.52 (1H, multiplet); 1.34 (1.8H, singlet); 1.35 (1.2H, singlet); 1.54–1.75 (2H, multiplet; 1H exchangeable for D$_2$O); 1.80–1.91 (1H, multiplet); 2.03–2.12 (1H, multiplet); 3.82–3.91 (1H, multiplet); 4.21–4.27 (2H, multiplet); 7.22–7.59 (8H, multiplet); 8.02 (2H, doublet, J=7.9 Hz).

Infrared Spectrum (CHCl$_3$) $v_{max}$ cm$^{-1}$: 3600, 2950, 1710, 1280, 1120.

Mass Spectrum m/e: 313 (M$^+$+1).

PREPARATION 12

(–)-(4S)-S-t-Butyldimethylsilyloxy-4-phenyl-4-methyl-1-hexanol

[Compound 8]

4.88 g (70.8 mmol) of imidazole and then 8.02 g (53.1 mmol) of t-butyldimethylsilyl chloride in a stream of nitrogen were added to a solution of 5.54 g (17.7 mmol) of a mixture of the two diastereomers of (–)-(3S)-6-benzoyloxy-3-phenyl-3-methyl-2-hexanol [prepared as described in Preparation 11, above] in 20 ml of dimethylformamide, and the resulting mixture was stirred at room temperature for 15 hours. At the end of this time, the reaction mixture was concentrated by evaporation under reduced pressure, and the concentrate was diluted with 400 ml of water. The diluted solution was extracted twice, each time with 300 ml of ethyl acetate. The extracts were combined, washed with a saturated aqueous solution of sodium chloride and then dried over anhydrous sodium sulfate. The solvent was then removed by distillation under reduced pressure, to provide a colorless oily substance. This material consisted of the two diastereomers derived from the starting compound. 53 ml of a 1N aqueous solution of sodium hydroxide were added to a solution of 8.03 g of the above diastereomeric mixture in 250 ml of ethanol, and the resulting mixture was stirred at 60° C. for 2.5 hours. At the end of this time, the reaction mixture was concentrated by evaporation under reduced pressure, and the concentrate was diluted with 400 ml of water. The diluted solution was extracted twice, each time with 300 ml of ethyl acetate, the extracts were combined, washed with a saturated aqueous solution of sodium chloride and then dried over anhydrous sodium sulfate. The solvent was removed by distillation under reduced pressure, to provide a colorless oily residue. This residue was purified by flash column chromatography through silica gel, using a 4:1 by volume mixture of hexane and ethyl acetate as the eluent, to give 5.37 g (94% yield) of the title compound, consisting of two diastereomers, as a colorless oil.

Nuclear Magnetic Resonance Spectrum (270 MHz, CDCl$_3$) δ ppm: 0.00–0.10 (6H, multiplet); 0.80 (1.8H, doublet, J=6.4 Hz); 0.90 (9H, singlet); 0.97 (1.2H, doublet, J=6.5 Hz); 1.03–1.14 (1H, multiplet); 1.26 (1.2H, singlet); 1.28 (1.8H, singlet); 1.32–1.55 (2H, multiplet; 1H exchangeable for D$_2$O); 1.72–1.84 (2H, multiplet); 3.49–3.57 (2H, multiplet); 3.79 (0.4H, quartet, J=6.4 Hz); 3.90 (0.6H, quartet, J=6.4 Hz); 7.14–7.33 (5H, multiplet).

Infrared Spectrum (CHCl$_3$) $v_{max}$ cm$^{-1}$: 3650, 2950, 1250, 1150, 1090, 840.

Mass Spectrum m/e: 321 (M$^+$–1).

PREPARATION 13

(–)-(3S)-2-t-Butyldimethylsilyloxy-3-phenyl-3-methyl-6-iodohexane

[Compound 9]

5.24 ml (33.2 mmol) of diethyl azodicarboxylate, followed by 3.11 ml (49.8 mmol) of methyl iodide, were added to a solution of 5.37 g (16.6 mmol) of a mixture of the two diastereomers of (–)-(4S)-5-t-butyldimethylsilyloxy-4-phenyl-4-methyl-1-hexanol [prepared as described in Preparation 12, above] and 8.73 g (33.2 mmol) of triphenylphosphine in 70 ml of dry tetrahydrofuran, whilst ice-cooling and in a stream of nitrogen, and the resulting mixture was stirred at room temperature for one hour. At the end of this time, 2.18 g (8.3 mmol) of triphenylphosphine were added to the mixture, and the mixture was ice-cooled. 2.62 ml (16.6 mmol) of diethyl azodicarboxylate, followed by 1.55 ml (49.8 mmol) of methyl iodide were then added to the mixture, and the resulting mixture was stirred at room temperature for 30 minutes. At the end of this time, the reaction mixture was concentrated by evaporation under reduced pressure, and the concentrate was purified by flash column chromatography through silica gel, using hexane as the eluent, to give 6.29 g (87% yield) of the title compound, consisting of two diastereomers, as a colorless oil.

Nuclear Magnetic Resonance Spectrum (270 MHz, CDCl$_3$) δ ppm: –0.22 (1.8H, singlet); –0.04 (1.8H, singlet); 0.04 (1.2H, singlet); 0.05 (1.2H, singlet); 0.79 (1.2H, doublet, J=5.9 Hz); 0.82 (5.4H, singlet); 0.92 (3.6H, singlet); 0.95 (1.8H, doublet, J=5.9 Hz); 1.25 (1.2H, singlet); 1.28 (1.8H, singlet); 1.28–1.40 (1H, multiplet); 1.54–1.65 (1H, multiplet); 1.74–2.10 (2H, multiplet); 3.02–3.14 (2H, multiplet); 3.77 (0.6H, quartet, J=6.6 Hz); 3.90 (0.4H, quartet, J=6.6 Hz); 7.16–7.32 (5H, multiplet).

Infrared Spectrum (CHCl$_3$) $v_{max}$ cm$^{-1}$: 2950, 1250, 1100, 980, 840, 700.

Mass Spectrum m/e: 431 (M$^+$–1).

PREPARATION 14

(–)-(3S)-2-Hydroxy-3-phenyl-3-methylhexane

[Compound 10]

19.2 ml (71.0 mmol) of tributyltin hydride and 3.51 g (21.3 mmol) of azobisisobutyronitrile in a stream of nitrogen were added to a solution of 6.16 g (14.2 mmol) of a mixture of the two diastereomers of (–)-(3S)-2-t-butyldimethylsilyloxy-3-phenyl-3-methyl-6-iodohexane [prepared as described in Preparation 13, above] in 80 ml of toluene, and the resulting mixture was stirred at 80° C. for one hour. At the end of this time, the reaction mixture was concentrated by evaporation under reduced pressure, and the concentrate was purified by flash column chromatography through silica gel, using hexane as the eluent. The product thus obtained was dissolved in 200 ml of acetonitrile, after which 20 ml of a 46% w/v aqueous solution of hydrogen fluoride were added to the mixture, which was then stirred at room temperature for 4 hours. At the end of this time, the reaction mixture was concentrated by evaporation under reduced pressure, and the concentrate was mixed with 300 ml of water. The aqueous mixture was then extracted twice, each time with 200 ml of ethyl acetate. The extracts were combined, washed with a saturated aqueous solution of sodium chloride and then dried over anhydrous sodium sulfate. The solvent was removed by distillation under reduced pressure, and the colorless oily residue was purified by flash column chromatography through silica gel, using a 4:1 by volume mixture of hexane and ethyl acetate as the eluent, to give 2.84 g (65% yield) of the title compound, consisting of two diastereomers, as a colorless oil.

Nuclear Magnetic Resonance Spectrum (270 MHz, CDCl$_3$) δ ppm: 0.82–0.97 (6H, multiplet); 1.10–1.21 (1H, multiplet); 1.29 (1.8H, singlet); 1.31 (1.2H, singlet); 1.35–1.93 (4H, multiplet; 1H exchangeable for D$_2$O); 3.83–3.92 (1H, multiplet); 7.22–7.41 (5H, multiplet).

Infrared Spectrum (CHCl$_3$) $v_{max}$ cm$^{-1}$: 3600, 2950, 1100, 700.

Mass Spectrum m/e: 177 (M$^+$–15).

PREPARATION 15

(+)-(3S)-3-Phenyl-3-methyl-2-hexanone

[Compound 11]

A solution of 1.86 ml (26.2 mmol) of dimethyl sulfoxide in 5 ml of dry methylene chloride was added dropwise over a period of 5 minutes, in a stream of nitrogen and at a temperature of –78° C., to a solution of 1.43 ml (16.4 mmol) of oxalyl chloride in 25 ml of dry methylene chloride, and the resulting mixture was stirred at –78° C. for 10 minutes. At the end of this time, a solution of 2.10 g (10.9 mmol) of a mixture of the two diastereomers of (–)-(3S)-2-hydroxy-3-phenyl-3-methylhexane [prepared as described in Prepartion 14, above] in 10 ml of dry methylene chloride was added dropwise to the mixture over a period of 5 minutes. The mixture thus obtained was stirred at −78° C. for 15 minutes, after which 7.0 ml (50 mmol) of triethylamine were added dropwise to the mixture over a period of 5 minutes. The mixture was then stirred at −78° C. for 20 minutes, after which the mixture was stirred at 0° C. for one hour, and then mixed with 50 ml of water. The aqueous mixture was extracted three times, each time with 100 ml of ethyl acetate. The extracts were combined, washed first with a saturated aqueous solution of sodium hydrogencarbonate and afterwards with a saturated aqueous solution of sodium chloride, and then dried over anhydrous sodium sulfate. The solvent was removed by distillation under reduced pressure, and the colorless oily residue formed was purified by flash column chromatography through silica gel, using a 20:1 by volume mixture of hexane and ethyl acetate as the eluent, to give 1.91 g (92% yield) of the title compound as a colorless oil.

Nuclear Magnetic Resonance Spectrum (270 MHz, CDCl$_3$) δ ppm: 0.91 (3H, triplet, J=7.3 Hz); 1.03–1.93 (2H, multiplet); 1.46 (3H, singlet); 1.87–1.93 (2H, multiplet); 1.89 (3H, singlet); 7.22–7.34 (5H, multiplet).

Infrared Spectrum (CHCl$_3$) ν$_{max}$ cm$^{-1}$: 2950, 1700, 1350, 1130, 700.

Mass Spectrum m/e: 190 (M$^+$).

$[α]_D^{25}$ +49.8° (c=2.08, ethanol).

PREPARATION 16

2-methyl-2[(−)-(2S)-1-methyl-1-phenylbutyl]-1,3-dithiane

[Compound 12]

0.99 ml (9.89 mmol) of 1,2-ethanediol and 0.17 ml of boron trifluoride diethyl etherate were added to a solution of 1.25 g (6.59 mmol) of (+)-(3S)-3-phenyl-3-methyl-2-hexanone [prepared as described in Preparation 15, above] in 25 ml of dry methylene chloride, and the resulting mixture was stirred at room temperature for 16 hours. At the end of this time, 0.33 ml of boron trifluoride diethyl etherate were added to the mixture and the mixture was stirred for a further for 16 hours. 30 ml of a 5% w/v aqueous solution of sodium hydroxide were then added to the mixture, and the resulting mixture was extracted twice, each time with 100 ml of ethyl acetate. The extracts were combined, washed with a saturated aqueous solution of sodium chloride and then dried over anhydrous sodium sulfate. The solvent was then removed by distillation under reduced pressure, and the colorless oily residue formed was purified by flash column chromatography through silica gel, using a 30:1 by volume mixture of hexane and ethyl acetate as the eluent, to give 1.20 g (65% yield) of the title compound as a colorless oil.

The eluate from the above chromatographic procedure also yielded 454 mg of the starting material, (+)-(3S)-3-phenyl-3-methyl-2-hexanone, which had not reacted.

Nuclear Magnetic Resonance Spectrum (270 MHz, CDCl$_3$) δ ppm: 0.88–0.94 (4H, multiplet); 1.12–1.28 (1H, multiplet); 1.66 (3H, singlet); 1.74 (3H, singlet); 1.76–1.82 (1H, multiplet) 1.95–2.06 (1H, multiplet); 2.41–2.50 (1H, multiplet); 2.58–2.67 (2H, multiplet); 2.86–3.00 (2H, multiplet); 7.23–7.33 (3H, multiplet);. 7.46 (2H, doublet, J=7.3 Hz).

Infrared Spectrum (CHCl$_3$) ν$_{max}$ cm$^{-1}$: 2950, 1450, 1270, 700.

Mass Spectrum m/e: 280 (M$^+$).

$[α]_D^{25}$ −7.4° (c=0.38, ethanol).

PREPARATION 17

(−)-(S)-3-Phenyl-3-methylhexane

[Compound 13]

20 g of Raney nickel (W-2) were added to a solution of 1.20 g (4.26 mmol) of 2-methyl-2[(−)-(2S)-1-methyl-1-phenylbutyl]-1,3-dithiane [prepared as described in Preparation 16, above] in 50 ml of absolute ethanol, and the mixture was heated to reflux for 4.5 hours. At the end of this time, the reaction mixture was cooled to room temperature and then filtered with the aid of a Celite™ filter aid. Any Raney nickel remaining on the filter aid was washed thoroughly with 1 liter of ethanol. The filtrate and the washings were combined and then concentrated by evaporation under reduced pressure. The resulting concentrate was purified by flash column chromatography through silica gel, using a 5:1 by volume mixture of hexane and ethyl acetate as the eluent, to give 536 mg (71% yield) of the title compound as a pale yellow oil.

Nuclear Magnetic Resonsance Spectrum (270 MHz, CDCl$_3$) δ ppm: 0.66 (3H, triplet, J=7.3 Hz); 0.81 (3H, triplet, J=7.3 Hz); 0.85–1.05 (2H, multiplet); 1.09–1.22 (2H, multiplet); 1.26 (3H, singlet); 1.43–1.78 (3H, multiplet); 7.15–7.18 (1H, multiplet); 7.28–7.33 (4H, multiplet).

Infrared Spectrum (CHCl$_3$) ν$_{max}$ cm$^{-1}$: 2950, 1600, 1500, 1460, 1380, 700.

Mass Spectrum m/e: 176 (M$^+$).

$[α]_D^{25}$ −7.5° (c=3.51, ethanol).

PREPARATION 18

(−)-(2S)-2-ethyl-2-methylvaleric acid

[Compound 14]

A stream of air including 10 g/m$^3$ of ozone was bubbled through a solution of 423 mg (2.4 mmol) of (−)-(S)-3-phenyl-3-methylhexane [prepared as described in Preparation 17, above] in 25 ml of acetic acid at room temperature for 8 hours. 8.4 ml of a 30% w/v aqueous hydrogen peroxide solution were then added to the reaction mixture, and the resulting mixture was stirred at room temperature for 14 hours. At the end of this time, 20 mg of platinum were added to the mixture, and the mixture was stirred for 4 hours. The mixture was then filtered with the aid of a Celite™ filter aid, the filtrate was concentrated by evaporation under reduced pressure, and the concentrate was mixed with a 10% w/v aqueous solution of sodium hydroxide and 50 ml of ethyl acetate. The aqueous layer was removed and the pH of this layer was adjusted to pH 2 by the addition of an appropriate amount of concentrated hydrochloric acid. The mixture was then extracted three times, each time with 50 ml of ethyl acetate. The extracts were combined, washed with a saturated aqueous solution of sodium chloride and then dried over anhydrous sodium sulfate. The solvent was then removed by distillation under reduced pressure, and the pale-yellow oily residue which formed was purified by bulb-to-bulb distillation (130° C./2 mmHg) to give 70 mg of the title compound as a colorless oil. The optical purity of the product was analyzed to be 93% enantiomeric excess by high-performance liquid chromatography through an optically active column.

Nuclear Magnetic Resonance Spectrum (270 MHz, CDCl$_3$) δ ppm: 0.87 (3H, triplet, J=7.3 Hz); 0.91 (3H, triplet, J=7.3 Hz); 1.12 (3H, singlet); 1.16–1.78 (6H, multiplet); 3.40–4.20 (1H, multiplet; exchangeable for D$_2$O).

Infrared Spectrum (CHCl$_3$) v$_{max}$ cm$^{-1}$: 3000, 2950, 1700, 1440, 1120

Mass Spectrum m/e: 145 (M$^+$+1).

[α]$_D^{25}$ −7.8° (c=5.87, ethanol).

The above procedure may also be used in the preparation of (+)-(2R)-2-ethyl-2-methylvaleric acid, using (−)-(2R)-2-methyl-2-phenylcyclopentane as the starting material.

FORMULATION 1

Hard Capsules

The following ingredients were filled into standard 2-piece hard gelatin capsules to prepare a unit capsule, which was then washed and dried.

| | |
|---|---|
| Compound of Example 50 | 5 mg |
| Hydroxypropyl cellulose (low substitution) | 10 mg |
| Hydroxypropyl cellulose | 3 mg |
| Magnesium stearate | 1 mg |
| Lactose | 81 mg |
| Total | 100 mg |

FORMULATION 2

Powder Formulation

A powdered formulation containing the ingredients listed below was prepared using conventional techniques.

| | |
|---|---|
| Compound of Example 64 | 5 mg |
| Hydroxypropyl cellulose (low Substitution) | 20 mg |
| Hydroxypropyi cellulose | 40 mg |
| Magnesum stearate | 5 mg |
| Lactose | 930 mg |
| Total | 1000 mg |

FORMULATION 3

Tablet Formulation

Tablets containing the ingredients listed below were prepared using conventional techniques.

| | |
|---|---|
| Compound of Example 65 | 5 mg |
| Hydroxypropyl cellulose (low substitution) | 10 mg |
| Hydroxypropyl cellulose | 3 mg |
| Magnesium stearate | 1 mg |
| Lactose | 81 mg |
| Total | 100 mg |

The tablets may, if desired, be coated. Coating procedures and the components of the coatings are well known in the art.

We claim:

1. A compound selected from the group consisting of
    3,5-dihydroxy-7-[6-hydroxy-2-methyl-8-(2-ethyl-2-methylpentanoyloxy)-1,2,6,7,8,8a-hexahydro-1-naphthyl]heptanoic acid,
    3,5-dihydroxy-7-[6-hydroxy-2-methyl-8-(2-ethyl-2-methylbutyryloxy)-1,2,6,7,8,8a-hexahydro-1-naphthyl]heptanoic acid,
    3,5-dihydroxy-7-[6-hydroxy-2-methyl-8-(2,2-diethylbutyryloxy)-1,2,6,7,8,8a-hexahydro-1-naphthyl]heptanoic acid,
    pharmaceutically acceptable salts thereof, pharmaceutically acceptable esters thereof and ring-closed lactones corresponding thereto.

2. A pharmaceutical composition comprising an effective amount of the compound of claim 1 to inhibit cholesterol biosynthesis in admixture with a pharmaceutically acceptable carrier or diluent.

3. A method of treating a mammal with hypercholesterolemia which comprises administering to said mammal an effective blood cholesterol reducing amount of the compound of claim 1.

4. The compound of claim 1, wherein the compound is selected from the group consisting of
    3,5-dihydroxy-7-[6-hydroxy-2-methyl-8-(2-ethyl-2-methylpentanoyloxy)-1,2,6,7,8,8a-hexahydro-1-naphthyl]heptanoic acid,
    3,5-dihydroxy-7-[6-hydroxy-2-methyl-8-(2-ethyl-2-methylbutyryloxy)-1,2,6,7,8,8a-hexahydro-1-naphthyl]heptanoic acid,
    pharmaceutically acceptable salts thereof, pharmaceutically acceptable esters thereof and ring-closed lactones corresponding thereto.

5. The compound of claim 1, wherein the compound is selected from the group consisting of
    3,5-dihydroxy-7-[6-hydroxy-2-methyl-8-(2-ethyl-2-methylpentanoyloxy)-1,2,6,7,8,8a-hexahydro-1-naphthyl]heptanoic acid,
    3,5-dihydroxy-7-[6-hydroxy-2-methyl-8-(2,2-diethylbutyryloxy)-1,2,6,7,8,8a-hexahydro-1-naphthyl]heptanoic acid,
    pharmaceutically acceptable salts thereof, pharmaceutically acceptable esters thereof and ring-closed lactones corresponding thereto.

6. The compound of claim 1, wherein the compound is selected from the group consisting of
    3,5-dihydroxy-7-[6-hydroxy-2-methyl-8-(2-ethyl-2-methylbutyryloxy)-1,2,6,7,8,8a-hexahydro-1-naphthyl]heptanoic acid,
    3,5-dihydroxy-7-[6-hydroxy-2-methyl-8-(2,2-diethylbutyryloxy)-1,2,6,7,8,8a-hexahydro-1-naphthyl]heptanoic acid,
    pharmaceutically acceptable salts thereof, pharmaceutically acceptable esters thereof and ring-closed lactones corresponding thereto.

7. A method of treating a mammal to inhibit the activity of 3-hydroxy-3-methylglutaryl-CoA reductase in the mammal which comprises administering to said mammal an effective amount of a compound of claim 1 to inhibit the activity of 3-hydroxy-3-methylglutaryl-CoA reductase.

* * * * *

UNITED STATES PATENT AND TRADEMARK OFFICE
CERTIFICATE OF CORRECTION

PATENT NO. : 5,827,855
DATED : October 27, 1998
INVENTOR(S) : Kogen et al

It is certified that error appears in the above-identified patent and that said Letters Patent is hereby corrected as shown below:

Title Page, right column: at top of page, before "Oct. 27, 1998" insert --*--.

Title Page, left column: under "[73] Assignee: Sankyo Company, Limited, Tokyo, Japan" insert
--[*] Notice: The term of this patent shall not extend beyond the expiration date of Pat. No. 5,451,688.--

Title Page, right column, under "OTHER PUBLICATIONS", 5th line, delete "Covergent" and insert --Convergent--.

Column 13, line 51: after "groups:" insert

```
--All     allyl
  Bu      butyl
  iBu     isobutyl
  tBu     t-butyl
  Et      ethyl
  Me      methyl
  Pr      propyl
  iPr     isopropyl--.
```

UNITED STATES PATENT AND TRADEMARK OFFICE
CERTIFICATE OF CORRECTION

PATENT NO. : 5,827,855
DATED : October 27, 1998
INVENTOR(S) : Kogen et al

It is certified that error appears in the above-identified patent and that said Letters Patent is hereby corrected as shown below:

Column 13, line 53: delete "          TABLE 1          ".

Column 14, line 1: delete "   TABLE 1-continued   ".

Column 14, line 40: below the structural formula (I-2a), insert --          TABLE 1          --.

Signed and Sealed this

Twenty-first Day of September, 1999

Q. TODD DICKINSON

*Attest:*

*Attesting Officer*          Acting Commissioner of Patents and Trademarks